US011732045B2

(12) United States Patent
Hipp et al.

(10) Patent No.: US 11,732,045 B2
(45) Date of Patent: Aug. 22, 2023

(54) MULTI-SPECIFIC BINDING PROTEINS FOR CANCER TREATMENT

(71) Applicant: Boehringer Ingelheim International GmbH, Ingelheim am Rhein (DE)

(72) Inventors: Susanne Hipp, Fuessen (DE); Paul Adam, Vienna (AT); Michael Dziegelewski, Newburgh, NY (US); Rajkumar Ganesan, Blue Bell, PA (US); Philip Nicholas Gorman, Prospect, CT (US); Pankaj Gupta, Scarsdale, NY (US); Priyanka Gupta, Danbury, CT (US); Marcio Lasaro, Sandy Hook, CT (US); Justin M. Scheer, Ridgefield, CT (US); Vladimir H. Voynov, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 224 days.

(21) Appl. No.: 17/060,111

(22) Filed: Oct. 1, 2020

(65) Prior Publication Data

US 2021/0107983 A1 Apr. 15, 2021

(30) Foreign Application Priority Data

Oct. 2, 2019 (EP) .................................... 19201200

(51) Int. Cl.
*C07K 16/28* (2006.01)
*A61P 35/00* (2006.01)

(52) U.S. Cl.
CPC .......... *C07K 16/2827* (2013.01); *A61P 35/00* (2018.01); *C07K 16/2809* (2013.01); *C07K 2317/31* (2013.01); *C07K 2317/565* (2013.01)

(58) Field of Classification Search
None
See application file for complete search history.

(56) References Cited

U.S. PATENT DOCUMENTS

| | | | | |
|---|---|---|---|---|
| 4,676,980 | A | 6/1987 | Segal et al. | |
| 11,034,766 | B2 * | 6/2021 | Sentman | C07K 14/7051 |
| 11,332,541 | B2 * | 5/2022 | Hipp | C07K 16/2809 |
| 2014/0072581 | A1 * | 3/2014 | Dixit | C07K 16/2809 435/69.6 |

FOREIGN PATENT DOCUMENTS

| | | | | |
|---|---|---|---|---|
| WO | 8801649 | A1 | 3/1988 | |
| WO | 9005144 | A1 | 5/1990 | |
| WO | 9308829 | A1 | 5/1993 | |
| WO | 9403678 | A1 | 2/1994 | |
| WO | 9404678 | A1 | 3/1994 | |
| WO | 9413804 | A1 | 6/1994 | |
| WO | 09429348 | | 12/1994 | |
| WO | 9634103 | A1 | 10/1996 | |
| WO | 02056910 | A1 | 7/2002 | |
| WO | 03050031 | A1 | 6/2003 | |
| WO | 2007042309 | A2 | 4/2007 | |
| WO | 2009046407 | A2 | 4/2009 | |
| WO | 2009089004 | A1 | 7/2009 | |
| WO | 2009117271 | A2 | 9/2009 | |
| WO | 2011007044 | A1 | 1/2011 | |
| WO | 2011075861 | A1 | 6/2011 | |
| WO | 2012162067 | | 11/2012 | |
| WO | 2012175741 | A2 | 12/2012 | |
| WO | 2013024059 | A2 | 2/2013 | |
| WO | 2013169691 | | 11/2013 | |
| WO | 2013169691 | A1 | 11/2013 | |
| WO | WO-2017165464 | A1 * | 9/2017 | ......... A61K 38/1764 |
| WO | 2017181001 | | 10/2017 | |
| WO | 2017198741 | A1 | 11/2017 | |

OTHER PUBLICATIONS

Altschul, Basic Local Alignment Search Tool, J. Mol. Biol., vol. 215, 1990, p. 403-410.
Karlin and Altschul, Applications and statistics for multiple high-scoring segments in molecular sequences, Proc. Natl. Acad. Sci, vol. 90, 1993, p. 5873-5877.
Ward, Binding activities of a repertoire of single immunoglobulin variable domains secreted from *Escerichia coli*, Letters to Nature, vol. 341, 1989, 3 pages.
Altschul, Gapped Blast and PSI-Blast, a new generation of protein databse search problems, Nucleic Acids Research, vol. 25, 1997, p. 3389-3402.
Knappik, Fully synthetic human combinatorial antibody libraries, JMB, vol. 296, 2002, p. 57-86.
Wang, the prognostic value of B7—H6 protein expression in human oral squamous cell carcinoma, vol. 10, 2017, 7 pages.
Atwell, Stable heterodimers from Remodeling the domain interface of a homeodimer using a phage display library, J. Mol. Biol., vol. 270, 1997, p. 26-35.
Kostelny, Formation of a bispecific antibody by the use of leucine zippers, the J. of Immunology, vol. 148, 1992, p. 1547-1553.
Xu, In vitro characterization of five humanized OKT3 effector Function variant antibodies, Cellular Immunology, vol. 200, 2000, p. 16-26.
Huston, medical Applications of single chain antibodies, Inter. rev. immunol., vol. 10, 1993, p. 195-217.
International Search Report and Written Opinion for PCT/EP2020/077586, dated Mar. 30, 2021.
Brandt, the B7 family member B7—H6 is a tumor cell ligand for the activating natural killer cell receptor NKp30 in humans, Experimental meds, vol. 163, 2009.
Anonymous, Human/Cynomolgus Monkey B7—H6 Antibody, R&D systems Product Catalog, 2019, retrieved from internet, https://resources.rndsystems.com/pdfs/datasheets/mab10162.pdf.

(Continued)

*Primary Examiner* — Laura B Goddard
(74) *Attorney, Agent, or Firm* — Wendy M. Gombert

(57) ABSTRACT

The present invention relates to novel B7H6/CD3 binding proteins. The invention also relates to nucleic acids encoding such proteins; to methods for preparing such proteins; to host cells expressing or capable of expressing such proteins; to compositions comprising such proteins; and to uses of such proteins or such compositions, in particular for therapeutic purposes in the field of cancer diseases.

20 Claims, 24 Drawing Sheets

Specification includes a Sequence Listing.

(56) References Cited

OTHER PUBLICATIONS

Angal, a single amino acid substitution abolishes the heterogeneity of chimeric mouse/human (IgG4) antibody, Molecular Immunology, vol. 30, No. 1, 1993. p. 105-108.
Kohler, Continuous cultures of fused cells secreting antibody of predefined specificity, Nature, vol. 256, 1975, p. 495-497.
Zhang, an NKp-30-based chimeric antigen receptor promotes T-cell effector functions and anti-tumor efficacy in vivo, J. Immunolgy, 2012, vol. 189, p. 2290-2299.
Billetta, Chimeric Antibodies, Intern. Rev. immun., vol. 10, 1993, p. 165-176.
Labrin, Therapeutic IgG4 antbodies engage in Fab-arm exchange with endogenous human IgG4 in vivo, Nature Biotechnology, vol. 27, 2009, 7 pages.
Zhang, Knockdown of B7H6 inhibits tumor progression in triple-negative breast cancer, Oncology letters, vol. 16, 2018, 6 pages.
Brennan, Abstract, Preparation of Bispecific Antibodies by Chemical Recmobination of monoclonal Immunoglobulin G1 Fragments, American Assoc. for the Advancement of Science, 1085, 4 pages.
Li, Structure of the human activating natural cytotoxicity receptor NKp30 bound to its tumor cell ligand B7—H6, JEM, 2011, 13 pages.
Zhao, Comprehensive molecular profilikng of the B7 family in gastrointestinal cancer, Cell Proliferation, vol. 10, 2018, 12 pages.
Bruggemann, Production of human antibody repertoires in transgenic mice, Protein Engineering, 1997, 4 pages.
Anonymous, Human/Cynomolgus Monkey B7—H6 Antibody, Biotechne, Catalog No. MAB10162, 2019, 2 pages.
Brandt, the B7 family member B7—H6 is a tumor cell ligand for the activating natural killer cell receptor NKp30 in humans, JEM, vol. 206, No. 7, 2009, 9 pages.
Lefranc, IMGT unique numbering for immunoglobulin and T cell receptor variable domains and Ig superfamily V-like domains, Developmental and Comparitive immunology, vol. 27, 2003, p. 55-77.
Zhang, B7—H6 expression in non-small cell lung centers, Int. J. Clin Exp. Pathology, vol. 7, 2014, p. 6936-6942.
Li, Alterations of the immunologic Co-Stimulator B7 and TNFR Families Correlate with Hepatocellular Carcinoma Prognosis and Metastasis by Inactivating STAT3, Int. J of Molecular Sciences, vol. 20, 2019, 18 pages.
Zhou, B7—H6 expression correlates with Cancer progression and patient's survival in human ovarian cancer, Int. J. Exp. Pathol., vol. 8, 2015, p. 9428-9433.
Carmen, Abstract, Concepts in antibody phage display, Briefings in Functional Genomics and Proteomics, vol. 1, 2002, p. 189-203.
Lonberg, Human Antibodies from Transgenic Mice, International Reviews of Immunology, vol. 13, 1995, 2 pages.
Giudicelli, IMGT-V-Quest: IMGT Standardized Analysis of the Immunolglobulin (IG) and T cell receptor (TR) Nuelceotide Sequences, CSH Protocols, vol. 10, 2011, 2 pages.
Chatenoud, CD3 Monoclonal Antibodies, Diabetic Studies, No. 4, 2012, 10 pages.
Malmqvist, Surface plamon resonance for detection and measurement of antibody-antigen affinity and kinetics, Scicen Direct, vol. 5, Issue 2, 1993, p. 282-286.
Chen, B7—H6 Protein Expression has no Prognostic Significance in human Gastric Carcinoma, Pathol. Oncol. Res., vol. 20, 2014, p. 203-207.
Marks, Human Antibodies from V-gene Libraries Displayed on Phage, J. Mole. Biol., vol. 222, 1991, p. 581-597.
Chothia, Domain Association in immunoglobulin Molecules, J. Mol. Biol., vol. 186, 1985, p. 651-663.
Matta, Induction of B7—H6, a ligand for the natural killer cell-activating receptor NKp30, Immunobiology, vol. 122, 2013, 11 pages.
Chothia and Lesk, Canonical Structures for the Hypervariable Regions of Immunoglobullins, J. Mol. Biol., vol. 196, 1987, p. 901-917.
Norderhaug, Versatile vectors for transient and stable expression of recombinant antibody molecules in mammalian cells, J. of Immunological Methods, vol. 204, 1997, p. 77-87.
Cunningham, Subgroups of amino acid sequences in the variable regions of immunoglobulin heavy chains, Biochemistry, vol. 64, 1969, 7 pages.
Pearson and Lipman, improved tools for Biological sequence comparison, Proc. Natl. Acad. Sci, vol. 85, 1988, p. 2444-2448.
Darling, Kinetic Exclusion Assay Technoloy, Assay and Drug Development technologies, vol. 2, No. 6, 2005, 1 page.
Pessano, Te T3/T cell receptor Complex, the EMBO Journal, vol. 4, No. 2, 1985, p. 337-344.
Dall'Acqua, Properties of human IgG1s Engineered for enhanced binding to the neonatal Fc receptor (FcRn)*, the J. of Biological Chem., vol. 281, No. 13, 2006, p. 23514-23524.
Ridgeway, Knobs-into-holes engineering of antibody CH3 domains for heavy chain heterodimerization, Protein Engineering vol. 9, No. 7, 1996, p. 617-621.
Edelman, the covalent structure of the entire i G Immunoglobulin Molecule*, Biochemistry, vol. 63, 1969, 8 pages.
Reichmann, Reshaping human antibodies for therapy, Nature, vol. 232, 1985 pages.
Greaves, the role of B7 family molecules in hematolgic malignancy, Blood, vol. 121, 2013, 11 pages.
Revets, Nanobodies as novel agents for cancer therapy, Expert Opinion on Biological Therapy, vol. 5, 2005, p. 111-124.
Gruber, Efficient tumor cell lysis mediated by a bispecific single chain antibody expressed in *Escherichia coli*, the J. of Immunology, vol. 152, 1994, p. 5368-5374.
Salmeron, a conformation epitope expressed upon association of CD-3-epsilon with either CD3-delta or CD-3gamma is the main target for recognition by anti-CD3 onoclonal antibodies, the J. of Immunology, vol. 147, 1991, p. 3047-3052.
Hezareh, Effector Function activities of a panel of mutants of a broadly neutralizing antibody against human immunodeficiency virus type 1, J. of Virology, vol. 10, 2001, p. 12161-12168.
Singh, Selective targeting of the IL23 pathway, MABS, vol. 7, Issue 4, 2015, 14 pages.
Higgins, Using CLUSTAL for multiple sequence alignments, Methods in Enzymology, vol. 266, 1996, 20 pages.
Srinivasan, Immunomodulatory Peptides from IgSF Proteins, vol. 6, Issue 2, 2005 3 pages.
Hollinger, Diabodies, small bivalent and bispecific antbody fragments, Proc. Natl. Acad. Sci, vol. 90, 1993, p. 6444-6448.
Shields, High resolution mapping of the binding site on human IgG1 for FcyRI, FcyRII, FcyRIII, and FcRn and Design of IgG1, the J. of Biological Chem., vol. 276, No. 9, 2001, p. 6591-9604.
Hua, Development of unique cytotoxic chimeric antigen receptors based on human scFv targeting B7H6, Protein Engineering, vol. 30, No. 10, 2017, p. 713-721.
Traunecker, Bispecific single chain molecules target cytotoxic lymphocytes on HIV infected cells, the EMBO journal, vol. 10, 1991, p. 3655-36.
Hust, Abstract, Single chain Fab (scFab) fragment, BMC Biotechnology, vol. 7, 2007, 15 pages.
Tutt, Trispecific F(ab')3 derivatives that use cooperative signaling via the TCR/D3 complex and CD2 to activate and redirect resting cytotoxic T cells, the J. of Immunology, vol. 147, 1991, p. 60-69.
Wu, B7H6-specific bispecific T cell engagers lead to tumor elimination and host anti-tumor immunity, J. Immunol., vol. 194, 2015, p. 5305-5311.

* cited by examiner

A

B

SEQUENCE LISTING

```
<160> NUMBER OF SEQ ID NOS: 350

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: B7H6#1 LCCDR1

<400> SEQUENCE: 1

Lys Ser Ser Gln Ser Leu Phe Tyr Ser Ser Asn Gln Lys Asn Tyr Leu
1               5                   10                  15

Ala


<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#1 LCCDR2

<400> SEQUENCE: 2

Trp Ala Ser Thr Arg Glu Ser
1               5


<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#1 LCCDR3

<400> SEQUENCE: 3

Gln Gln Tyr Tyr Asn Tyr Pro Arg Thr
1               5


<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#1 HCCDR1

<400> SEQUENCE: 4

Gly Tyr Thr Phe Thr Asp Tyr Tyr Met Asn
1               5                   10


<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#1 HCCDR2

<400> SEQUENCE: 5

Tyr Ile Tyr Pro Lys Thr Gly Gly Asn Gly Tyr Asn Gln Lys Phe Lys
1               5                   10                  15

Asp


<210> SEQ ID NO 6
<211> LENGTH: 10
```

<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#1 HCCDR3

<400> SEQUENCE: 6

Glu Asn Trp Asp Gly Tyr Thr Met Ala Tyr
1 5 10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#2 LCCDR1

<400> SEQUENCE: 7

Arg Ala Thr Ser Ser Leu Tyr Ser Met His
1 5 10

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#2 LCCDR2

<400> SEQUENCE: 8

Ala Thr Phe Asn Leu Ala Ser
1 5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#2 LCCDR3

<400> SEQUENCE: 9

Gln Gln Trp Ser Thr Asn Pro Pro Lys Leu Thr
1 5 10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#2 HCCDR1

<400> SEQUENCE: 10

Gly Phe Asn Ile Lys Asn Thr Phe Ile His
1 5 10

<210> SEQ ID NO 11

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#2 HCCDR2

<400> SEQUENCE: 11

Arg Ile Asp Pro Ala Asn Gly Asn Thr Ile Tyr Ala Ser Lys Phe Gln
1               5                   10                  15

Gly


<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#2 HCCDR3

<400> SEQUENCE: 12

Thr Tyr Gly Gly Thr Asn Tyr Phe Asp Tyr
1               5                   10


<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#3 LCCDR1

<400> SEQUENCE: 13

Lys Ala Ser His Asn Val Gly Val Tyr Val Ala
1               5                   10


<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#3 LCCDR2

<400> SEQUENCE: 14

Ser Ala Ser Asn Arg Tyr Ser
1               5


<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#3 LCCDR3

<400> SEQUENCE: 15

Gln Gln Tyr Asn Ser Tyr Pro Leu Thr
1               5
```

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#3 HCCDR1

<400> SEQUENCE: 16

Gly Phe Thr Phe Ser Asp Tyr Tyr Met Thr
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#3 HCCDR2

<400> SEQUENCE: 17

Asn Ile Asp Tyr Asp Gly Ser Arg Ile Tyr Tyr Leu Asp Ser Leu Lys
1               5                   10                  15

Ser

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#3 HCCDR3

<400> SEQUENCE: 18

Asp Asp Pro Ala Trp Leu Ala Tyr
1               5

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#4 LCCDR1

<400> SEQUENCE: 19

Lys Ala Ser Gln Asn Val Gly Lys Tyr Val Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#4 LCCDR2

<400> SEQUENCE: 20

Ser Ala Ser Asn Arg Tyr Asp
1 5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#4 LCCDR3

<400> SEQUENCE: 21

Gln Gln Tyr Ile Ser Tyr Pro Leu Thr
1 5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#4 HCCDR1

<400> SEQUENCE: 22

Gly Tyr Thr Phe Thr Asn Tyr Trp Met Asn
1 5 10

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#4 HCCDR2

<400> SEQUENCE: 23

Gly Ile Tyr Leu Asn Gly Asp Ser Thr Asp Tyr Asn Glu Lys Phe Lys
1 5 10 15

Gly

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#4 HCCDR3

<400> SEQUENCE: 24

Arg Gly Asp Tyr Phe Gly Asp Phe
1 5

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:

<223> OTHER INFORMATION: B7H6#5 LCCDR1

<400> SEQUENCE: 25

Arg Ala Ser Gln Asp Ile Arg Asn Asp Leu Gly
1 5 10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#5 LCCDR2

<400> SEQUENCE: 26

Ala Ala Ser Ser Leu Glu Ser
1 5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#5 LCCDR3

<400> SEQUENCE: 27

Leu Gln Tyr Tyr Asn His Pro Leu Thr
1 5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#5 HCCDR1

<400> SEQUENCE: 28

Gly Tyr Thr Phe Thr Gly Tyr Tyr Ile His
1 5 10

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#5 HCCDR2

<400> SEQUENCE: 29

Trp Ile Asn Pro His Ser Gly Ala Thr Asn Tyr Ala Gln Asn Phe Gln
1 5 10 15

Gly

<210> SEQ ID NO 30
<211> LENGTH: 10
<212> TYPE: PRT
<213> ORGANISM: Artificial Sequence
<220> FEATURE:

<223> OTHER INFORMATION: Description of Artificial Sequence: Synthetic peptide
<220> FEATURE:
<223> OTHER INFORMATION: B7H6#5 HCCDR3

<400> SEQUENCE: 30

Glu Arg Trp Gly Ser Gly Thr Phe Asn Ile
1 5 10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#6 LCCDR1

<400> SEQUENCE: 31

Lys Ala Ser Gln Ser Val Ser Asn Asp Val Val
1 5 10

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#6 LCCDR2

<400> SEQUENCE: 32

Ser Thr Ser Asn Arg Tyr Ile
1 5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#6 LCCDR3

<400> SEQUENCE: 33

Gln Gln Asp Tyr Ser Ser Pro Tyr Thr
1 5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#6 HCCDR1

<400> SEQUENCE: 34

Gly Tyr Thr Phe Thr Asp Tyr Thr Met His
1 5 10

<210> SEQ ID NO 35
<211> LENGTH: 17
<212> TYPE: PRT
<213> ORGANISM: Artificial Sequence -continued
<220> FEATURE:
<223> OTHER INFORMATION: Description of Artificial Sequence: Synthetic
peptide
<220> FEATURE:
<223> OTHER INFORMATION: B7H6#6 HCCDR2

<400> SEQUENCE: 35

Gly Ile Asn Pro Asn Tyr Asp Asn Thr Gly Tyr Ser Glu Lys Phe Lys
1 5 10 15

Asp

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#6 HCCDR3

<400> SEQUENCE: 36

Ser Gly Ser Arg Arg Ser Phe Tyr Phe Asp Tyr
1 5 10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#7 LCCDR1

<400> SEQUENCE: 37

Arg Ala Ser Gln Gly Ile Ser Ser Trp Leu Ala
1 5 10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#7 LCCDR2

<400> SEQUENCE: 38

Ala Ala Ser Ser Leu Gln Ser
1 5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#7 LCCDR3

<400> SEQUENCE: 39

Gln Gln Ala Asn Ser Phe Pro Arg Thr
1 5

<210> SEQ ID NO 40

<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#7 HCCDR1

<400> SEQUENCE: 40

Gly Gly Ser Ile Ser Tyr Asn Tyr Trp Ser
1 5 10

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#7 HCCDR2

<400> SEQUENCE: 41

His Ile Tyr Tyr Ser Gly Ser Thr Asn Tyr Asn Pro Ser Leu Lys Ser
1 5 10 15

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#7 HCCDR3

<400> SEQUENCE: 42

Val Gly Thr Trp Gly Ser Phe Asp Asp
1 5

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#8 LCCDR1

<400> SEQUENCE: 43

Arg Ser Ser Gln Ser Leu Leu Tyr Asn Asn Arg Tyr Asn Tyr Leu Asp
1 5 10 15

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#8 LCCDR2

<400> SEQUENCE: 44

Leu Gly Ser Asn Arg Ala Ser
1 5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#8 LCCDR3

<400> SEQUENCE: 45

Met Gln Thr Leu Gln Ile Pro Ile Thr
1               5

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#8 HCCDR1

<400> SEQUENCE: 46

Gly Asp Thr Leu Asn Ser Tyr Gly Ile Ser
1               5                   10

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#8 HCCDR2

<400> SEQUENCE: 47

Gly Ile Ile Pro Ile Phe Asp Thr Thr Lys Tyr Ala Gln Lys Phe Gln
1               5                   10                  15

Gly

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#8 HCCDR3

<400> SEQUENCE: 48

Glu Arg Gly Tyr Arg Phe Ser Glu Asp Tyr Tyr Phe Tyr Tyr Gly Met
1               5                   10                  15

Asp Val

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#9 LCCDR1

<400> SEQUENCE: 49

Arg Ala Ser Glu Ser Val Asp Asn Phe Gly Val Ser Phe Met Asn
1 5 10 15

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#9 LCCDR2

<400> SEQUENCE: 50

Ala Ala Ser Asn Gln Gly Ser
1 5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#9 LCCDR3

<400> SEQUENCE: 51

Gln Gln Ser Lys Glu Val Pro Trp Thr
1 5

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#9 HCCDR1

<400> SEQUENCE: 52

Asp Tyr Thr Phe Thr His Tyr Trp Ile His
1 5 10

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#9 HCCDR2

<400> SEQUENCE: 53

Ile Ile Gly Pro Ser Asp Asn Glu Ile His Tyr Asn Gln Asp Phe Lys
1 5 10 15

Asp

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:

<223> OTHER INFORMATION: B7H6#9 HCCDR3

<400> SEQUENCE: 54

Gln Ile Ile Ser Met Val Val Gly Thr Glu Tyr Phe Asp Val
1 5 10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#10 LCCDR1

<400> SEQUENCE: 55

Arg Ala Ser Gln Gly Ile Ser Ser Trp Leu Ala
1 5 10

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#10 LCCDR2

<400> SEQUENCE: 56

Val Ala Ser Ser Leu Gln Arg
1 5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#10 LCCDR3

<400> SEQUENCE: 57

Gln Gln Ala Asn Ser Phe Pro Arg Thr
1 5

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#10 HCCDR1

<400> SEQUENCE: 58

Gly Asp Ser Ile Ser Ser Tyr Tyr Trp Ser
1 5 10

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<220> FEATURE:
<223> OTHER INFORMATION: B7H6#10 HCCDR2

<400> SEQUENCE: 59

His Ile Tyr Thr Ser Glu Lys Asn Asn Tyr Asn Pro Ser Leu Lys Ser
1 5 10 15

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#10 HCCDR3

<400> SEQUENCE: 60

Val Gly Asn Trp Gly Ser His Asp Ala
1 5

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#11 LCCDR1

<400> SEQUENCE: 61

Arg Ser Ser Gln Ser Leu Leu His Ser Asn Gly Tyr Asn Tyr Leu Asp
1 5 10 15

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#11 LCCDR2

<400> SEQUENCE: 62

Leu Gly Ser Asn Arg Ala Ser
1 5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#11 LCCDR3

<400> SEQUENCE: 63

Met Gln Ala Leu Gln Thr Pro Leu Thr
1 5

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#11 HCCDR1

<400> SEQUENCE: 64

Gly Ile Thr Phe Ser Tyr Tyr Thr Met Asn
1 5 10

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#11 HCCDR2

<400> SEQUENCE: 65

Ser Ile Ser Ser Arg Ser Ser Tyr Ile Tyr Tyr Ala Asp Ser Val Lys
1 5 10 15

Gly

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#11 HCCDR3

<400> SEQUENCE: 66

Asp Lys Gly Asp Tyr Ser Lys Asp Ile Tyr Tyr Tyr Tyr Gly Met Asp
1 5 10 15

Val

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#12 LCCDR1

<400> SEQUENCE: 67

Lys Ala Ser Gln Asn Val Gly Lys Tyr Val Ala
1 5 10

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#12 LCCDR2

<400> SEQUENCE: 68

Ser Ala Ser Asn Arg Tyr Asp
1 5

<210> SEQ ID NO 69

<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#12 LCCDR3

<400> SEQUENCE: 69

Gln Gln Tyr Ile Ser Tyr Pro Leu Thr
1 5

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#12 HCCDR1

<400> SEQUENCE: 70

Gly Tyr Thr Phe Thr Asn Tyr Trp Met Asn
1 5 10

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#12 HCCDR2

<400> SEQUENCE: 71

Gly Ile Tyr Leu Asn Gly Asp Ser Thr Asp Tyr Asn Glu Lys Phe Lys
1 5 10 15

Gly

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#12 HCCDR3

<400> SEQUENCE: 72

Arg Gly Asp Tyr Phe Gly Asp Phe
1 5

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#13 LCCDR1

<400> SEQUENCE: 73

Lys Ala Ser Gln Asn Val Gly Lys Tyr Val Ala
1 5 10

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#13 LCCDR2

<400> SEQUENCE: 74

Ser Ala Ser Asn Arg Tyr Asp
1 5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#13 LCCDR3

<400> SEQUENCE: 75

Gln Gln Tyr Ile Ser Tyr Pro Leu Thr
1 5

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#13 HCCDR1

<400> SEQUENCE: 76

Gly Tyr Thr Phe Thr Ser Tyr Trp Met Asn
1 5 10

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#13 HCCDR2

<400> SEQUENCE: 77

Gly Ile Tyr Leu Asn Gly Asp Ser Thr Asp Tyr Asn Glu Lys Phe Lys
1 5 10 15

Gly

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#13 HCCDR3

<400> SEQUENCE: 78

Arg Gly Asp Tyr Phe Gly Asp Phe
1 5

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#14 LCCDR1

<400> SEQUENCE: 79

Lys Ala Ser Gln Asn Val Gly Lys Tyr Val Ala
1 5 10

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#14 LCCDR2

<400> SEQUENCE: 80

Ser Ala Ser Asn Arg Tyr Asp
1 5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#14 LCCDR3

<400> SEQUENCE: 81

Gln Gln Tyr Ile Ser Tyr Pro Leu Thr
1 5

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#14 HCCDR1

<400> SEQUENCE: 82

Gly Tyr Thr Phe Thr Asn Tyr Trp Met Asn
1 5 10

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#14 HCCDR2

<400> SEQUENCE: 83

Gly Ile Tyr Leu Asn Gly Asp Ser Thr Asp Tyr Asn Glu Lys Phe Lys
1 5 10 15

Gly

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#14 HCCDR3

<400> SEQUENCE: 84

Arg Gly Asp Tyr Phe Gly Asp Phe
1 5

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#15 LCCDR1

<400> SEQUENCE: 85

Lys Ala Ser Gln Asn Val Gly Lys Tyr Val Ala
1 5 10

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#15 LCCDR2

<400> SEQUENCE: 86

Ser Ala Ser Asn Arg Tyr Asp
1 5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#15 LCCDR3

<400> SEQUENCE: 87

Gln Gln Tyr Ile Ser Tyr Pro Leu Thr
1 5

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<220> FEATURE:
<223> OTHER INFORMATION: B7H6#15 HCCDR1

<400> SEQUENCE: 88

Gly Tyr Thr Phe Thr Asn Tyr Trp Met Asn
1 5 10

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#15 HCCDR2

<400> SEQUENCE: 89

Gly Ile Tyr Leu Ser Gly Asp Ser Thr Asp Tyr Asn Glu Lys Phe Lys
1 5 10 15

Gly

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#15 HCCDR3

<400> SEQUENCE: 90

Arg Gly Asp Tyr Phe Gly Asp Phe
1 5

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#16 LCCDR1

<400> SEQUENCE: 91

Lys Ala Ser Gln Asn Val Gly Lys Tyr Val Ala
1 5 10

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#16 LCCDR2

<400> SEQUENCE: 92

Ser Ala Ser Asn Arg Tyr Asp
1 5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#16 LCCDR3

<400> SEQUENCE: 93

Gln Gln Tyr Ile Ser Tyr Pro Leu Thr
1 5

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#16 HCCDR1

<400> SEQUENCE: 94

Gly Tyr Thr Phe Thr Ser Tyr Trp Met Asn
1 5 10

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#16 HCCDR2

<400> SEQUENCE: 95

Gly Ile Tyr Leu Ser Gly Glu Ser Thr Asp Tyr Asn Glu Lys Phe Lys
1 5 10 15

Gly

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#16 HCCDR3

<400> SEQUENCE: 96

Arg Gly Asp Tyr Phe Gly Asp Phe
1 5

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: B7H6#17 LCCDR1

<400> SEQUENCE: 97

Lys Ala Ser Gln Asn Val Gly Lys Tyr Val Ala
1 5 10

<210> SEQ ID NO 98

<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#17 LCCDR2

<400> SEQUENCE: 98

Ser Ala Ser Asn Arg Tyr Asp
1 5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#17 LCCDR3

<400> SEQUENCE: 99

Gln Gln Tyr Ile Ser Tyr Pro Leu Thr
1 5

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#17 HCCDR1

<400> SEQUENCE: 100

Gly Tyr Thr Phe Thr Ser Tyr Trp Met Asn
1 5 10

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#17 HCCDR2

<400> SEQUENCE: 101

Gly Ile Tyr Leu Ser Gly Asp Ser Thr Asp Tyr Asn Glu Lys Phe Lys
1 5 10 15

Gly

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#17 HCCDR3

<400> SEQUENCE: 102

Arg Gly Asp Tyr Phe Gly Asp Phe
1 5

```
<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#18 LCCDR1

<400> SEQUENCE: 103

Lys Ala Ser Gln Asn Val Gly Lys Tyr Val Ala
1               5                   10


<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#18 LCCDR2

<400> SEQUENCE: 104

Ser Ala Ser Asn Arg Tyr Asp
1               5


<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#18 LCCDR3

<400> SEQUENCE: 105

Gln Gln Tyr Ile Ser Tyr Pro Leu Thr
1               5


<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#18 HCCDR1

<400> SEQUENCE: 106

Gly Tyr Thr Phe Thr Ser Tyr Trp Met Asn
1               5                   10


<210> SEQ ID NO 107
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#18 HCCDR2

<400> SEQUENCE: 107

Gly Ile Tyr Leu Ser Gly Asp Ser Thr Asp Tyr Asn Glu Lys Phe Lys
```

1 5 10 15

Gly

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#18 HCCDR3

<400> SEQUENCE: 108

Arg Gly Asp Tyr Phe Gly Asp Phe
1 5

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#19 LCCDR1

<400> SEQUENCE: 109

Lys Ala Ser Gln Asn Val Gly Lys Tyr Val Ala
1 5 10

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#19 LCCDR2

<400> SEQUENCE: 110

Ser Ala Ser Asn Arg Tyr Asp
1 5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#19 LCCDR3

<400> SEQUENCE: 111

Gln Gln Tyr Ile Ser Tyr Pro Leu Thr
1 5

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#19 HCCDR1

<400> SEQUENCE: 112

Gly Tyr Thr Phe Thr Ser Tyr Trp Met Asn
1 5 10

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#19 HCCDR2

<400> SEQUENCE: 113

Gly Ile Tyr Leu Ser Gly Glu Ser Thr Asp Tyr Asn Glu Lys Phe Lys
1 5 10 15

Gly

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#19 HCCDR3

<400> SEQUENCE: 114

Arg Gly Asp Tyr Phe Gly Asp Phe
1 5

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#20 LCCDR1

<400> SEQUENCE: 115

Lys Ala Ser Gln Asn Val Gly Lys Tyr Val Ala
1 5 10

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#20 LCCDR2

<400> SEQUENCE: 116

Ser Ala Ser Asn Arg Tyr Asp
1 5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<220> FEATURE:
<223> OTHER INFORMATION: B7H6#20 LCCDR3

<400> SEQUENCE: 117

Gln Gln Tyr Ile Ser Tyr Pro Leu Thr
1 5

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#20 HCCDR1

<400> SEQUENCE: 118

Gly Tyr Thr Phe Thr Ser Tyr Trp Met Asn
1 5 10

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#20 HCCDR2

<400> SEQUENCE: 119

Gly Ile Tyr Leu Ser Gly Asp Ser Thr Asp Tyr Asn Glu Lys Phe Lys
1 5 10 15

Gly

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#20 HCCDR3

<400> SEQUENCE: 120

Arg Gly Asp Tyr Phe Gly Asp Phe
1 5

<210> SEQ ID NO 121
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#21 LCCDR1

<400> SEQUENCE: 121

Lys Ala Ser Gln Asn Val Gly Lys Tyr Val Ala
1 5 10

<210> SEQ ID NO 122
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: B7H6#21 LCCDR2

<400> SEQUENCE: 122

Ser Ala Ser Asn Arg Tyr Asp
1               5


<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#21 LCCDR3

<400> SEQUENCE: 123

Gln Gln Tyr Ile Ser Tyr Pro Leu Thr
1               5


<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#21 HCCDR1

<400> SEQUENCE: 124

Gly Tyr Thr Phe Thr Ser Tyr Trp Met Asn
1               5                   10


<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#21 HCCDR2

<400> SEQUENCE: 125

Gly Ile Tyr Leu Ser Gly Glu Ser Thr Asp Tyr Asn Glu Lys Phe Lys
1               5                   10                  15

Gly


<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#21 HCCDR3

<400> SEQUENCE: 126

Arg Gly Asp Tyr Phe Gly Asp Phe
1               5


<210> SEQ ID NO 127
```

<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#22 LCCDR1

<400> SEQUENCE: 127

Lys Ala Ser Gln Asn Val Gly Lys Tyr Val Ala
1               5                   10

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#22 LCCDR2

<400> SEQUENCE: 128

Ser Ala Ser Asn Arg Tyr Asp
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#22 LCCDR3

<400> SEQUENCE: 129

Gln Gln Tyr Ile Ser Tyr Pro Leu Thr
1               5

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#22 HCCDR1

<400> SEQUENCE: 130

Gly Tyr Thr Phe Thr Ser Tyr Trp Met Asn
1               5                   10

<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#22 HCCDR2

<400> SEQUENCE: 131

Gly Ile Tyr Leu Ser Gly Asp Ser Thr Asp Tyr Asn Glu Lys Phe Lys
1               5                   10                  15

Gly

```
<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#22 HCCDR3

<400> SEQUENCE: 132

Arg Gly Asp Tyr Phe Gly Asp Phe
1               5


<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#23 LCCDR1

<400> SEQUENCE: 133

Lys Ala Ser Gln Asn Val Gly Lys Tyr Val Ala
1               5                   10


<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#23 LCCDR2

<400> SEQUENCE: 134

Ser Ala Ser Asn Arg Tyr Asp
1               5


<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#23 LCCDR3

<400> SEQUENCE: 135

Gln Gln Tyr Ile Ser Tyr Pro Leu Thr
1               5


<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#23 HCCDR1

<400> SEQUENCE: 136

Gly Tyr Thr Phe Thr Ser Tyr Trp Met Asn
```

1 5 10

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#23 HCCDR2

<400> SEQUENCE: 137

Gly Ile Tyr Leu Ser Gly Glu Ser Thr Asp Tyr Asn Glu Lys Phe Lys
1 5 10 15

Gly

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#23 HCCDR3

<400> SEQUENCE: 138

Arg Gly Asp Tyr Phe Gly Asp Phe
1 5

<210> SEQ ID NO 139
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#24 LCCDR1

<400> SEQUENCE: 139

Lys Ala Ser Gln Asn Val Gly Lys Tyr Val Ala
1 5 10

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#24 LCCDR2

<400> SEQUENCE: 140

Ser Ala Ser Asn Arg Tyr Asp
1 5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: B7H6#24 LCCDR3

<400> SEQUENCE: 141

Gln Gln Tyr Ile Ser Tyr Pro Leu Thr
1               5

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#24 HCCDR1

<400> SEQUENCE: 142

Gly Tyr Thr Phe Thr Asn Tyr Trp Met Asn
1               5                   10

<210> SEQ ID NO 143
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#24 HCCDR2

<400> SEQUENCE: 143

Gly Ile Tyr Leu Ser Gly Asp Ser Thr Asp Tyr Asn Glu Lys Phe Lys
1               5                   10                  15

Gly

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B7H6#24 HCCDR3

<400> SEQUENCE: 144

Arg Gly Asp Tyr Phe Gly Asp Phe
1               5

<210> SEQ ID NO 145
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#1 VL

<400> SEQUENCE: 145

Asp Ile Val Met Ser Gln Ser Pro Ser Ser Leu Ala Val Ser Val Gly
1               5                   10                  15

Glu Lys Val Thr Met Asn Cys Lys Ser Ser Gln Ser Leu Phe Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

-continued

Pro Asp Arg Phe Thr Gly Ser Gly Ser Gly Thr Asp Phe Thr Leu Thr
65 70 75 80

Ile Ser Ser Val Lys Ala Glu Asp Leu Ala Val Tyr Tyr Cys Gln Gln
85 90 95

Tyr Tyr Asn Tyr Pro Arg Thr Phe Gly Gly Gly Thr Lys Leu Glu Ile
100 105 110

Lys

<210> SEQ ID NO 146
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#1 VH

<400> SEQUENCE: 146

Glu Val Gln Leu Gln Gln Ser Gly Pro Glu Leu Val Lys Pro Gly Thr
1 5 10 15

Ser Val Lys Met Ser Cys Lys Ala Ser Gly Tyr Thr Phe Thr Asp Tyr
20 25 30

Tyr Met Asn Trp Val Lys Gln Ser Gln Gly Lys Asn Leu Glu Trp Ile
35 40 45

Ala Tyr Ile Tyr Pro Lys Thr Gly Gly Asn Gly Tyr Asn Gln Lys Phe
50 55 60

Lys Asp Lys Ala Thr Leu Thr Val Asp Lys Ser Ser Asn Thr Ala Tyr
65 70 75 80

Met Glu Leu Arg Ser Leu Thr Ser Asp Asp Ser Ala Val Tyr Tyr Cys
85 90 95

Gly Arg Glu Asn Trp Asp Gly Tyr Thr Met Ala Tyr Trp Gly Gln Gly
100 105 110

Thr Ser Val Thr Val Ser Ser
115

<210> SEQ ID NO 147
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#2 VL

<400> SEQUENCE: 147

Glu Ile Val Leu Thr Gln Ser Pro Asp Phe Leu Ser Ala Ser Pro Gly
1 5 10 15

Glu Lys Val Thr Met Thr Cys Arg Ala Thr Ser Ser Leu Tyr Ser Met
20 25 30

His Trp Tyr Gln Gln Lys Pro Gly Ser Ser Pro Lys Pro Trp Ile Tyr
35 40 45

Ala Thr Phe Asn Leu Ala Ser Gly Val Pro Ala Arg Phe Ser Gly Ser
50 55 60

Gly Ser Gly Thr Ser Tyr Ser Leu Thr Ile Thr Arg Val Glu Ala Glu
65 70 75 80

Asp Ala Ala Thr Tyr Tyr Cys Gln Gln Trp Ser Thr Asn Pro Pro Lys
85 90 95

```
Leu Thr Phe Gly Ala Gly Thr Lys Leu Glu Leu Lys
            100                 105


<210> SEQ ID NO 148
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#2 VH

<400> SEQUENCE: 148

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asn Thr
            20                  25                  30

Phe Ile His Trp Val Asn Gln Arg Pro Glu Gln Gly Leu Glu Trp Ile
        35                  40                  45

Gly Arg Ile Asp Pro Ala Asn Gly Asn Thr Ile Tyr Ala Ser Lys Phe
    50                  55                  60

Gln Gly Arg Ala Thr Ile Thr Thr Asp Thr Ser Ser Asn Thr Ala Tyr
65                  70                  75                  80

Met His Leu Ser Ser Leu Thr Ser Gly Asp Thr Ala Val Tyr Tyr Cys
                85                  90                  95

Ala Arg Thr Tyr Gly Gly Thr Asn Tyr Phe Asp Tyr Trp Gly Gln Gly
            100                 105                 110

Thr Thr Leu Thr Val Ser Ser
        115


<210> SEQ ID NO 149
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#3 VL

<400> SEQUENCE: 149

Asp Ile Val Met Thr Gln Ser Gln Lys Leu Leu Ser Thr Ser Val Gly
1               5                   10                  15

Asp Arg Ile Ser Val Thr Cys Lys Ala Ser His Asn Val Gly Val Tyr
            20                  25                  30

Val Ala Trp Tyr Gln Gln Lys Pro Gly His Ser Pro Lys Ala Leu Ile
        35                  40                  45

His Ser Ala Ser Asn Arg Tyr Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Leu Ile
            100                 105


<210> SEQ ID NO 150
<211> LENGTH: 117
<212> TYPE: PRT
```

<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#3 VH

<400> SEQUENCE: 150

```
Glu Val Lys Leu Val Glu Ser Glu Gly Gly Leu Val Gln Pro Gly Ser
1               5                   10                  15

Ser Met Lys Leu Ser Cys Thr Ala Ser Gly Phe Thr Phe Ser Asp Tyr
            20                  25                  30

Tyr Met Thr Trp Val Arg Gln Val Pro Glu Lys Gly Leu Glu Trp Val
        35                  40                  45

Gly Asn Ile Asp Tyr Asp Gly Ser Arg Ile Tyr Tyr Leu Asp Ser Leu
    50                  55                  60

Lys Ser Arg Phe Ile Ile Ser Arg Asp Asn Ala Lys Asn Ile Leu Tyr
65                  70                  75                  80

Leu Gln Met Asn Ser Leu Lys Ser Glu Asp Thr Ala Thr Tyr Tyr Cys
                85                  90                  95

Ala Arg Asp Asp Pro Ala Trp Leu Ala Tyr Trp Gly Gln Gly Thr Leu
            100                 105                 110

Val Thr Val Ser Ser
        115
```

<210> SEQ ID NO 151
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#4 VL

<400> SEQUENCE: 151

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Lys Tyr
            20                  25                  30

Val Ala Trp Tyr Gln Gln Lys Pro Gly Gln Ser Pro Lys Ala Leu Ile
        35                  40                  45

Tyr Ser Ala Ser Asn Arg Tyr Asp Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Thr Glu Tyr Phe Cys Gln Gln Tyr Ile Ser Tyr Pro Leu
                85                  90                  95

Thr Phe Gly Ala Gly Thr Lys Leu Glu Leu Lys
            100                 105
```

<210> SEQ ID NO 152
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#4 VH

<400> SEQUENCE: 152

```
Gln Val Gln Leu Gln Gln Pro Gly Ser Val Leu Val Arg Pro Gly Ala
1               5                   10                  15

Ser Val Arg Leu Ser Cys Lys Ala Ser Gly Tyr Thr Phe Thr Asn Tyr
            20                  25                  30

Trp Met Asn Trp Met Lys Gln Arg Pro Gly Gln Gly Leu Glu Trp Ile
        35                  40                  45

Gly Gly Ile Tyr Leu Asn Gly Asp Ser Thr Asp Tyr Asn Glu Lys Phe
    50                  55                  60

Lys Gly Lys Ala Thr Leu Thr Val Asp Thr Ser Ser Ser Thr Thr Tyr
65                  70                  75                  80

Met Asp Leu Ser Ser Leu Thr Tyr Glu Asp Ser Ala Val Tyr Tyr Cys
                85                  90                  95

Thr Thr Arg Gly Asp Tyr Phe Gly Asp Phe Trp Gly Gln Gly Thr Thr
            100                 105                 110

Leu Thr Val Ser Ser
        115


<210> SEQ ID NO 153
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#5 VL

<400> SEQUENCE: 153

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Phe Gln Gln Arg Pro Gly Lys Ala Pro Asn Leu Leu Ile
        35                  40                  45

Tyr Ala Ala Ser Ser Leu Glu Ser Gly Val Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Tyr Asn His Pro Leu
                85                  90                  95

Thr Phe Gly Gly Gly Thr Lys Val Glu Ile Lys
            100                 105


<210> SEQ ID NO 154
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#5 VH

<400> SEQUENCE: 154

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
```

```
        35                  40                  45

Gly Trp Ile Asn Pro His Ser Gly Ala Thr Asn Tyr Ala Gln Asn Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Ala Ala Val Tyr Tyr Cys
                85                  90                  95

Ala Arg Glu Arg Trp Gly Ser Gly Thr Phe Asn Ile Trp Gly Gln Gly
            100                 105                 110

Thr Met Val Thr Val Ser Ser
        115


<210> SEQ ID NO 155
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#6 VL

<400> SEQUENCE: 155

Asp Ile Val Met Thr Gln Ser Pro Asp Ser Leu Pro Val Ser Ala Gly
1               5                   10                  15

Asp Arg Val Thr Ile Thr Cys Lys Ala Ser Gln Ser Val Ser Asn Asp
            20                  25                  30

Val Val Trp Tyr Gln Gln Lys Pro Gly Gln Ser Pro Lys Leu Leu Met
        35                  40                  45

Tyr Ser Thr Ser Asn Arg Tyr Ile Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105


<210> SEQ ID NO 156
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#6 VH

<400> SEQUENCE: 156

Glu Val Gln Leu Gln Gln Ser Gly Pro Glu Leu Leu Lys Pro Gly Ala
1               5                   10                  15

Ser Val Lys Ile Ser Cys Lys Thr Ser Gly Tyr Thr Phe Thr Asp Tyr
            20                  25                  30

Thr Met His Trp Val Lys Gln Ser His Gly Lys Ser Leu Glu Trp Ile
        35                  40                  45

Gly Gly Ile Asn Pro Asn Tyr Asp Asn Thr Gly Tyr Ser Glu Lys Phe
    50                  55                  60

Lys Asp Lys Ala Thr Leu Thr Val Asp Lys Ser Ser Ser Thr Ala Tyr
65                  70                  75                  80
```

```
Met Glu Leu Arg Ser Leu Thr Ser Glu Asp Ser Ala Val Tyr Tyr Cys
                85                  90                  95

Thr Arg Ser Gly Ser Arg Arg Ser Phe Tyr Phe Asp Tyr Trp Gly Gln
            100                 105                 110

Gly Thr Thr Leu Thr Val Ser Ser
        115                 120


<210> SEQ ID NO 157
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#7 VL

<400> SEQUENCE: 157

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105


<210> SEQ ID NO 158
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#7 VH

<400> SEQUENCE: 158

Gln Val Gln Leu Gln Glu Ser Gly Pro Gly Leu Val Lys Pro Ser Glu
1               5                   10                  15

Thr Leu Ser Leu Thr Tyr Thr Val Ser Gly Gly Ser Ile Ser Tyr Asn
            20                  25                  30

Tyr Trp Ser Trp Ile Arg Gln Pro Pro Glu Lys Gly Leu Glu Trp Ile
        35                  40                  45

Gly His Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Val Gly Thr Trp Gly Ser Phe Asp Asp Trp Gly Gln Gly Thr Leu
            100                 105                 110

Val Thr Val Ser Ser
        115
```

<210> SEQ ID NO 159
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#8 VL

<400> SEQUENCE: 159

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Asn
            20                  25                  30

Asn Arg Tyr Asn Tyr Leu Asp Trp Tyr Leu Gln Lys Pro Gly Gln Ser
        35                  40                  45

Pro Glu Val Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Phe Gly Val Tyr Tyr Cys Met Gln Thr
                85                  90                  95

Leu Gln Ile Pro Ile Thr Phe Gly Gln Gly Thr Arg Leu Glu Ile Lys
            100                 105                 110
```

<210> SEQ ID NO 160
<211> LENGTH: 127
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#8 VH

<400> SEQUENCE: 160

```
Gln Val Gln Val Val Gln Ser Gly Ala Glu Val Lys Lys Pro Gly Ser
1               5                   10                  15

Ser Val Lys Val Ser Cys Lys Gly Ser Gly Asp Thr Leu Asn Ser Tyr
            20                  25                  30

Gly Ile Ser Trp Met Arg Gln Ala Pro Gly Gln Gly Leu Glu Trp Met
        35                  40                  45

Gly Gly Ile Ile Pro Ile Phe Asp Thr Thr Lys Tyr Ala Gln Lys Phe
    50                  55                  60

Gln Gly Arg Val Thr Ile Thr Ala Asp Lys Ser Thr Thr Thr Val Tyr
65                  70                  75                  80

Met Glu Leu Ser Ser Leu Arg Phe Glu Asp Thr Ala Val Tyr Tyr Cys
                85                  90                  95

Ala Arg Glu Arg Gly Tyr Arg Phe Ser Glu Asp Tyr Tyr Phe Tyr Tyr
            100                 105                 110

Gly Met Asp Val Trp Gly Gln Gly Thr Thr Val Thr Val Ser Ser
        115                 120                 125
```

<210> SEQ ID NO 161
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#9 VL

<400> SEQUENCE: 161

Asp Ile Val Leu Thr Gln Ser Pro Val Ser Leu Ala Val Ser Leu Gly
1               5                   10                  15

Gln Arg Ala Thr Ile Ser Cys Arg Ala Ser Glu Ser Val Asp Asn Phe
            20                  25                  30

Gly Val Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Leu Glu Glu Asp Asp Thr Ala Met Tyr Phe Cys Gln Gln Ser Lys
                85                  90                  95

Glu Val Pro Trp Thr Phe Gly Gly Gly Thr Arg Leu Glu Ile Lys
            100                 105                 110

<210> SEQ ID NO 162
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#9 VH

<400> SEQUENCE: 162

Gln Val Gln Leu Gln Gln Pro Gly Ala Glu Met Val Arg Pro Gly Ser
1               5                   10                  15

Ser Val Lys Leu Ser Cys Lys Ala Ser Asp Tyr Thr Phe Thr His Tyr
            20                  25                  30

Trp Ile His Trp Val Lys Gln Arg Pro Leu Glu Gly Leu Glu Trp Ile
        35                  40                  45

Gly Ile Ile Gly Pro Ser Asp Asn Glu Ile His Tyr Asn Gln Asp Phe
    50                  55                  60

Lys Asp Lys Ala Thr Leu Thr Val Asp Lys Ser Ser Asn Thr Ala Tyr
65                  70                  75                  80

Leu His Leu Asn Ser Leu Thr Ser Glu Asp Ser Ala Val Tyr Tyr Cys
                85                  90                  95

Ala Arg Gln Ile Ile Ser Met Val Val Gly Thr Glu Tyr Phe Asp Val
            100                 105                 110

Trp Gly Thr Gly Thr Thr Val Thr Val Ser Ser
        115                 120

<210> SEQ ID NO 163
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#10 VL

<400> SEQUENCE: 163

Asp Ile Gln Met Thr Gln Ser Pro Ser Ser Val Ser Ala Ser Val Gly
1               5                   10                  15

```
Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Val Ala Ser Ser Leu Gln Arg Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105


<210> SEQ ID NO 164
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#10 VH

<400> SEQUENCE: 164

Gln Val His Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Tyr
            20                  25                  30

Tyr Trp Ser Trp Ile Arg Gln Pro Ala Gly Lys Gly Leu Glu Trp Ile
        35                  40                  45

Gly His Ile Tyr Thr Ser Glu Lys Asn Asn Tyr Asn Pro Ser Leu Lys
    50                  55                  60

Ser Arg Val Ile Met Ser Val Asp Thr Ser Lys Asn Gln Phe Ser Leu
65                  70                  75                  80

Asn Leu Ser Ser Val Thr Ala Ala Asp Thr Ala Val Tyr Tyr Cys Ala
                85                  90                  95

Arg Val Gly Asn Trp Gly Ser His Asp Ala Trp Gly Gln Gly Thr Leu
            100                 105                 110

Val Thr Val Ser Ser
        115


<210> SEQ ID NO 165
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#11 VL

<400> SEQUENCE: 165

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Val Leu Ile Tyr Leu Gly Ser Asn Arg Ala Ser Gly Val Pro
```

```
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110


<210> SEQ ID NO 166
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#11 VH

<400> SEQUENCE: 166

Glu Leu Gln Leu Val Asn Ser Gly Gly Gly Leu Val Lys Ser Gly Gly
1               5                   10                  15

Ser Leu Arg Leu Ser Cys Ala Ala Ser Gly Ile Thr Phe Ser Tyr Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Ser Tyr Ile Tyr Tyr Ala Asp Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Gly Asp Tyr Ser Lys Asp Ile Tyr Tyr Tyr Tyr Gly
            100                 105                 110

Met Asp Val Trp Gly Gln Gly Thr Thr Val Thr Val Ser Ser
        115                 120                 125


<210> SEQ ID NO 167
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#12 VL

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Tyr Ile Ser Tyr Pro Leu
                85                  90                  95
```

```
Thr Phe Gly Ala Gly Thr Lys Leu Glu Ile Lys
            100                 105


<210> SEQ ID NO 168
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#12 VH

<400> SEQUENCE: 168

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Asn Trp Val Lys Gln Ala Pro Gly Gln Gly Leu Glu Trp Met
        35                  40                  45

Gly Gly Ile Tyr Leu Asn Gly Asp Ser Thr Asp Tyr Asn Glu Lys Phe
    50                  55                  60

Lys Gly Lys Ala Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Arg Gly Asp Tyr Phe Gly Asp Phe Trp Gly Gln Gly Thr Leu
            100                 105                 110

Val Thr Val Ser Ser
        115


<210> SEQ ID NO 169
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#13 VL

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Tyr Ile Ser Tyr Pro Leu
                85                  90                  95

Thr Phe Gly Ala Gly Thr Lys Leu Glu Ile Lys
            100                 105


<210> SEQ ID NO 170
<211> LENGTH: 117
<212> TYPE: PRT
<213> ORGANISM: Artificial Sequence
```

<220> FEATURE:
<223> OTHER INFORMATION: Description of Artificial Sequence: Synthetic
polypeptide
<220> FEATURE:
<223> OTHER INFORMATION: B7H6#13 VH

<400> SEQUENCE: 170

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Met Lys Gln Ala Pro Gly Gln Gly Leu Glu Trp Met
        35                  40                  45

Gly Gly Ile Tyr Leu Asn Gly Asp Ser Thr Asp Tyr Asn Glu Lys Phe
    50                  55                  60

Lys Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Arg Gly Asp Tyr Phe Gly Asp Phe Trp Gly Gln Gly Thr Leu
            100                 105                 110

Val Thr Val Ser Ser
        115
```

<210> SEQ ID NO 171
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#14 VL

<400> SEQUENCE: 171

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ile Ser Tyr Pro Leu
                85                  90                  95

Thr Phe Gly Ala Gly Thr Lys Leu Glu Ile Lys
            100                 105
```

<210> SEQ ID NO 172
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#14 VH

<400> SEQUENCE: 172

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Asn Trp Met Lys Gln Ala Pro Gly Gln Gly Leu Glu Trp Ile
        35                  40                  45

Gly Gly Ile Tyr Leu Asn Gly Asp Ser Thr Asp Tyr Asn Glu Lys Phe
    50                  55                  60

Lys Gly Lys Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Arg Gly Asp Tyr Phe Gly Asp Phe Trp Gly Gln Gly Thr Leu
            100                 105                 110

Val Thr Val Ser Ser
        115


<210> SEQ ID NO 173
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#15 VL

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Tyr Ile Ser Tyr Pro Leu
                85                  90                  95

Thr Phe Gly Ala Gly Thr Lys Leu Glu Ile Lys
            100                 105


<210> SEQ ID NO 174
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#15 VH

<400> SEQUENCE: 174

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Asn Trp Met Arg Gln Ala Pro Gly Gln Gly Leu Glu Trp Met
        35                  40                  45
```

```
Gly Gly Ile Tyr Leu Ser Gly Asp Ser Thr Asp Tyr Asn Glu Lys Phe
    50                  55                  60

Lys Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Arg Gly Asp Tyr Phe Gly Asp Phe Trp Gly Gln Gly Thr Leu
            100                 105                 110

Val Thr Val Ser Ser
        115


<210> SEQ ID NO 175
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#16 VL

<400> SEQUENCE: 175

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Tyr Ile Ser Tyr Pro Leu
                85                  90                  95

Thr Phe Gly Ala Gly Thr Lys Leu Glu Ile Lys
            100                 105


<210> SEQ ID NO 176
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#16 VH

<400> SEQUENCE: 176

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Met Arg Gln Ala Pro Gly Gln Gly Leu Glu Trp Met
        35                  40                  45

Gly Gly Ile Tyr Leu Ser Gly Glu Ser Thr Asp Tyr Asn Glu Lys Phe
    50                  55                  60

Lys Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
```

```
                85                  90                  95

Thr Arg Arg Gly Asp Tyr Phe Gly Asp Phe Trp Gly Gln Gly Thr Leu
            100                 105                 110

Val Thr Val Ser Ser
        115


<210> SEQ ID NO 177
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#17 VL

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Tyr Ile Ser Tyr Pro Leu
                85                  90                  95

Thr Phe Gly Ala Gly Thr Lys Leu Glu Ile Lys
            100                 105


<210> SEQ ID NO 178
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#17 VH

<400> SEQUENCE: 178

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Met Arg Gln Ala Pro Gly Gln Gly Leu Glu Trp Met
        35                  40                  45

Gly Gly Ile Tyr Leu Ser Gly Asp Ser Thr Asp Tyr Asn Glu Lys Phe
    50                  55                  60

Lys Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Arg Gly Asp Tyr Phe Gly Asp Phe Trp Gly Gln Gly Thr Leu
            100                 105                 110

Val Thr Val Ser Ser
        115
```

<210> SEQ ID NO 179
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#18 VL

<400> SEQUENCE: 179

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Ala Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Tyr Ile Ser Tyr Pro Leu
                85                  90                  95

Thr Phe Gly Ala Gly Thr Lys Leu Glu Ile Lys
            100                 105
```

<210> SEQ ID NO 180
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#18 VH

<400> SEQUENCE: 180

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Met Arg Gln Ala Pro Gly Gln Gly Leu Glu Trp Met
        35                  40                  45

Gly Gly Ile Tyr Leu Ser Gly Asp Ser Thr Asp Tyr Asn Glu Lys Phe
    50                  55                  60

Lys Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Arg Gly Asp Tyr Phe Gly Asp Phe Trp Gly Gln Gly Thr Leu
            100                 105                 110

Val Thr Val Ser Ser
        115
```

<210> SEQ ID NO 181
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<220> FEATURE:
<223> OTHER INFORMATION: B7H6#19 VL

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Tyr Ile Ser Tyr Pro Leu
                85                  90                  95

Thr Phe Gly Ala Gly Thr Lys Leu Glu Ile Lys
            100                 105

<210> SEQ ID NO 182
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#19 VH

<400> SEQUENCE: 182

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Lys Gln Ala Pro Gly Gln Gly Leu Glu Trp Met
        35                  40                  45

Gly Gly Ile Tyr Leu Ser Gly Glu Ser Thr Asp Tyr Asn Glu Lys Phe
    50                  55                  60

Lys Gly Lys Ala Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Arg Gly Asp Tyr Phe Gly Asp Phe Trp Gly Gln Gly Thr Leu
            100                 105                 110

Val Thr Val Ser Ser
        115

<210> SEQ ID NO 183
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#20 VL

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Ala Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Thr Thr Tyr Tyr Cys Gln Gln Tyr Ile Ser Tyr Pro Leu
85 90 95

Thr Phe Gly Ala Gly Thr Lys Leu Glu Ile Lys
100 105

<210> SEQ ID NO 184
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#20 VH

<400> SEQUENCE: 184

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met Asn Trp Val Lys Gln Ala Pro Gly Gln Gly Leu Glu Trp Met
35 40 45

Gly Gly Ile Tyr Leu Ser Gly Asp Ser Thr Asp Tyr Asn Glu Lys Phe
50 55 60

Lys Gly Lys Ala Thr Met Thr Val Asp Thr Ser Thr Ser Thr Val Tyr
65 70 75 80

Met Glu Leu Ser Ser Leu Arg Ser Glu Asp Thr Ala Val Tyr Tyr Cys
85 90 95

Thr Arg Arg Gly Asp Tyr Phe Gly Asp Phe Trp Gly Gln Gly Thr Leu
100 105 110

Val Thr Val Ser Ser
115

<210> SEQ ID NO 185
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#21 VL

<400> SEQUENCE: 185

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Phe Cys Gln Gln Tyr Ile Ser Tyr Pro Leu
85 90 95

Thr Phe Gly Ala Gly Thr Lys Leu Glu Ile Lys
100 105

<210> SEQ ID NO 186
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#21 VH

<400> SEQUENCE: 186

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met Asn Trp Met Lys Gln Ala Pro Gly Gln Gly Leu Glu Trp Ile
35 40 45

Gly Gly Ile Tyr Leu Ser Gly Glu Ser Thr Asp Tyr Asn Glu Lys Phe
50 55 60

Lys Gly Lys Val Thr Met Thr Val Asp Thr Ser Thr Ser Thr Val Tyr
65 70 75 80

Met Glu Leu Ser Ser Leu Arg Ser Glu Asp Thr Ala Val Tyr Tyr Cys
85 90 95

Thr Arg Arg Gly Asp Tyr Phe Gly Asp Phe Trp Gly Gln Gly Thr Leu
100 105 110

Val Thr Val Ser Ser
115

<210> SEQ ID NO 187
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#22 VL

<400> SEQUENCE: 187

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Ala Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Phe Cys Gln Gln Tyr Ile Ser Tyr Pro Leu
85 90 95

Thr Phe Gly Ala Gly Thr Lys Leu Glu Ile Lys 100 105

<210> SEQ ID NO 188
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#22 VH

<400> SEQUENCE: 188

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met Asn Trp Met Lys Gln Ala Pro Gly Gln Gly Leu Glu Trp Ile
35 40 45

Gly Gly Ile Tyr Leu Ser Gly Asp Ser Thr Asp Tyr Asn Glu Lys Phe
50 55 60

Lys Gly Lys Val Thr Met Thr Val Asp Thr Ser Thr Ser Thr Val Tyr
65 70 75 80

Met Glu Leu Ser Ser Leu Arg Ser Glu Asp Thr Ala Val Tyr Tyr Cys
85 90 95

Thr Arg Arg Gly Asp Tyr Phe Gly Asp Phe Trp Gly Gln Gly Thr Leu
100 105 110

Val Thr Val Ser Ser
115

<210> SEQ ID NO 189
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#23 VL

<400> SEQUENCE: 189

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Ala Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Phe Cys Gln Gln Tyr Ile Ser Tyr Pro Leu
85 90 95

Thr Phe Gly Ala Gly Thr Lys Leu Glu Ile Lys
100 105

<210> SEQ ID NO 190
<211> LENGTH: 117
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<223> OTHER INFORMATION: B7H6#23 VH

<400> SEQUENCE: 190

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Met Lys Gln Ala Pro Gly Gln Gly Leu Glu Trp Ile
        35                  40                  45

Gly Gly Ile Tyr Leu Ser Gly Glu Ser Thr Asp Tyr Asn Glu Lys Phe
    50                  55                  60

Lys Gly Lys Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Arg Gly Asp Tyr Phe Gly Asp Phe Trp Gly Gln Gly Thr Leu
            100                 105                 110

Val Thr Val Ser Ser
        115


<210> SEQ ID NO 191
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#24 VL

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Ala Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Tyr Ile Ser Tyr Pro Leu
                85                  90                  95

Thr Phe Gly Ala Gly Thr Lys Leu Glu Ile Lys
            100                 105


<210> SEQ ID NO 192
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#24 VH

<400> SEQUENCE: 192

Gln Val Gln Leu Val Gln Ser Gly Ala Glu Val Lys Lys Pro Gly Ala
```

```
1               5                   10                  15

Ser Val Lys Val Ser Cys Lys Ala Ser Gly Tyr Thr Phe Thr Asn Tyr
            20                  25                  30

Trp Met Asn Trp Met Arg Gln Ala Pro Gly Gln Gly Leu Glu Trp Met
        35                  40                  45

Gly Gly Ile Tyr Leu Ser Gly Asp Ser Thr Asp Tyr Asn Glu Lys Phe
    50                  55                  60

Lys Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Arg Gly Asp Tyr Phe Gly Asp Phe Trp Gly Gln Gly Thr Leu
            100                 105                 110

Val Thr Val Ser Ser
        115


<210> SEQ ID NO 193
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#1 scFab

<400> SEQUENCE: 193

Asp Ile Val Met Ser Gln Ser Pro Ser Ser Leu Ala Val Ser Val Gly
1               5                   10                  15

Glu Lys Val Thr Met Asn Cys Lys Ser Ser Gln Ser Leu Phe Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Asn Tyr Pro Arg Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gly Gly Gly Gly
    210                 215                 220

Ser Glu Gly Lys Ser Ser Gly Ser Gly Ser Glu Ser Lys Ser Thr Glu
```

225 230 235 240

Gly Lys Ser Ser Gly Ser Gly Ser Glu Ser Lys Ser Thr Gly Gly Gly
245 250 255

Gly Ser Glu Val Gln Leu Gln Gln Ser Gly Pro Glu Leu Val Lys Pro
260 265 270

Gly Thr Ser Val Lys Met Ser Cys Lys Ala Ser Gly Tyr Thr Phe Thr
275 280 285

Asp Tyr Tyr Met Asn Trp Val Lys Gln Ser Gln Gly Lys Asn Leu Glu
290 295 300

Trp Ile Ala Tyr Ile Tyr Pro Lys Thr Gly Gly Asn Gly Tyr Asn Gln
305 310 315 320

Lys Phe Lys Asp Lys Ala Thr Leu Thr Val Asp Lys Ser Ser Asn Thr
325 330 335

Ala Tyr Met Glu Leu Arg Ser Leu Thr Ser Asp Asp Ser Ala Val Tyr
340 345 350

Tyr Cys Gly Arg Glu Asn Trp Asp Gly Tyr Thr Met Ala Tyr Trp Gly
355 360 365

Gln Gly Thr Ser Val Thr Val Ser Ser Ala Ser Thr Lys Gly Pro Ser
370 375 380

Val Phe Pro Leu Ala Pro Ser Ser Lys Ser Thr Ser Gly Gly Thr Ala
385 390 395 400

Ala Leu Gly Cys Leu Val Lys Asp Tyr Phe Pro Glu Pro Val Thr Val
405 410 415

Ser Trp Asn Ser Gly Ala Leu Thr Ser Gly Val His Thr Phe Pro Ala
420 425 430

Val Leu Gln Ser Ser Gly Leu Tyr Ser Leu Ser Ser Val Val Thr Val
435 440 445

Pro Ser Ser Ser Leu Gly Thr Gln Thr Tyr Ile Cys Asn Val Asn His
450 455 460

Lys Pro Ser Asn Thr Lys Val Asp Lys Arg Val Glu Pro Lys Ser Cys
465 470 475 480

<210> SEQ ID NO 194
<211> LENGTH: 475
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#2 scFab

<400> SEQUENCE: 194

Glu Ile Val Leu Thr Gln Ser Pro Asp Phe Leu Ser Ala Ser Pro Gly
1 5 10 15

Glu Lys Val Thr Met Thr Cys Arg Ala Thr Ser Ser Leu Tyr Ser Met
20 25 30

His Trp Tyr Gln Gln Lys Pro Gly Ser Ser Pro Lys Pro Trp Ile Tyr
35 40 45

Ala Thr Phe Asn Leu Ala Ser Gly Val Pro Ala Arg Phe Ser Gly Ser
50 55 60

Gly Ser Gly Thr Ser Tyr Ser Leu Thr Ile Thr Arg Val Glu Ala Glu
65 70 75 80

Asp Ala Ala Thr Tyr Tyr Cys Gln Gln Trp Ser Thr Asn Pro Pro Lys
85 90 95

Leu Thr Phe Gly Ala Gly Thr Lys Leu Glu Leu Lys Arg Thr Val Ala

```
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Gly Ser Glu Gly Lys Ser
    210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Gly Ser Glu Val Gln
                245                 250                 255

Leu Gln Gln Ser Gly Ala Glu Leu Val Arg Pro Gly Ala Ser Val Lys
            260                 265                 270

Leu Ser Cys Thr Ala Ser Gly Phe Asn Ile Lys Asn Thr Phe Ile His
        275                 280                 285

Trp Val Asn Gln Arg Pro Glu Gln Gly Leu Glu Trp Ile Gly Arg Ile
    290                 295                 300

Asp Pro Ala Asn Gly Asn Thr Ile Tyr Ala Ser Lys Phe Gln Gly Arg
305                 310                 315                 320

Ala Thr Ile Thr Thr Asp Thr Ser Ser Asn Thr Ala Tyr Met His Leu
                325                 330                 335

Ser Ser Leu Thr Ser Gly Asp Thr Ala Val Tyr Tyr Cys Ala Arg Thr
            340                 345                 350

Tyr Gly Gly Thr Asn Tyr Phe Asp Tyr Trp Gly Gln Gly Thr Thr Leu
        355                 360                 365

Thr Val Ser Ser Ala Ser Thr Lys Gly Pro Ser Val Phe Pro Leu Ala
    370                 375                 380

Pro Ser Ser Lys Ser Thr Ser Gly Gly Thr Ala Ala Leu Gly Cys Leu
385                 390                 395                 400

Val Lys Asp Tyr Phe Pro Glu Pro Val Thr Val Ser Trp Asn Ser Gly
                405                 410                 415

Ala Leu Thr Ser Gly Val His Thr Phe Pro Ala Val Leu Gln Ser Ser
            420                 425                 430

Gly Leu Tyr Ser Leu Ser Ser Val Val Thr Val Pro Ser Ser Ser Leu
        435                 440                 445

Gly Thr Gln Thr Tyr Ile Cys Asn Val Asn His Lys Pro Ser Asn Thr
    450                 455                 460

Lys Val Asp Lys Arg Val Glu Pro Lys Ser Cys
465                 470                 475
```

<210> SEQ ID NO 195
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<223> OTHER INFORMATION: B7H6#3 scFab

<400> SEQUENCE: 195

Asp Ile Val Met Thr Gln Ser Gln Lys Leu Leu Ser Thr Ser Val Gly
1 5 10 15

Asp Arg Ile Ser Val Thr Cys Lys Ala Ser His Asn Val Gly Val Tyr
20 25 30

Val Ala Trp Tyr Gln Gln Lys Pro Gly His Ser Pro Lys Ala Leu Ile
35 40 45

His Ser Ala Ser Asn Arg Tyr Ser Gly Val Pro Asp Arg Phe Thr Gly
50 55 60

Ser Gly Ser Gly Thr Asp Phe Thr Leu Thr Ile Thr Asn Val Gln Ser
65 70 75 80

Glu Asp Leu Ala Glu Tyr Phe Cys Gln Gln Tyr Asn Ser Tyr Pro Leu
85 90 95

Thr Phe Gly Ala Gly Thr Lys Leu Glu Leu Ile Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Glu Gly Lys Ser Ser
210 215 220

Gly Ser Gly Ser Glu Ser Lys Ser Thr Glu Gly Lys Ser Ser Gly Ser
225 230 235 240

Gly Ser Glu Ser Lys Ser Thr Gly Gly Gly Gly Ser Glu Val Lys Leu
245 250 255

Val Glu Ser Glu Gly Gly Leu Val Gln Pro Gly Ser Ser Met Lys Leu
260 265 270

Ser Cys Thr Ala Ser Gly Phe Thr Phe Ser Asp Tyr Tyr Met Thr Trp
275 280 285

Val Arg Gln Val Pro Glu Lys Gly Leu Glu Trp Val Gly Asn Ile Asp
290 295 300

Tyr Asp Gly Ser Arg Ile Tyr Tyr Leu Asp Ser Leu Lys Ser Arg Phe
305 310 315 320

Ile Ile Ser Arg Asp Asn Ala Lys Asn Ile Leu Tyr Leu Gln Met Asn
325 330 335

Ser Leu Lys Ser Glu Asp Thr Ala Thr Tyr Tyr Cys Ala Arg Asp Asp
340 345 350

Pro Ala Trp Leu Ala Tyr Trp Gly Gln Gly Thr Leu Val Thr Val Ser
355 360 365

Ser Ala Ser Thr Lys Gly Pro Ser Val Phe Pro Leu Ala Pro Ser Ser
370 375 380

Lys Ser Thr Ser Gly Gly Thr Ala Ala Leu Gly Cys Leu Val Lys Asp
385 390 395 400

```
Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys
465                 470


<210> SEQ ID NO 196
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#4 scFab

<400> SEQUENCE: 196

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Lys Tyr
            20                  25                  30

Val Ala Trp Tyr Gln Gln Lys Pro Gly Gln Ser Pro Lys Ala Leu Ile
        35                  40                  45

Tyr Ser Ala Ser Asn Arg Tyr Asp Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Thr Glu Tyr Phe Cys Gln Gln Tyr Ile Ser Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Gln Gln Pro Gly Ser Val Leu Val Arg Pro Gly Ala Ser Val Arg Leu
            260                 265                 270
```

Ser Cys Lys Ala Ser Gly Tyr Thr Phe Thr Asn Tyr Trp Met Asn Trp
275 280 285

Met Lys Gln Arg Pro Gly Gln Gly Leu Glu Trp Ile Gly Gly Ile Tyr
290 295 300

Leu Asn Gly Asp Ser Thr Asp Tyr Asn Glu Lys Phe Lys Gly Lys Ala
305 310 315 320

Thr Leu Thr Val Asp Thr Ser Ser Ser Thr Thr Tyr Met Asp Leu Ser
325 330 335

Ser Leu Thr Tyr Glu Asp Ser Ala Val Tyr Tyr Cys Thr Thr Arg Gly
340 345 350

Asp Tyr Phe Gly Asp Phe Trp Gly Gln Gly Thr Thr Leu Thr Val Ser
355 360 365

Ser Ala Ser Thr Lys Gly Pro Ser Val Phe Pro Leu Ala Pro Ser Ser
370 375 380

Lys Ser Thr Ser Gly Gly Thr Ala Ala Leu Gly Cys Leu Val Lys Asp
385 390 395 400

Tyr Phe Pro Glu Pro Val Thr Val Ser Trp Asn Ser Gly Ala Leu Thr
405 410 415

Ser Gly Val His Thr Phe Pro Ala Val Leu Gln Ser Ser Gly Leu Tyr
420 425 430

Ser Leu Ser Ser Val Val Thr Val Pro Ser Ser Ser Leu Gly Thr Gln
435 440 445

Thr Tyr Ile Cys Asn Val Asn His Lys Pro Ser Asn Thr Lys Val Asp
450 455 460

Lys Arg Val Glu Pro Lys Ser Cys
465 470

<210> SEQ ID NO 197
<211> LENGTH: 474
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#5 scFab

<400> SEQUENCE: 197

Ala Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Arg Asn Asp
20 25 30

Leu Gly Trp Phe Gln Gln Arg Pro Gly Lys Ala Pro Asn Leu Leu Ile
35 40 45

Tyr Ala Ala Ser Ser Leu Glu Ser Gly Val Pro Ser Arg Phe Ser Gly
50 55 60

Arg Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Tyr Asn His Pro Leu
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Glu Gly Lys Ser Ser
210 215 220

Gly Ser Gly Ser Glu Ser Lys Ser Thr Glu Gly Lys Ser Ser Gly Ser
225 230 235 240

Gly Ser Glu Ser Lys Ser Thr Gly Gly Gly Gly Ser Gln Val Gln Leu
245 250 255

Val Gln Ser Gly Ala Glu Val Lys Lys Pro Gly Ala Ser Val Lys Val
260 265 270

Ser Cys Lys Ala Ser Gly Tyr Thr Phe Thr Gly Tyr Tyr Ile His Trp
275 280 285

Val Arg Gln Ala Pro Gly Gln Gly Leu Glu Trp Met Gly Trp Ile Asn
290 295 300

Pro His Ser Gly Ala Thr Asn Tyr Ala Gln Asn Phe Gln Gly Arg Val
305 310 315 320

Thr Met Thr Arg Asp Thr Ser Ile Ser Thr Ala Tyr Met Glu Leu Ser
325 330 335

Arg Leu Arg Ser Asp Asp Ala Ala Val Tyr Tyr Cys Ala Arg Glu Arg
340 345 350

Trp Gly Ser Gly Thr Phe Asn Ile Trp Gly Gln Gly Thr Met Val Thr
355 360 365

Val Ser Ser Ala Ser Thr Lys Gly Pro Ser Val Phe Pro Leu Ala Pro
370 375 380

Ser Ser Lys Ser Thr Ser Gly Gly Thr Ala Ala Leu Gly Cys Leu Val
385 390 395 400

Lys Asp Tyr Phe Pro Glu Pro Val Thr Val Ser Trp Asn Ser Gly Ala
405 410 415

Leu Thr Ser Gly Val His Thr Phe Pro Ala Val Leu Gln Ser Ser Gly
420 425 430

Leu Tyr Ser Leu Ser Ser Val Val Thr Val Pro Ser Ser Ser Leu Gly
435 440 445

Thr Gln Thr Tyr Ile Cys Asn Val Asn His Lys Pro Ser Asn Thr Lys
450 455 460

Val Asp Lys Arg Val Glu Pro Lys Ser Cys
465 470

<210> SEQ ID NO 198
<211> LENGTH: 475
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#6 scFab

<400> SEQUENCE: 198

Asp Ile Val Met Thr Gln Ser Pro Asp Ser Leu Pro Val Ser Ala Gly
1 5 10 15

-continued

```
Asp Arg Val Thr Ile Thr Cys Lys Ala Ser Gln Ser Val Ser Asn Asp
            20                  25                  30

Val Val Trp Tyr Gln Gln Lys Pro Gly Gln Ser Pro Lys Leu Leu Met
        35                  40                  45

Tyr Ser Thr Ser Asn Arg Tyr Ile Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Glu Val Gln Leu
                245                 250                 255

Gln Gln Ser Gly Pro Glu Leu Leu Lys Pro Gly Ala Ser Val Lys Ile
            260                 265                 270

Ser Cys Lys Thr Ser Gly Tyr Thr Phe Thr Asp Tyr Thr Met His Trp
        275                 280                 285

Val Lys Gln Ser His Gly Lys Ser Leu Glu Trp Ile Gly Gly Ile Asn
    290                 295                 300

Pro Asn Tyr Asp Asn Thr Gly Tyr Ser Glu Lys Phe Lys Asp Lys Ala
305                 310                 315                 320

Thr Leu Thr Val Asp Lys Ser Ser Ser Thr Ala Tyr Met Glu Leu Arg
                325                 330                 335

Ser Leu Thr Ser Glu Asp Ser Ala Val Tyr Tyr Cys Thr Arg Ser Gly
            340                 345                 350

Ser Arg Arg Ser Phe Tyr Phe Asp Tyr Trp Gly Gln Gly Thr Thr Leu
        355                 360                 365

Thr Val Ser Ser Ala Ser Thr Lys Gly Pro Ser Val Phe Pro Leu Ala
    370                 375                 380

Pro Ser Ser Lys Ser Thr Ser Gly Gly Thr Ala Ala Leu Gly Cys Leu
385                 390                 395                 400

Val Lys Asp Tyr Phe Pro Glu Pro Val Thr Val Ser Trp Asn Ser Gly
                405                 410                 415

Ala Leu Thr Ser Gly Val His Thr Phe Pro Ala Val Leu Gln Ser Ser
            420                 425                 430
```

-continued

```
Gly Leu Tyr Ser Leu Ser Ser Val Val Thr Val Pro Ser Ser Ser Leu
        435                 440                 445

Gly Thr Gln Thr Tyr Ile Cys Asn Val Asn His Lys Pro Ser Asn Thr
    450                 455                 460

Lys Val Asp Lys Arg Val Glu Pro Lys Ser Cys
465                 470                 475


<210> SEQ ID NO 199
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#7 scFab

<400> SEQUENCE: 199

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Gln Glu Ser Gly Pro Gly Leu Val Lys Pro Ser Glu Thr Leu Ser Leu
            260                 265                 270

Thr Tyr Thr Val Ser Gly Gly Ser Ile Ser Tyr Asn Tyr Trp Ser Trp
        275                 280                 285

Ile Arg Gln Pro Pro Glu Lys Gly Leu Glu Trp Ile Gly His Ile Tyr
    290                 295                 300
```

```
Tyr Ser Gly Ser Thr Asn Tyr Asn Pro Ser Leu Lys Ser Arg Val Thr
305                 310                 315                 320

Ile Ser Val Asp Thr Ser Lys Asn Gln Phe Ser Leu Lys Leu Asn Ser
                325                 330                 335

Val Thr Ala Ala Asp Thr Ala Val Tyr Tyr Cys Ala Arg Val Gly Thr
            340                 345                 350

Trp Gly Ser Phe Asp Asp Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys
465                 470


<210> SEQ ID NO 200
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#8 scFab

<400> SEQUENCE: 200

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Asn
            20                  25                  30

Asn Arg Tyr Asn Tyr Leu Asp Trp Tyr Leu Gln Lys Pro Gly Gln Ser
        35                  40                  45

Pro Glu Val Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Phe Gly Val Tyr Tyr Cys Met Gln Thr
                85                  90                  95

Leu Gln Ile Pro Ile Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Glu Gly Lys Ser Ser Gly Ser Gly Ser Glu Ser Lys Ser Thr Glu Gly
225                 230                 235                 240

Lys Ser Ser Gly Ser Gly Ser Glu Ser Lys Ser Thr Gly Gly Gly Gly
                245                 250                 255

Ser Gln Val Gln Val Val Gln Ser Gly Ala Glu Val Lys Lys Pro Gly
            260                 265                 270

Ser Ser Val Lys Val Ser Cys Lys Gly Ser Gly Asp Thr Leu Asn Ser
        275                 280                 285

Tyr Gly Ile Ser Trp Met Arg Gln Ala Pro Gly Gln Gly Leu Glu Trp
    290                 295                 300

Met Gly Gly Ile Ile Pro Ile Phe Asp Thr Thr Lys Tyr Ala Gln Lys
305                 310                 315                 320

Phe Gln Gly Arg Val Thr Ile Thr Ala Asp Lys Ser Thr Thr Thr Val
                325                 330                 335

Tyr Met Glu Leu Ser Ser Leu Arg Phe Glu Asp Thr Ala Val Tyr Tyr
            340                 345                 350

Cys Ala Arg Glu Arg Gly Tyr Arg Phe Ser Glu Asp Tyr Tyr Phe Tyr
        355                 360                 365

Tyr Gly Met Asp Val Trp Gly Gln Gly Thr Thr Val Thr Val Ser Ser
    370                 375                 380

Ala Ser Thr Lys Gly Pro Ser Val Phe Pro Leu Ala Pro Ser Ser Lys
385                 390                 395                 400

Ser Thr Ser Gly Gly Thr Ala Ala Leu Gly Cys Leu Val Lys Asp Tyr
                405                 410                 415

Phe Pro Glu Pro Val Thr Val Ser Trp Asn Ser Gly Ala Leu Thr Ser
            420                 425                 430

Gly Val His Thr Phe Pro Ala Val Leu Gln Ser Ser Gly Leu Tyr Ser
        435                 440                 445

Leu Ser Ser Val Val Thr Val Pro Ser Ser Ser Leu Gly Thr Gln Thr
    450                 455                 460

Tyr Ile Cys Asn Val Asn His Lys Pro Ser Asn Thr Lys Val Asp Lys
465                 470                 475                 480

Arg Val Glu Pro Lys Ser Cys
                485


<210> SEQ ID NO 201
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#9 scFab

<400> SEQUENCE: 201

Asp Ile Val Leu Thr Gln Ser Pro Val Ser Leu Ala Val Ser Leu Gly
1               5                   10                  15

Gln Arg Ala Thr Ile Ser Cys Arg Ala Ser Glu Ser Val Asp Asn Phe
            20                  25                  30
```

```
Gly Val Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Leu Glu Glu Asp Asp Thr Ala Met Tyr Phe Cys Gln Gln Ser Lys
                85                  90                  95

Glu Val Pro Trp Thr Phe Gly Gly Gly Thr Arg Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Gly Ser Glu
    210                 215                 220

Gly Lys Ser Ser Gly Ser Gly Ser Glu Ser Lys Ser Thr Glu Gly Lys
225                 230                 235                 240

Ser Ser Gly Ser Gly Ser Glu Ser Lys Ser Thr Gly Gly Gly Gly Ser
                245                 250                 255

Gln Val Gln Leu Gln Gln Pro Gly Ala Glu Met Val Arg Pro Gly Ser
            260                 265                 270

Ser Val Lys Leu Ser Cys Lys Ala Ser Asp Tyr Thr Phe Thr His Tyr
        275                 280                 285

Trp Ile His Trp Val Lys Gln Arg Pro Leu Glu Gly Leu Glu Trp Ile
    290                 295                 300

Gly Ile Ile Gly Pro Ser Asp Asn Glu Ile His Tyr Asn Gln Asp Phe
305                 310                 315                 320

Lys Asp Lys Ala Thr Leu Thr Val Asp Lys Ser Ser Asn Thr Ala Tyr
                325                 330                 335

Leu His Leu Asn Ser Leu Thr Ser Glu Asp Ser Ala Val Tyr Tyr Cys
            340                 345                 350

Ala Arg Gln Ile Ile Ser Met Val Val Gly Thr Glu Tyr Phe Asp Val
        355                 360                 365

Trp Gly Thr Gly Thr Thr Val Thr Val Ser Ser Ala Ser Thr Lys Gly
    370                 375                 380

Pro Ser Val Phe Pro Leu Ala Pro Ser Ser Lys Ser Thr Ser Gly Gly
385                 390                 395                 400

Thr Ala Ala Leu Gly Cys Leu Val Lys Asp Tyr Phe Pro Glu Pro Val
                405                 410                 415

Thr Val Ser Trp Asn Ser Gly Ala Leu Thr Ser Gly Val His Thr Phe
            420                 425                 430

Pro Ala Val Leu Gln Ser Ser Gly Leu Tyr Ser Leu Ser Ser Val Val
        435                 440                 445

Thr Val Pro Ser Ser Ser Leu Gly Thr Gln Thr Tyr Ile Cys Asn Val
```

```
    450                 455                 460

Asn His Lys Pro Ser Asn Thr Lys Val Asp Lys Arg Val Glu Pro Lys
465                 470                 475                 480

Ser Cys


<210> SEQ ID NO 202
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#10 scFab

<400> SEQUENCE: 202

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Val Ala Ser Ser Leu Gln Arg Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val His Leu
                245                 250                 255

Gln Glu Ser Gly Pro Gly Leu Val Lys Pro Ser Glu Thr Leu Ser Leu
            260                 265                 270

Thr Cys Thr Val Ser Gly Asp Ser Ile Ser Ser Tyr Tyr Trp Ser Trp
        275                 280                 285

Ile Arg Gln Pro Ala Gly Lys Gly Leu Glu Trp Ile Gly His Ile Tyr
    290                 295                 300

Thr Ser Glu Lys Asn Asn Tyr Asn Pro Ser Leu Lys Ser Arg Val Ile
305                 310                 315                 320
```

```
Met Ser Val Asp Thr Ser Lys Asn Gln Phe Ser Leu Asn Leu Ser Ser
                325                 330                 335

Val Thr Ala Ala Asp Thr Ala Val Tyr Tyr Cys Ala Arg Val Gly Asn
            340                 345                 350

Trp Gly Ser His Asp Ala Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys
465                 470
```

<210> SEQ ID NO 203
<211> LENGTH: 486
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#11 scFab

<400> SEQUENCE: 203

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Val Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

Lys His Lys Val Tyr Ala Cys Glu Val Thr His Gln Gly Leu Ser Ser
195 200 205

Pro Val Thr Lys Ser Phe Asn Arg Gly Glu Cys Gly Gly Gly Gly Ser
210 215 220

Glu Gly Lys Ser Ser Gly Ser Gly Ser Glu Ser Lys Ser Thr Glu Gly
225 230 235 240

Lys Ser Ser Gly Ser Gly Ser Glu Ser Lys Ser Thr Gly Gly Gly Gly
245 250 255

Ser Glu Leu Gln Leu Val Asn Ser Gly Gly Gly Leu Val Lys Ser Gly
260 265 270

Gly Ser Leu Arg Leu Ser Cys Ala Ala Ser Gly Ile Thr Phe Ser Tyr
275 280 285

Tyr Thr Met Asn Trp Val Arg Gln Ala Pro Gly Lys Gly Leu Glu Trp
290 295 300

Val Ser Ser Ile Ser Ser Arg Ser Ser Tyr Ile Tyr Tyr Ala Asp Ser
305 310 315 320

Val Lys Gly Arg Phe Thr Ile Ser Arg Asp Asn Ala Glu Asn Ser Leu
325 330 335

Tyr Leu Gln Met Asn Ser Leu Arg Ala Glu Asp Thr Ala Val Tyr Tyr
340 345 350

Cys Ala Arg Asp Lys Gly Asp Tyr Ser Lys Asp Ile Tyr Tyr Tyr Tyr
355 360 365

Gly Met Asp Val Trp Gly Gln Gly Thr Thr Val Thr Val Ser Ser Ala
370 375 380

Ser Thr Lys Gly Pro Ser Val Phe Pro Leu Ala Pro Ser Ser Lys Ser
385 390 395 400

Thr Ser Gly Gly Thr Ala Ala Leu Gly Cys Leu Val Lys Asp Tyr Phe
405 410 415

Pro Glu Pro Val Thr Val Ser Trp Asn Ser Gly Ala Leu Thr Ser Gly
420 425 430

Val His Thr Phe Pro Ala Val Leu Gln Ser Ser Gly Leu Tyr Ser Leu
435 440 445

Ser Ser Val Val Thr Val Pro Ser Ser Ser Leu Gly Thr Gln Thr Tyr
450 455 460

Ile Cys Asn Val Asn His Lys Pro Ser Asn Thr Lys Val Asp Lys Arg
465 470 475 480

Val Glu Pro Lys Ser Cys
485

<210> SEQ ID NO 204
<211> LENGTH: 472
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#12 scFab

<400> SEQUENCE: 204

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

```
Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Tyr Ile Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Asn Tyr Trp Met Asn Trp
        275                 280                 285

Val Lys Gln Ala Pro Gly Gln Gly Leu Glu Trp Met Gly Gly Ile Tyr
    290                 295                 300

Leu Asn Gly Asp Ser Thr Asp Tyr Asn Glu Lys Phe Lys Gly Lys Ala
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460
```

Lys Arg Val Glu Pro Lys Ser Cys
465 470

<210> SEQ ID NO 205
<211> LENGTH: 472
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#13 scFab

<400> SEQUENCE: 205

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Thr Thr Tyr Tyr Cys Gln Gln Tyr Ile Ser Tyr Pro Leu
85 90 95

Thr Phe Gly Ala Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Glu Gly Lys Ser Ser
210 215 220

Gly Ser Gly Ser Glu Ser Lys Ser Thr Glu Gly Lys Ser Ser Gly Ser
225 230 235 240

Gly Ser Glu Ser Lys Ser Thr Gly Gly Gly Gly Ser Gln Val Gln Leu
245 250 255

Val Gln Ser Gly Ala Glu Val Lys Lys Pro Gly Ala Ser Val Lys Val
260 265 270

Ser Cys Lys Ala Ser Gly Tyr Thr Phe Thr Ser Tyr Trp Met Asn Trp
275 280 285

Met Lys Gln Ala Pro Gly Gln Gly Leu Glu Trp Met Gly Gly Ile Tyr
290 295 300

Leu Asn Gly Asp Ser Thr Asp Tyr Asn Glu Lys Phe Lys Gly Arg Val
305 310 315 320

Thr Met Thr Val Asp Thr Ser Thr Ser Thr Val Tyr Met Glu Leu Ser
325 330 335

```
Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys
465                 470


<210> SEQ ID NO 206
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#14 scFab

<400> SEQUENCE: 206

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ile Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Asn Tyr Trp Met Asn Trp
        275                 280                 285

Met Lys Gln Ala Pro Gly Gln Gly Leu Glu Trp Ile Gly Gly Ile Tyr
    290                 295                 300

Leu Asn Gly Asp Ser Thr Asp Tyr Asn Glu Lys Phe Lys Gly Lys Val
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys
465                 470

<210> SEQ ID NO 207
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#15 scFab

<400> SEQUENCE: 207

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Thr Thr Tyr Tyr Cys Gln Gln Tyr Ile Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Asn Tyr Trp Met Asn Trp
        275                 280                 285

Met Arg Gln Ala Pro Gly Gln Gly Leu Glu Trp Met Gly Gly Ile Tyr
    290                 295                 300

Leu Ser Gly Asp Ser Thr Asp Tyr Asn Glu Lys Phe Lys Gly Arg Val
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys
465                 470
```

<210> SEQ ID NO 208
<211> LENGTH: 472
<212> TYPE: PRT

<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#16 scFab

<400> SEQUENCE: 208

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Thr Thr Tyr Tyr Cys Gln Gln Tyr Ile Ser Tyr Pro Leu
85 90 95

Thr Phe Gly Ala Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Glu Gly Lys Ser Ser
210 215 220

Gly Ser Gly Ser Glu Ser Lys Ser Thr Glu Gly Lys Ser Ser Gly Ser
225 230 235 240

Gly Ser Glu Ser Lys Ser Thr Gly Gly Gly Gly Ser Gln Val Gln Leu
245 250 255

Val Gln Ser Gly Ala Glu Val Lys Lys Pro Gly Ala Ser Val Lys Val
260 265 270

Ser Cys Lys Ala Ser Gly Tyr Thr Phe Thr Ser Tyr Trp Met Asn Trp
275 280 285

Met Arg Gln Ala Pro Gly Gln Gly Leu Glu Trp Met Gly Gly Ile Tyr
290 295 300

Leu Ser Gly Glu Ser Thr Asp Tyr Asn Glu Lys Phe Lys Gly Arg Val
305 310 315 320

Thr Met Thr Val Asp Thr Ser Thr Ser Thr Val Tyr Met Glu Leu Ser
325 330 335

Ser Leu Arg Ser Glu Asp Thr Ala Val Tyr Tyr Cys Thr Arg Arg Gly
340 345 350

Asp Tyr Phe Gly Asp Phe Trp Gly Gln Gly Thr Leu Val Thr Val Ser
355 360 365

Ser Ala Ser Thr Lys Gly Pro Ser Val Phe Pro Leu Ala Pro Ser Ser 370 375 380

Lys Ser Thr Ser Gly Gly Thr Ala Ala Leu Gly Cys Leu Val Lys Asp
385 390 395 400

Tyr Phe Pro Glu Pro Val Thr Val Ser Trp Asn Ser Gly Ala Leu Thr
405 410 415

Ser Gly Val His Thr Phe Pro Ala Val Leu Gln Ser Ser Gly Leu Tyr
420 425 430

Ser Leu Ser Ser Val Val Thr Val Pro Ser Ser Ser Leu Gly Thr Gln
435 440 445

Thr Tyr Ile Cys Asn Val Asn His Lys Pro Ser Asn Thr Lys Val Asp
450 455 460

Lys Arg Val Glu Pro Lys Ser Cys
465 470

<210> SEQ ID NO 209
<211> LENGTH: 472
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#17 scFab

<400> SEQUENCE: 209

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Thr Thr Tyr Tyr Cys Gln Gln Tyr Ile Ser Tyr Pro Leu
85 90 95

Thr Phe Gly Ala Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Glu Gly Lys Ser Ser
210 215 220

Gly Ser Gly Ser Glu Ser Lys Ser Thr Glu Gly Lys Ser Ser Gly Ser
225 230 235 240

Gly Ser Glu Ser Lys Ser Thr Gly Gly Gly Gly Ser Gln Val Gln Leu

```
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Ser Tyr Trp Met Asn Trp
        275                 280                 285

Met Arg Gln Ala Pro Gly Gln Gly Leu Glu Trp Met Gly Gly Ile Tyr
    290                 295                 300

Leu Ser Gly Asp Ser Thr Asp Tyr Asn Glu Lys Phe Lys Gly Arg Val
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys
465                 470


<210> SEQ ID NO 210
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#18 scFab

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Ala Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Tyr Ile Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
```

```
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Ser Tyr Trp Met Asn Trp
        275                 280                 285

Met Arg Gln Ala Pro Gly Gln Gly Leu Glu Trp Met Gly Gly Ile Tyr
    290                 295                 300

Leu Ser Gly Asp Ser Thr Asp Tyr Asn Glu Lys Phe Lys Gly Arg Val
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys
465                 470


<210> SEQ ID NO 211
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#19 scFab
```

<400> SEQUENCE: 211

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Thr Thr Tyr Tyr Cys Gln Gln Tyr Ile Ser Tyr Pro Leu
85 90 95

Thr Phe Gly Ala Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Glu Gly Lys Ser Ser
210 215 220

Gly Ser Gly Ser Glu Ser Lys Ser Thr Glu Gly Lys Ser Ser Gly Ser
225 230 235 240

Gly Ser Glu Ser Lys Ser Thr Gly Gly Gly Gly Ser Gln Val Gln Leu
245 250 255

Val Gln Ser Gly Ala Glu Val Lys Lys Pro Gly Ala Ser Val Lys Val
260 265 270

Ser Cys Lys Ala Ser Gly Tyr Thr Phe Thr Ser Tyr Trp Met Asn Trp
275 280 285

Val Lys Gln Ala Pro Gly Gln Gly Leu Glu Trp Met Gly Gly Ile Tyr
290 295 300

Leu Ser Gly Glu Ser Thr Asp Tyr Asn Glu Lys Phe Lys Gly Lys Ala
305 310 315 320

Thr Met Thr Val Asp Thr Ser Thr Ser Thr Val Tyr Met Glu Leu Ser
325 330 335

Ser Leu Arg Ser Glu Asp Thr Ala Val Tyr Tyr Cys Thr Arg Arg Gly
340 345 350

Asp Tyr Phe Gly Asp Phe Trp Gly Gln Gly Thr Leu Val Thr Val Ser
355 360 365

Ser Ala Ser Thr Lys Gly Pro Ser Val Phe Pro Leu Ala Pro Ser Ser
370 375 380

Lys Ser Thr Ser Gly Gly Thr Ala Ala Leu Gly Cys Leu Val Lys Asp
385 390 395 400

Tyr Phe Pro Glu Pro Val Thr Val Ser Trp Asn Ser Gly Ala Leu Thr
405 410 415

Ser Gly Val His Thr Phe Pro Ala Val Leu Gln Ser Ser Gly Leu Tyr
420 425 430

Ser Leu Ser Ser Val Val Thr Val Pro Ser Ser Ser Leu Gly Thr Gln
435 440 445

Thr Tyr Ile Cys Asn Val Asn His Lys Pro Ser Asn Thr Lys Val Asp
450 455 460

Lys Arg Val Glu Pro Lys Ser Cys
465 470

<210> SEQ ID NO 212
<211> LENGTH: 472
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#20 scFab

<400> SEQUENCE: 212

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Ala Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Thr Thr Tyr Tyr Cys Gln Gln Tyr Ile Ser Tyr Pro Leu
85 90 95

Thr Phe Gly Ala Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Glu Gly Lys Ser Ser
210 215 220

Gly Ser Gly Ser Glu Ser Lys Ser Thr Glu Gly Lys Ser Ser Gly Ser
225 230 235 240

Gly Ser Glu Ser Lys Ser Thr Gly Gly Gly Gly Ser Gln Val Gln Leu
245 250 255

Val Gln Ser Gly Ala Glu Val Lys Lys Pro Gly Ala Ser Val Lys Val
260 265 270

Ser Cys Lys Ala Ser Gly Tyr Thr Phe Thr Ser Tyr Trp Met Asn Trp
275 280 285

```
Val Lys Gln Ala Pro Gly Gln Gly Leu Glu Trp Met Gly Gly Ile Tyr
    290                 295                 300

Leu Ser Gly Asp Ser Thr Asp Tyr Asn Glu Lys Phe Lys Gly Lys Ala
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys
465                 470


<210> SEQ ID NO 213
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#21 scFab

<400> SEQUENCE: 213

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ile Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Ser Tyr Trp Met Asn Trp
        275                 280                 285

Met Lys Gln Ala Pro Gly Gln Gly Leu Glu Trp Ile Gly Gly Ile Tyr
    290                 295                 300

Leu Ser Gly Glu Ser Thr Asp Tyr Asn Glu Lys Phe Lys Gly Lys Val
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys
465                 470
```

<210> SEQ ID NO 214
<211> LENGTH: 472
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#22 scFab

<400> SEQUENCE: 214

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30
```

```
Val Ala Trp Tyr Gln Gln Lys Pro Gly Lys Ala Pro Lys Ser Leu Ile
        35                  40                  45

Tyr Ser Ala Ser Asn Arg Tyr Asp Ala Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ile Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Ser Tyr Trp Met Asn Trp
        275                 280                 285

Met Lys Gln Ala Pro Gly Gln Gly Leu Glu Trp Ile Gly Gly Ile Tyr
    290                 295                 300

Leu Ser Gly Asp Ser Thr Asp Tyr Asn Glu Lys Phe Lys Gly Lys Val
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445
```

Thr Tyr Ile Cys Asn Val Asn His Lys Pro Ser Asn Thr Lys Val Asp
    450                 455                 460

Lys Arg Val Glu Pro Lys Ser Cys
465                 470

<210> SEQ ID NO 215
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#23 scFab

<400> SEQUENCE: 215

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Ala Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ile Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Ser Tyr Trp Met Asn Trp
        275                 280                 285

Met Lys Gln Ala Pro Gly Gln Gly Leu Glu Trp Ile Gly Gly Ile Tyr
    290                 295                 300

Leu Ser Gly Glu Ser Thr Asp Tyr Asn Glu Lys Phe Lys Gly Lys Val
305                 310                 315                 320

Thr Met Thr Val Asp Thr Ser Thr Ser Thr Val Tyr Met Glu Leu Ser
325 330 335

Ser Leu Arg Ser Glu Asp Thr Ala Val Tyr Tyr Cys Thr Arg Arg Gly
340 345 350

Asp Tyr Phe Gly Asp Phe Trp Gly Gln Gly Thr Leu Val Thr Val Ser
355 360 365

Ser Ala Ser Thr Lys Gly Pro Ser Val Phe Pro Leu Ala Pro Ser Ser
370 375 380

Lys Ser Thr Ser Gly Gly Thr Ala Ala Leu Gly Cys Leu Val Lys Asp
385 390 395 400

Tyr Phe Pro Glu Pro Val Thr Val Ser Trp Asn Ser Gly Ala Leu Thr
405 410 415

Ser Gly Val His Thr Phe Pro Ala Val Leu Gln Ser Ser Gly Leu Tyr
420 425 430

Ser Leu Ser Ser Val Val Thr Val Pro Ser Ser Ser Leu Gly Thr Gln
435 440 445

Thr Tyr Ile Cys Asn Val Asn His Lys Pro Ser Asn Thr Lys Val Asp
450 455 460

Lys Arg Val Glu Pro Lys Ser Cys
465 470

<210> SEQ ID NO 216
<211> LENGTH: 472
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#24 scFab

<400> SEQUENCE: 216

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Ala Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Thr Thr Tyr Tyr Cys Gln Gln Tyr Ile Ser Tyr Pro Leu
85 90 95

Thr Phe Gly Ala Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

```
Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Asn Tyr Trp Met Asn Trp
        275                 280                 285

Met Arg Gln Ala Pro Gly Gln Gly Leu Glu Trp Met Gly Gly Ile Tyr
    290                 295                 300

Leu Ser Gly Asp Ser Thr Asp Tyr Asn Glu Lys Phe Lys Gly Arg Val
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys
465                 470


<210> SEQ ID NO 217
<211> LENGTH: 706
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#1 chain

<400> SEQUENCE: 217

Asp Ile Val Met Ser Gln Ser Pro Ser Ser Leu Ala Val Ser Val Gly
1               5                   10                  15

Glu Lys Val Thr Met Asn Cys Lys Ser Ser Gln Ser Leu Phe Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60
```

```
Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Asn Tyr Pro Arg Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gly Gly Gly Gly
    210                 215                 220

Ser Glu Gly Lys Ser Ser Gly Ser Gly Ser Glu Ser Lys Ser Thr Glu
225                 230                 235                 240

Gly Lys Ser Ser Gly Ser Gly Ser Glu Ser Lys Ser Thr Gly Gly Gly
                245                 250                 255

Gly Ser Glu Val Gln Leu Gln Gln Ser Gly Pro Glu Leu Val Lys Pro
            260                 265                 270

Gly Thr Ser Val Lys Met Ser Cys Lys Ala Ser Gly Tyr Thr Phe Thr
        275                 280                 285

Asp Tyr Tyr Met Asn Trp Val Lys Gln Ser Gln Gly Lys Asn Leu Glu
    290                 295                 300

Trp Ile Ala Tyr Ile Tyr Pro Lys Thr Gly Gly Asn Gly Tyr Asn Gln
305                 310                 315                 320

Lys Phe Lys Asp Lys Ala Thr Leu Thr Val Asp Lys Ser Ser Asn Thr
                325                 330                 335

Ala Tyr Met Glu Leu Arg Ser Leu Thr Ser Asp Asp Ser Ala Val Tyr
            340                 345                 350

Tyr Cys Gly Arg Glu Asn Trp Asp Gly Tyr Thr Met Ala Tyr Trp Gly
        355                 360                 365

Gln Gly Thr Ser Val Thr Val Ser Ser Ala Ser Thr Lys Gly Pro Ser
    370                 375                 380

Val Phe Pro Leu Ala Pro Ser Ser Lys Ser Thr Ser Gly Gly Thr Ala
385                 390                 395                 400

Ala Leu Gly Cys Leu Val Lys Asp Tyr Phe Pro Glu Pro Val Thr Val
                405                 410                 415

Ser Trp Asn Ser Gly Ala Leu Thr Ser Gly Val His Thr Phe Pro Ala
            420                 425                 430

Val Leu Gln Ser Ser Gly Leu Tyr Ser Leu Ser Ser Val Val Thr Val
        435                 440                 445

Pro Ser Ser Ser Leu Gly Thr Gln Thr Tyr Ile Cys Asn Val Asn His
    450                 455                 460

Lys Pro Ser Asn Thr Lys Val Asp Lys Arg Val Glu Pro Lys Ser Cys
465                 470                 475                 480

Asp Lys Thr His Thr Cys Pro Pro Cys Pro Ala Pro Glu Ala Ala Gly
```

485 490 495

Gly Pro Ser Val Phe Leu Phe Pro Pro Lys Pro Lys Asp Thr Leu Met
500 505 510

Ile Ser Arg Thr Pro Glu Val Thr Cys Val Val Val Asp Val Ser His
515 520 525

Glu Asp Pro Glu Val Lys Phe Asn Trp Tyr Val Asp Gly Val Glu Val
530 535 540

His Asn Ala Lys Thr Lys Pro Arg Glu Glu Gln Tyr Asn Ser Thr Tyr
545 550 555 560

Arg Val Val Ser Val Leu Thr Val Leu His Gln Asp Trp Leu Asn Gly
565 570 575

Lys Glu Tyr Lys Cys Lys Val Ser Asn Lys Ala Leu Pro Ala Pro Ile
580 585 590

Glu Lys Thr Ile Ser Lys Ala Lys Gly Gln Pro Arg Glu Pro Gln Val
595 600 605

Tyr Thr Leu Pro Pro Ser Arg Glu Glu Met Thr Lys Asn Gln Val Ser
610 615 620

Leu Trp Cys Leu Val Lys Gly Phe Tyr Pro Ser Asp Ile Ala Val Glu
625 630 635 640

Trp Glu Ser Asn Gly Gln Pro Glu Asn Asn Tyr Lys Thr Thr Pro Pro
645 650 655

Val Leu Asp Ser Asp Gly Ser Phe Phe Leu Tyr Ser Lys Leu Thr Val
660 665 670

Asp Lys Ser Arg Trp Gln Gln Gly Asn Val Phe Ser Cys Ser Val Met
675 680 685

His Glu Ala Leu His Asn His Tyr Thr Gln Lys Ser Leu Ser Leu Ser
690 695 700

Pro Gly
705

<210> SEQ ID NO 218
<211> LENGTH: 701
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#2 chain

<400> SEQUENCE: 218

Glu Ile Val Leu Thr Gln Ser Pro Asp Phe Leu Ser Ala Ser Pro Gly
1 5 10 15

Glu Lys Val Thr Met Thr Cys Arg Ala Thr Ser Ser Leu Tyr Ser Met
20 25 30

His Trp Tyr Gln Gln Lys Pro Gly Ser Ser Pro Lys Pro Trp Ile Tyr
35 40 45

Ala Thr Phe Asn Leu Ala Ser Gly Val Pro Ala Arg Phe Ser Gly Ser
50 55 60

Gly Ser Gly Thr Ser Tyr Ser Leu Thr Ile Thr Arg Val Glu Ala Glu
65 70 75 80

Asp Ala Ala Thr Tyr Tyr Cys Gln Gln Trp Ser Thr Asn Pro Pro Lys
85 90 95

Leu Thr Phe Gly Ala Gly Thr Lys Leu Glu Leu Lys Arg Thr Val Ala
100 105 110

Ala Pro Ser Val Phe Ile Phe Pro Pro Ser Asp Glu Gln Leu Lys Ser

-continued

```
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Gly Ser Glu Gly Lys Ser
    210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Gly Ser Glu Val Gln
                245                 250                 255

Leu Gln Gln Ser Gly Ala Glu Leu Val Arg Pro Gly Ala Ser Val Lys
            260                 265                 270

Leu Ser Cys Thr Ala Ser Gly Phe Asn Ile Lys Asn Thr Phe Ile His
        275                 280                 285

Trp Val Asn Gln Arg Pro Glu Gln Gly Leu Glu Trp Ile Gly Arg Ile
    290                 295                 300

Asp Pro Ala Asn Gly Asn Thr Ile Tyr Ala Ser Lys Phe Gln Gly Arg
305                 310                 315                 320

Ala Thr Ile Thr Thr Asp Thr Ser Ser Asn Thr Ala Tyr Met His Leu
                325                 330                 335

Ser Ser Leu Thr Ser Gly Asp Thr Ala Val Tyr Tyr Cys Ala Arg Thr
            340                 345                 350

Tyr Gly Gly Thr Asn Tyr Phe Asp Tyr Trp Gly Gln Gly Thr Thr Leu
        355                 360                 365

Thr Val Ser Ser Ala Ser Thr Lys Gly Pro Ser Val Phe Pro Leu Ala
    370                 375                 380

Pro Ser Ser Lys Ser Thr Ser Gly Gly Thr Ala Ala Leu Gly Cys Leu
385                 390                 395                 400

Val Lys Asp Tyr Phe Pro Glu Pro Val Thr Val Ser Trp Asn Ser Gly
                405                 410                 415

Ala Leu Thr Ser Gly Val His Thr Phe Pro Ala Val Leu Gln Ser Ser
            420                 425                 430

Gly Leu Tyr Ser Leu Ser Ser Val Val Thr Val Pro Ser Ser Ser Leu
        435                 440                 445

Gly Thr Gln Thr Tyr Ile Cys Asn Val Asn His Lys Pro Ser Asn Thr
    450                 455                 460

Lys Val Asp Lys Arg Val Glu Pro Lys Ser Cys Asp Lys Thr His Thr
465                 470                 475                 480

Cys Pro Pro Cys Pro Ala Pro Glu Ala Ala Gly Gly Pro Ser Val Phe
                485                 490                 495

Leu Phe Pro Pro Lys Pro Lys Asp Thr Leu Met Ile Ser Arg Thr Pro
            500                 505                 510

Glu Val Thr Cys Val Val Val Asp Val Ser His Glu Asp Pro Glu Val
        515                 520                 525

Lys Phe Asn Trp Tyr Val Asp Gly Val Glu Val His Asn Ala Lys Thr
    530                 535                 540
```

Lys Pro Arg Glu Glu Gln Tyr Asn Ser Thr Tyr Arg Val Val Ser Val
545 550 555 560

Leu Thr Val Leu His Gln Asp Trp Leu Asn Gly Lys Glu Tyr Lys Cys
565 570 575

Lys Val Ser Asn Lys Ala Leu Pro Ala Pro Ile Glu Lys Thr Ile Ser
580 585 590

Lys Ala Lys Gly Gln Pro Arg Glu Pro Gln Val Tyr Thr Leu Pro Pro
595 600 605

Ser Arg Glu Glu Met Thr Lys Asn Gln Val Ser Leu Trp Cys Leu Val
610 615 620

Lys Gly Phe Tyr Pro Ser Asp Ile Ala Val Glu Trp Glu Ser Asn Gly
625 630 635 640

Gln Pro Glu Asn Asn Tyr Lys Thr Thr Pro Pro Val Leu Asp Ser Asp
645 650 655

Gly Ser Phe Phe Leu Tyr Ser Lys Leu Thr Val Asp Lys Ser Arg Trp
660 665 670

Gln Gln Gly Asn Val Phe Ser Cys Ser Val Met His Glu Ala Leu His
675 680 685

Asn His Tyr Thr Gln Lys Ser Leu Ser Leu Ser Pro Gly
690 695 700

<210> SEQ ID NO 219
<211> LENGTH: 698
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#3 chain

<400> SEQUENCE: 219

Asp Ile Val Met Thr Gln Ser Gln Lys Leu Leu Ser Thr Ser Val Gly
1 5 10 15

Asp Arg Ile Ser Val Thr Cys Lys Ala Ser His Asn Val Gly Val Tyr
20 25 30

Val Ala Trp Tyr Gln Gln Lys Pro Gly His Ser Pro Lys Ala Leu Ile
35 40 45

His Ser Ala Ser Asn Arg Tyr Ser Gly Val Pro Asp Arg Phe Thr Gly
50 55 60

Ser Gly Ser Gly Thr Asp Phe Thr Leu Thr Ile Thr Asn Val Gln Ser
65 70 75 80

Glu Asp Leu Ala Glu Tyr Phe Cys Gln Gln Tyr Asn Ser Tyr Pro Leu
85 90 95

Thr Phe Gly Ala Gly Thr Lys Leu Glu Leu Ile Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

-continued

```
Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Glu Val Lys Leu
                245                 250                 255

Val Glu Ser Glu Gly Gly Leu Val Gln Pro Gly Ser Ser Met Lys Leu
            260                 265                 270

Ser Cys Thr Ala Ser Gly Phe Thr Phe Ser Asp Tyr Tyr Met Thr Trp
        275                 280                 285

Val Arg Gln Val Pro Glu Lys Gly Leu Glu Trp Val Gly Asn Ile Asp
    290                 295                 300

Tyr Asp Gly Ser Arg Ile Tyr Tyr Leu Asp Ser Leu Lys Ser Arg Phe
305                 310                 315                 320

Ile Ile Ser Arg Asp Asn Ala Lys Asn Ile Leu Tyr Leu Gln Met Asn
                325                 330                 335

Ser Leu Lys Ser Glu Asp Thr Ala Thr Tyr Tyr Cys Ala Arg Asp Asp
            340                 345                 350

Pro Ala Trp Leu Ala Tyr Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys Asp Lys Thr His Thr Cys Pro Pro
465                 470                 475                 480

Cys Pro Ala Pro Glu Ala Ala Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
        595                 600                 605
```

-continued

```
Glu Met Thr Lys Asn Gln Val Ser Leu Trp Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
        675                 680                 685

Thr Gln Lys Ser Leu Ser Leu Ser Pro Gly
    690                 695


<210> SEQ ID NO 220
<211> LENGTH: 698
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#4 chain

<400> SEQUENCE: 220

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Lys Tyr
            20                  25                  30

Val Ala Trp Tyr Gln Gln Lys Pro Gly Gln Ser Pro Lys Ala Leu Ile
        35                  40                  45

Tyr Ser Ala Ser Asn Arg Tyr Asp Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Thr Glu Tyr Phe Cys Gln Gln Tyr Ile Ser Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255
```

-continued

```
Gln Gln Pro Gly Ser Val Leu Val Arg Pro Gly Ala Ser Val Arg Leu
            260                 265                 270

Ser Cys Lys Ala Ser Gly Tyr Thr Phe Thr Asn Tyr Trp Met Asn Trp
        275                 280                 285

Met Lys Gln Arg Pro Gly Gln Gly Leu Glu Trp Ile Gly Gly Ile Tyr
    290                 295                 300

Leu Asn Gly Asp Ser Thr Asp Tyr Asn Glu Lys Phe Lys Gly Lys Ala
305                 310                 315                 320

Thr Leu Thr Val Asp Thr Ser Ser Ser Thr Thr Tyr Met Asp Leu Ser
                325                 330                 335

Ser Leu Thr Tyr Glu Asp Ser Ala Val Tyr Tyr Cys Thr Thr Arg Gly
            340                 345                 350

Asp Tyr Phe Gly Asp Phe Trp Gly Gln Gly Thr Thr Leu Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys Asp Lys Thr His Thr Cys Pro Pro
465                 470                 475                 480

Cys Pro Ala Pro Glu Ala Ala Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
        595                 600                 605

Glu Met Thr Lys Asn Gln Val Ser Leu Trp Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
```

```
        675                 680                 685

Thr Gln Lys Ser Leu Ser Leu Ser Pro Gly
    690                 695


<210> SEQ ID NO 221
<211> LENGTH: 700
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#5 chain

<400> SEQUENCE: 221

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Phe Gln Gln Arg Pro Gly Lys Ala Pro Asn Leu Leu Ile
        35                  40                  45

Tyr Ala Ala Ser Ser Leu Glu Ser Gly Val Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Tyr Asn His Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Gly Tyr Tyr Ile His Trp
        275                 280                 285

Val Arg Gln Ala Pro Gly Gln Gly Leu Glu Trp Met Gly Trp Ile Asn
    290                 295                 300

Pro His Ser Gly Ala Thr Asn Tyr Ala Gln Asn Phe Gln Gly Arg Val
305                 310                 315                 320

Thr Met Thr Arg Asp Thr Ser Ile Ser Thr Ala Tyr Met Glu Leu Ser
```

```
                325                 330                 335

Arg Leu Arg Ser Asp Asp Ala Ala Val Tyr Tyr Cys Ala Arg Glu Arg
            340                 345                 350

Trp Gly Ser Gly Thr Phe Asn Ile Trp Gly Gln Gly Thr Met Val Thr
        355                 360                 365

Val Ser Ser Ala Ser Thr Lys Gly Pro Ser Val Phe Pro Leu Ala Pro
    370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
                405                 410                 415

Leu Thr Ser Gly Val His Thr Phe Pro Ala Val Leu Gln Ser Ser Gly
            420                 425                 430

Leu Tyr Ser Leu Ser Ser Val Val Thr Val Pro Ser Ser Ser Leu Gly
        435                 440                 445

Thr Gln Thr Tyr Ile Cys Asn Val Asn His Lys Pro Ser Asn Thr Lys
    450                 455                 460

Val Asp Lys Arg Val Glu Pro Lys Ser Cys Asp Lys Thr His Thr Cys
465                 470                 475                 480

Pro Pro Cys Pro Ala Pro Glu Ala Ala Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Glu Glu Met Thr Lys Asn Gln Val Ser Leu Trp Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly
    690                 695                 700
```

<210> SEQ ID NO 222
<211> LENGTH: 701
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<223> OTHER INFORMATION: B7H6#6 chain

<400> SEQUENCE: 222

Asp Ile Val Met Thr Gln Ser Pro Asp Ser Leu Pro Val Ser Ala Gly
1               5                   10                  15

Asp Arg Val Thr Ile Thr Cys Lys Ala Ser Gln Ser Val Ser Asn Asp
            20                  25                  30

Val Val Trp Tyr Gln Gln Lys Pro Gly Gln Ser Pro Lys Leu Leu Met
        35                  40                  45

Tyr Ser Thr Ser Asn Arg Tyr Ile Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Glu Val Gln Leu
                245                 250                 255

Gln Gln Ser Gly Pro Glu Leu Leu Lys Pro Gly Ala Ser Val Lys Ile
            260                 265                 270

Ser Cys Lys Thr Ser Gly Tyr Thr Phe Thr Asp Tyr Thr Met His Trp
        275                 280                 285

Val Lys Gln Ser His Gly Lys Ser Leu Glu Trp Ile Gly Gly Ile Asn
    290                 295                 300

Pro Asn Tyr Asp Asn Thr Gly Tyr Ser Glu Lys Phe Lys Asp Lys Ala
305                 310                 315                 320

Thr Leu Thr Val Asp Lys Ser Ser Ser Thr Ala Tyr Met Glu Leu Arg
                325                 330                 335

Ser Leu Thr Ser Glu Asp Ser Ala Val Tyr Tyr Cys Thr Arg Ser Gly
            340                 345                 350

Ser Arg Arg Ser Phe Tyr Phe Asp Tyr Trp Gly Gln Gly Thr Thr Leu
        355                 360                 365

Thr Val Ser Ser Ala Ser Thr Lys Gly Pro Ser Val Phe Pro Leu Ala
    370                 375                 380

Pro Ser Ser Lys Ser Thr Ser Gly Gly Thr Ala Ala Leu Gly Cys Leu
385                 390                 395                 400
```

Val Lys Asp Tyr Phe Pro Glu Pro Val Thr Val Ser Trp Asn Ser Gly
405 410 415

Ala Leu Thr Ser Gly Val His Thr Phe Pro Ala Val Leu Gln Ser Ser
420 425 430

Gly Leu Tyr Ser Leu Ser Ser Val Val Thr Val Pro Ser Ser Ser Leu
435 440 445

Gly Thr Gln Thr Tyr Ile Cys Asn Val Asn His Lys Pro Ser Asn Thr
450 455 460

Lys Val Asp Lys Arg Val Glu Pro Lys Ser Cys Asp Lys Thr His Thr
465 470 475 480

Cys Pro Pro Cys Pro Ala Pro Glu Ala Ala Gly Gly Pro Ser Val Phe
485 490 495

Leu Phe Pro Pro Lys Pro Lys Asp Thr Leu Met Ile Ser Arg Thr Pro
500 505 510

Glu Val Thr Cys Val Val Val Asp Val Ser His Glu Asp Pro Glu Val
515 520 525

Lys Phe Asn Trp Tyr Val Asp Gly Val Glu Val His Asn Ala Lys Thr
530 535 540

Lys Pro Arg Glu Glu Gln Tyr Asn Ser Thr Tyr Arg Val Val Ser Val
545 550 555 560

Leu Thr Val Leu His Gln Asp Trp Leu Asn Gly Lys Glu Tyr Lys Cys
565 570 575

Lys Val Ser Asn Lys Ala Leu Pro Ala Pro Ile Glu Lys Thr Ile Ser
580 585 590

Lys Ala Lys Gly Gln Pro Arg Glu Pro Gln Val Tyr Thr Leu Pro Pro
595 600 605

Ser Arg Glu Glu Met Thr Lys Asn Gln Val Ser Leu Trp Cys Leu Val
610 615 620

Lys Gly Phe Tyr Pro Ser Asp Ile Ala Val Glu Trp Glu Ser Asn Gly
625 630 635 640

Gln Pro Glu Asn Asn Tyr Lys Thr Thr Pro Pro Val Leu Asp Ser Asp
645 650 655

Gly Ser Phe Phe Leu Tyr Ser Lys Leu Thr Val Asp Lys Ser Arg Trp
660 665 670

Gln Gln Gly Asn Val Phe Ser Cys Ser Val Met His Glu Ala Leu His
675 680 685

Asn His Tyr Thr Gln Lys Ser Leu Ser Leu Ser Pro Gly
690 695 700

<210> SEQ ID NO 223
<211> LENGTH: 698
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#7 chain

<400> SEQUENCE: 223

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Asn Leu Leu Ile
35 40 45

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Gln Glu Ser Gly Pro Gly Leu Val Lys Pro Ser Glu Thr Leu Ser Leu
            260                 265                 270

Thr Tyr Thr Val Ser Gly Gly Ser Ile Ser Tyr Asn Tyr Trp Ser Trp
        275                 280                 285

Ile Arg Gln Pro Pro Glu Lys Gly Leu Glu Trp Ile Gly His Ile Tyr
    290                 295                 300

Tyr Ser Gly Ser Thr Asn Tyr Asn Pro Ser Leu Lys Ser Arg Val Thr
305                 310                 315                 320

Ile Ser Val Asp Thr Ser Lys Asn Gln Phe Ser Leu Lys Leu Asn Ser
                325                 330                 335

Val Thr Ala Ala Asp Thr Ala Val Tyr Tyr Cys Ala Arg Val Gly Thr
            340                 345                 350

Trp Gly Ser Phe Asp Asp Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460
```

Lys Arg Val Glu Pro Lys Ser Cys Asp Lys Thr His Thr Cys Pro Pro
465 470 475 480

Cys Pro Ala Pro Glu Ala Ala Gly Gly Pro Ser Val Phe Leu Phe Pro
485 490 495

Pro Lys Pro Lys Asp Thr Leu Met Ile Ser Arg Thr Pro Glu Val Thr
500 505 510

Cys Val Val Val Asp Val Ser His Glu Asp Pro Glu Val Lys Phe Asn
515 520 525

Trp Tyr Val Asp Gly Val Glu Val His Asn Ala Lys Thr Lys Pro Arg
530 535 540

Glu Glu Gln Tyr Asn Ser Thr Tyr Arg Val Val Ser Val Leu Thr Val
545 550 555 560

Leu His Gln Asp Trp Leu Asn Gly Lys Glu Tyr Lys Cys Lys Val Ser
565 570 575

Asn Lys Ala Leu Pro Ala Pro Ile Glu Lys Thr Ile Ser Lys Ala Lys
580 585 590

Gly Gln Pro Arg Glu Pro Gln Val Tyr Thr Leu Pro Pro Ser Arg Glu
595 600 605

Glu Met Thr Lys Asn Gln Val Ser Leu Trp Cys Leu Val Lys Gly Phe
610 615 620

Tyr Pro Ser Asp Ile Ala Val Glu Trp Glu Ser Asn Gly Gln Pro Glu
625 630 635 640

Asn Asn Tyr Lys Thr Thr Pro Pro Val Leu Asp Ser Asp Gly Ser Phe
645 650 655

Phe Leu Tyr Ser Lys Leu Thr Val Asp Lys Ser Arg Trp Gln Gln Gly
660 665 670

Asn Val Phe Ser Cys Ser Val Met His Glu Ala Leu His Asn His Tyr
675 680 685

Thr Gln Lys Ser Leu Ser Leu Ser Pro Gly
690 695

<210> SEQ ID NO 224
<211> LENGTH: 713
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#8 chain

<400> SEQUENCE: 224

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu Tyr Asn
20 25 30

Asn Arg Tyr Asn Tyr Leu Asp Trp Tyr Leu Gln Lys Pro Gly Gln Ser
35 40 45

Pro Glu Val Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Phe Gly Val Tyr Tyr Cys Met Gln Thr
85 90 95

Leu Gln Ile Pro Ile Thr Phe Gly Gln Gly Thr Arg Leu Glu Ile Lys
100 105 110

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Glu Gly Lys Ser Ser Gly Ser Gly Ser Glu Ser Lys Ser Thr Glu Gly
225                 230                 235                 240

Lys Ser Ser Gly Ser Gly Ser Glu Ser Lys Ser Thr Gly Gly Gly Gly
                245                 250                 255

Ser Gln Val Gln Val Val Gln Ser Gly Ala Glu Val Lys Lys Pro Gly
            260                 265                 270

Ser Ser Val Lys Val Ser Cys Lys Gly Ser Gly Asp Thr Leu Asn Ser
        275                 280                 285

Tyr Gly Ile Ser Trp Met Arg Gln Ala Pro Gly Gln Gly Leu Glu Trp
    290                 295                 300

Met Gly Gly Ile Ile Pro Ile Phe Asp Thr Thr Lys Tyr Ala Gln Lys
305                 310                 315                 320

Phe Gln Gly Arg Val Thr Ile Thr Ala Asp Lys Ser Thr Thr Thr Val
                325                 330                 335

Tyr Met Glu Leu Ser Ser Leu Arg Phe Glu Asp Thr Ala Val Tyr Tyr
            340                 345                 350

Cys Ala Arg Glu Arg Gly Tyr Arg Phe Ser Glu Asp Tyr Tyr Phe Tyr
        355                 360                 365

Tyr Gly Met Asp Val Trp Gly Gln Gly Thr Thr Val Thr Val Ser Ser
    370                 375                 380

Ala Ser Thr Lys Gly Pro Ser Val Phe Pro Leu Ala Pro Ser Ser Lys
385                 390                 395                 400

Ser Thr Ser Gly Gly Thr Ala Ala Leu Gly Cys Leu Val Lys Asp Tyr
                405                 410                 415

Phe Pro Glu Pro Val Thr Val Ser Trp Asn Ser Gly Ala Leu Thr Ser
            420                 425                 430

Gly Val His Thr Phe Pro Ala Val Leu Gln Ser Ser Gly Leu Tyr Ser
        435                 440                 445

Leu Ser Ser Val Val Thr Val Pro Ser Ser Ser Leu Gly Thr Gln Thr
    450                 455                 460

Tyr Ile Cys Asn Val Asn His Lys Pro Ser Asn Thr Lys Val Asp Lys
465                 470                 475                 480

Arg Val Glu Pro Lys Ser Cys Asp Lys Thr His Thr Cys Pro Pro Cys
                485                 490                 495

Pro Ala Pro Glu Ala Ala Gly Gly Pro Ser Val Phe Leu Phe Pro Pro
            500                 505                 510

Lys Pro Lys Asp Thr Leu Met Ile Ser Arg Thr Pro Glu Val Thr Cys
        515                 520                 525

Val Val Val Asp Val Ser His Glu Asp Pro Glu Val Lys Phe Asn Trp
```

```
    530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Ala Leu Pro Ala Pro Ile Glu Lys Thr Ile Ser Lys Ala Lys Gly
        595                 600                 605

Gln Pro Arg Glu Pro Gln Val Tyr Thr Leu Pro Pro Ser Arg Glu Glu
    610                 615                 620

Met Thr Lys Asn Gln Val Ser Leu Trp Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
            660                 665                 670

Leu Tyr Ser Lys Leu Thr Val Asp Lys Ser Arg Trp Gln Gln Gly Asn
        675                 680                 685

Val Phe Ser Cys Ser Val Met His Glu Ala Leu His Asn His Tyr Thr
    690                 695                 700

Gln Lys Ser Leu Ser Leu Ser Pro Gly
705                 710


<210> SEQ ID NO 225
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#9 chain

<400> SEQUENCE: 225

Asp Ile Val Leu Thr Gln Ser Pro Val Ser Leu Ala Val Ser Leu Gly
1               5                   10                  15

Gln Arg Ala Thr Ile Ser Cys Arg Ala Ser Glu Ser Val Asp Asn Phe
            20                  25                  30

Gly Val Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Leu Glu Glu Asp Asp Thr Ala Met Tyr Phe Cys Gln Gln Ser Lys
                85                  90                  95

Glu Val Pro Trp Thr Phe Gly Gly Gly Thr Arg Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
```

-continued

```
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys Gly Gly Gly Gly Ser Glu
    210                 215                 220
Gly Lys Ser Ser Gly Ser Gly Ser Glu Ser Lys Ser Thr Glu Gly Lys
225                 230                 235                 240
Ser Ser Gly Ser Gly Ser Glu Ser Lys Ser Thr Gly Gly Gly Gly Ser
                245                 250                 255
Gln Val Gln Leu Gln Gln Pro Gly Ala Glu Met Val Arg Pro Gly Ser
            260                 265                 270
Ser Val Lys Leu Ser Cys Lys Ala Ser Asp Tyr Thr Phe Thr His Tyr
        275                 280                 285
Trp Ile His Trp Val Lys Gln Arg Pro Leu Glu Gly Leu Glu Trp Ile
    290                 295                 300
Gly Ile Ile Gly Pro Ser Asp Asn Glu Ile His Tyr Asn Gln Asp Phe
305                 310                 315                 320
Lys Asp Lys Ala Thr Leu Thr Val Asp Lys Ser Ser Asn Thr Ala Tyr
                325                 330                 335
Leu His Leu Asn Ser Leu Thr Ser Glu Asp Ser Ala Val Tyr Tyr Cys
            340                 345                 350
Ala Arg Gln Ile Ile Ser Met Val Val Gly Thr Glu Tyr Phe Asp Val
        355                 360                 365
Trp Gly Thr Gly Thr Thr Val Thr Val Ser Ser Ala Ser Thr Lys Gly
    370                 375                 380
Pro Ser Val Phe Pro Leu Ala Pro Ser Ser Lys Ser Thr Ser Gly Gly
385                 390                 395                 400
Thr Ala Ala Leu Gly Cys Leu Val Lys Asp Tyr Phe Pro Glu Pro Val
                405                 410                 415
Thr Val Ser Trp Asn Ser Gly Ala Leu Thr Ser Gly Val His Thr Phe
            420                 425                 430
Pro Ala Val Leu Gln Ser Ser Gly Leu Tyr Ser Leu Ser Ser Val Val
        435                 440                 445
Thr Val Pro Ser Ser Ser Leu Gly Thr Gln Thr Tyr Ile Cys Asn Val
    450                 455                 460
Asn His Lys Pro Ser Asn Thr Lys Val Asp Lys Arg Val Glu Pro Lys
465                 470                 475                 480
Ser Cys Asp Lys Thr His Thr Cys Pro Pro Cys Pro Ala Pro Glu Ala
                485                 490                 495
Ala Gly Gly Pro Ser Val Phe Leu Phe Pro Pro Lys Pro Lys Asp Thr
            500                 505                 510
Leu Met Ile Ser Arg Thr Pro Glu Val Thr Cys Val Val Val Asp Val
        515                 520                 525
Ser His Glu Asp Pro Glu Val Lys Phe Asn Trp Tyr Val Asp Gly Val
    530                 535                 540
Glu Val His Asn Ala Lys Thr Lys Pro Arg Glu Glu Gln Tyr Asn Ser
545                 550                 555                 560
Thr Tyr Arg Val Val Ser Val Leu Thr Val Leu His Gln Asp Trp Leu
                565                 570                 575
Asn Gly Lys Glu Tyr Lys Cys Lys Val Ser Asn Lys Ala Leu Pro Ala
            580                 585                 590
```

```
Pro Ile Glu Lys Thr Ile Ser Lys Ala Lys Gly Gln Pro Arg Glu Pro
        595                 600                 605

Gln Val Tyr Thr Leu Pro Pro Ser Arg Glu Glu Met Thr Lys Asn Gln
    610                 615                 620

Val Ser Leu Trp Cys Leu Val Lys Gly Phe Tyr Pro Ser Asp Ile Ala
625                 630                 635                 640

Val Glu Trp Glu Ser Asn Gly Gln Pro Glu Asn Asn Tyr Lys Thr Thr
                645                 650                 655

Pro Pro Val Leu Asp Ser Asp Gly Ser Phe Phe Leu Tyr Ser Lys Leu
            660                 665                 670

Thr Val Asp Lys Ser Arg Trp Gln Gln Gly Asn Val Phe Ser Cys Ser
        675                 680                 685

Val Met His Glu Ala Leu His Asn His Tyr Thr Gln Lys Ser Leu Ser
    690                 695                 700

Leu Ser Pro Gly
705


<210> SEQ ID NO 226
<211> LENGTH: 698
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#10 chain

<400> SEQUENCE: 226

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Val Ala Ser Ser Leu Gln Arg Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220
```

-continued

```
Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val His Leu
                245                 250                 255

Gln Glu Ser Gly Pro Gly Leu Val Lys Pro Ser Glu Thr Leu Ser Leu
            260                 265                 270

Thr Cys Thr Val Ser Gly Asp Ser Ile Ser Ser Tyr Tyr Trp Ser Trp
        275                 280                 285

Ile Arg Gln Pro Ala Gly Lys Gly Leu Glu Trp Ile Gly His Ile Tyr
    290                 295                 300

Thr Ser Glu Lys Asn Asn Tyr Asn Pro Ser Leu Lys Ser Arg Val Ile
305                 310                 315                 320

Met Ser Val Asp Thr Ser Lys Asn Gln Phe Ser Leu Asn Leu Ser Ser
                325                 330                 335

Val Thr Ala Ala Asp Thr Ala Val Tyr Tyr Cys Ala Arg Val Gly Asn
            340                 345                 350

Trp Gly Ser His Asp Ala Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys Asp Lys Thr His Thr Cys Pro Pro
465                 470                 475                 480

Cys Pro Ala Pro Glu Ala Ala Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
        595                 600                 605

Glu Met Thr Lys Asn Gln Val Ser Leu Trp Cys Leu Val Lys Gly Phe
    610                 615                 620

Tyr Pro Ser Asp Ile Ala Val Glu Trp Glu Ser Asn Gly Gln Pro Glu
625                 630                 635                 640
```

```
Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
        675                 680                 685

Thr Gln Lys Ser Leu Ser Leu Ser Pro Gly
    690                 695


<210> SEQ ID NO 227
<211> LENGTH: 712
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#11 chain

<400> SEQUENCE: 227

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Val Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Glu Gly Lys Ser Ser Gly Ser Gly Ser Glu Ser Lys Ser Thr Glu Gly
225                 230                 235                 240

Lys Ser Ser Gly Ser Gly Ser Glu Ser Lys Ser Thr Gly Gly Gly Gly
                245                 250                 255

Ser Glu Leu Gln Leu Val Asn Ser Gly Gly Gly Leu Val Lys Ser Gly
            260                 265                 270

Gly Ser Leu Arg Leu Ser Cys Ala Ala Ser Gly Ile Thr Phe Ser Tyr
        275                 280                 285
```

```
Tyr Thr Met Asn Trp Val Arg Gln Ala Pro Gly Lys Gly Leu Glu Trp
    290                 295                 300

Val Ser Ser Ile Ser Ser Arg Ser Ser Tyr Ile Tyr Tyr Ala Asp Ser
305                 310                 315                 320

Val Lys Gly Arg Phe Thr Ile Ser Arg Asp Asn Ala Glu Asn Ser Leu
                325                 330                 335

Tyr Leu Gln Met Asn Ser Leu Arg Ala Glu Asp Thr Ala Val Tyr Tyr
            340                 345                 350

Cys Ala Arg Asp Lys Gly Asp Tyr Ser Lys Asp Ile Tyr Tyr Tyr Tyr
        355                 360                 365

Gly Met Asp Val Trp Gly Gln Gly Thr Thr Val Thr Val Ser Ser Ala
    370                 375                 380

Ser Thr Lys Gly Pro Ser Val Phe Pro Leu Ala Pro Ser Ser Lys Ser
385                 390                 395                 400

Thr Ser Gly Gly Thr Ala Ala Leu Gly Cys Leu Val Lys Asp Tyr Phe
                405                 410                 415

Pro Glu Pro Val Thr Val Ser Trp Asn Ser Gly Ala Leu Thr Ser Gly
            420                 425                 430

Val His Thr Phe Pro Ala Val Leu Gln Ser Ser Gly Leu Tyr Ser Leu
        435                 440                 445

Ser Ser Val Val Thr Val Pro Ser Ser Ser Leu Gly Thr Gln Thr Tyr
    450                 455                 460

Ile Cys Asn Val Asn His Lys Pro Ser Asn Thr Lys Val Asp Lys Arg
465                 470                 475                 480

Val Glu Pro Lys Ser Cys Asp Lys Thr His Thr Cys Pro Pro Cys Pro
                485                 490                 495

Ala Pro Glu Ala Ala Gly Gly Pro Ser Val Phe Leu Phe Pro Pro Lys
            500                 505                 510

Pro Lys Asp Thr Leu Met Ile Ser Arg Thr Pro Glu Val Thr Cys Val
        515                 520                 525

Val Val Asp Val Ser His Glu Asp Pro Glu Val Lys Phe Asn Trp Tyr
    530                 535                 540

Val Asp Gly Val Glu Val His Asn Ala Lys Thr Lys Pro Arg Glu Glu
545                 550                 555                 560

Gln Tyr Asn Ser Thr Tyr Arg Val Val Ser Val Leu Thr Val Leu His
                565                 570                 575

Gln Asp Trp Leu Asn Gly Lys Glu Tyr Lys Cys Lys Val Ser Asn Lys
            580                 585                 590

Ala Leu Pro Ala Pro Ile Glu Lys Thr Ile Ser Lys Ala Lys Gly Gln
        595                 600                 605

Pro Arg Glu Pro Gln Val Tyr Thr Leu Pro Pro Ser Arg Glu Glu Met
    610                 615                 620

Thr Lys Asn Gln Val Ser Leu Trp Cys Leu Val Lys Gly Phe Tyr Pro
625                 630                 635                 640

Ser Asp Ile Ala Val Glu Trp Glu Ser Asn Gly Gln Pro Glu Asn Asn
                645                 650                 655

Tyr Lys Thr Thr Pro Pro Val Leu Asp Ser Asp Gly Ser Phe Phe Leu
            660                 665                 670

Tyr Ser Lys Leu Thr Val Asp Lys Ser Arg Trp Gln Gln Gly Asn Val
        675                 680                 685

Phe Ser Cys Ser Val Met His Glu Ala Leu His Asn His Tyr Thr Gln
    690                 695                 700

Lys Ser Leu Ser Leu Ser Pro Gly
```

705 710

<210> SEQ ID NO 228
<211> LENGTH: 698
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#12 chain

<400> SEQUENCE: 228

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Tyr Ile Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Asn Tyr Trp Met Asn Trp
        275                 280                 285

Val Lys Gln Ala Pro Gly Gln Gly Leu Glu Trp Met Gly Gly Ile Tyr
    290                 295                 300

Leu Asn Gly Asp Ser Thr Asp Tyr Asn Glu Lys Phe Lys Gly Lys Ala
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
```

```
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys Asp Lys Thr His Thr Cys Pro Pro
465                 470                 475                 480

Cys Pro Ala Pro Glu Ala Ala Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
        595                 600                 605

Glu Met Thr Lys Asn Gln Val Ser Leu Trp Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
        675                 680                 685

Thr Gln Lys Ser Leu Ser Leu Ser Pro Gly
    690                 695
```

<210> SEQ ID NO 229
<211> LENGTH: 698
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#13 chain

<400> SEQUENCE: 229

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Tyr Ile Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Ser Tyr Trp Met Asn Trp
        275                 280                 285

Met Lys Gln Ala Pro Gly Gln Gly Leu Glu Trp Met Gly Gly Ile Tyr
    290                 295                 300

Leu Asn Gly Asp Ser Thr Asp Tyr Asn Glu Lys Phe Lys Gly Arg Val
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415
```

Ser Gly Val His Thr Phe Pro Ala Val Leu Gln Ser Ser Gly Leu Tyr
420 425 430

Ser Leu Ser Ser Val Val Thr Val Pro Ser Ser Ser Leu Gly Thr Gln
435 440 445

Thr Tyr Ile Cys Asn Val Asn His Lys Pro Ser Asn Thr Lys Val Asp
450 455 460

Lys Arg Val Glu Pro Lys Ser Cys Asp Lys Thr His Thr Cys Pro Pro
465 470 475 480

Cys Pro Ala Pro Glu Ala Ala Gly Gly Pro Ser Val Phe Leu Phe Pro
485 490 495

Pro Lys Pro Lys Asp Thr Leu Met Ile Ser Arg Thr Pro Glu Val Thr
500 505 510

Cys Val Val Val Asp Val Ser His Glu Asp Pro Glu Val Lys Phe Asn
515 520 525

Trp Tyr Val Asp Gly Val Glu Val His Asn Ala Lys Thr Lys Pro Arg
530 535 540

Glu Glu Gln Tyr Asn Ser Thr Tyr Arg Val Val Ser Val Leu Thr Val
545 550 555 560

Leu His Gln Asp Trp Leu Asn Gly Lys Glu Tyr Lys Cys Lys Val Ser
565 570 575

Asn Lys Ala Leu Pro Ala Pro Ile Glu Lys Thr Ile Ser Lys Ala Lys
580 585 590

Gly Gln Pro Arg Glu Pro Gln Val Tyr Thr Leu Pro Pro Ser Arg Glu
595 600 605

Glu Met Thr Lys Asn Gln Val Ser Leu Trp Cys Leu Val Lys Gly Phe
610 615 620

Tyr Pro Ser Asp Ile Ala Val Glu Trp Glu Ser Asn Gly Gln Pro Glu
625 630 635 640

Asn Asn Tyr Lys Thr Thr Pro Pro Val Leu Asp Ser Asp Gly Ser Phe
645 650 655

Phe Leu Tyr Ser Lys Leu Thr Val Asp Lys Ser Arg Trp Gln Gln Gly
660 665 670

Asn Val Phe Ser Cys Ser Val Met His Glu Ala Leu His Asn His Tyr
675 680 685

Thr Gln Lys Ser Leu Ser Leu Ser Pro Gly
690 695

<210> SEQ ID NO 230
<211> LENGTH: 698
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#14 chain

<400> SEQUENCE: 230

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Phe Cys Gln Gln Tyr Ile Ser Tyr Pro Leu
85 90 95

Thr Phe Gly Ala Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Glu Gly Lys Ser Ser
210 215 220

Gly Ser Gly Ser Glu Ser Lys Ser Thr Glu Gly Lys Ser Ser Gly Ser
225 230 235 240

Gly Ser Glu Ser Lys Ser Thr Gly Gly Gly Gly Ser Gln Val Gln Leu
245 250 255

Val Gln Ser Gly Ala Glu Val Lys Lys Pro Gly Ala Ser Val Lys Val
260 265 270

Ser Cys Lys Ala Ser Gly Tyr Thr Phe Thr Asn Tyr Trp Met Asn Trp
275 280 285

Met Lys Gln Ala Pro Gly Gln Gly Leu Glu Trp Ile Gly Gly Ile Tyr
290 295 300

Leu Asn Gly Asp Ser Thr Asp Tyr Asn Glu Lys Phe Lys Gly Lys Val
305 310 315 320

Thr Met Thr Val Asp Thr Ser Thr Ser Thr Val Tyr Met Glu Leu Ser
325 330 335

Ser Leu Arg Ser Glu Asp Thr Ala Val Tyr Tyr Cys Thr Arg Arg Gly
340 345 350

Asp Tyr Phe Gly Asp Phe Trp Gly Gln Gly Thr Leu Val Thr Val Ser
355 360 365

Ser Ala Ser Thr Lys Gly Pro Ser Val Phe Pro Leu Ala Pro Ser Ser
370 375 380

Lys Ser Thr Ser Gly Gly Thr Ala Ala Leu Gly Cys Leu Val Lys Asp
385 390 395 400

Tyr Phe Pro Glu Pro Val Thr Val Ser Trp Asn Ser Gly Ala Leu Thr
405 410 415

Ser Gly Val His Thr Phe Pro Ala Val Leu Gln Ser Ser Gly Leu Tyr
420 425 430

Ser Leu Ser Ser Val Val Thr Val Pro Ser Ser Ser Leu Gly Thr Gln
435 440 445

Thr Tyr Ile Cys Asn Val Asn His Lys Pro Ser Asn Thr Lys Val Asp
450 455 460

Lys Arg Val Glu Pro Lys Ser Cys Asp Lys Thr His Thr Cys Pro Pro
465 470 475 480

Cys Pro Ala Pro Glu Ala Ala Gly Gly Pro Ser Val Phe Leu Phe Pro
485 490 495

Pro Lys Pro Lys Asp Thr Leu Met Ile Ser Arg Thr Pro Glu Val Thr
500 505 510

Cys Val Val Val Asp Val Ser His Glu Asp Pro Glu Val Lys Phe Asn
515 520 525

Trp Tyr Val Asp Gly Val Glu Val His Asn Ala Lys Thr Lys Pro Arg
530 535 540

Glu Glu Gln Tyr Asn Ser Thr Tyr Arg Val Val Ser Val Leu Thr Val
545 550 555 560

Leu His Gln Asp Trp Leu Asn Gly Lys Glu Tyr Lys Cys Lys Val Ser
565 570 575

Asn Lys Ala Leu Pro Ala Pro Ile Glu Lys Thr Ile Ser Lys Ala Lys
580 585 590

Gly Gln Pro Arg Glu Pro Gln Val Tyr Thr Leu Pro Pro Ser Arg Glu
595 600 605

Glu Met Thr Lys Asn Gln Val Ser Leu Trp Cys Leu Val Lys Gly Phe
610 615 620

Tyr Pro Ser Asp Ile Ala Val Glu Trp Glu Ser Asn Gly Gln Pro Glu
625 630 635 640

Asn Asn Tyr Lys Thr Thr Pro Pro Val Leu Asp Ser Asp Gly Ser Phe
645 650 655

Phe Leu Tyr Ser Lys Leu Thr Val Asp Lys Ser Arg Trp Gln Gln Gly
660 665 670

Asn Val Phe Ser Cys Ser Val Met His Glu Ala Leu His Asn His Tyr
675 680 685

Thr Gln Lys Ser Leu Ser Leu Ser Pro Gly
690 695

<210> SEQ ID NO 231
<211> LENGTH: 698
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#15 chain

<400> SEQUENCE: 231

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Thr Thr Tyr Tyr Cys Gln Gln Tyr Ile Ser Tyr Pro Leu
85 90 95

Thr Phe Gly Ala Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

-continued

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Asn Tyr Trp Met Asn Trp
        275                 280                 285

Met Arg Gln Ala Pro Gly Gln Gly Leu Glu Trp Met Gly Gly Ile Tyr
    290                 295                 300

Leu Ser Gly Asp Ser Thr Asp Tyr Asn Glu Lys Phe Lys Gly Arg Val
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys Asp Lys Thr His Thr Cys Pro Pro
465                 470                 475                 480

Cys Pro Ala Pro Glu Ala Ala Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
```

```
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
        595                 600                 605

Glu Met Thr Lys Asn Gln Val Ser Leu Trp Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
        675                 680                 685

Thr Gln Lys Ser Leu Ser Leu Ser Pro Gly
    690                 695


<210> SEQ ID NO 232
<211> LENGTH: 698
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#16 chain

<400> SEQUENCE: 232

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Tyr Ile Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

```
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Ser Tyr Trp Met Asn Trp
        275                 280                 285

Met Arg Gln Ala Pro Gly Gln Gly Leu Glu Trp Met Gly Gly Ile Tyr
    290                 295                 300

Leu Ser Gly Glu Ser Thr Asp Tyr Asn Glu Lys Phe Lys Gly Arg Val
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys Asp Lys Thr His Thr Cys Pro Pro
465                 470                 475                 480

Cys Pro Ala Pro Glu Ala Ala Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
        595                 600                 605

Glu Met Thr Lys Asn Gln Val Ser Leu Trp Cys Leu Val Lys Gly Phe
    610                 615                 620
```

Tyr Pro Ser Asp Ile Ala Val Glu Trp Glu Ser Asn Gly Gln Pro Glu
625 630 635 640

Asn Asn Tyr Lys Thr Thr Pro Pro Val Leu Asp Ser Asp Gly Ser Phe
645 650 655

Phe Leu Tyr Ser Lys Leu Thr Val Asp Lys Ser Arg Trp Gln Gln Gly
660 665 670

Asn Val Phe Ser Cys Ser Val Met His Glu Ala Leu His Asn His Tyr
675 680 685

Thr Gln Lys Ser Leu Ser Leu Ser Pro Gly
690 695

<210> SEQ ID NO 233
<211> LENGTH: 698
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#17 chain

<400> SEQUENCE: 233

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Thr Thr Tyr Tyr Cys Gln Gln Tyr Ile Ser Tyr Pro Leu
85 90 95

Thr Phe Gly Ala Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Glu Gly Lys Ser Ser
210 215 220

Gly Ser Gly Ser Glu Ser Lys Ser Thr Glu Gly Lys Ser Ser Gly Ser
225 230 235 240

Gly Ser Glu Ser Lys Ser Thr Gly Gly Gly Gly Ser Gln Val Gln Leu
245 250 255

Val Gln Ser Gly Ala Glu Val Lys Lys Pro Gly Ala Ser Val Lys Val
260 265 270

```
Ser Cys Lys Ala Ser Gly Tyr Thr Phe Thr Ser Tyr Trp Met Asn Trp
        275                 280                 285

Met Arg Gln Ala Pro Gly Gln Gly Leu Glu Trp Met Gly Gly Ile Tyr
    290                 295                 300

Leu Ser Gly Asp Ser Thr Asp Tyr Asn Glu Lys Phe Lys Gly Arg Val
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys Asp Lys Thr His Thr Cys Pro Pro
465                 470                 475                 480

Cys Pro Ala Pro Glu Ala Ala Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
        595                 600                 605

Glu Met Thr Lys Asn Gln Val Ser Leu Trp Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
        675                 680                 685
```

-continued

Thr Gln Lys Ser Leu Ser Leu Ser Pro Gly
690 695

<210> SEQ ID NO 234
<211> LENGTH: 698
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#18 chain

<400> SEQUENCE: 234

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Ala Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Thr Thr Tyr Tyr Cys Gln Gln Tyr Ile Ser Tyr Pro Leu
85 90 95

Thr Phe Gly Ala Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Glu Gly Lys Ser Ser
210 215 220

Gly Ser Gly Ser Glu Ser Lys Ser Thr Glu Gly Lys Ser Ser Gly Ser
225 230 235 240

Gly Ser Glu Ser Lys Ser Thr Gly Gly Gly Gly Ser Gln Val Gln Leu
245 250 255

Val Gln Ser Gly Ala Glu Val Lys Lys Pro Gly Ala Ser Val Lys Val
260 265 270

Ser Cys Lys Ala Ser Gly Tyr Thr Phe Thr Ser Tyr Trp Met Asn Trp
275 280 285

Met Arg Gln Ala Pro Gly Gln Gly Leu Glu Trp Met Gly Gly Ile Tyr
290 295 300

Leu Ser Gly Asp Ser Thr Asp Tyr Asn Glu Lys Phe Lys Gly Arg Val
305 310 315 320

Thr Met Thr Val Asp Thr Ser Thr Ser Thr Val Tyr Met Glu Leu Ser
325 330 335

Ser Leu Arg Ser Glu Asp Thr Ala Val Tyr Tyr Cys Thr Arg Arg Gly
340 345 350

Asp Tyr Phe Gly Asp Phe Trp Gly Gln Gly Thr Leu Val Thr Val Ser
355 360 365

Ser Ala Ser Thr Lys Gly Pro Ser Val Phe Pro Leu Ala Pro Ser Ser
370 375 380

Lys Ser Thr Ser Gly Gly Thr Ala Ala Leu Gly Cys Leu Val Lys Asp
385 390 395 400

Tyr Phe Pro Glu Pro Val Thr Val Ser Trp Asn Ser Gly Ala Leu Thr
405 410 415

Ser Gly Val His Thr Phe Pro Ala Val Leu Gln Ser Ser Gly Leu Tyr
420 425 430

Ser Leu Ser Ser Val Val Thr Val Pro Ser Ser Ser Leu Gly Thr Gln
435 440 445

Thr Tyr Ile Cys Asn Val Asn His Lys Pro Ser Asn Thr Lys Val Asp
450 455 460

Lys Arg Val Glu Pro Lys Ser Cys Asp Lys Thr His Thr Cys Pro Pro
465 470 475 480

Cys Pro Ala Pro Glu Ala Ala Gly Gly Pro Ser Val Phe Leu Phe Pro
485 490 495

Pro Lys Pro Lys Asp Thr Leu Met Ile Ser Arg Thr Pro Glu Val Thr
500 505 510

Cys Val Val Val Asp Val Ser His Glu Asp Pro Glu Val Lys Phe Asn
515 520 525

Trp Tyr Val Asp Gly Val Glu Val His Asn Ala Lys Thr Lys Pro Arg
530 535 540

Glu Glu Gln Tyr Asn Ser Thr Tyr Arg Val Val Ser Val Leu Thr Val
545 550 555 560

Leu His Gln Asp Trp Leu Asn Gly Lys Glu Tyr Lys Cys Lys Val Ser
565 570 575

Asn Lys Ala Leu Pro Ala Pro Ile Glu Lys Thr Ile Ser Lys Ala Lys
580 585 590

Gly Gln Pro Arg Glu Pro Gln Val Tyr Thr Leu Pro Pro Ser Arg Glu
595 600 605

Glu Met Thr Lys Asn Gln Val Ser Leu Trp Cys Leu Val Lys Gly Phe
610 615 620

Tyr Pro Ser Asp Ile Ala Val Glu Trp Glu Ser Asn Gly Gln Pro Glu
625 630 635 640

Asn Asn Tyr Lys Thr Thr Pro Pro Val Leu Asp Ser Asp Gly Ser Phe
645 650 655

Phe Leu Tyr Ser Lys Leu Thr Val Asp Lys Ser Arg Trp Gln Gln Gly
660 665 670

Asn Val Phe Ser Cys Ser Val Met His Glu Ala Leu His Asn His Tyr
675 680 685

Thr Gln Lys Ser Leu Ser Leu Ser Pro Gly
690 695

<210> SEQ ID NO 235
<211> LENGTH: 698
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#19 chain

<400> SEQUENCE: 235

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Tyr Ile Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Ser Tyr Trp Met Asn Trp
        275                 280                 285

Val Lys Gln Ala Pro Gly Gln Gly Leu Glu Trp Met Gly Gly Ile Tyr
    290                 295                 300

Leu Ser Gly Glu Ser Thr Asp Tyr Asn Glu Lys Phe Lys Gly Lys Ala
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr

-continued

```
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys Asp Lys Thr His Thr Cys Pro Pro
465                 470                 475                 480

Cys Pro Ala Pro Glu Ala Ala Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
        595                 600                 605

Glu Met Thr Lys Asn Gln Val Ser Leu Trp Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
        675                 680                 685

Thr Gln Lys Ser Leu Ser Leu Ser Pro Gly
    690                 695


<210> SEQ ID NO 236
<211> LENGTH: 698
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#20 chain

<400> SEQUENCE: 236

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Ala Val Pro Ser Arg Phe Ser Gly
```

```
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Tyr Ile Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Ser Tyr Trp Met Asn Trp
        275                 280                 285

Val Lys Gln Ala Pro Gly Gln Gly Leu Glu Trp Met Gly Gly Ile Tyr
    290                 295                 300

Leu Ser Gly Asp Ser Thr Asp Tyr Asn Glu Lys Phe Lys Gly Lys Ala
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys Asp Lys Thr His Thr Cys Pro Pro
465                 470                 475                 480
```

```
Cys Pro Ala Pro Glu Ala Ala Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
        595                 600                 605

Glu Met Thr Lys Asn Gln Val Ser Leu Trp Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
        675                 680                 685

Thr Gln Lys Ser Leu Ser Leu Ser Pro Gly
    690                 695


<210> SEQ ID NO 237
<211> LENGTH: 698
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#21 chain

<400> SEQUENCE: 237

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ile Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Ser Tyr Trp Met Asn Trp
        275                 280                 285

Met Lys Gln Ala Pro Gly Gln Gly Leu Glu Trp Ile Gly Gly Ile Tyr
    290                 295                 300

Leu Ser Gly Glu Ser Thr Asp Tyr Asn Glu Lys Phe Lys Gly Lys Val
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys Asp Lys Thr His Thr Cys Pro Pro
465                 470                 475                 480

Cys Pro Ala Pro Glu Ala Ala Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540
```

Glu Glu Gln Tyr Asn Ser Thr Tyr Arg Val Val Ser Val Leu Thr Val
545 550 555 560

Leu His Gln Asp Trp Leu Asn Gly Lys Glu Tyr Lys Cys Lys Val Ser
565 570 575

Asn Lys Ala Leu Pro Ala Pro Ile Glu Lys Thr Ile Ser Lys Ala Lys
580 585 590

Gly Gln Pro Arg Glu Pro Gln Val Tyr Thr Leu Pro Pro Ser Arg Glu
595 600 605

Glu Met Thr Lys Asn Gln Val Ser Leu Trp Cys Leu Val Lys Gly Phe
610 615 620

Tyr Pro Ser Asp Ile Ala Val Glu Trp Glu Ser Asn Gly Gln Pro Glu
625 630 635 640

Asn Asn Tyr Lys Thr Thr Pro Pro Val Leu Asp Ser Asp Gly Ser Phe
645 650 655

Phe Leu Tyr Ser Lys Leu Thr Val Asp Lys Ser Arg Trp Gln Gln Gly
660 665 670

Asn Val Phe Ser Cys Ser Val Met His Glu Ala Leu His Asn His Tyr
675 680 685

Thr Gln Lys Ser Leu Ser Leu Ser Pro Gly
690 695

<210> SEQ ID NO 238
<211> LENGTH: 698
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: B7H6#22 chain

<400> SEQUENCE: 238

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Ala Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Phe Cys Gln Gln Tyr Ile Ser Tyr Pro Leu
85 90 95

Thr Phe Gly Ala Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

-continued

```
Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
            260                 265                 270

Ser Cys Lys Ala Ser Gly Tyr Thr Phe Thr Ser Tyr Trp Met Asn Trp
        275                 280                 285

Met Lys Gln Ala Pro Gly Gln Gly Leu Glu Trp Ile Gly Gly Ile Tyr
    290                 295                 300

Leu Ser Gly Asp Ser Thr Asp Tyr Asn Glu Lys Phe Lys Gly Lys Val
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys Asp Lys Thr His Thr Cys Pro Pro
465                 470                 475                 480

Cys Pro Ala Pro Glu Ala Ala Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
        595                 600                 605

Glu Met Thr Lys Asn Gln Val Ser Leu Trp Cys Leu Val Lys Gly Phe
```

```
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
        675                 680                 685

Thr Gln Lys Ser Leu Ser Leu Ser Pro Gly
    690                 695


<210> SEQ ID NO 239
<211> LENGTH: 698
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B7H6#23 chain

<400> SEQUENCE: 239

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Lys Tyr
            20                  25                  30

Val Ala Trp Tyr Gln Gln Lys Pro Gly Lys Ala Pro Lys Ser Leu Ile
        35                  40                  45

Tyr Ser Ala Ser Asn Arg Tyr Asp Ala Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ile Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Glu Gly Lys Ser Ser
    210                 215                 220

Gly Ser Gly Ser Glu Ser Lys Ser Thr Glu Gly Lys Ser Ser Gly Ser
225                 230                 235                 240

Gly Ser Glu Ser Lys Ser Thr Gly Gly Gly Gly Ser Gln Val Gln Leu
                245                 250                 255

Val Gln Ser Gly Ala Glu Val Lys Lys Pro Gly Ala Ser Val Lys Val
```

```
            260                 265                 270

Ser Cys Lys Ala Ser Gly Tyr Thr Phe Thr Ser Tyr Trp Met Asn Trp
        275                 280                 285

Met Lys Gln Ala Pro Gly Gln Gly Leu Glu Trp Ile Gly Gly Ile Tyr
    290                 295                 300

Leu Ser Gly Glu Ser Thr Asp Tyr Asn Glu Lys Phe Lys Gly Lys Val
305                 310                 315                 320

Thr Met Thr Val Asp Thr Ser Thr Ser Thr Val Tyr Met Glu Leu Ser
                325                 330                 335

Ser Leu Arg Ser Glu Asp Thr Ala Val Tyr Tyr Cys Thr Arg Arg Gly
            340                 345                 350

Asp Tyr Phe Gly Asp Phe Trp Gly Gln Gly Thr Leu Val Thr Val Ser
        355                 360                 365

Ser Ala Ser Thr Lys Gly Pro Ser Val Phe Pro Leu Ala Pro Ser Ser
    370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
        435                 440                 445

Thr Tyr Ile Cys Asn Val Asn His Lys Pro Ser Asn Thr Lys Val Asp
    450                 455                 460

Lys Arg Val Glu Pro Lys Ser Cys Asp Lys Thr His Thr Cys Pro Pro
465                 470                 475                 480

Cys Pro Ala Pro Glu Ala Ala Gly Gly Pro Ser Val Phe Leu Phe Pro
                485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
        515                 520                 525

Trp Tyr Val Asp Gly Val Glu Val His Asn Ala Lys Thr Lys Pro Arg
    530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
        595                 600                 605

Glu Met Thr Lys Asn Gln Val Ser Leu Trp Cys Leu Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
        675                 680                 685
```

Thr Gln Lys Ser Leu Ser Leu Ser Pro Gly
690 695

<210> SEQ ID NO 240
<211> LENGTH: 698
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: B7H6#24 chain

<400> SEQUENCE: 240

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Val Gly Lys Tyr
20 25 30

Val Ala Trp Tyr Gln Gln Lys Pro Gly Lys Ala Pro Lys Ser Leu Ile
35 40 45

Tyr Ser Ala Ser Asn Arg Tyr Asp Ala Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Thr Thr Tyr Tyr Cys Gln Gln Tyr Ile Ser Tyr Pro Leu
85 90 95

Thr Phe Gly Ala Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Glu Gly Lys Ser Ser
210 215 220

Gly Ser Gly Ser Glu Ser Lys Ser Thr Glu Gly Lys Ser Ser Gly Ser
225 230 235 240

Gly Ser Glu Ser Lys Ser Thr Gly Gly Gly Gly Ser Gln Val Gln Leu
245 250 255

Val Gln Ser Gly Ala Glu Val Lys Lys Pro Gly Ala Ser Val Lys Val
260 265 270

Ser Cys Lys Ala Ser Gly Tyr Thr Phe Thr Asn Tyr Trp Met Asn Trp
275 280 285

Met Arg Gln Ala Pro Gly Gln Gly Leu Glu Trp Met Gly Gly Ile Tyr
290 295 300

Leu Ser Gly Asp Ser Thr Asp Tyr Asn Glu Lys Phe Lys Gly Arg Val
305 310 315 320

Thr Met Thr Val Asp Thr Ser Thr Ser Thr Val Tyr Met Glu Leu Ser
325 330 335

Ser Leu Arg Ser Glu Asp Thr Ala Val Tyr Tyr Cys Thr Arg Arg Gly
340 345 350

Asp Tyr Phe Gly Asp Phe Trp Gly Gln Gly Thr Leu Val Thr Val Ser
355 360 365

Ser Ala Ser Thr Lys Gly Pro Ser Val Phe Pro Leu Ala Pro Ser Ser
370 375 380

Lys Ser Thr Ser Gly Gly Thr Ala Ala Leu Gly Cys Leu Val Lys Asp
385 390 395 400

Tyr Phe Pro Glu Pro Val Thr Val Ser Trp Asn Ser Gly Ala Leu Thr
405 410 415

Ser Gly Val His Thr Phe Pro Ala Val Leu Gln Ser Ser Gly Leu Tyr
420 425 430

Ser Leu Ser Ser Val Val Thr Val Pro Ser Ser Ser Leu Gly Thr Gln
435 440 445

Thr Tyr Ile Cys Asn Val Asn His Lys Pro Ser Asn Thr Lys Val Asp
450 455 460

Lys Arg Val Glu Pro Lys Ser Cys Asp Lys Thr His Thr Cys Pro Pro
465 470 475 480

Cys Pro Ala Pro Glu Ala Ala Gly Gly Pro Ser Val Phe Leu Phe Pro
485 490 495

Pro Lys Pro Lys Asp Thr Leu Met Ile Ser Arg Thr Pro Glu Val Thr
500 505 510

Cys Val Val Val Asp Val Ser His Glu Asp Pro Glu Val Lys Phe Asn
515 520 525

Trp Tyr Val Asp Gly Val Glu Val His Asn Ala Lys Thr Lys Pro Arg
530 535 540

Glu Glu Gln Tyr Asn Ser Thr Tyr Arg Val Val Ser Val Leu Thr Val
545 550 555 560

Leu His Gln Asp Trp Leu Asn Gly Lys Glu Tyr Lys Cys Lys Val Ser
565 570 575

Asn Lys Ala Leu Pro Ala Pro Ile Glu Lys Thr Ile Ser Lys Ala Lys
580 585 590

Gly Gln Pro Arg Glu Pro Gln Val Tyr Thr Leu Pro Pro Ser Arg Glu
595 600 605

Glu Met Thr Lys Asn Gln Val Ser Leu Trp Cys Leu Val Lys Gly Phe
610 615 620

Tyr Pro Ser Asp Ile Ala Val Glu Trp Glu Ser Asn Gly Gln Pro Glu
625 630 635 640

Asn Asn Tyr Lys Thr Thr Pro Pro Val Leu Asp Ser Asp Gly Ser Phe
645 650 655

Phe Leu Tyr Ser Lys Leu Thr Val Asp Lys Ser Arg Trp Gln Gln Gly
660 665 670

Asn Val Phe Ser Cys Ser Val Met His Glu Ala Leu His Asn His Tyr
675 680 685

Thr Gln Lys Ser Leu Ser Leu Ser Pro Gly
690 695

<210> SEQ ID NO 241
<211> LENGTH: 226
<212> TYPE: PRT
<213> ORGANISM: Artificial Sequence
<220> FEATURE:
<223> OTHER INFORMATION: Description of Artificial Sequence: Synthetic
polypeptide
<220> FEATURE:

<223> OTHER INFORMATION: Fc domain* (IgG1)

<400> SEQUENCE: 241

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Ser Arg Glu Glu Met Thr Lys Asn Gln Val Ser
130 135 140

Leu Thr Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly
225

<210> SEQ ID NO 242
<211> LENGTH: 226
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Fc W domain (IgG1, LALA)

<400> SEQUENCE: 242

Asp Lys Thr His Thr Cys Pro Pro Cys Pro Ala Pro Glu Ala Ala Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Ser Arg Glu Glu Met Thr Lys Asn Gln Val Ser
130 135 140

Leu Trp Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly
225

<210> SEQ ID NO 243
<211> LENGTH: 226
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Fc, SAV domain (IgG1, RF/LALA)

<400> SEQUENCE: 243

Asp Lys Thr His Thr Cys Pro Pro Cys Pro Ala Pro Glu Ala Ala Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Ser Arg Glu Glu Met Thr Lys Asn Gln Val Ser
130 135 140

Leu Ser Cys Ala Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Val Ser Lys Leu Thr Val
180 185 190

Asp Lys Ser Arg Trp Gln Gln Gly Asn Val Phe Ser Cys Ser Val Met
195 200 205

His Glu Ala Leu His Asn Arg Phe Thr Gln Lys Ser Leu Ser Leu Ser
    210                 215                 220

Pro Gly
225

<210> SEQ ID NO 244
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fc domain (IgG4Pro)

<400> SEQUENCE: 244

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 245
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fc W domain (IgG4Pro)

<400> SEQUENCE: 245

Glu Ser Lys Tyr Gly Pro Pro Cys Pro Pro Cys Pro Ala Pro Glu Phe

```
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225


<210> SEQ ID NO 246
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fc SAV domain (IgG4Pro, RF)

<400> SEQUENCE: 246

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
```

```
        115                 120                 125

Gln Val Tyr Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn Arg Phe Thr Gln Lys Ser Leu Ser
    210                 215                 220

Leu Ser Leu Gly
225


<210> SEQ ID NO 247
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: constant region of a kappa light chain

<400> SEQUENCE: 247

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 248
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: constant region of a lambda light chain

<400> SEQUENCE: 248

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45
```

-continued

```
Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105


<210> SEQ ID NO 249
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Constant region of heavy chain CH1

<400> SEQUENCE: 249

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys
            100


<210> SEQ ID NO 250
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Linker

<400> SEQUENCE: 250

Gly Gly Gly Gly Ser Glu Gly Lys Ser Ser Gly Ser Gly Ser Glu Ser
1               5                   10                  15

Lys Ser Thr Glu Gly Lys Ser Ser Gly Ser Gly Ser Glu Ser Lys Ser
            20                  25                  30

Thr Gly Gly Gly Gly Ser
        35


<210> SEQ ID NO 251
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker
```

<400> SEQUENCE: 251

Gly Gly Gly Gly Ser Gly Gly Gly Gly Ser Gly Gly Ser Gly Gly Ser
1               5                   10                  15

Gly Gly Gly Gly Gly Ser
            20

<210> SEQ ID NO 252
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker

<400> SEQUENCE: 252

Gly Gly Gly Gly Ser Gly Gly Gly Gly Ser Gly Gly Gly Gly Ser Gly
1               5                   10                  15

Gly Gly Gly Ser Gly Gly Gly Gly Gly Ser
            20                  25

<210> SEQ ID NO 253
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Linker

<400> SEQUENCE: 253

Gly Gly Gly Gly Ser Gly Gly Gly Gly Gly Gly Ser Gly Gly Gly Gly
1               5                   10                  15

Gly Gly Ser Gly Gly Gly Gly Ser Gly Gly Gly Gly Gly Ser
            20                  25                  30

<210> SEQ ID NO 254
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Linker

<400> SEQUENCE: 254

Gly Gly Gly Gly Ser Gly Gly Gly Gly Ser Gly Gly Gly Ser Gly Gly
1               5                   10                  15

Gly Ser Gly Gly Gly Gly Ser Gly Gly Gly Gly Ser Gly Gly Gly Gly
            20                  25                  30

Gly Ser

<210> SEQ ID NO 255
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Linker

<400> SEQUENCE: 255

```
Gly Gly Gly Gly Ser Gly Gly Gly Gly Ser Gly Gly Gly Ser Gly Gly
1               5                   10                  15

Gly Ser Gly Gly Gly Ser Gly Gly Gly Gly Ser Gly Gly Gly Gly Ser
            20                  25                  30

Gly Gly Gly Gly Gly Ser
        35
```

```
<210> SEQ ID NO 256
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Linker

<400> SEQUENCE: 256

Gly Gly Gly Gly Ser Gly Gly Gly Gly Ser Gly Gly Gly Ser Gly Gly
1               5                   10                  15

Gly Ser Gly Gly Gly Ser Gly Gly Gly Gly Ser Gly Gly Gly Gly Gly
            20                  25                  30

Ser Gly Gly Gly Ser Gly Gly Gly Gly Ser
        35                  40
```

```
<210> SEQ ID NO 257
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#1 LCCDR1

<400> SEQUENCE: 257

Arg Ser Ser Thr Gly Ala Val Thr Thr Ser Asn Tyr Ala Asn
1               5                   10
```

```
<210> SEQ ID NO 258
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#1 LCCDR2

<400> SEQUENCE: 258

Gly Thr Asn Lys Arg Ala Pro
1               5
```

```
<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#1 LCCDR3

<400> SEQUENCE: 259

Ala Leu Trp Tyr Ser Asn Leu Trp Val
1               5
```

<210> SEQ ID NO 260
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#1 HCCDR1

<400> SEQUENCE: 260

Gly Phe Thr Phe Asn Thr Tyr Ala Met Asn
1               5                   10

<210> SEQ ID NO 261
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#1 HCCDR2

<400> SEQUENCE: 261

Arg Ile Arg Ser Lys Tyr Asn Asn Tyr Ala Thr Tyr Tyr Ala Asp Ser
1               5                   10                  15

Val Lys Asp

<210> SEQ ID NO 262
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#1 HCCDR3

<400> SEQUENCE: 262

His Gly Asn Phe Gly Asn Ser Tyr Val Ser Trp Phe Ala Tyr
1               5                   10

<210> SEQ ID NO 263
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#2 LCCDR1

<400> SEQUENCE: 263

Lys Ser Ser Gln Ser Leu Leu Asn Ser Arg Thr Arg Lys Asn Tyr Leu
1               5                   10                  15

Ala

<210> SEQ ID NO 264
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#2 LCCDR2

<400> SEQUENCE: 264

Trp Ala Ser Thr Arg Glu Ser
1               5

<210> SEQ ID NO 265
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#2 LCCDR3

<400> SEQUENCE: 265

Lys Gln Ser Phe Ile Leu Arg Thr
1               5

<210> SEQ ID NO 266
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#2 HCCDR1

<400> SEQUENCE: 266

Gly Tyr Ser Phe Thr Asp Tyr Tyr Val His
1               5                   10

<210> SEQ ID NO 267
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#2 HCCDR2

<400> SEQUENCE: 267

Trp Ile Tyr Pro Gly Asn Gly Asn Ile Lys Tyr Asn Glu Arg Phe Arg
1               5                   10                  15

Gly

<210> SEQ ID NO 268
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#2 HCCDR3

<400> SEQUENCE: 268

Asp Asn Tyr Ser Ala Tyr Tyr Phe Ala Tyr
1               5                   10

<210> SEQ ID NO 269
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CD3#3 LCCDR1

<400> SEQUENCE: 269

Lys Ser Ser Gln Ser Leu Leu Asn Ser Arg Thr Arg Lys Val Tyr Leu
1               5                   10                  15

Ala

<210> SEQ ID NO 270
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CD3#3 LCCDR2

<400> SEQUENCE: 270

Trp Ala Ser Thr Arg Glu Ser
1               5

<210> SEQ ID NO 271
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CD3#3 LCCDR3

<400> SEQUENCE: 271

Lys Gln Ser Phe Ile Leu Arg Thr
1               5

<210> SEQ ID NO 272
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CD3#3 HCCDR1

<400> SEQUENCE: 272

Gly Tyr Thr Phe Thr Ser Tyr Tyr Val His
1               5                   10

<210> SEQ ID NO 273
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CD3#3 HCCDR2

<400> SEQUENCE: 273

Trp Ile Tyr Pro Gly Gly Gly Asn Ile Lys Tyr Ala Gln Lys Phe Gln
1               5                   10                  15

Gly

<210> SEQ ID NO 274

<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CD3#3 HCCDR3

<400> SEQUENCE: 274

Asp Gln Tyr Ser Ala Tyr Tyr Phe Ala Tyr
1 5 10

<210> SEQ ID NO 275
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CD3#4 LCCDR1

<400> SEQUENCE: 275

Lys Ser Ser Gln Ser Leu Leu Asn Ser Arg Thr Arg Lys Val Tyr Leu
1 5 10 15

Ala

<210> SEQ ID NO 276
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CD3#4 LCCDR2

<400> SEQUENCE: 276

Trp Ala Ser Thr Arg Glu Ser
1 5

<210> SEQ ID NO 277
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CD3#4 LCCDR3

<400> SEQUENCE: 277

Lys Gln Ser Phe Ile Leu Arg Thr
1 5

<210> SEQ ID NO 278
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CD3#4 HCCDR1

<400> SEQUENCE: 278

Gly Tyr Ser Phe Thr Ser Tyr Tyr Val His
1 5 10

<210> SEQ ID NO 279
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CD3#4 HCCDR2

<400> SEQUENCE: 279

Trp Ile Tyr Pro Gly Gly Gly Asn Ile Lys Tyr Asn Gln Lys Phe Gln
1 5 10 15

Gly

<210> SEQ ID NO 280
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CD3#4 HCCDR3

<400> SEQUENCE: 280

Asp His Tyr Ser Ala Tyr Tyr Phe Ala Tyr
1 5 10

<210> SEQ ID NO 281
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CD3#5 LCCDR1

<400> SEQUENCE: 281

Lys Ser Ser Gln Ser Leu Leu Asn Ser Arg Thr Arg Lys Thr Tyr Leu
1 5 10 15

Ala

<210> SEQ ID NO 282
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CD3#5 LCCDR2

<400> SEQUENCE: 282

Trp Ala Ser Thr Arg Glu Ser
1 5

<210> SEQ ID NO 283
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CD3#5 LCCDR3

<400> SEQUENCE: 283

Lys Gln Ser Phe Ile Leu Arg Thr
1 5

<210> SEQ ID NO 284
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CD3#5 HCCDR1

<400> SEQUENCE: 284

Gly Tyr Thr Phe Thr Gly Tyr Tyr Val His
1 5 10

<210> SEQ ID NO 285
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CD3#5 HCCDR2

<400> SEQUENCE: 285

Trp Ile Tyr Pro Gly Gly Gly Ser Thr Lys Tyr Ala Gln Lys Phe Gln
1 5 10 15

Gly

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CD3#5 HCCDR3

<400> SEQUENCE: 286

Asp Gln Tyr Ser Ala Tyr Tyr Phe Ala Tyr
1 5 10

<210> SEQ ID NO 287
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CD3#6 LCCDR1

<400> SEQUENCE: 287

Lys Ser Ser Gln Ser Leu Leu Asn Ser Arg Thr Arg Lys Thr Tyr Leu
1 5 10 15

Ala

<210> SEQ ID NO 288
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#6 LCCDR2

<400> SEQUENCE: 288

Trp Ala Ser Thr Arg Glu Ser
1               5

<210> SEQ ID NO 289
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#6 LCCDR3

<400> SEQUENCE: 289

Lys Gln Ser Phe Ile Leu Arg Thr
1               5

<210> SEQ ID NO 290
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#6 HCCDR1

<400> SEQUENCE: 290

Gly Tyr Thr Phe Thr Ser Tyr Tyr Val His
1               5                   10

<210> SEQ ID NO 291
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#6 HCCDR2

<400> SEQUENCE: 291

Trp Ile Tyr Pro Gly Gly Gly Asn Ile Lys Tyr Ala Gln Lys Phe Gln
1               5                   10                  15

Gly

<210> SEQ ID NO 292
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD3#6 HCCDR3

<400> SEQUENCE: 292

Asp Gln Tyr Ser Ala Tyr Tyr Phe Ala Tyr
1               5                   10

<210> SEQ ID NO 293

<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD3#1 VL

<400> SEQUENCE: 293

```
Glu Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Leu Pro Arg Gly
        35                  40                  45

Leu Ile Gly Gly Thr Asn Lys Arg Ala Pro Trp Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 294
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD3#1 VH

<400> SEQUENCE: 294

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125
```

<210> SEQ ID NO 295
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD3#2 VL

<400> SEQUENCE: 295

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Leu Glu Ile Lys
            100                 105                 110
```

<210> SEQ ID NO 296
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CD3#2 VH

<400> SEQUENCE: 296

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Val His Trp Val Arg Gln Ala Pro Gly Gln Gly Leu Glu Trp Met
        35                  40                  45

Gly Trp Ile Tyr Pro Gly Asn Gly Asn Ile Lys Tyr Asn Glu Arg Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asn Tyr Ser Ala Tyr Tyr Phe Ala Tyr Trp Gly Gln Gly
            100                 105                 110

Thr Thr Val Thr Val Ser Ser
        115
```

<210> SEQ ID NO 297
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CD3#3 VL

<400> SEQUENCE: 297

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30
```

```
Arg Thr Arg Lys Val Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Leu Glu Ile Lys
            100                 105                 110


<210> SEQ ID NO 298
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD3#3 VH

<400> SEQUENCE: 298

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Val His Trp Val Arg Gln Ala Pro Gly Gln Gly Leu Glu Trp Ile
        35                  40                  45

Gly Trp Ile Tyr Pro Gly Gly Gly Asn Ile Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gln Tyr Ser Ala Tyr Tyr Phe Ala Tyr Trp Gly Gln Gly
            100                 105                 110

Thr Thr Val Thr Val Ser Ser
        115


<210> SEQ ID NO 299
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD3#4 VL

<400> SEQUENCE: 299

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Val Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
```

65 70 75 80

Ile Ser Ser Leu Gln Ala Glu Asp Val Ala Val Tyr Tyr Cys Lys Gln
85 90 95

Ser Phe Ile Leu Arg Thr Phe Gly Gln Gly Thr Lys Leu Glu Ile Lys
100 105 110

<210> SEQ ID NO 300
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CD3#4 VH

<400> SEQUENCE: 300

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Ser Tyr
20 25 30

Tyr Val His Trp Val Arg Gln Ala Pro Gly Gln Gly Leu Glu Trp Ile
35 40 45

Gly Trp Ile Tyr Pro Gly Gly Gly Asn Ile Lys Tyr Asn Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Asp His Tyr Ser Ala Tyr Tyr Phe Ala Tyr Trp Gly Gln Gly
100 105 110

Thr Thr Val Thr Val Ser Ser
115

<210> SEQ ID NO 301
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CD3#5 VL

<400> SEQUENCE: 301

Asp Ile Val Met Thr Gln Ser Pro Asp Ser Leu Ala Val Ser Leu Gly
1 5 10 15

Glu Arg Ala Thr Ile Ser Cys Lys Ser Ser Gln Ser Leu Leu Asn Ser
20 25 30

Arg Thr Arg Lys Thr Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Lys Gln
85 90 95

Ser Phe Ile Leu Arg Thr Phe Gly Gln Gly Thr Lys Leu Glu Ile Lys
100 105 110

<210> SEQ ID NO 302
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CD3#5 VH

<400> SEQUENCE: 302

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Val His Trp Val Arg Gln Ala Pro Gly Gln Gly Leu Glu Trp Met
        35                  40                  45

Gly Trp Ile Tyr Pro Gly Gly Gly Ser Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gln Tyr Ser Ala Tyr Tyr Phe Ala Tyr Trp Gly Gln Gly
            100                 105                 110

Thr Thr Val Thr Val Ser Ser
        115
```

<210> SEQ ID NO 303
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CD3#6 VL

<400> SEQUENCE: 303

```
Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Arg Thr Arg Lys Thr Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Leu Glu Ile Lys
            100                 105                 110
```

<210> SEQ ID NO 304
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<220> FEATURE:
<223> OTHER INFORMATION: CD3#6 VH

<400> SEQUENCE: 304

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Val His Trp Val Arg Gln Ala Pro Gly Gln Gly Leu Glu Trp Ile
35 40 45

Gly Trp Ile Tyr Pro Gly Gly Gly Asn Ile Lys Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Asp Gln Tyr Ser Ala Tyr Tyr Phe Ala Tyr Trp Gly Gln Gly
100 105 110

Thr Thr Val Thr Val Ser Ser
115

<210> SEQ ID NO 305
<211> LENGTH: 481
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CD3#1 scFab

<400> SEQUENCE: 305

Glu Ala Val Val Thr Gln Glu Pro Ser Leu Thr Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Glu Lys Pro Gly Gln Leu Pro Arg Gly
35 40 45

Leu Ile Gly Gly Thr Asn Lys Arg Ala Pro Trp Val Pro Ala Arg Phe
50 55 60

Ser Gly Ser Leu Leu Gly Gly Lys Ala Ala Leu Thr Leu Ser Gly Ala
65 70 75 80

Gln Pro Glu Asp Glu Ala Glu Tyr Phe Cys Ala Leu Trp Tyr Ser Asn
85 90 95

Leu Trp Val Phe Gly Gly Gly Thr Lys Leu Thr Val Leu Gly Gln Pro
100 105 110

Lys Ala Ala Pro Ser Val Thr Leu Phe Pro Pro Ser Ser Glu Glu Leu
115 120 125

Gln Ala Asn Lys Ala Thr Leu Val Cys Leu Ile Ser Asp Phe Tyr Pro
130 135 140

Gly Ala Val Lys Val Ala Trp Lys Ala Asp Gly Ser Pro Val Asn Thr
145 150 155 160

Gly Val Glu Thr Thr Thr Pro Ser Lys Gln Ser Asn Asn Lys Tyr Ala
165 170 175

Ala Ser Ser Tyr Leu Ser Leu Thr Pro Glu Gln Trp Lys Ser His Arg
180 185 190

Ser Tyr Ser Cys Gln Val Thr His Glu Gly Ser Thr Val Glu Lys Thr

```
        195                 200                 205

Val Ala Pro Ala Glu Cys Ser Gly Gly Gly Gly Ser Glu Gly Lys Ser
    210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Gly Ser Glu Val Gln
                245                 250                 255

Leu Val Glu Ser Gly Gly Gly Leu Val Gln Pro Gly Gly Ser Leu Lys
            260                 265                 270

Leu Ser Cys Ala Ala Ser Gly Phe Thr Phe Asn Thr Tyr Ala Met Asn
        275                 280                 285

Trp Val Arg Gln Ala Pro Gly Lys Gly Leu Glu Trp Val Ala Arg Ile
    290                 295                 300

Arg Ser Lys Tyr Asn Asn Tyr Ala Thr Tyr Tyr Ala Asp Ser Val Lys
305                 310                 315                 320

Asp Arg Phe Thr Ile Ser Arg Asp Asp Ser Lys Asn Thr Ala Tyr Leu
                325                 330                 335

Gln Met Asn Asn Leu Lys Thr Glu Asp Thr Ala Val Tyr Tyr Cys Val
            340                 345                 350

Arg His Gly Asn Phe Gly Asn Ser Tyr Val Ser Trp Phe Ala Tyr Trp
        355                 360                 365

Gly Gln Gly Thr Leu Val Thr Val Ser Ala Ala Ser Thr Lys Gly Pro
    370                 375                 380

Ser Val Phe Pro Leu Ala Pro Ser Ser Lys Ser Thr Ser Gly Gly Thr
385                 390                 395                 400

Ala Ala Leu Gly Cys Leu Val Lys Asp Tyr Phe Pro Glu Pro Val Thr
                405                 410                 415

Val Ser Trp Asn Ser Gly Ala Leu Thr Ser Gly Val His Thr Phe Pro
            420                 425                 430

Ala Val Leu Gln Ser Ser Gly Leu Tyr Ser Leu Ser Ser Val Val Thr
        435                 440                 445

Val Pro Ser Ser Ser Leu Gly Thr Gln Thr Tyr Ile Cys Asn Val Asn
    450                 455                 460

His Lys Pro Ser Asn Thr Lys Val Asp Lys Arg Val Glu Pro Lys Ser
465                 470                 475                 480

Cys


<210> SEQ ID NO 306
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD3#2 scFab

<400> SEQUENCE: 306

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60
```

```
Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Glu Gly Lys Ser Ser Gly Ser Gly Ser Glu Ser Lys Ser Thr Glu Gly
225                 230                 235                 240

Lys Ser Ser Gly Ser Gly Ser Glu Ser Lys Ser Thr Gly Gly Gly Gly
                245                 250                 255

Ser Gln Val Gln Leu Val Gln Ser Gly Ala Glu Val Lys Lys Pro Gly
            260                 265                 270

Ala Ser Val Lys Val Ser Cys Lys Ala Ser Gly Tyr Ser Phe Thr Asp
        275                 280                 285

Tyr Tyr Val His Trp Val Arg Gln Ala Pro Gly Gln Gly Leu Glu Trp
    290                 295                 300

Met Gly Trp Ile Tyr Pro Gly Asn Gly Asn Ile Lys Tyr Asn Glu Arg
305                 310                 315                 320

Phe Arg Gly Arg Val Thr Met Thr Arg Asp Thr Ser Thr Ser Thr Val
                325                 330                 335

Tyr Met Glu Leu Ser Ser Leu Arg Ser Glu Asp Thr Ala Val Tyr Tyr
            340                 345                 350

Cys Ala Arg Asp Asn Tyr Ser Ala Tyr Tyr Phe Ala Tyr Trp Gly Gln
        355                 360                 365

Gly Thr Thr Val Thr Val Ser Ser Ala Ser Thr Lys Gly Pro Ser Val
    370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
        435                 440                 445

Ser Ser Ser Leu Gly Thr Gln Thr Tyr Ile Cys Asn Val Asn His Lys
    450                 455                 460

Pro Ser Asn Thr Lys Val Asp Lys Arg Val Glu Pro Lys Ser Cys
465                 470                 475
```

<210> SEQ ID NO 307
<211> LENGTH: 479
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CD3#3 scFab

<400> SEQUENCE: 307

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Val Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Glu Gly Lys Ser Ser Gly Ser Gly Ser Glu Ser Lys Ser Thr Glu Gly
225                 230                 235                 240

Lys Ser Ser Gly Ser Gly Ser Glu Ser Lys Ser Thr Gly Gly Gly Gly
                245                 250                 255

Ser Gln Val Gln Leu Val Gln Ser Gly Ala Glu Val Lys Lys Pro Gly
            260                 265                 270

Ala Ser Val Lys Val Ser Cys Lys Ala Ser Gly Tyr Thr Phe Thr Ser
        275                 280                 285

Tyr Tyr Val His Trp Val Arg Gln Ala Pro Gly Gln Gly Leu Glu Trp
    290                 295                 300

Ile Gly Trp Ile Tyr Pro Gly Gly Gly Asn Ile Lys Tyr Ala Gln Lys
305                 310                 315                 320

Phe Gln Gly Arg Val Thr Met Thr Arg Asp Thr Ser Thr Ser Thr Val
                325                 330                 335

Tyr Met Glu Leu Ser Ser Leu Arg Ser Glu Asp Thr Ala Val Tyr Tyr
            340                 345                 350
```

```
Cys Ala Arg Asp Gln Tyr Ser Ala Tyr Tyr Phe Ala Tyr Trp Gly Gln
        355                 360                 365

Gly Thr Thr Val Thr Val Ser Ser Ala Ser Thr Lys Gly Pro Ser Val
    370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
        435                 440                 445

Ser Ser Ser Leu Gly Thr Gln Thr Tyr Ile Cys Asn Val Asn His Lys
    450                 455                 460

Pro Ser Asn Thr Lys Val Asp Lys Arg Val Glu Pro Lys Ser Cys
465                 470                 475


<210> SEQ ID NO 308
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD3#4 scFab

<400> SEQUENCE: 308

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Val Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220
```

```
Glu Gly Lys Ser Ser Gly Ser Gly Ser Glu Ser Lys Ser Thr Glu Gly
225                 230                 235                 240

Lys Ser Ser Gly Ser Gly Ser Glu Ser Lys Ser Thr Gly Gly Gly Gly
                245                 250                 255

Ser Gln Val Gln Leu Val Gln Ser Gly Ala Glu Val Lys Lys Pro Gly
            260                 265                 270

Ala Ser Val Lys Val Ser Cys Lys Ala Ser Gly Tyr Ser Phe Thr Ser
        275                 280                 285

Tyr Tyr Val His Trp Val Arg Gln Ala Pro Gly Gln Gly Leu Glu Trp
    290                 295                 300

Ile Gly Trp Ile Tyr Pro Gly Gly Gly Asn Ile Lys Tyr Asn Gln Lys
305                 310                 315                 320

Phe Gln Gly Arg Val Thr Met Thr Arg Asp Thr Ser Thr Ser Thr Val
                325                 330                 335

Tyr Met Glu Leu Ser Ser Leu Arg Ser Glu Asp Thr Ala Val Tyr Tyr
            340                 345                 350

Cys Ala Arg Asp His Tyr Ser Ala Tyr Tyr Phe Ala Tyr Trp Gly Gln
        355                 360                 365

Gly Thr Thr Val Thr Val Ser Ser Ala Ser Thr Lys Gly Pro Ser Val
    370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
        435                 440                 445

Ser Ser Ser Leu Gly Thr Gln Thr Tyr Ile Cys Asn Val Asn His Lys
    450                 455                 460

Pro Ser Asn Thr Lys Val Asp Lys Arg Val Glu Pro Lys Ser Cys
465                 470                 475
```

<210> SEQ ID NO 309
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD3#5 scFab

<400> SEQUENCE: 309

```
Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Arg Thr Arg Lys Thr Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95
```

-continued

```
Ser Phe Ile Leu Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Glu Gly Lys Ser Ser Gly Ser Gly Ser Glu Ser Lys Ser Thr Glu Gly
225                 230                 235                 240

Lys Ser Ser Gly Ser Gly Ser Glu Ser Lys Ser Thr Gly Gly Gly Gly
                245                 250                 255

Ser Gln Val Gln Leu Val Gln Ser Gly Ala Glu Val Lys Lys Pro Gly
            260                 265                 270

Ala Ser Val Lys Val Ser Cys Lys Ala Ser Gly Tyr Thr Phe Thr Gly
        275                 280                 285

Tyr Tyr Val His Trp Val Arg Gln Ala Pro Gly Gln Gly Leu Glu Trp
    290                 295                 300

Met Gly Trp Ile Tyr Pro Gly Gly Gly Ser Thr Lys Tyr Ala Gln Lys
305                 310                 315                 320

Phe Gln Gly Arg Val Thr Met Thr Arg Asp Thr Ser Thr Ser Thr Val
                325                 330                 335

Tyr Met Glu Leu Ser Ser Leu Arg Ser Glu Asp Thr Ala Val Tyr Tyr
            340                 345                 350

Cys Ala Arg Asp Gln Tyr Ser Ala Tyr Tyr Phe Ala Tyr Trp Gly Gln
        355                 360                 365

Gly Thr Thr Val Thr Val Ser Ser Ala Ser Thr Lys Gly Pro Ser Val
    370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
        435                 440                 445

Ser Ser Ser Leu Gly Thr Gln Thr Tyr Ile Cys Asn Val Asn His Lys
    450                 455                 460

Pro Ser Asn Thr Lys Val Asp Lys Arg Val Glu Pro Lys Ser Cys
465                 470                 475
```

<210> SEQ ID NO 310
<211> LENGTH: 479
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CD3#6 scFab

<400> SEQUENCE: 310

Asp Ile Val Met Thr Gln Ser Pro Asp Ser Leu Ala Val Ser Leu Gly
1 5 10 15

Glu Arg Ala Thr Ile Ser Cys Lys Ser Ser Gln Ser Leu Leu Asn Ser
20 25 30

Arg Thr Arg Lys Thr Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Lys Gln
85 90 95

Ser Phe Ile Leu Arg Thr Phe Gly Gln Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys Gly Gly Gly Gly Ser
210 215 220

Glu Gly Lys Ser Ser Gly Ser Gly Ser Glu Ser Lys Ser Thr Glu Gly
225 230 235 240

Lys Ser Ser Gly Ser Gly Ser Glu Ser Lys Ser Thr Gly Gly Gly Gly
245 250 255

Ser Gln Val Gln Leu Val Gln Ser Gly Ala Glu Val Lys Lys Pro Gly
260 265 270

Ala Ser Val Lys Val Ser Cys Lys Ala Ser Gly Tyr Thr Phe Thr Ser
275 280 285

Tyr Tyr Val His Trp Val Arg Gln Ala Pro Gly Gln Gly Leu Glu Trp
290 295 300

Ile Gly Trp Ile Tyr Pro Gly Gly Gly Asn Ile Lys Tyr Ala Gln Lys
305 310 315 320

Phe Gln Gly Arg Val Thr Met Thr Arg Asp Thr Ser Thr Ser Thr Val
325 330 335

Tyr Met Glu Leu Ser Ser Leu Arg Ser Glu Asp Thr Ala Val Tyr Tyr
340 345 350

Cys Ala Arg Asp Gln Tyr Ser Ala Tyr Tyr Phe Ala Tyr Trp Gly Gln
355 360 365

Gly Thr Thr Val Thr Val Ser Ser Ala Ser Thr Lys Gly Pro Ser Val
370 375 380

Phe Pro Leu Ala Pro Ser Ser Lys Ser Thr Ser Gly Gly Thr Ala Ala

```
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
        435                 440                 445

Ser Ser Ser Leu Gly Thr Gln Thr Tyr Ile Cys Asn Val Asn His Lys
    450                 455                 460

Pro Ser Asn Thr Lys Val Asp Lys Arg Val Glu Pro Lys Ser Cys
465                 470                 475


<210> SEQ ID NO 311
<211> LENGTH: 707
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD3#1 chain

<400> SEQUENCE: 311

Glu Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Leu Pro Arg Gly
        35                  40                  45

Leu Ile Gly Gly Thr Asn Lys Arg Ala Pro Trp Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Lys Val Ala Trp Lys Ala Asp Gly Ser Pro Val Asn Thr
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Ala Glu Cys Ser Gly Gly Gly Gly Ser Glu Gly Lys Ser
    210                 215                 220

Ser Gly Ser Gly Ser Glu Ser Lys Ser Thr Glu Gly Lys Ser Ser Gly
225                 230                 235                 240

Ser Gly Ser Glu Ser Lys Ser Thr Gly Gly Gly Gly Ser Glu Val Gln
                245                 250                 255

Leu Val Glu Ser Gly Gly Gly Leu Val Gln Pro Gly Gly Ser Leu Lys
```

```
        260                 265                 270

Leu Ser Cys Ala Ala Ser Gly Phe Thr Phe Asn Thr Tyr Ala Met Asn
    275                 280                 285

Trp Val Arg Gln Ala Pro Gly Lys Gly Leu Glu Trp Val Ala Arg Ile
    290                 295                 300

Arg Ser Lys Tyr Asn Asn Tyr Ala Thr Tyr Tyr Ala Asp Ser Val Lys
305                 310                 315                 320

Asp Arg Phe Thr Ile Ser Arg Asp Asp Ser Lys Asn Thr Ala Tyr Leu
                325                 330                 335

Gln Met Asn Asn Leu Lys Thr Glu Asp Thr Ala Val Tyr Tyr Cys Val
            340                 345                 350

Arg His Gly Asn Phe Gly Asn Ser Tyr Val Ser Trp Phe Ala Tyr Trp
        355                 360                 365

Gly Gln Gly Thr Leu Val Thr Val Ser Ala Ala Ser Thr Lys Gly Pro
    370                 375                 380

Ser Val Phe Pro Leu Ala Pro Ser Ser Lys Ser Thr Ser Gly Gly Thr
385                 390                 395                 400

Ala Ala Leu Gly Cys Leu Val Lys Asp Tyr Phe Pro Glu Pro Val Thr
                405                 410                 415

Val Ser Trp Asn Ser Gly Ala Leu Thr Ser Gly Val His Thr Phe Pro
            420                 425                 430

Ala Val Leu Gln Ser Ser Gly Leu Tyr Ser Leu Ser Ser Val Val Thr
        435                 440                 445

Val Pro Ser Ser Ser Leu Gly Thr Gln Thr Tyr Ile Cys Asn Val Asn
    450                 455                 460

His Lys Pro Ser Asn Thr Lys Val Asp Lys Arg Val Glu Pro Lys Ser
465                 470                 475                 480

Cys Asp Lys Thr His Thr Cys Pro Pro Cys Pro Ala Pro Glu Ala Ala
                485                 490                 495

Gly Gly Pro Ser Val Phe Leu Phe Pro Pro Lys Pro Lys Asp Thr Leu
            500                 505                 510

Met Ile Ser Arg Thr Pro Glu Val Thr Cys Val Val Val Asp Val Ser
        515                 520                 525

His Glu Asp Pro Glu Val Lys Phe Asn Trp Tyr Val Asp Gly Val Glu
    530                 535                 540

Val His Asn Ala Lys Thr Lys Pro Arg Glu Glu Gln Tyr Asn Ser Thr
545                 550                 555                 560

Tyr Arg Val Val Ser Val Leu Thr Val Leu His Gln Asp Trp Leu Asn
                565                 570                 575

Gly Lys Glu Tyr Lys Cys Lys Val Ser Asn Lys Ala Leu Pro Ala Pro
            580                 585                 590

Ile Glu Lys Thr Ile Ser Lys Ala Lys Gly Gln Pro Arg Glu Pro Gln
        595                 600                 605

Val Tyr Thr Leu Pro Pro Ser Arg Glu Glu Met Thr Lys Asn Gln Val
    610                 615                 620

Ser Leu Ser Cys Ala Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
                645                 650                 655

Pro Val Leu Asp Ser Asp Gly Ser Phe Phe Leu Val Ser Lys Leu Thr
            660                 665                 670

Val Asp Lys Ser Arg Trp Gln Gln Gly Asn Val Phe Ser Cys Ser Val
        675                 680                 685
```

```
Met His Glu Ala Leu His Asn Arg Phe Thr Gln Lys Ser Leu Ser Leu
    690                 695                 700

Ser Pro Gly
705


<210> SEQ ID NO 312
<211> LENGTH: 705
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD3#2 chain

<400> SEQUENCE: 312

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Glu Gly Lys Ser Ser Gly Ser Gly Ser Glu Ser Lys Ser Thr Glu Gly
225                 230                 235                 240

Lys Ser Ser Gly Ser Gly Ser Glu Ser Lys Ser Thr Gly Gly Gly Gly
                245                 250                 255

Ser Gln Val Gln Leu Val Gln Ser Gly Ala Glu Val Lys Lys Pro Gly
            260                 265                 270

Ala Ser Val Lys Val Ser Cys Lys Ala Ser Gly Tyr Ser Phe Thr Asp
        275                 280                 285

Tyr Tyr Val His Trp Val Arg Gln Ala Pro Gly Gln Gly Leu Glu Trp
    290                 295                 300

Met Gly Trp Ile Tyr Pro Gly Asn Gly Asn Ile Lys Tyr Asn Glu Arg
305                 310                 315                 320
```

```
Phe Arg Gly Arg Val Thr Met Thr Arg Asp Thr Ser Thr Ser Thr Val
                325                 330                 335

Tyr Met Glu Leu Ser Ser Leu Arg Ser Glu Asp Thr Ala Val Tyr Tyr
            340                 345                 350

Cys Ala Arg Asp Asn Tyr Ser Ala Tyr Tyr Phe Ala Tyr Trp Gly Gln
        355                 360                 365

Gly Thr Thr Val Thr Val Ser Ser Ala Ser Thr Lys Gly Pro Ser Val
    370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
        435                 440                 445

Ser Ser Ser Leu Gly Thr Gln Thr Tyr Ile Cys Asn Val Asn His Lys
    450                 455                 460

Pro Ser Asn Thr Lys Val Asp Lys Arg Val Glu Pro Lys Ser Cys Asp
465                 470                 475                 480

Lys Thr His Thr Cys Pro Pro Cys Pro Ala Pro Glu Ala Ala Gly Gly
                485                 490                 495

Pro Ser Val Phe Leu Phe Pro Pro Lys Pro Lys Asp Thr Leu Met Ile
            500                 505                 510

Ser Arg Thr Pro Glu Val Thr Cys Val Val Val Asp Val Ser His Glu
        515                 520                 525

Asp Pro Glu Val Lys Phe Asn Trp Tyr Val Asp Gly Val Glu Val His
    530                 535                 540

Asn Ala Lys Thr Lys Pro Arg Glu Glu Gln Tyr Asn Ser Thr Tyr Arg
545                 550                 555                 560

Val Val Ser Val Leu Thr Val Leu His Gln Asp Trp Leu Asn Gly Lys
                565                 570                 575

Glu Tyr Lys Cys Lys Val Ser Asn Lys Ala Leu Pro Ala Pro Ile Glu
            580                 585                 590

Lys Thr Ile Ser Lys Ala Lys Gly Gln Pro Arg Glu Pro Gln Val Tyr
        595                 600                 605

Thr Leu Pro Pro Ser Arg Glu Glu Met Thr Lys Asn Gln Val Ser Leu
    610                 615                 620

Ser Cys Ala Val Lys Gly Phe Tyr Pro Ser Asp Ile Ala Val Glu Trp
625                 630                 635                 640

Glu Ser Asn Gly Gln Pro Glu Asn Asn Tyr Lys Thr Thr Pro Pro Val
                645                 650                 655

Leu Asp Ser Asp Gly Ser Phe Phe Leu Val Ser Lys Leu Thr Val Asp
            660                 665                 670

Lys Ser Arg Trp Gln Gln Gly Asn Val Phe Ser Cys Ser Val Met His
        675                 680                 685

Glu Ala Leu His Asn Arg Phe Thr Gln Lys Ser Leu Ser Leu Ser Pro
    690                 695                 700

Gly
705

<210> SEQ ID NO 313
<211> LENGTH: 705
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD3#3 chain

<400> SEQUENCE: 313

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Val Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Glu Gly Lys Ser Ser Gly Ser Gly Ser Glu Ser Lys Ser Thr Glu Gly
225                 230                 235                 240

Lys Ser Ser Gly Ser Gly Ser Glu Ser Lys Ser Thr Gly Gly Gly Gly
                245                 250                 255

Ser Gln Val Gln Leu Val Gln Ser Gly Ala Glu Val Lys Lys Pro Gly
            260                 265                 270

Ala Ser Val Lys Val Ser Cys Lys Ala Ser Gly Tyr Thr Phe Thr Ser
        275                 280                 285

Tyr Tyr Val His Trp Val Arg Gln Ala Pro Gly Gln Gly Leu Glu Trp
    290                 295                 300

Ile Gly Trp Ile Tyr Pro Gly Gly Gly Asn Ile Lys Tyr Ala Gln Lys
305                 310                 315                 320

Phe Gln Gly Arg Val Thr Met Thr Arg Asp Thr Ser Thr Ser Thr Val
                325                 330                 335

Tyr Met Glu Leu Ser Ser Leu Arg Ser Glu Asp Thr Ala Val Tyr Tyr
            340                 345                 350

Cys Ala Arg Asp Gln Tyr Ser Ala Tyr Tyr Phe Ala Tyr Trp Gly Gln
        355                 360                 365
```

```
Gly Thr Thr Val Thr Val Ser Ser Ala Ser Thr Lys Gly Pro Ser Val
    370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
        435                 440                 445

Ser Ser Ser Leu Gly Thr Gln Thr Tyr Ile Cys Asn Val Asn His Lys
    450                 455                 460

Pro Ser Asn Thr Lys Val Asp Lys Arg Val Glu Pro Lys Ser Cys Asp
465                 470                 475                 480

Lys Thr His Thr Cys Pro Pro Cys Pro Ala Pro Glu Ala Ala Gly Gly
                485                 490                 495

Pro Ser Val Phe Leu Phe Pro Pro Lys Pro Lys Asp Thr Leu Met Ile
            500                 505                 510

Ser Arg Thr Pro Glu Val Thr Cys Val Val Val Asp Val Ser His Glu
        515                 520                 525

Asp Pro Glu Val Lys Phe Asn Trp Tyr Val Asp Gly Val Glu Val His
    530                 535                 540

Asn Ala Lys Thr Lys Pro Arg Glu Glu Gln Tyr Asn Ser Thr Tyr Arg
545                 550                 555                 560

Val Val Ser Val Leu Thr Val Leu His Gln Asp Trp Leu Asn Gly Lys
                565                 570                 575

Glu Tyr Lys Cys Lys Val Ser Asn Lys Ala Leu Pro Ala Pro Ile Glu
            580                 585                 590

Lys Thr Ile Ser Lys Ala Lys Gly Gln Pro Arg Glu Pro Gln Val Tyr
        595                 600                 605

Thr Leu Pro Pro Ser Arg Glu Glu Met Thr Lys Asn Gln Val Ser Leu
    610                 615                 620

Ser Cys Ala Val Lys Gly Phe Tyr Pro Ser Asp Ile Ala Val Glu Trp
625                 630                 635                 640

Glu Ser Asn Gly Gln Pro Glu Asn Asn Tyr Lys Thr Thr Pro Pro Val
                645                 650                 655

Leu Asp Ser Asp Gly Ser Phe Phe Leu Val Ser Lys Leu Thr Val Asp
            660                 665                 670

Lys Ser Arg Trp Gln Gln Gly Asn Val Phe Ser Cys Ser Val Met His
        675                 680                 685

Glu Ala Leu His Asn Arg Phe Thr Gln Lys Ser Leu Ser Leu Ser Pro
    690                 695                 700

Gly
705
```

<210> SEQ ID NO 314
<211> LENGTH: 705
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CD3#4 chain

<400> SEQUENCE: 314

-continued

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Val Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Glu Gly Lys Ser Ser Gly Ser Gly Ser Glu Ser Lys Ser Thr Glu Gly
225                 230                 235                 240

Lys Ser Ser Gly Ser Gly Ser Glu Ser Lys Ser Thr Gly Gly Gly Gly
                245                 250                 255

Ser Gln Val Gln Leu Val Gln Ser Gly Ala Glu Val Lys Lys Pro Gly
            260                 265                 270

Ala Ser Val Lys Val Ser Cys Lys Ala Ser Gly Tyr Ser Phe Thr Ser
        275                 280                 285

Tyr Tyr Val His Trp Val Arg Gln Ala Pro Gly Gln Gly Leu Glu Trp
    290                 295                 300

Ile Gly Trp Ile Tyr Pro Gly Gly Gly Asn Ile Lys Tyr Asn Gln Lys
305                 310                 315                 320

Phe Gln Gly Arg Val Thr Met Thr Arg Asp Thr Ser Thr Ser Thr Val
                325                 330                 335

Tyr Met Glu Leu Ser Ser Leu Arg Ser Glu Asp Thr Ala Val Tyr Tyr
            340                 345                 350

Cys Ala Arg Asp His Tyr Ser Ala Tyr Tyr Phe Ala Tyr Trp Gly Gln
        355                 360                 365

Gly Thr Thr Val Thr Val Ser Ser Ala Ser Thr Lys Gly Pro Ser Val
    370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
```

```
            420                 425                 430

Leu Gln Ser Ser Gly Leu Tyr Ser Leu Ser Ser Val Val Thr Val Pro
        435                 440                 445

Ser Ser Ser Leu Gly Thr Gln Thr Tyr Ile Cys Asn Val Asn His Lys
    450                 455                 460

Pro Ser Asn Thr Lys Val Asp Lys Arg Val Glu Pro Lys Ser Cys Asp
465                 470                 475                 480

Lys Thr His Thr Cys Pro Pro Cys Pro Ala Pro Glu Ala Ala Gly Gly
                485                 490                 495

Pro Ser Val Phe Leu Phe Pro Pro Lys Pro Lys Asp Thr Leu Met Ile
            500                 505                 510

Ser Arg Thr Pro Glu Val Thr Cys Val Val Val Asp Val Ser His Glu
        515                 520                 525

Asp Pro Glu Val Lys Phe Asn Trp Tyr Val Asp Gly Val Glu Val His
    530                 535                 540

Asn Ala Lys Thr Lys Pro Arg Glu Glu Gln Tyr Asn Ser Thr Tyr Arg
545                 550                 555                 560

Val Val Ser Val Leu Thr Val Leu His Gln Asp Trp Leu Asn Gly Lys
                565                 570                 575

Glu Tyr Lys Cys Lys Val Ser Asn Lys Ala Leu Pro Ala Pro Ile Glu
            580                 585                 590

Lys Thr Ile Ser Lys Ala Lys Gly Gln Pro Arg Glu Pro Gln Val Tyr
        595                 600                 605

Thr Leu Pro Pro Ser Arg Glu Glu Met Thr Lys Asn Gln Val Ser Leu
    610                 615                 620

Ser Cys Ala Val Lys Gly Phe Tyr Pro Ser Asp Ile Ala Val Glu Trp
625                 630                 635                 640

Glu Ser Asn Gly Gln Pro Glu Asn Asn Tyr Lys Thr Thr Pro Pro Val
                645                 650                 655

Leu Asp Ser Asp Gly Ser Phe Phe Leu Val Ser Lys Leu Thr Val Asp
            660                 665                 670

Lys Ser Arg Trp Gln Gln Gly Asn Val Phe Ser Cys Ser Val Met His
        675                 680                 685

Glu Ala Leu His Asn Arg Phe Thr Gln Lys Ser Leu Ser Leu Ser Pro
    690                 695                 700

Gly
705


<210> SEQ ID NO 315
<211> LENGTH: 705
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD3#5 chain

<400> SEQUENCE: 315

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Arg Thr Arg Lys Thr Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
```

```
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Glu Gly Lys Ser Ser Gly Ser Gly Ser Glu Ser Lys Ser Thr Glu Gly
225                 230                 235                 240

Lys Ser Ser Gly Ser Gly Ser Glu Ser Lys Ser Thr Gly Gly Gly Gly
                245                 250                 255

Ser Gln Val Gln Leu Val Gln Ser Gly Ala Glu Val Lys Lys Pro Gly
            260                 265                 270

Ala Ser Val Lys Val Ser Cys Lys Ala Ser Gly Tyr Thr Phe Thr Gly
        275                 280                 285

Tyr Tyr Val His Trp Val Arg Gln Ala Pro Gly Gln Gly Leu Glu Trp
    290                 295                 300

Met Gly Trp Ile Tyr Pro Gly Gly Gly Ser Thr Lys Tyr Ala Gln Lys
305                 310                 315                 320

Phe Gln Gly Arg Val Thr Met Thr Arg Asp Thr Ser Thr Ser Thr Val
                325                 330                 335

Tyr Met Glu Leu Ser Ser Leu Arg Ser Glu Asp Thr Ala Val Tyr Tyr
            340                 345                 350

Cys Ala Arg Asp Gln Tyr Ser Ala Tyr Tyr Phe Ala Tyr Trp Gly Gln
        355                 360                 365

Gly Thr Thr Val Thr Val Ser Ser Ala Ser Thr Lys Gly Pro Ser Val
    370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
        435                 440                 445

Ser Ser Ser Leu Gly Thr Gln Thr Tyr Ile Cys Asn Val Asn His Lys
    450                 455                 460

Pro Ser Asn Thr Lys Val Asp Lys Arg Val Glu Pro Lys Ser Cys Asp
465                 470                 475                 480
```

```
Lys Thr His Thr Cys Pro Pro Cys Pro Ala Pro Glu Ala Ala Gly Gly
                485                 490                 495

Pro Ser Val Phe Leu Phe Pro Pro Lys Pro Lys Asp Thr Leu Met Ile
            500                 505                 510

Ser Arg Thr Pro Glu Val Thr Cys Val Val Val Asp Val Ser His Glu
        515                 520                 525

Asp Pro Glu Val Lys Phe Asn Trp Tyr Val Asp Gly Val Glu Val His
    530                 535                 540

Asn Ala Lys Thr Lys Pro Arg Glu Glu Gln Tyr Asn Ser Thr Tyr Arg
545                 550                 555                 560

Val Val Ser Val Leu Thr Val Leu His Gln Asp Trp Leu Asn Gly Lys
                565                 570                 575

Glu Tyr Lys Cys Lys Val Ser Asn Lys Ala Leu Pro Ala Pro Ile Glu
            580                 585                 590

Lys Thr Ile Ser Lys Ala Lys Gly Gln Pro Arg Glu Pro Gln Val Tyr
        595                 600                 605

Thr Leu Pro Pro Ser Arg Glu Glu Met Thr Lys Asn Gln Val Ser Leu
    610                 615                 620

Ser Cys Ala Val Lys Gly Phe Tyr Pro Ser Asp Ile Ala Val Glu Trp
625                 630                 635                 640

Glu Ser Asn Gly Gln Pro Glu Asn Asn Tyr Lys Thr Thr Pro Pro Val
                645                 650                 655

Leu Asp Ser Asp Gly Ser Phe Phe Leu Val Ser Lys Leu Thr Val Asp
            660                 665                 670

Lys Ser Arg Trp Gln Gln Gly Asn Val Phe Ser Cys Ser Val Met His
        675                 680                 685

Glu Ala Leu His Asn Arg Phe Thr Gln Lys Ser Leu Ser Leu Ser Pro
    690                 695                 700

Gly
705


<210> SEQ ID NO 316
<211> LENGTH: 705
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD3#6 chain

<400> SEQUENCE: 316

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Arg Thr Arg Lys Thr Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Leu Glu Ile Lys
            100                 105                 110
```

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Glu Gly Lys Ser Ser Gly Ser Gly Ser Glu Ser Lys Ser Thr Glu Gly
225                 230                 235                 240

Lys Ser Ser Gly Ser Gly Ser Glu Ser Lys Ser Thr Gly Gly Gly Gly
                245                 250                 255

Ser Gln Val Gln Leu Val Gln Ser Gly Ala Glu Val Lys Lys Pro Gly
            260                 265                 270

Ala Ser Val Lys Val Ser Cys Lys Ala Ser Gly Tyr Thr Phe Thr Ser
        275                 280                 285

Tyr Tyr Val His Trp Val Arg Gln Ala Pro Gly Gln Gly Leu Glu Trp
    290                 295                 300

Ile Gly Trp Ile Tyr Pro Gly Gly Gly Asn Ile Lys Tyr Ala Gln Lys
305                 310                 315                 320

Phe Gln Gly Arg Val Thr Met Thr Arg Asp Thr Ser Thr Ser Thr Val
                325                 330                 335

Tyr Met Glu Leu Ser Ser Leu Arg Ser Glu Asp Thr Ala Val Tyr Tyr
            340                 345                 350

Cys Ala Arg Asp Gln Tyr Ser Ala Tyr Tyr Phe Ala Tyr Trp Gly Gln
        355                 360                 365

Gly Thr Thr Val Thr Val Ser Ser Ala Ser Thr Lys Gly Pro Ser Val
    370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
        435                 440                 445

Ser Ser Ser Leu Gly Thr Gln Thr Tyr Ile Cys Asn Val Asn His Lys
    450                 455                 460

Pro Ser Asn Thr Lys Val Asp Lys Arg Val Glu Pro Lys Ser Cys Asp
465                 470                 475                 480

Lys Thr His Thr Cys Pro Pro Cys Pro Ala Pro Glu Ala Ala Gly Gly
                485                 490                 495

Pro Ser Val Phe Leu Phe Pro Pro Lys Pro Lys Asp Thr Leu Met Ile
            500                 505                 510

Ser Arg Thr Pro Glu Val Thr Cys Val Val Val Asp Val Ser His Glu
        515                 520                 525
```

Asp Pro Glu Val Lys Phe Asn Trp Tyr Val Asp Gly Val Glu Val His
    530                 535                 540

Asn Ala Lys Thr Lys Pro Arg Glu Glu Gln Tyr Asn Ser Thr Tyr Arg
545                 550                 555                 560

Val Val Ser Val Leu Thr Val Leu His Gln Asp Trp Leu Asn Gly Lys
                565                 570                 575

Glu Tyr Lys Cys Lys Val Ser Asn Lys Ala Leu Pro Ala Pro Ile Glu
            580                 585                 590

Lys Thr Ile Ser Lys Ala Lys Gly Gln Pro Arg Glu Pro Gln Val Tyr
        595                 600                 605

Thr Leu Pro Pro Ser Arg Glu Glu Met Thr Lys Asn Gln Val Ser Leu
    610                 615                 620

Ser Cys Ala Val Lys Gly Phe Tyr Pro Ser Asp Ile Ala Val Glu Trp
625                 630                 635                 640

Glu Ser Asn Gly Gln Pro Glu Asn Asn Tyr Lys Thr Thr Pro Pro Val
                645                 650                 655

Leu Asp Ser Asp Gly Ser Phe Phe Leu Val Ser Lys Leu Thr Val Asp
            660                 665                 670

Lys Ser Arg Trp Gln Gln Gly Asn Val Phe Ser Cys Ser Val Met His
        675                 680                 685

Glu Ala Leu His Asn Arg Phe Thr Gln Lys Ser Leu Ser Leu Ser Pro
    690                 695                 700

Gly
705

<210> SEQ ID NO 317
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: His-tagged human B7H6 ECD ECD

<400> SEQUENCE: 317

Asp Leu Lys Val Glu Met Met Ala Gly Gly Thr Gln Ile Thr Pro Leu
1               5                   10                  15

Asn Asp Asn Val Thr Ile Phe Cys Asn Ile Phe Tyr Ser Gln Pro Leu
            20                  25                  30

Asn Ile Thr Ser Met Gly Ile Thr Trp Phe Trp Lys Ser Leu Thr Phe
        35                  40                  45

Asp Lys Glu Val Lys Val Phe Glu Phe Phe Gly Asp His Gln Glu Ala
    50                  55                  60

Phe Arg Pro Gly Ala Ile Val Ser Pro Trp Arg Leu Lys Ser Gly Asp
65                  70                  75                  80

Ala Ser Leu Arg Leu Pro Gly Ile Gln Leu Glu Glu Ala Gly Glu Tyr
                85                  90                  95

Arg Cys Glu Val Val Val Thr Pro Leu Lys Ala Gln Gly Thr Val Gln
            100                 105                 110

Leu Glu Val Val Ala Ser Pro Ala Ser Arg Leu Leu Leu Asp Gln Val
        115                 120                 125

Gly Met Lys Glu Asn Glu Asp Lys Tyr Met Cys Glu Ser Ser Gly Phe
    130                 135                 140

Tyr Pro Glu Ala Ile Asn Ile Thr Trp Glu Lys Gln Thr Gln Lys Phe
145                 150                 155                 160

```
Pro His Pro Ile Glu Ile Ser Glu Asp Val Ile Thr Gly Pro Thr Ile
                165                 170                 175

Lys Asn Met Asp Gly Thr Phe Asn Val Thr Ser Cys Leu Lys Leu Asn
            180                 185                 190

Ser Ser Gln Glu Asp Pro Gly Thr Val Tyr Gln Cys Val Val Arg His
        195                 200                 205

Ala Ser Leu His Thr Pro Leu Arg Ser Asn Phe Thr Leu Thr Ala Ala
    210                 215                 220

Arg His Ser Leu Ser Glu Thr Glu Lys Thr Asp Asn Phe Ser Ala Gly
225                 230                 235                 240

Ser Gly His His His His His His
                245


<210> SEQ ID NO 318
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fc-His-tagged human B7H6 ECD

<400> SEQUENCE: 318

Asp Leu Lys Val Glu Met Met Ala Gly Gly Thr Gln Ile Thr Pro Leu
1               5                   10                  15

Asn Asp Asn Val Thr Ile Phe Cys Asn Ile Phe Tyr Ser Gln Pro Leu
            20                  25                  30

Asn Ile Thr Ser Met Gly Ile Thr Trp Phe Trp Lys Ser Leu Thr Phe
        35                  40                  45

Asp Lys Glu Val Lys Val Phe Glu Phe Phe Gly Asp His Gln Glu Ala
    50                  55                  60

Phe Arg Pro Gly Ala Ile Val Ser Pro Trp Arg Leu Lys Ser Gly Asp
65                  70                  75                  80

Ala Ser Leu Arg Leu Pro Gly Ile Gln Leu Glu Glu Ala Gly Glu Tyr
                85                  90                  95

Arg Cys Glu Val Val Val Thr Pro Leu Lys Ala Gln Gly Thr Val Gln
            100                 105                 110

Leu Glu Val Val Ala Ser Pro Ala Ser Arg Leu Leu Leu Asp Gln Val
        115                 120                 125

Gly Met Lys Glu Asn Glu Asp Lys Tyr Met Cys Glu Ser Ser Gly Phe
    130                 135                 140

Tyr Pro Glu Ala Ile Asn Ile Thr Trp Glu Lys Gln Thr Gln Lys Phe
145                 150                 155                 160

Pro His Pro Ile Glu Ile Ser Glu Asp Val Ile Thr Gly Pro Thr Ile
                165                 170                 175

Lys Asn Met Asp Gly Thr Phe Asn Val Thr Ser Cys Leu Lys Leu Asn
            180                 185                 190

Ser Ser Gln Glu Asp Pro Gly Thr Val Tyr Gln Cys Val Val Arg His
        195                 200                 205

Ala Ser Leu His Thr Pro Leu Arg Ser Asn Phe Thr Leu Thr Ala Ala
    210                 215                 220

Arg His Ser Leu Ser Glu Thr Glu Lys Thr Asp Asn Phe Ser Gly Gly
225                 230                 235                 240

Ser Gly Gly Ser Gly Gly Ser Gly Gly Ser Gly Gly Ser Gly Gly Ser
                245                 250                 255
```

```
Gly Gly Glu Pro Lys Ser Cys Asp Lys Thr His Thr Cys Pro Pro Cys
            260                 265                 270

Pro Ala Pro Glu Ala Ala Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys Ala Gly Ser Gly His His
                485                 490                 495

His His His His
            500


<210> SEQ ID NO 319
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fc-His-tagged human Ala-mutated B7H6 ECD (NKp30
      interaction sites aa35-38 and aa102-105 substituted by Ala)

<400> SEQUENCE: 319

Asp Leu Lys Val Glu Met Met Ala Gly Gly Thr Gln Ile Thr Pro Leu
1               5                   10                  15

Asn Asp Asn Val Thr Ile Phe Cys Asn Ile Phe Tyr Ser Gln Pro Leu
            20                  25                  30

Asn Ile Ala Ala Ala Ala Ile Thr Trp Phe Trp Lys Ser Leu Thr Phe
        35                  40                  45

Asp Lys Glu Val Lys Val Phe Glu Phe Phe Gly Asp His Gln Glu Ala
    50                  55                  60

Phe Arg Pro Gly Ala Ile Val Ser Pro Trp Arg Leu Lys Ser Gly Asp
65                  70                  75                  80

Ala Ser Leu Arg Leu Pro Gly Ile Gln Leu Glu Glu Ala Gly Glu Tyr
                85                  90                  95
```

-continued

```
Arg Cys Glu Val Val Val Ala Ala Ala Ala Ala Gln Gly Thr Val Gln
            100                 105                 110

Leu Glu Val Val Ala Ser Pro Ala Ser Arg Leu Leu Leu Asp Gln Val
        115                 120                 125

Gly Met Lys Glu Asn Glu Asp Lys Tyr Met Cys Glu Ser Ser Gly Phe
    130                 135                 140

Tyr Pro Glu Ala Ile Asn Ile Thr Trp Glu Lys Gln Thr Gln Lys Phe
145                 150                 155                 160

Pro His Pro Ile Glu Ile Ser Glu Asp Val Ile Thr Gly Pro Thr Ile
                165                 170                 175

Lys Asn Met Asp Gly Thr Phe Asn Val Thr Ser Cys Leu Lys Leu Asn
            180                 185                 190

Ser Ser Gln Glu Asp Pro Gly Thr Val Tyr Gln Cys Val Val Arg His
        195                 200                 205

Ala Ser Leu His Thr Pro Leu Arg Ser Asn Phe Thr Leu Thr Ala Ala
    210                 215                 220

Arg His Ser Leu Ser Glu Thr Glu Lys Thr Asp Asn Phe Ser Gly Gly
225                 230                 235                 240

Ser Gly Gly Ser Gly Gly Ser Gly Gly Ser Gly Gly Ser Gly Gly Ser
                245                 250                 255

Gly Gly Glu Pro Lys Ser Cys Asp Lys Thr His Thr Cys Pro Pro Cys
            260                 265                 270

Pro Ala Pro Glu Ala Ala Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys Ala Gly Ser Gly His His
                485                 490                 495

His His His His
            500
```

<210> SEQ ID NO 320
<211> LENGTH: 245
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: His-tagged cyno B7H6 ECD

<400> SEQUENCE: 320

Asp Leu Lys Val Glu Met Met Ala Arg Gly Ile Gln Ala Thr Arg Leu
1 5 10 15

Asn Asp Ser Val Thr Ile Ser Cys Lys Val Ile Tyr Ser Gln Pro Leu
20 25 30

Asn Ile Thr Ser Met Gly Ile Thr Trp Phe Arg Lys Ser Leu Thr Leu
35 40 45

Asp Lys Glu Val Lys Val Phe Glu Phe Phe Gly Asp His Gln Lys Ala
50 55 60

Phe Arg Pro Gly Ala Asn Val Ser Leu Trp Arg Leu Lys Ser Gly Asp
65 70 75 80

Ala Ser Leu Lys Leu Pro Gly Val Gln Leu Glu Glu Ala Gly Glu Tyr
85 90 95

Arg Cys Glu Val Val Val Thr Pro Leu Lys Ala Gln Gly Thr Val Gln
100 105 110

Leu Lys Val Val Ala Ser Pro Thr Ser Arg Leu Phe Gln Asp Gln Ala
115 120 125

Val Val Lys Glu Asn Glu Gly Lys Tyr Met Cys Glu Ser Ser Arg Phe
130 135 140

Tyr Pro Lys Asp Ile Asn Ile Thr Trp Glu Lys Trp Thr Gln Lys Ser
145 150 155 160

Pro His His Val Val Ile Ser Glu Asn Val Ile Thr Gly Pro Thr Ile
165 170 175

Lys Asn Met Asp Gly Thr Phe Asn Ile Thr Ser Tyr Leu Lys Leu Asn
180 185 190

Ser Ser Gln Glu Asp Pro Gly Thr Val Tyr Arg Cys Val Ile Arg His
195 200 205

Glu Ser Leu His Thr Pro Val Ser Ile Asp Phe Ile Leu Thr Ala Pro
210 215 220

Gln Gln Ser Leu Ser Glu Pro Glu Lys Thr Asp Ala Gly Ser Gly His
225 230 235 240

His His His His His
245

<210> SEQ ID NO 321
<211> LENGTH: 497
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Fc-His-tagged cyno B7H6 ECD

<400> SEQUENCE: 321

Asp Leu Lys Val Glu Met Met Ala Arg Gly Ile Gln Ala Thr Arg Leu
1 5 10 15

Asn Asp Ser Val Thr Ile Ser Cys Lys Val Ile Tyr Ser Gln Pro Leu
20 25 30

-continued

```
Asn Ile Thr Ser Met Gly Ile Thr Trp Phe Arg Lys Ser Leu Thr Leu
        35                  40                  45

Asp Lys Glu Val Lys Val Phe Glu Phe Phe Gly Asp His Gln Lys Ala
    50                  55                  60

Phe Arg Pro Gly Ala Asn Val Ser Leu Trp Arg Leu Lys Ser Gly Asp
65                  70                  75                  80

Ala Ser Leu Lys Leu Pro Gly Val Gln Leu Glu Glu Ala Gly Glu Tyr
                85                  90                  95

Arg Cys Glu Val Val Val Thr Pro Leu Lys Ala Gln Gly Thr Val Gln
            100                 105                 110

Leu Lys Val Val Ala Ser Pro Thr Ser Arg Leu Phe Gln Asp Gln Ala
        115                 120                 125

Val Val Lys Glu Asn Glu Gly Lys Tyr Met Cys Glu Ser Ser Arg Phe
    130                 135                 140

Tyr Pro Lys Asp Ile Asn Ile Thr Trp Glu Lys Trp Thr Gln Lys Ser
145                 150                 155                 160

Pro His His Val Val Ile Ser Glu Asn Val Ile Thr Gly Pro Thr Ile
                165                 170                 175

Lys Asn Met Asp Gly Thr Phe Asn Ile Thr Ser Tyr Leu Lys Leu Asn
            180                 185                 190

Ser Ser Gln Glu Asp Pro Gly Thr Val Tyr Arg Cys Val Ile Arg His
        195                 200                 205

Glu Ser Leu His Thr Pro Val Ser Ile Asp Phe Ile Leu Thr Ala Pro
    210                 215                 220

Gln Gln Ser Leu Ser Glu Pro Glu Lys Thr Asp Gly Gly Ser Gly Gly
225                 230                 235                 240

Ser Gly Gly Ser Gly Gly Ser Gly Gly Ser Gly Gly Ser Gly Gly Glu
                245                 250                 255

Pro Lys Ser Cys Asp Lys Thr His Thr Cys Pro Pro Cys Pro Ala Pro
            260                 265                 270

Glu Ala Ala Gly Gly Pro Ser Val Phe Leu Phe Pro Pro Lys Pro Lys
        275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
        355                 360                 365

Pro Ala Pro Ile Glu Lys Thr Ile Ser Lys Ala Lys Gly Gln Pro Arg
    370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
        435                 440                 445
```

Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Pro Gly Lys Ala Gly Ser Gly His His His His His
                485                 490                 495

His

<210> SEQ ID NO 322
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human CD3E+G-HuFc-His

<400> SEQUENCE: 322

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Gly Gly Gly Ser Gly Gly Gly
            100                 105                 110

Ser Gly Gly Gly Ser Gly Gly Gly Ser Gly Gly Gly Ser Gly Gly Gly
        115                 120                 125

Ser Gly Gly Gln Ser Ile Lys Gly Asn His Leu Val Lys Val Tyr Asp
    130                 135                 140

Tyr Gln Glu Asp Gly Ser Val Leu Leu Thr Cys Asp Ala Glu Ala Lys
145                 150                 155                 160

Asn Ile Thr Trp Phe Lys Asp Gly Lys Met Ile Gly Phe Leu Thr Glu
                165                 170                 175

Asp Lys Lys Lys Trp Asn Leu Gly Ser Asn Ala Lys Asp Pro Arg Gly
            180                 185                 190

Met Tyr Gln Cys Lys Gly Ser Gln Asn Lys Ser Lys Pro Leu Gln Val
        195                 200                 205

Tyr Tyr Arg Met Cys Gln Asn Cys Ile Glu Leu Asn Ala Ala Thr Ile
    210                 215                 220

Ser Gly Gly Ser Gly Gly Ser Gly Gly Ser Gly Gly Ser Gly Gly Ser
225                 230                 235                 240

Gly Gly Ser Gly Gly Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys

```
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys Ala Gly Ser
465                 470                 475                 480

Ala His His His His His His
                485


<210> SEQ ID NO 323
<211> LENGTH: 477
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cyno CD3 E+G huFc-His

<400> SEQUENCE: 323

Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
            20                  25                  30

Gly Ser Glu Ala Gln Trp Gln His Asn Gly Lys Asn Lys Gly Asp Ser
        35                  40                  45

Gly Asp Gln Leu Phe Leu Pro Glu Phe Ser Glu Met Glu Gln Ser Gly
    50                  55                  60

Tyr Tyr Val Cys Tyr Pro Arg Gly Ser Asn Pro Glu Asp Ala Ser His
65                  70                  75                  80

His Leu Tyr Leu Lys Ala Arg Val Cys Glu Asn Cys Met Glu Met Asp
                85                  90                  95

Val Met Gly Gly Gly Ser Gly Gly Gly Ser Gly Gly Gly Ser Gly Gly
            100                 105                 110

Gly Ser Gly Gly Gly Ser Gly Gly Gly Ser Gly Gly Gln Ser Phe Glu
        115                 120                 125

Glu Asn Arg Lys Leu Asn Val Tyr Asn Gln Glu Asp Gly Ser Val Leu
    130                 135                 140

Leu Thr Cys His Val Lys Asn Thr Asn Ile Thr Trp Phe Lys Glu Gly
```

```
145                 150                 155                 160

Lys Met Ile Asp Ile Leu Thr Ala His Lys Asn Lys Trp Asn Leu Gly
                165                 170                 175

Ser Asn Thr Lys Asp Pro Arg Gly Val Tyr Gln Cys Lys Gly Ser Lys
            180                 185                 190

Asp Lys Ser Lys Thr Leu Gln Val Tyr Tyr Arg Met Cys Gln Asn Cys
        195                 200                 205

Ile Glu Leu Asn Ala Ala Thr Gly Gly Ser Gly Gly Ser Gly Gly Ser
    210                 215                 220

Gly Gly Ser Gly Gly Ser Gly Gly Ser Gly Gly Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys Ala Gly Ser Ala His His His His His His
465                 470                 475
```

<210> SEQ ID NO 324
<211> LENGTH: 461
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Human B7H1-Fc

<400> SEQUENCE: 324

```
Thr Val Thr Val Pro Lys Asp Leu Tyr Val Val Glu Tyr Gly Ser Asn
1               5                   10                  15

Met Thr Ile Glu Cys Lys Phe Pro Val Glu Lys Gln Leu Asp Leu Ala
```

-continued

```
            20                  25                  30

Ala Leu Ile Val Tyr Trp Glu Met Glu Asp Lys Asn Ile Ile Gln Phe
        35                  40                  45

Val His Gly Glu Glu Asp Leu Lys Val Gln His Ser Ser Tyr Arg Gln
    50                  55                  60

Arg Ala Arg Leu Leu Lys Asp Gln Leu Ser Leu Gly Asn Ala Ala Leu
65                  70                  75                  80

Gln Ile Thr Asp Val Lys Leu Gln Asp Ala Gly Val Tyr Arg Cys Met
                85                  90                  95

Ile Ser Tyr Gly Gly Ala Asp Tyr Lys Arg Ile Thr Val Lys Val Asn
            100                 105                 110

Ala Pro Tyr Asn Lys Ile Asn Gln Arg Ile Leu Val Val Asp Pro Val
        115                 120                 125

Thr Ser Glu His Glu Leu Thr Cys Gln Ala Glu Gly Tyr Pro Lys Ala
    130                 135                 140

Glu Val Ile Trp Thr Ser Ser Asp His Gln Val Leu Ser Gly Lys Thr
145                 150                 155                 160

Thr Thr Thr Asn Ser Lys Arg Glu Glu Lys Leu Phe Asn Val Thr Ser
                165                 170                 175

Thr Leu Arg Ile Asn Thr Thr Thr Asn Glu Ile Phe Tyr Cys Thr Phe
            180                 185                 190

Arg Arg Leu Asp Pro Glu Glu Asn His Thr Ala Glu Leu Val Ile Pro
        195                 200                 205

Glu Leu Pro Leu Ala His Pro Pro Asn Glu Arg Thr Glu Gln Lys Leu
    210                 215                 220

Ile Ser Glu Glu Asp Leu Leu Val Pro Arg Gly Ser Arg Ser Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Gly Leu Pro Ser Ser Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Gly Leu His Asn
        435                 440                 445
```

```
His Tyr Thr Gln Lys Ser Leu Ser Leu Ser Pro Gly Lys
    450                 455                 460


<210> SEQ ID NO 325
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Vk leader

<400> SEQUENCE: 325

Met Glu Thr Asp Thr Leu Leu Leu Trp Val Leu Leu Leu Trp Val Pro
1               5                   10                  15

Gly Ser Thr Gly Asp
            20


<210> SEQ ID NO 326
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 6-His-myc tag

<400> SEQUENCE: 326

His His His His His His Glu Gln Lys Leu Ile Ser Glu Glu Asp Leu
1               5                   10                  15


<210> SEQ ID NO 327
<211> LENGTH: 238
<212> TYPE: PRT
<213> ORGANISM: Macaca fascicularis
<220> FEATURE:
<223> OTHER INFORMATION: Cynomolgus B7-H6 extracellular domain (NCBI
      XP_005578557.1, aa25-262)

<400> SEQUENCE: 327

Asp Leu Lys Val Glu Met Met Ala Arg Gly Ile Gln Ala Thr Arg Leu
1               5                   10                  15

Asn Asp Ser Val Thr Ile Ser Cys Lys Val Ile Tyr Ser Gln Pro Leu
            20                  25                  30

Asn Ile Thr Ser Met Gly Ile Thr Trp Phe Arg Lys Ser Leu Thr Leu
        35                  40                  45

Asp Lys Glu Val Lys Val Phe Glu Phe Phe Gly Asp His Gln Lys Ala
    50                  55                  60

Phe Arg Pro Gly Ala Asn Val Ser Leu Trp Arg Leu Lys Ser Gly Asp
65                  70                  75                  80

Ala Ser Leu Lys Leu Pro Gly Val Gln Leu Glu Glu Ala Gly Glu Tyr
                85                  90                  95

Arg Cys Glu Val Val Val Thr Pro Leu Lys Ala Gln Gly Thr Val Gln
            100                 105                 110

Leu Lys Val Val Ala Ser Pro Thr Ser Arg Leu Phe Gln Asp Gln Ala
        115                 120                 125

Val Val Lys Glu Asn Glu Gly Lys Tyr Met Cys Glu Ser Ser Arg Phe
    130                 135                 140

Tyr Pro Lys Asp Ile Asn Ile Thr Trp Glu Lys Trp Thr Gln Lys Ser
145                 150                 155                 160
```

```
Pro His His Val Val Ile Ser Glu Asn Val Ile Thr Gly Pro Thr Ile
                165                 170                 175

Lys Asn Met Asp Gly Thr Phe Asn Ile Thr Ser Tyr Leu Lys Leu Asn
            180                 185                 190

Ser Ser Gln Glu Asp Pro Gly Thr Val Tyr Arg Cys Val Ile Arg His
        195                 200                 205

Glu Ser Leu His Thr Pro Val Ser Ile Asp Phe Ile Leu Thr Ala Pro
    210                 215                 220

Gln Gln Ser Leu Ser Glu Pro Glu Lys Thr Asp Ile Phe Ser
225                 230                 235
```

<210> SEQ ID NO 328
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Linker

<400> SEQUENCE: 328

```
Ser Gly Gly Gly Gly Ser
1               5
```

<210> SEQ ID NO 329
<211> LENGTH: 23
<212> TYPE: PRT
<213> ORGANISM: Homo sapiens
<220> FEATURE:
<223> OTHER INFORMATION: Human EpCAM transmembrane domain (Uniprot P16422, aa266-288)

<400> SEQUENCE: 329

```
Ala Gly Val Ile Ala Val Ile Val Val Val Val Ile Ala Val Val Ala
1               5                   10                  15

Gly Ile Val Val Leu Val Ile
            20
```

<210> SEQ ID NO 330
<211> LENGTH: 26
<212> TYPE: PRT
<213> ORGANISM: Homo sapiens
<220> FEATURE:
<223> OTHER INFORMATION: Human EpCAM intracellular domain (Uniprot P16422, aa289-314)

<400> SEQUENCE: 330

```
Ser Arg Lys Lys Arg Met Ala Lys Tyr Glu Lys Ala Glu Ile Lys Glu
1               5                   10                  15

Met Gly Glu Met His Arg Glu Leu Asn Ala
            20                  25
```

<210> SEQ ID NO 331
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PD1-1 HC

<400> SEQUENCE: 331

-continued

```
Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
```

```
            420                 425                 430

His Asn His Tyr Thr Gln Lys Ser Leu Ser Leu Ser Leu Gly
        435                 440                 445


<210> SEQ ID NO 332
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PD1-1 LC

<400> SEQUENCE: 332

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 333
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PD1-2 HC

<400> SEQUENCE: 333

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30
```

```
Ala Met Ser Trp Val Arg Gln Ala Pro Gly Lys Gly Leu Glu Trp Val
        35                  40                  45

Ala Tyr Ile Ser Gly Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Pro Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 334
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PD1-2 LC

<400> SEQUENCE: 334

```
Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 335
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PD1-3 HC

<400> SEQUENCE: 335

```
Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Gly Asp Thr Tyr Tyr Ser Ser Ser Val
    50                  55                  60
```

-continued

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 336
<211> LENGTH: 218
<212> TYPE: PRT
<213> ORGANISM: Artificial Sequence
<220> FEATURE:
<223> OTHER INFORMATION: Description of Artificial Sequence: Synthetic

```
      polypeptide
<220> FEATURE:
<223> OTHER INFORMATION: PD1-3 LC

<400> SEQUENCE: 336

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 337
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PD1-4 HC

<400> SEQUENCE: 337

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 338
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PD1-4 LC

<400> SEQUENCE: 338

```
Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 339
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PD1-5 HC

<400> SEQUENCE: 339

```
Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 340
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PD1-5 LC

<400> SEQUENCE: 340

```
Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30
```

Gly Ile Ser Phe Met Asn Trp Tyr Gln Gln Lys Pro Gly Gln Ala Pro
35 40 45

Lys Leu Leu Ile Tyr Val Ala Ser Asn Gln Gly Ser Gly Ile Pro Ala
50 55 60

Arg Phe Ser Gly Ser Gly Ser Gly Thr Asp Phe Thr Leu Thr Ile Ser
65 70 75 80

Arg Leu Glu Pro Glu Asp Phe Ala Val Tyr Tyr Cys Gln Gln Ser Lys
85 90 95

Glu Val Pro Trp Thr Phe Gly Gln Gly Thr Lys Leu Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 341
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 341

Gly Gly Gly Gly Ser Gly Gly Gly Gly Ser Gly Gly Gly Gly Ser
1 5 10 15

<210> SEQ ID NO 342
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 342

Gly Gly Gly Gly Ser Gly Gly Gly Gly Ser Gly Gly Gly Gly Ser Gly
1 5 10 15

Gly Gly Gly Ser Gly Gly Gly Gly Ser
20 25

<210> SEQ ID NO 343
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 343

Gly Gly Gly Gly Ser Gly Gly Gly Gly Ser Gly Gly Gly Gly Ser Gly 1 5 10 15

Gly Gly Gly Ser Gly Gly Gly Gly Ser Gly Gly Gly Gly Ser Gly Gly
20 25 30

Gly Gly Ser
35

<210> SEQ ID NO 344
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 344

Gly Gly Gly Ser Gly Gly Gly Ser Gly Gly Gly Ser
1 5 10

<210> SEQ ID NO 345
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 345

Gly Gly Gly Ser Gly Gly Gly Ser Gly Gly Gly Ser Gly Gly Gly Ser
1 5 10 15

Gly Gly Gly Ser
20

<210> SEQ ID NO 346
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 346

Gly Gly Gly Ser Gly Gly Gly Ser Gly Gly Gly Ser Gly Gly Gly Ser
1 5 10 15

Gly Gly Gly Ser Gly Gly Gly Ser Gly Gly Gly Ser
20 25

<210> SEQ ID NO 347
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 347

Gly Gly Gly Ser Ser Gly Gly Gly Ser Ser Gly Gly Gly Ser Ser
1 5 10 15

<210> SEQ ID NO 348
<211> LENGTH: 25
<212> TYPE: PRT
<213> ORGANISM: Artificial Sequence
<220> FEATURE:
<223> OTHER INFORMATION: Description of Artificial Sequence: Synthetic peptide -continued

```
<400> SEQUENCE: 348

Gly Gly Gly Ser Ser Gly Gly Gly Ser Ser Gly Gly Gly Ser Ser Gly
1               5                   10                  15

Gly Gly Ser Ser Gly Gly Gly Ser Ser
            20                  25


<210> SEQ ID NO 349
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Gly Gly Gly Ser Ser Gly Gly Gly Ser Ser Gly Gly Gly Ser Ser Gly
1               5                   10                  15

Gly Gly Ser Ser Gly Gly Gly Ser Ser Gly Gly Gly Ser Ser Gly Gly
            20                  25                  30

Gly Ser Ser
        35


<210> SEQ ID NO 350
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 350

His His His His His His
1               5
```

MULTI-SPECIFIC BINDING PROTEINS FOR CANCER TREATMENT

BACKGROUND OF THE INVENTION

The instant application contains a Sequence Listing which has been submitted electronically in ASCII format and is hereby incorporated by reference in its entirety. Said ASCII copy, created on Sep. 28, 2020, is named 12-0442-US-1_SL.txt and is 517,149 bytes in size.

TECHNICAL FIELD

The present invention relates to multi-specific binding proteins comprising a first antigen binding unit specific for B7H6 (also referred to herein as "B7-H6") and a second antigen binding unit specific for CD3. The invention also relates to nucleic acids encoding such binding proteins, to methods for preparing such binding proteins; host cells expressing or capable of expressing such binding proteins, compositions comprising such binding proteins and to uses of such binding proteins or such compositions, in particular for therapeutic purposes in the field of cancer diseases.

BACKGROUND INFORMATION

B7H6 is a tumor-selective B7 family member that has been described to attract innate immunity to target cells and shares a similar function as other B7 family members with two Ig-like domains in the extracellular domain, an N-terminal IgV-like domain and a C-terminal IgC1-like domain B7H6 triggers NKp30 mediated activation of human natural killer (NK) cells leading to degranulation and IFNγ secretion. (Brandt et al., J. Exp. Med. 2009 206(7); 1495-1503). Currently available data suggest a role of B7H6 in inflammatory responses to infectious conditions as well as in solid tumors.

B7H6 has been shown to be expressed on $CD14^{+}CD16^{+}$ cells isolated from the peripheral blood of sepsis patients as a result of the inflammatory process in this acute disease state. These findings have been confirmed by in vitro analysis of the upregulation of B7H6 on the cell surface of $CD14^{+}CD16^{+}$ proinflammatory monocytes and neutrophils upon stimulation by IL-1β and TNFα. (Matta et al., Blood 2013 122(3)), suggesting a role of B7H6 in inflammatory responses to sepsis conditions.

With the exception of the aforementioned sepsis conditions, B7H6 is otherwise selectively expressed in tumor cells and could not be detected in normal human tissues at steady state. For example, expression of B7H6 has been described for T cell lymphoma, myeloid leukemia, colon carcinoma, breast cancer and ovarian carcinoma cell lines (Brandt et al., J. Exp. Med. 2009 206(7): 1495-1503; Li et al., J. Exp. Med. 2011 208(4); Greaves et al., Blood 2013 121(5); Zhang et al. Oncology Letters 2018 16:91-96), non-small cell lung cancer tissues (Zhang et al., Int J clin Exp Pathol 2014; 7(10):6936-6942), gastro-intestinal tumor tissues (Chen et al., Pathol. Oncol. Res. 2014 20:203-207; Zhao et al., Cell Proliferation 2018; e12468), ovarian carcinoma tissues (Zhou et al., Int clin Exp Pathol at 2015 8(8), oral squamous carcinoma tissues (Wang et al., J Oral Pathol Med. 2017; 46:766-772), and hepatocellular carcinoma tissues (Li et al., Int. J. Mol. Sci. 2019, 20, 156), however, the function of B7H6 in tumors is not fully understood.

Therapeutic applications including the treatment of cancer using anti-B7H6 antibodies which engage the ADCC/

CDC pathway or anti-B7H6 antibody-drug conjugates are described in WO2009/046407A2 and WO2011/07044A2.

However, B7H6 targeted therapy based on ADCC/CDC activity is not an optimal mode of action because of the low cell surface expression of B7H6 and low success rates using conventional antibodies with ADCC/CDC activity in solid tumors.

Targeted therapy based on B7H6-specific antibody drug conjugates (ADCs) might have limitations as well, since the majority of patients relapse after chemotherapy treatment and due to the low expression of B7H6 on the cell surface. In addition, ADC approaches often have off-target toxicities caused by free drug as a result of linker instability or degradation.

CAR-T-cells and T cell engaging antibodies are further approaches for targeted therapy of B7H6-expressing solid tumors (Wu et al., Gene 2015 22, 675-684; Hua et al. Protein Engineering, Design & Selection 201730(10), 713-721; WO2017/181001). For example, Wu et al. (J Immunol. 2015 Jun. 1; 194(11):5305-11) describes preclinical data with a B7H6-specific-BiTE, BiTE standing for Bi-specific T cell Engager which is an approximately 55 Kda fusion protein consisting of two single-chain variable fragments (scFvs)). In that case the B7H6-specific-BiTE was engineered based on the OKT3-CD3-binder and a previously published B7H6 antibody (Zhang et al., J Immunol. 2012 Sep. 1; 189(5): 2290-9; WO 2013/169691). However, the OKT3 antibody is not cross-reactive with cynomolgus monkey CD3 and therefore does not allow preclinical toxicological testing in cynomolgus monkeys which is the preferred testing species for preparation of clinical trials (Chatenoud et al., The Rev Diabet Stud 2012; 9(4):372-381). An additional challenge is the short half-life of the relatively small, easily degraded BiTE molecules, which requires continuous intravenous dosing in the clinic. Therefore, it is unproven whether this approach will be successful. To date, no targeted therapies for B7-H6-expressing tumors are available, and there remains an unmet need unaddressed by current approaches.

For example, colorectal cancer (CRC) shows a high prevalence and predictable expression of B7-H6. It is one of the leading causes of cancer morbidity and mortality worldwide. Approximately 25% of CRC patients initially present with overt metastasis and metastatic disease develops in 40-50% of newly diagnosed patients. Although recent improvements in chemotherapy and targeted therapies have extended survival durations of metastatic CRC, most patients will succumb to their disease.

In view of the poor outlook for cancer patients with advanced disease, there is a need to identify more efficacious therapies, particularly efficacious therapies with improved tolerability.

Thus, it is an object of the invention to provide pharmacologically active agents, compositions and/or methods of treatment that provide certain advantages compared to the agents, compositions and/or methods currently used and/or known in the art. These advantages include improved therapeutic and pharmacological properties, such as in vivo efficacy, less side effects, reduced immunogenicity, improved therapeutic window, reduced administration (e.g. infusion) times, lower dosage, extended half-life to allow less frequent dosing and other advantageous properties such as improved ease of preparation, stability, compatibility with conventional antibody processes or reduced costs of goods, especially as compared to candidate drugs already known in the art.

BRIEF SUMMARY OF THE INVENTION

The present invention is based on a bispecific T cell engaging approach employing multi-specific binding proteins with a binding arm to CD3, which is expressed on T cells, and a binding arm to B7H6, which is expressed on the cell surface of tumor cells. Through simultaneously binding to T cells and tumors cells, the T cell engagers of the present invention force the formation of a cytolytic synapse between the two cells and thereby redirect the T cell activity selectively to the targeted tumor cells.

In one aspect, the invention provides a multi-specific binding protein comprising a first antigen binding unit specifically binding to B7H6 and a second antigen binding unit specifically binding to CD3, wherein said first antigen binding unit specifically binding to B7H6 is selected from the group consisting of i) to xxiv):

i) an antigen binding unit comprising light chain CDRs comprising the amino acid sequences of SEQ ID NO:1 (CDR1), SEQ ID NO:2 (CDR2) and SEQ ID NO:3 (CDR3) and heavy chain CDRs comprising the amino acid sequences of SEQ ID NO:4 (CDR1), SEQ ID NO:5 (CDR2) and SEQ ID NO:6 (CDR3);

ii) an antigen binding unit comprising light chain CDRs comprising the amino acid sequences of SEQ ID NO:7 (CDR1), SEQ ID NO:8 (CDR2) and SEQ ID NO:9 (CDR3) and heavy chain CDRs comprising the amino acid sequences of SEQ ID NO:10 (CDR1), SEQ ID NO:11 (CDR2) and SEQ ID NO:12 (CDR3);

iii) an antigen binding unit comprising light chain CDRs comprising the amino acid sequences of SEQ ID NO:13 (CDR1), SEQ ID NO:14 (CDR2) and SEQ ID NO:15 (CDR3) and heavy chain CDRs comprising the amino acid sequences of SEQ ID NO:16 (CDR1), SEQ ID NO:17 (CDR2) and SEQ ID NO:18 (CDR3);

iv) an antigen binding unit comprising light chain CDRs comprising the amino acid sequences of SEQ ID NO:19 (CDR1), SEQ ID NO:20 (CDR2) and SEQ ID NO:21 (CDR3) and heavy chain CDRs comprising the amino acid sequences of SEQ ID NO:22 (CDR1), SEQ ID NO:23 (CDR2) and SEQ ID NO:24 (CDR3);

v) an antigen binding unit comprising light chain CDRs comprising the amino acid sequences of SEQ ID NO:25 (CDR1), SEQ ID NO:26 (CDR2) and SEQ ID NO:27 (CDR3) and heavy chain CDRs comprising the amino acid sequences of SEQ ID NO:28 (CDR1), SEQ ID NO:29 (CDR2) and SEQ ID NO:30 (CDR3);

vi) an antigen binding unit comprising light chain CDRs comprising the amino acid sequences of SEQ ID NO:31 (CDR1), SEQ ID NO:32 (CDR2) and SEQ ID NO:33 (CDR3) and heavy chain CDRs comprising the amino acid sequences of SEQ ID NO:34 (CDR1), SEQ ID NO:35 (CDR2) and SEQ ID NO:36 (CDR3);

vii) an antigen binding unit comprising light chain CDRs comprising the amino acid sequences of SEQ ID NO:37 (CDR1), SEQ ID NO:38 (CDR2) and SEQ ID NO:39 (CDR3) and heavy chain CDRs comprising the amino acid sequences of SEQ ID NO:40 (CDR1), SEQ ID NO:41 (CDR2) and SEQ ID NO:42 (CDR3);

viii) an antigen binding unit comprising light chain CDRs comprising the amino acid sequences of SEQ ID NO:43 (CDR1), SEQ ID NO:44 (CDR2) and SEQ ID NO:45 (CDR3) and heavy chain CDRs comprising the amino acid sequences of SEQ ID NO:46 (CDR1), SEQ ID NO:47 (CDR2) and SEQ ID NO:48 (CDR3);

ix) an antigen binding unit comprising light chain CDRs comprising the amino acid sequences of SEQ ID NO:49 (CDR1), SEQ ID NO:50 (CDR2) and SEQ ID NO:51 (CDR3) and heavy chain CDRs comprising the amino acid sequences of SEQ ID NO:52 (CDR1), SEQ ID NO:53 (CDR2) and SEQ ID NO:54 (CDR3);

x) an antigen binding unit comprising light chain CDRs comprising the amino acid sequences of SEQ ID NO:55 (CDR1), SEQ ID NO:56 (CDR2) and SEQ ID NO:57 (CDR3) and heavy chain CDRs comprising the amino acid sequences of SEQ ID NO:58 (CDR1), SEQ ID NO:59 (CDR2) and SEQ ID NO:60 (CDR3);

xi) an antigen binding unit comprising light chain CDRs comprising the amino acid sequences of SEQ ID NO:61 (CDR1), SEQ ID NO:62 (CDR2) and SEQ ID NO:63 (CDR3) and heavy chain CDRs comprising the amino acid sequences of SEQ ID NO:64 (CDR1), SEQ ID NO:65 (CDR2) and SEQ ID NO:66 (CDR3);

xii) an antigen binding unit comprising light chain CDRs comprising the amino acid sequences of SEQ ID NO:67 (CDR1), SEQ ID NO:68 (CDR2) and SEQ ID NO:69 (CDR3) and heavy chain CDRs comprising the amino acid sequences of SEQ ID NO:70 (CDR1), SEQ ID NO:71 (CDR2) and SEQ ID NO:72 (CDR3);

xiii) an antigen binding unit comprising light chain CDRs comprising the amino acid sequences of SEQ ID NO:73 (CDR1), SEQ ID NO:74 (CDR2) and SEQ ID NO:75 (CDR3) and heavy chain CDRs comprising the amino acid sequences of SEQ ID NO:76 (CDR1), SEQ ID NO:77 (CDR2) and SEQ ID NO:78 (CDR3);

xiv) an antigen binding unit comprising light chain CDRs comprising the amino acid sequences of SEQ ID NO:79 (CDR1), SEQ ID NO:80 (CDR2) and SEQ ID NO:81 (CDR3) and heavy chain CDRs comprising the amino acid sequences of SEQ ID NO:82 (CDR1), SEQ ID NO:83 (CDR2) and SEQ ID NO:84 (CDR3);

xv) an antigen binding unit comprising light chain CDRs comprising the amino acid sequences of SEQ ID NO:85 (CDR1), SEQ ID NO:86 (CDR2) and SEQ ID NO:87 (CDR3) and heavy chain CDRs comprising the amino acid sequences of SEQ ID NO:88 (CDR1), SEQ ID NO:89 (CDR2) and SEQ ID NO:90 (CDR3);

xvi) an antigen binding unit comprising light chain CDRs comprising the amino acid sequences of SEQ ID NO:91 (CDR1), SEQ ID NO:92 (CDR2) and SEQ ID NO:93 (CDR3) and heavy chain CDRs comprising the amino acid sequences of SEQ ID NO:94 (CDR1), SEQ ID NO:95 (CDR2) and SEQ ID NO:96 (CDR3);

xvii) an antigen binding unit comprising light chain CDRs comprising the amino acid sequences of SEQ ID NO:97 (CDR1), SEQ ID NO:98 (CDR2) and SEQ ID NO:99 (CDR3) and heavy chain CDRs comprising the amino acid sequences of SEQ ID NO:100 (CDR1), SEQ ID NO:101 (CDR2) and SEQ ID NO:102 (CDR3);

xviii) an antigen binding unit comprising light chain CDRs comprising the amino acid sequences of SEQ ID NO:103 (CDR1), SEQ ID NO:104 (CDR2) and SEQ ID NO:105 (CDR3) and heavy chain CDRs comprising the amino acid sequences of SEQ ID NO:106 (CDR1), SEQ ID NO:107 (CDR2) and SEQ ID NO:108 (CDR3);

xix) an antigen binding unit comprising light chain CDRs comprising the amino acid sequences of SEQ ID NO:109 (CDR1), SEQ ID NO:110 (CDR2) and SEQ ID NO:111 (CDR3) and heavy chain CDRs comprising the amino acid sequences of SEQ ID NO:112 (CDR1), SEQ ID NO:113 (CDR2) and SEQ ID NO:114 (CDR3);

xx) an antigen binding unit comprising light chain CDRs comprising the amino acid sequences of SEQ ID NO:115 (CDR1), SEQ ID NO:116 (CDR2) and SEQ ID NO:117 (CDR3) and heavy chain CDRs comprising the amino acid sequences of SEQ ID NO:118 (CDR1), SEQ ID NO:119 (CDR2) and SEQ ID NO:120 (CDR3);

xxi) an antigen binding unit comprising light chain CDRs comprising the amino acid sequences of SEQ ID NO:121 (CDR1), SEQ ID NO:122 (CDR2) and SEQ ID NO:123 (CDR3) and heavy chain CDRs comprising the amino acid sequences of SEQ ID NO:124 (CDR1), SEQ ID NO:125 (CDR2) and SEQ ID NO:126 (CDR3);

xxii) an antigen binding unit comprising light chain CDRs comprising the amino acid sequences of SEQ ID NO:127 (CDR1), SEQ ID NO:128 (CDR2) and SEQ ID NO:129 (CDR3) and heavy chain CDRs comprising the amino acid sequences of SEQ ID NO:130 (CDR1), SEQ ID NO:131 (CDR2) and SEQ ID NO:132 (CDR3);

xxiii) an antigen binding unit comprising light chain CDRs comprising the amino acid sequences of SEQ ID NO:133 (CDR1), SEQ ID NO:134 (CDR2) and SEQ ID NO:135 (CDR3) and heavy chain CDRs comprising the amino acid sequences of SEQ ID NO:136 (CDR1), SEQ ID NO:137 (CDR2) and SEQ ID NO:138 (CDR3); and xxiv) an antigen binding unit comprising light chain CDRs comprising the amino acid sequences of SEQ ID NO:139 (CDR1), SEQ ID NO:140 (CDR2) and SEQ ID NO:141 (CDR3) and heavy chain CDRs comprising the amino acid sequences of SEQ ID NO:142 (CDR1), SEQ ID NO:143 (CDR2) and SEQ ID NO:144 (CDR3).

In some embodiments of the binding protein of the invention, the first antigen binding unit specifically binding to B7H6 is selected from the group consisting of i) to xxiv):

i) a light chain variable domain comprising the amino acid sequence of SEQ ID NO:145 and heavy chain variable domain comprising the amino acid sequence of SEQ ID NO:146;

ii) a light chain variable domain comprising the amino acid sequences of SEQ ID NO:147 and heavy chain variable domain comprising the amino acid sequences of SEQ ID NO:148;

iii) a light chain variable domain comprising the amino acid sequence of SEQ ID NO:149 and heavy chain variable domain comprising the amino acid sequence of SEQ ID NO:150;

iv) a light chain variable domain comprising the amino acid sequence of SEQ ID NO:151 and heavy chain variable domain comprising the amino acid sequence of SEQ ID NO:152;

v) a light chain variable domain comprising the amino acid sequence of SEQ ID NO:153 and heavy chain variable domain comprising the amino acid sequence of SEQ ID NO:154;

vi) a light chain variable domain comprising the amino acid sequence of SEQ ID NO:155 and heavy chain variable domain comprising the amino acid sequence of SEQ ID NO:156;

vii) a light chain variable domain comprising the amino acid sequence of SEQ ID NO:157 and heavy chain variable domain comprising the amino acid sequence of SEQ ID NO:158;

viii) a light chain variable domain comprising the amino acid sequence of SEQ ID NO:159 and heavy chain variable domain comprising the amino acid sequence of SEQ ID NO:160;

ix) a light chain variable domain comprising the amino acid sequence of SEQ ID NO:161 and heavy chain variable domain comprising the amino acid sequence of SEQ ID NO:162;

x) a light chain variable domain comprising the amino acid sequence of SEQ ID NO:163 and heavy chain variable domain comprising the amino acid sequence of SEQ ID NO:164;

xi) a light chain variable domain comprising the amino acid sequence of SEQ ID NO:165 and heavy chain variable domain comprising the amino acid sequence of SEQ ID NO:166;

xii) a light chain variable domain comprising the amino acid sequence of SEQ ID NO:167 and heavy chain variable domain comprising the amino acid sequence of SEQ ID NO:168;

xiii) a light chain variable domain comprising the amino acid sequence of SEQ ID NO:169 and heavy chain variable domain comprising the amino acid sequence of SEQ ID NO:170;

xiv) a light chain variable domain comprising the amino acid sequence of SEQ ID NO:171 and heavy chain variable domain comprising the amino acid sequence of SEQ ID NO:172;

xv) a light chain variable domain comprising the amino acid sequence of SEQ ID NO:173 and heavy chain variable domain comprising the amino acid sequence of SEQ ID NO:174;

xvi) a light chain variable domain comprising the amino acid sequence of SEQ ID NO:175 and heavy chain variable domain comprising the amino acid sequence of SEQ ID NO:176;

xvii) a light chain variable domain comprising the amino acid sequence of SEQ ID NO:177 and heavy chain variable domain comprising the amino acid sequence of SEQ ID NO:178;

xviii) a light chain variable domain comprising the amino acid sequence of SEQ ID NO:179 and heavy chain variable domain comprising the amino acid sequence of SEQ ID NO:180;

xix) a light chain variable domain comprising the amino acid sequence of SEQ ID NO:181 and heavy chain variable domain comprising the amino acid sequence of SEQ ID NO:182;

xx) a light chain variable domain comprising the amino acid sequence of SEQ ID NO:183 and heavy chain variable domain comprising the amino acid sequence of SEQ ID NO:184;

xxi) a light chain variable domain comprising the amino acid sequence of SEQ ID NO:185 and heavy chain variable domain comprising the amino acid sequence of SEQ ID NO:186;

xxii) a light chain variable domain comprising the amino acid sequence of SEQ ID NO:187 and heavy chain variable domain comprising the amino acid sequence of SEQ ID NO:188;

xxiii) a light chain variable domain comprising the amino acid sequence of SEQ ID NO:189 and heavy chain variable domain comprising the amino acid sequence of SEQ ID NO:190; and xxiv) a light chain variable domain comprising the amino acid sequence of SEQ ID NO:191 and heavy chain variable domain comprising the amino acid sequence of SEQ ID NO:192.

In some embodiments of the binding protein of the invention, the second antigen binding unit specifically binding to CD3 is selected from the group consisting of i)-vi):

i) an antigen binding unit comprising light chain CDRs comprising the amino acid sequences of SEQ ID NO:257 (CDR1), SEQ ID NO:258 (CDR2) and SEQ ID NO:259 (CDR3) and heavy chain CDRs comprising the amino acid sequences of SEQ ID NO:260 (CDR1), SEQ ID NO:261 (CDR2) and SEQ ID NO:262 (CDR3);

ii) an antigen binding unit comprising light chain CDRs comprising the amino acid sequences of SEQ ID NO:263 (CDR1), SEQ ID NO:264 (CDR2) and SEQ ID NO:265 (CDR3) and heavy chain CDRs comprising the amino acid sequences of SEQ ID NO:266 (CDR1), SEQ ID NO:267 (CDR2) and SEQ ID NO:268 (CDR3);

iii) an antigen binding unit comprising light chain CDRs comprising the amino acid sequences of SEQ ID NO:269 (CDR1), SEQ ID NO:270 (CDR2) and SEQ ID NO:271 (CDR3) and heavy chain CDRs comprising the amino acid sequences of SEQ ID NO:272 (CDR1), SEQ ID NO:273 (CDR2) and SEQ ID NO:274 (CDR3);

iv) an antigen binding unit comprising light chain CDRs comprising the amino acid sequences of SEQ ID NO:275 (CDR1), SEQ ID NO:276 (CDR2) and SEQ ID NO:277 (CDR3) and heavy chain CDRs comprising the amino acid sequences of SEQ ID NO:278 (CDR1), SEQ ID NO:279 (CDR2) and SEQ ID NO:280 (CDR3);

v) an antigen binding unit comprising light chain CDRs comprising the amino acid sequences of SEQ ID NO:281 (CDR1), SEQ ID NO:282 (CDR2) and SEQ ID NO:283 (CDR3) and heavy chain CDRs comprising the amino acid sequences of SEQ ID NO:284 (CDR1), SEQ ID NO:285 (CDR2) and SEQ ID NO:286 (CDR3); and vi) an antigen binding unit comprising light chain CDRs comprising the amino acid sequences of SEQ ID NO:287 (CDR1), SEQ ID NO:288 (CDR2) and SEQ ID NO:289 (CDR3) and heavy chain CDRs comprising the amino acid sequences of SEQ ID NO:290 (CDR1), SEQ ID NO:291 (CDR2) and SEQ ID NO:292 (CDR3).

In some embodiments of the binding protein of the invention, the second antigen binding unit specifically binding to CD3 is selected from the group consisting of i) to vi):

i) a light chain variable domain comprising the amino acid sequence of SEQ ID NO:293 and a heavy chain variable domain comprising the amino acid sequence of SEQ ID NO:294;

ii) a light chain variable domain comprising the amino acid sequence of SEQ ID NO:295 and a heavy chain variable domain comprising the amino acid sequence of SEQ ID NO:296;

iii) a light chain variable domain comprising the amino acid sequence of SEQ ID NO:297 and a heavy chain variable domain comprising the amino acid sequence of SEQ ID NO:298;

iv) a light chain variable domain comprising the amino acid sequence of SEQ ID NO:299 and a heavy chain variable domain comprising the amino acid sequence of SEQ ID NO:300;

v) a light chain variable domain comprising the amino acid sequence of SEQ ID NO:301 and a heavy chain variable domain comprising the amino acid sequence of SEQ ID NO:302; and vi) a light chain variable domain comprising the amino acid sequence of SEQ ID NO:303 and a heavy chain variable domain comprising the amino acid sequence of SEQ ID NO:304.

In some embodiments of the binding protein of the invention, the first antigen binding unit specifically binding to B7H6 comprises from its N- to C-terminus a first light chain variable domain, a first light chain constant domain, a first peptide linker, a first heavy chain variable domain and a first heavy chain constant CH1 domain; and the second antigen binding unit specifically binding to CD3 comprises from its N- to C-terminus a second light chain variable domain, a second light chain constant domain, a second peptide linker, a second heavy chain variable domain and a second heavy chain constant CH1 domain. In some embodiments of the binding protein of the invention, the first and/or second peptide linker comprises 26 to 42 amino acids, preferably any one of 30 to 40 amino acids, 34 to 40 amino acids, or 36 to 39 amino acids, more preferably 38 amino acids. In some embodiments of the invention, the first linker and/or second linker is a Gly-Ser linker, preferably comprising the amino acid sequence of SEQ ID NO:250, more preferably said first and second peptide linker comprise the same sequence (e.g. SEQ ID NO:250). In some embodiments of the invention, the first light chain constant domain and the second light chain constant domain comprise independently a human kappa or lambda domain.

In some embodiments, the first antigen binding unit specific for B7H6 of the binding protein of the invention comprises an amino acid sequence selected from the group consisting of SEQ ID NO:193, SEQ ID NO:194, SEQ ID NO:195, SEQ ID NO:196 SEQ ID NO:197 SEQ ID NO:198 SEQ ID NO:199 SEQ ID NO:200 SEQ ID NO:201 SEQ ID NO:202 SEQ ID NO:203 SEQ ID NO:204 SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, and SEQ ID NO:216 and the second antigen binding unit specific for CD3 comprises an amino acid sequence selected from the group consisting of SEQ ID NO:305, SEQ ID NO:306, SEQ ID NO:307, SEQ ID NO:308, SEQ ID NO:309, and SEQ ID NO:310, preferably SEQ ID NO:305.

In some embodiments, the binding protein of the invention further comprises a first and a second Fc domain, wherein said first Fc domain is covalently linked to said first antigen binding unit, preferably to the C-terminus of said first antigen binding unit, and said second Fc domain is covalently linked to said second antigen binding unit, preferably to the C-terminus of said second antigen binding unit.

In some embodiments of the invention, i) the first Fc domain comprises a tyrosine (Y) at position 366 [T366Y], and the second Fc domain comprises a threonine (T) at position 407 [Y407T], or ii) the first Fc domain comprises a tryptophan (W) at position 366 [T366W], and the second Fc domain comprises a serine (S) at position 366 [T366S], an alanine (A) at position 368 [L368A] and a valine (V) at position 407 [Y407V], or iii) the second Fc domain comprises a tyrosine (Y) at position 366 [T366Y], and the first Fc domain comprises a threonine (T) at position 407 [Y407T], or iv) the second Fc domain comprises a tryptophan (W) at position 366 [T366W], and the first Fc domain comprises a serine (S) at position 366 [T366S], an alanine (A) at position 368 [L368A] and a valine (V) at position 407 [Y407V], preferably wherein the first or the second Fc domain further comprises an arginine at position 435 [H435R] and a phenylalanine at position 436 [Y436F]. In some embodiments, the first and/or second Fc domain comprises an alanine at position 234 [L234A] and at position 235 [L235A].

In some embodiments, the binding protein of the invention comprises a first polypeptide chain specifically binding to B7H6 comprising an amino acid sequence selected from the group consisting of SEQ ID NO:217, SEQ ID NO:218, SEQ ID NO:219, SEQ ID NO:220, SEQ ID NO:221, SEQ ID NO:222, SEQ ID NO:223, SEQ ID NO; 224, SEQ ID NO:225, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, and SEQ ID NO:240 and a second polypeptide chain specifically binding to CD3 comprising the amino acid sequence selected from the group consisting of SEQ ID NO:311, SEQ ID NO:312, SEQ ID NO:313, SEQ ID NO:314, SEQ ID NO:315, and SEQ ID NO:316, preferably SEQ ID NO:311.

In a further aspect, the invention provides an isolated nucleic acid molecule i) encoding a first antigen binding unit and/or a second antigen binding unit of a binding protein of the invention, optionally further encoding a first and/or a second Fc domain, or ii) encoding the first and/or the second polypeptide chain of binding protein of the invention. In further aspects provided herein are expression vectors comprising the nucleic acid molecule of the invention, host cells transfected with such expression vectors, and methods of manufacturing a protein of the invention.

In a further aspect of the invention, provided herein is a multi-specific binding protein comprising a first polypeptide chain specifically binding to B7H6 and a second polypeptide chain specifically binding to CD3, where the first polypeptide chain comprises a first light chain, a first linker, and a first heavy chain and the second polypeptide chain comprises a second light chain, a second linker, and a second heavy chain, preferably the C-terminus of the first light chain is covalently bound to the N-terminus of the first heavy chain via the first peptide linker and the C-terminus of the second light chain is covalently bound to the N-terminus of the second heavy chain via the second peptide linker. The skilled person would understand that any reference herein to a "light chain" or "heavy chain" refers to an antibody light chain or antibody heavy chain, respectively.

In some embodiments of the protein of the invention, the first polypeptide chain specifically binding to B7H6 comprises a light chain variable and heavy chain variable domain comprising CDR sequences, VH/VL sequences and/or single chain Fab sequences as defined for the antigen binding units of any one of B7H6 #1, B7H6 #2, B7H6 #3, B7H6 #4, B7H6 #5, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23 and B7H6 #24 described herein. In some embodiments, the second polypeptide chain specifically binding to CD3 comprises a light chain variable and heavy chain variable domain comprising CDR sequences, VH/VL sequences and/or scFab sequences as defined for the antigen binding units of CD3 #1, as described herein.

Further aspects, embodiments, uses and methods involving the binding proteins of the invention will become clear from the following detailed description of the invention and from the appended claims.

The invention provides for novel binding proteins that allow a more efficient treatment of B7H6 expressing cancers, such as (metastatic) colorectal cancer ((m)CRC), non-small cell lung cancer (NSCLC), or head and neck squamous cell carcinoma (HNSCC).

DETAILED DESCRIPTION OF THE INVENTION

Used Terms and Definitions

Figure 1:
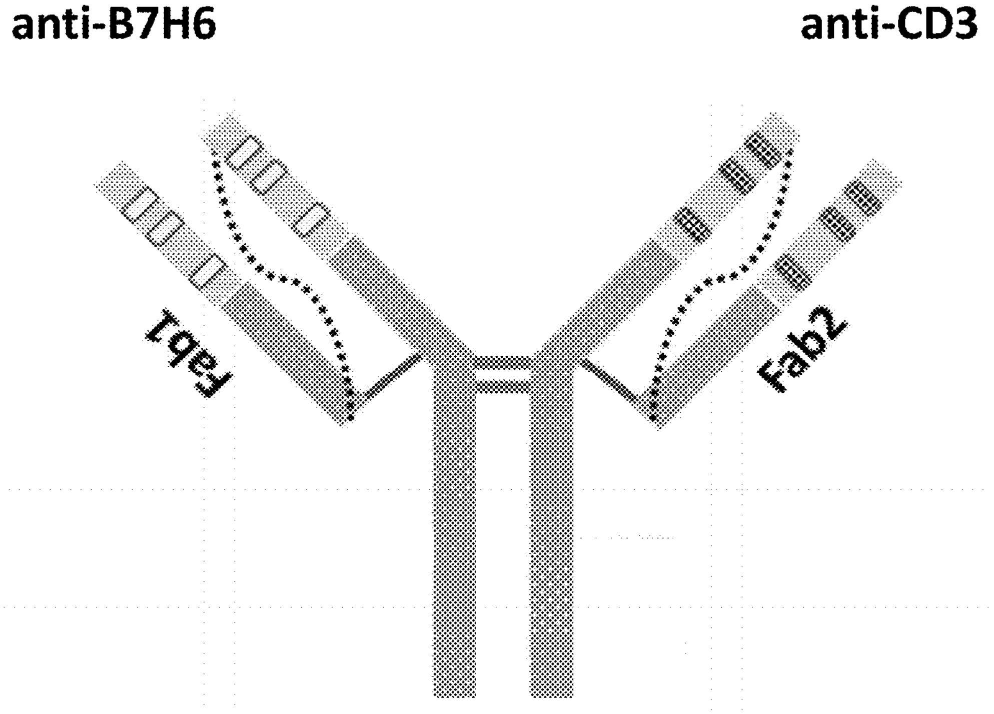
FIG. 1: Schematic representation of a bispecific binding protein of the invention

The above and other aspects and embodiments of the invention will become clear from the further description herein, in which:

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Roitt et al., "Immunology" (2nd Ed.), Gower Medical Publishing, London, New York (1989), as well as to the general background art cited herein. Furthermore, unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

When used herein the term "comprising" and variations thereof such as "comprises" and "comprise" can be substituted with the term "containing" or "including" or "having."

The term "sequence" as used herein (for example in terms like "heavy/light chain sequence", "antibody sequence", "variable domain sequence", "constant domain sequence" or "protein sequence"), should generally be understood to include both the relevant amino acid sequence as well as nucleic acid sequences or nucleotide sequences encoding the same, unless the context requires a more limited interpretation.

The term "antigen binding unit" as used herein comprises the minimal structural requirements derived from an antibody (i.e., the minimal structural requirements typically present in an antibody) which allow for binding to its specific target or antigen. Thus, an antigen binding unit comprises at least the three light chain and three heavy chain CDR sequences; preferably it comprises at least a light chain variable domain and a heavy chain variable domain.

The generalized structure of an antibody or immunoglobulin is well known to those of skill in the art. These molecules are heterotetrameric glycoproteins, typically of about 150,000 daltons, composed of two identical light (L) chains and two identical heavy (H) chains and are typically referred to as full length antibodies. Each light chain is covalently linked to a heavy chain by one disulfide bond to form a heterodimer, and the heterotetrameric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the N-terminus a variable domain (VH), followed by three or four (in case of IgE) constant domains (CH1, CH2, CH3, and CH4), as well as a hinge region between CH1 and CH2. Each light chain has two domains, an N-terminal variable domain (VL) and a C-terminal constant domain (CL). The VL domain associates non-covalently with the VH domain, whereas the CL domain is commonly covalently linked to the CH1 domain via a disulfide bond. Particular amino acid residues are believed to form an interface between the light and heavy chain variable domains (Chothia et al., 1985, J. Mol. Biol. 186:651-663). Variable domains are also referred to herein as variable regions or Fv and denote the part that confers specificity to an antibody for the antigen by carrying the antigen-binding site.

The "light chain variable domain" (or "light chain variable region") and "heavy chain variable domain" (or "heavy chain variable region") as used herein have the same general structure and each domain essentially consists of four framework (FR) regions whose sequences are widely conserved, which are referred to in the art and herein below as "framework region 1" or "FR1"; as "framework region 2" or "FR2"; as "framework region 3" or "1-R3"; and as "framework region 4" or "1-R4", respectively; which framework regions are interrupted by three hypervariable regions, HVRs (or CDRs), which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-1-R2-CDR2-FR3-CDR3-1-R4. The framework regions adopt a beta-sheet conformation and the CDRs may form loops connecting the beta-sheet structure. The CDRs in each chain are held in their three-dimensional structure by the framework regions and form together with the CDRs from the other chain the antigen binding site.

Various definitions of CDRs are known in the art, for example, the definition based on CCG, also referred to as IMGT (Lefranc M P, Pommié C, Ruiz M, Giudicelli V, Foulquier E, Truong L, Thouvenin-Contet V, Lefranc G. "IMGT unique numbering for immunoglobulin and T cell receptor variable domains and Ig superfamily V-like domains." Dev Comp Immunol. 2003 January; 27(1):55-77; Giudicelli V, Brochet X, Lefranc M P. "IMGT/V-QUEST: IMGT standardized analysis of the immunoglobulin (IG) and T cell receptor (TR) nucleotide sequences". Cold Spring Harb Protoc. 2011; 2011(6):695-715) or the definition based on Chothia (Chothia and Lesk, J. Mol. Biol. 1987, 196: 901-917), together with Kabat (E. A. Kabat, T. T. Wu, H. Bilofsky, M. Reid-Miller and H. Perry, Sequence of Proteins of Immunological Interest, National Institutes of Health, Bethesda (1983)). Within the context of this invention, reference to CDR's is based on the definition of CCG (IMGT).

The term "constant domains" or "constant region" as used within the current application denotes the sum of the domains of an antibody other than the variable region. Such constant domains and regions are well known in the state of the art and e.g. described by Kabat et al. ("Sequence of proteins of immunological interest", US Public Health Services, NIH Bethesda, Md., Publication No. 91-3242 (1991)). Depending on the amino acid sequence of the constant region of their heavy chains, antibodies or immunoglobulins are divided in the classes: IgA, IgD, IgE, IgG and IgM. According to the heavy chain constant regions the different classes of immunoglobulins are called α, δ, ε, γ, and μ respectively. Several of these may be further divided into subclasses (isotypes), e.g. IgG1, IgG2, IgG3, and IgG4, IgA1, and IgA2.

The "Fc part" or "Fc domain" of an antibody is not involved directly in binding of an antibody to an antigen, but exhibits various effector functions. An "Fc part/domain of an antibody" is a term well known to the skilled artisan and defined on the basis of papain cleavage of antibodies. The Fc part of an antibody is directly involved in ADCC (antibody dependent cell-mediated cytotoxicity) and CDC (complement-dependent cytotoxicity) based on complement activation, Clq binding and Fc receptor binding. Complement activation (CDC) is initiated by binding of complement factor Clq to the Fc part of most IgG antibody subclasses. While the influence of an antibody on the complement system is dependent on certain conditions, binding to Clq is caused by defined binding sites in the Fc part. Such binding sites are e.g. L234, L235, D270, N297, E318, K320, K322, P331 and P329 (numbering according to Eu numbering (Edelman et al, Proc Natl Acad Sci USA. 1969 May; 63(1):78-85)). Most crucial among these residues in mediating Clq and Fcgamma receptor binding in IgG1 are L234 and L235 (Hezareh et al., J. Virology 75 (2001) 12161-12168, Shields et al (2001) JBC, 276 (9): 6591-6604). Antibodies of subclass IgG1 and IgG3 usually show complement activation and Clq and C3 binding, whereas IgG2 and IgG4 do not activate the complement system and do not bind Clq and C3.

The term "antibody" or "antibody molecule" (used synonymously herein) encompasses a monoclonal antibody, a polyclonal antibody, a human antibody, a humanized antibody, a sequence-optimized antibody, a chimeric antibody, multispecific antibodies (e.g., bispecific antibodies), a fragment of an antibody, in particular a Fv, Fab, Fab', or F(ab')2 fragment, a single chain antibody, in particular a single chain variable fragment (scFv), a single chain Fab fragment (scFab), a Small Modular Immunopharmaceutical (SMIP), a domain antibody, a Nanobody®, a diabody. The antibody may have an effector function, such as ADCC or CDC, that is usually mediated by the Fc part of the antibody, or it may have no effector function, e.g. by lacking a Fc part or having a blocked, masked Fc part, in essence a Fc part that is not or insufficiently recognized by immune cells or immune system components, like the complement system.

Monoclonal antibodies (mAb) are monospecific antibodies that are identical in amino acid sequence. They may be produced by hybridoma technology from a hybrid cell line (called hybridoma) representing a clone of a fusion of a specific antibody-producing B cell with a myeloma (B cell cancer) cell (Kohler G, Milstein C. Continuous cultures of fused cells secreting antibody of predefined specificity. Nature 1975; 256:495-7.). Alternatively, monoclonal antibodies may be produced by recombinant expression in host cells (Norderhaug L, Olafsen T, Michaelsen T E, Sandlie I. (May 1997). "Versatile vectors for transient and stable expression of recombinant antibody molecules in mammalian cells." J Immunol Methods 204 (1): 77-87; see also below). A "recombinant antibody" or "recombinant binding protein" is an antibody or binding protein which has been produced by a recombinantly engineered host cell. It is optionally isolated or purified.

Antibody molecules according to the present invention also include fragments of immunoglobulins which retain antigen binding properties, like Fab, Fab', or F(ab')2 fragments. Such fragments may be obtained by fragmentation of immunoglobulins e.g. by proteolytic digestion, or by recombinant expression of such fragments. For example, immunoglobulin digestion can be accomplished by means of routine techniques, e.g. using papain or pepsin (WO 94/29348). Papain digestion of antibodies typically produces two identical antigen binding fragments (Fabs). A Fab fragment is composed of one constant and one variable domain of each of the heavy and the light chain. Pepsin treatment yields an F(ab')2. In Fab fragments, the variable domains are each fused to an immunoglobulin constant domain, preferably of human origin. Thus, the heavy chain variable domain is fused to a CH1 domain (a so-called Fd fragment), and the light chain variable domain is fused to a CL domain. Fab fragments may be produced by recombinant expression of respective nucleic acids in host cells, see below.

A number of technologies have been developed for placing variable domains of immunoglobulins, or molecules derived from such variable domains, in a different molecular context. Those should also be considered as "antibodies" or "antibody molecules" in accordance with the present invention. In general, these antibody molecules are smaller in size compared to immunoglobulins, and may comprise a single amino acid chain or several amino acid chains. For example, a "single-chain variable fragment (scFv)" is a fusion of the variable regions of the heavy and light chains of immunoglobulins, linked together with a short linker, usually serine (S) or glycine (G) (WO 88/01649; WO 91/17271; Huston et al; International Reviews of Immunology, Volume 10, 1993, 195-217). "Single domain antibodies" or a "Nanobody®" harbour an antigen-binding site in a single Ig-like domain (WO 94/04678; WO 03/050531, Ward et al., Nature. 1989 Oct. 12; 341(6242):544-6; Revets et al., Expert Opin Biol Ther. 5(1):111-24, 2005). One or more single domain antibodies with binding specificity for the same or a different antigen may be linked together. "Diabodies" are bivalent antibody molecules consisting of two amino acid chains comprising two variable domains (WO 94/13804, Holliger et al., Proc Natl Acad Sci USA. 1993 Jul. 15; 90(14):6444-8). Other examples of antibody-like molecules are "immunoglobulin super family antibodies" (IgSF; Srinivasan and Roeske, Current Protein Pept. Sci. 2005, 6(2): 185-96). A different concept leads to the so-called "Small Modular Immunopharmaceutical (SMIP)" which comprises a Fv domain linked to single-chain hinge and effector domains devoid of the constant domain CH1 (WO 02/056910). A "single-chain Fab" or "scFab" is a fusion of a light chain Fab domain (i.e. a light chain variable domain (VL) that is linked to one light chain constant domain (CL)) with a heavy chain Fab domain (i.e. a heavy chain variable domain (VH) that is linked to one heavy chain constant domain (CH1)). The single chain Fab is capable of recognizing and binding an antigen. The scFab may optionally also contain a linker (e.g., a peptide linker) positioned between the CL and VH domain (Hust et al. BMC Biotechnology 2007, 7:14).

For application in man, it is often desirable to reduce immunogenicity of therapeutic molecules, such as antibodies or binding proteins comprising an antigen binding unit as described herein, originally derived from other species, like mouse. This can be done by construction of chimeric antibodies/binding proteins, or by a process called "humanization". In this context, a "chimeric antibody"; or "chimeric antigen binding unit" is understood to be an antibody or an antigen binding unit comprising a sequence part (e.g. a variable domain) derived from one species (e.g. mouse) fused to a sequence part (e.g. the constant domains) derived from a different species (e.g. human) In this context, a "humanized antibody", "humanized antigen binding unit" or a "a humanized VL/VH domain" is an antibody, antigen binding unit or VH/VL domain comprising a variable domain originally derived from a non-human species, wherein certain amino acids have been mutated to make the overall sequence of that variable domain more closely resemble a sequence of a human variable domain. Methods of humanization of antibodies are well-known in the art (Billetta R, Lobuglio A F. "Chimeric antibodies". Int Rev Immunol. 1993; 10(2-3):165-76; Riechmann L, Clark M, Waldmann H, Winter G (1988). "Reshaping human antibodies for therapy". Nature: 332:323).

The terms "human antibody", "human antigen binding unit", or "human VH/VL domain" as used herein, include antibodies, antigen binding units or VH/VL domains having variable (and constant, if applicable) regions derived from human germline immunoglobulin sequences. The term "human antibody", "human antigen binding unit", or "human VH/VL domain" as used herein, is not intended to include antibodies in which CDR sequences derived from the germline of another (mammalian) species, such as a mouse, rat or rabbit, have been grafted onto human framework sequences. Thus, as used herein, the terms "human antibody", "human antigen binding unit", or "human VH/VL domain" refer to an antibody, antigen binding unit or VH/VL domain in which every part of the protein (e.g., CDR, framework, CL, CH domains (e.g., CH1, CH2, CH3), hinge, VL, VH) is substantially non-immunogenic in humans, with only minor sequence changes or variations as further described herein below.

Technologies for creating such "human antibodies", "human antigen binding units", or "human VH/VL domains" have been described and include without being limiting phage display or use of transgenic animals (WWW-.Ablexis.com/technology-alivamab.php; WO 90/05144; D. Marks, H. R. Hoogenboom, T. P. Bonnert, J. McCafferty, A. D. Griffiths and G. Winter (1991) "By-passing immunisation. Human antibodies from V-gene libraries displayed on phage." J. Mol. Biol., 222, 581-597; Knappik et al., J. Mol. Biol. 296: 57-86, 2000; S. Carmen and L. Jermutus, "Concepts in antibody phage display". Briefings in Functional Genomics and Proteomics 2002 1(2):189-203; Lonberg N, Huszar D. "Human antibodies from transgenic mice". Int Rev Immunol. 1995; 13(1):65-93; Brüggemann M, Taussig M J. "Production of human antibody repertoires in transgenic mice". Curr Opin Biotechnol. 1997 August; 8(4):455-8).

Thus, a human antibody, human antigen binding unit or human VH/VL domain is distinct from e.g., a chimeric or humanized antibody. It is pointed out that a human antibody, human antigen binding unit or human VH/VL domain can be produced by a non-human animal or prokaryotic or eukaryotic cell that is capable of expressing functionally rearranged human immunoglobulin (e.g., heavy chain and/or light chain) genes.

The chimeric, humanized or human antibodies, antigen binding units, or VH/VL domains of the present invention may further be optimized; also referred to herein as "optimized" or "sequence-optimized" antibodies, antigen binding units, or VH/VL domains. Such optimization includes without limitation the removal or exchange of undesired amino acids, for example to reduce immunogenicity in humans, or to avoid deamidation, undesirable charges or lipophilicity or non-specific binding. Such removal or exchange of undesired amino acids can, for example, be introduced by random or site-specific mutagenesis in vitro or by somatic mutation in vivo. Moreover, in connection with chimeric or humanized antibodies, antigen binding units or VH/VL domains, it will be understood that certain mouse FR residues may be important to the function of the optimized antibodies, antigen binding units and VH/VL domains. Therefore these important amino acid residues may be retained in an optimized antibody, antigen binding unit and VH/VL domain.

The term "monomer" refers to a homogenous form of an antibody or a multispecific protein as described herein. For example, for a full-length antibody, monomer means a monomeric antibody having two identical heavy chains and two identical light chains. In the context of the present invention, a monomer means a protein of the present invention having a single antigen binding unit specific for B7H6, and a single antigen binding unit specific for CD3 as described herein. For example, a monomer of a binding protein described herein may have two polypeptide chains, a first polypeptide chain comprising a single chain Fab specific for B7H6 and a first Fc domain and a second polypeptide chain comprising a single chain Fab specific for CD3 and a second Fc domain.

An epitope is a region of an antigen that is bound by an antibody or antigen binding moiety (e.g. the antigen binding unit of the proteins described herein). The term "epitope" includes any polypeptide determinant capable of specific binding to an antibody or antigen binding moiety. In certain embodiments, epitope determinants include chemically active surface groupings of molecules such as amino acids, glycan side chains, phosphoryl, or sulfonyl, and, in certain embodiments, may have specific three dimensional structural characteristics, and/or specific charge characteristics. Conformational and non-conformational epitopes are distinguished in that the binding to the former but not the latter is lost in the presence of denaturing solvents.

An antigen binding molecule/protein (such as an immunoglobulin, an antibody, an antigen binding unit, or a fragment of such antigen binding molecule/protein) that can "bind", "bind to", "specifically bind", or "specifically bind to", is "binding (to)" or "specifically binding to" that "has affinity for", "is specific for" and/or that "has specificity for" a certain epitope, antigen or protein (or for at least one part, fragment or epitope thereof) is said to be "against" or "directed against" said epitope, antigen or protein or is a "binding" molecule/protein with respect to such epitope, antigen or protein. These terms are used herein interchangeably.

As used herein, the terms "binding" and "specific binding" refer to the binding of an antigen binding molecule/protein (such as an immunoglobulin, an antibody, an antigen binding unit, or a fragment of such antigen binding molecule/protein) to an epitope of the antigen in an in vitro assay, preferably in a plasmon resonance assay ((Malmqvist M., "Surface plasmon resonance for detection and measurement of antibody-antigen affinity and kinetics.", Curr Opin Immunol. 1993 April; 5(2):282-6)) with purified wild-type antigen. Antibody affinity can also be measured using kinetic exclusion assay (KinExA) technology (Darling, R. J., and Brault P-A., "Kinetic exclusion assay technology: Characterization of Molecular Interactions." ASSAY and Drug Development Technologies. 2004, December 2(6): 647-657). For example, a binding protein or protein of the invention binds to an epitope of B7H6 with its first antigen binding unit/first polypeptide chain and to an epitope of CD3 with its second antigen binding unit/second polypeptide chain.

Generally, the term "specificity" refers to the number of different types of antigens or epitopes to which a particular antigen binding molecule/protein (such as an immunoglobulin, an antibody, an antigen binding unit, or a fragment of such antigen binding molecule/protein) can bind. Binding specificity for B7H6 means that the antigen binding protein/molecule of the invention (e.g. the first antigen binding unit of such binding protein) has a significantly higher binding affinity to B7H6 than to structurally unrelated molecules. Binding specificity for CD3 means that the antigen binding protein/molecule of the invention (e.g. the second antigen binding unit of such binding protein) has a significantly higher binding affinity to CD3 than to structurally unrelated molecules. The specificity of an antigen-binding molecule/protein can be determined based on its affinity and/or avidity. The affinity, represented by the equilibrium constant for the dissociation of an antigen with an antigen-binding protein ($K_D$), is a measure for the binding strength between an epitope and an antigen-binding site on the antigen-binding molecule/protein: the lesser the value of the $K_D$, the stronger the binding strength between an epitope and the antigen-binding site (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule/protein (such as an immunoglobulin, an antibody, an antigen binding unit, or fragment of such antigen binding molecule/protein) and the pertinent antigen. Avidity is related to both the affinity between an epitope and its antigen binding site on the antigen-binding molecule/protein and the number of pertinent binding sites present on the antigen-binding molecule/protein.

When referring to an antigen binding unit/antigen, ligand/receptor, or other binding pair, the term “specifically binds” or “selectively binds” indicates a binding reaction which is determinative of the presence of the protein in a heterogeneous population of proteins and other biologics. Thus, under designated conditions, a specified antigen binding unit binds to a particular antigen and does not bind in a significant amount to other proteins present in the sample. The antigen binding unit binds to its antigen with an affinity that is at least two fold greater, preferably at least ten times greater, more preferably at least 20-times greater, and most preferably at least 100-times greater under the designated conditions than the affinity with unrelated antigens.

The term “isolated,” as used herein, refers to material that is removed from its original or native environment (e.g. the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature. For example, a nucleic acid, protein/polypeptide molecule is considered to be “(in) essentially isolated (form)”—when compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or protein/polypeptide molecule is considered “essentially isolated” when it has been purified at least 2-fold, in particular at least 10-fold, more in particular at least 100-fold, and up to 1000-fold or more. A nucleic acid or protein/polypeptide molecule that is “in essentially isolated form” is preferably essentially homogeneous, as determined using a suitable technique, such as a suitable chromatographical technique, e.g., polyacrylamide-gel electrophoresis.

As used herein, the terms “identical” or “percent identity,” in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader (signal peptide) and/or constant domain sequences are not considered. For sequence comparisons between two sequences, a “corresponding” CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to a protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

The term “covalently linked” or “covalently bound” as used herein means either a direct covalent bond between residues, or an indirect link/bond where two residues are not directly bonded but are both covalently bonded to an intermediate molecule or domain, e.g. an intermediate domain of an immunoglobulin or a linker.

Multi-Specific Binding Proteins of the Invention

The present invention provides multi-specific binding proteins comprising at least one antigen binding unit specifically binding to B7H6 (a first antigen binding unit), and at least one antigen binding unit specifically binding to CD3 (a second antigen binding unit). Through simultaneous binding to a tumor cell antigen and CD3 on a T cell, the binding proteins act as T cell activating proteins and are also referred to herein as T cell engagers. The term “(multi-specific) binding protein” is used herein interchangeably with the term “(multi-specific) binding molecule”. Further terms used herein to refer to the multi-specific binding protein of the invention are “protein of the invention”, “binding protein of the invention”, “antigen-binding protein” as well as “multi-specific protein”.

The inventors have surprisingly found that multi-specific binding proteins of the invention is induce potent and selective lysis of B7H6-positive colorectal cancer cell lines in the presence of T cells and are already active at low effector to target cell ratios. Importantly, the binding proteins of the invention do not lyse B7H6-negative cells and do not cause T cell activation, T cell proliferation, and cytokine secretion in the absence of B7H6-positive cells. Notably, proteins of the invention that do not inhibit B7H6-dependent NK cell activation via NKp30 in vitro, are more potent in lysing B7H6-positive tumor cells. This activity is described, for example, in the in vitro assay in Example 11.

For avoidance of doubt, B7H6 as used herein refers to human B7H6 of UniProt Q68D85 and the nucleic acid sequence encoding that protein. CD3 as used herein refers to human CD3epsilon (UniProt P07766) and CD3 gamma (Uniprot: P09693) complexes, (human CD3εγ complexes). The skilled person would appreciate that the terms B7H6 and B7-H6 are used interchangeably herein.

In one aspect, the multi-specific binding protein of the invention comprises a first antigen binding unit specifically binding to B7H6 and a second antigen binding unit specifically binding to CD3, wherein said first binding unit is selected from the group consisting of i) to xxiv):

i) an antigen binding unit comprising light chain CDRs comprising the amino acid sequences of SEQ ID NO:1 (CDR1), SEQ ID NO:2 (CDR2) and SEQ ID NO:3 (CDR3) and heavy chain CDRs comprising the amino acid sequences of SEQ ID NO:4 (CDR1), SEQ ID NO:5 (CDR2) and SEQ ID NO:6 (CDR3) (antigen binding unit B7H6 #1);

ii) an antigen binding unit comprising light chain CDRs comprising the amino acid sequences of SEQ ID NO:7 (CDR1), SEQ ID NO:8 (CDR2) and SEQ ID NO:9 (CDR3) and heavy chain CDRs comprising the amino acid sequences of SEQ ID NO:10 (CDR1), SEQ ID NO:11 (CDR2) and SEQ ID NO:12 (CDR3) (antigen binding unit B7H6 #2);

iii) an antigen binding unit comprising light chain CDRs comprising the amino acid sequences of SEQ ID NO:13 (CDR1), SEQ ID NO:14 (CDR2) and SEQ ID NO:15 (CDR3) and heavy chain CDRs comprising the amino acid sequences of SEQ ID NO:16 (CDR1), SEQ ID NO:17 (CDR2) and SEQ ID NO:18 (CDR3) (antigen binding unit B7H6 #3);

iv) an antigen binding unit comprising light chain CDRs comprising the amino acid sequences of SEQ ID NO:19 (CDR1), SEQ ID NO:20 (CDR2) and SEQ ID NO:21 (CDR3) and heavy chain CDRs comprising the amino acid sequences of SEQ ID NO:22 (CDR1), SEQ ID NO:23 (CDR2) and SEQ ID NO:24 (CDR3) (antigen binding unit B7H6 #4);

v) an antigen binding unit comprising light chain CDRs comprising the amino acid sequences of SEQ ID NO:25 (CDR1), SEQ ID NO:26 (CDR2) and SEQ ID NO:27 (CDR3) and heavy chain CDRs comprising the amino acid sequences of SEQ ID NO:28 (CDR1), SEQ ID NO:29 (CDR2) and SEQ ID NO:30 (CDR3) (antigen binding unit B7H6 #5);

vi) an antigen binding unit comprising light chain CDRs comprising the amino acid sequences of SEQ ID NO:31 (CDR1), SEQ ID NO:32 (CDR2) and SEQ ID NO:33 (CDR3) and heavy chain CDRs comprising the amino acid sequences of SEQ ID NO:34 (CDR1), SEQ ID NO:35 (CDR2) and SEQ ID NO:36 (CDR3) (antigen binding unit B7H6 #6);

vii) an antigen binding unit comprising light chain CDRs comprising the amino acid sequences of SEQ ID NO:37 (CDR1), SEQ ID NO:38 (CDR2) and SEQ ID NO:39 (CDR3) and heavy chain CDRs comprising the amino acid sequences of SEQ ID NO:40 (CDR1), SEQ ID NO:41 (CDR2) and SEQ ID NO:42 (CDR3) (antigen binding unit B7H6 #7);

viii) an antigen binding unit comprising light chain CDRs comprising the amino acid sequences of SEQ ID NO:43 (CDR1), SEQ ID NO:44 (CDR2) and SEQ ID NO:45 (CDR3) and heavy chain CDRs comprising the amino acid sequences of SEQ ID NO:46 (CDR1), SEQ ID NO:47 (CDR2) and SEQ ID NO:48 (CDR3) (antigen binding unit B7H6 #8);

ix) an antigen binding unit comprising light chain CDRs comprising the amino acid sequences of SEQ ID NO:49 (CDR1), SEQ ID NO:50 (CDR2) and SEQ ID NO:51 (CDR3) and heavy chain CDRs comprising the amino acid sequences of SEQ ID NO:52 (CDR1), SEQ ID NO:53 (CDR2) and SEQ ID NO:54 (CDR3) (antigen binding unit B7H6 #9);

x) an antigen binding unit comprising light chain CDRs comprising the amino acid sequences of SEQ ID NO:55 (CDR1), SEQ ID NO:56 (CDR2) and SEQ ID NO:57 (CDR3) and heavy chain CDRs comprising the amino acid sequences of SEQ ID NO:58 (CDR1), SEQ ID NO:59 (CDR2) and SEQ ID NO:60 (CDR3) (antigen binding unit B7H6 #10);

xi) an antigen binding unit comprising light chain CDRs comprising the amino acid sequences of SEQ ID NO:61 (CDR1), SEQ ID NO:62 (CDR2) and SEQ ID NO:63 (CDR3) and heavy chain CDRs comprising the amino acid sequences of SEQ ID NO:64 (CDR1), SEQ ID NO:65 (CDR2) and SEQ ID NO:66 (CDR3) (antigen binding unit B7H6 #11);

xii) an antigen binding unit comprising light chain CDRs comprising the amino acid sequences of SEQ ID NO:67 (CDR1), SEQ ID NO:68 (CDR2) and SEQ ID NO:69 (CDR3) and heavy chain CDRs comprising the amino acid sequences of SEQ ID NO:70 (CDR1), SEQ ID NO:71 (CDR2) and SEQ ID NO:72 (CDR3 (antigen binding unit B7H6 #12));

xiii) an antigen binding unit comprising light chain CDRs comprising the amino acid sequences of SEQ ID NO:73 (CDR1), SEQ ID NO:74 (CDR2) and SEQ ID NO:75 (CDR3) and heavy chain CDRs comprising the amino acid sequences of SEQ ID NO:76 (CDR1), SEQ ID NO:77 (CDR2) and SEQ ID NO:78 (CDR3) (antigen binding unit B7H6 #13);

xiv) an antigen binding unit comprising light chain CDRs comprising the amino acid sequences of SEQ ID NO:79 (CDR1), SEQ ID NO:80 (CDR2) and SEQ ID NO:81 (CDR3) and heavy chain CDRs comprising the amino acid sequences of SEQ ID NO:82 (CDR1), SEQ ID NO:83 (CDR2) and SEQ ID NO:84 (CDR3) (antigen binding unit B7H6 #14);

xv) an antigen binding unit comprising light chain CDRs comprising the amino acid sequences of SEQ ID NO:85 (CDR1), SEQ ID NO:86 (CDR2) and SEQ ID NO:87 (CDR3) and heavy chain CDRs comprising the amino acid sequences of SEQ ID NO:88 (CDR1), SEQ ID NO:89 (CDR2) and SEQ ID NO:90 (CDR3) (antigen binding unit B7H6 #15);

xvi) an antigen binding unit comprising light chain CDRs comprising the amino acid sequences of SEQ ID NO:91 (CDR1), SEQ ID NO:92 (CDR2) and SEQ ID NO:93 (CDR3) and heavy chain CDRs comprising the amino acid sequences of SEQ ID NO:94 (CDR1), SEQ ID NO:95 (CDR2) and SEQ ID NO:96 (CDR3) (antigen binding unit B7H6 #16);

xvii) an antigen binding unit comprising light chain CDRs comprising the amino acid sequences of SEQ ID NO:97 (CDR1), SEQ ID NO:98 (CDR2) and SEQ ID NO:99 (CDR3) and heavy chain CDRs comprising the amino acid sequences of SEQ ID NO:100 (CDR1), SEQ ID NO:101 (CDR2) and SEQ ID NO:102 (CDR3) (antigen binding unit B7H6 #17);

xviii) an antigen binding unit comprising light chain CDRs comprising the amino acid sequences of SEQ ID NO:103 (CDR1), SEQ ID NO:104 (CDR2) and SEQ ID NO:105 (CDR3) and heavy chain CDRs comprising the amino acid sequences of SEQ ID NO:106 (CDR1), SEQ ID NO:107 (CDR2) and SEQ ID NO:108 (CDR3) (antigen binding unit B7H6 #18);

xix) an antigen binding unit comprising light chain CDRs comprising the amino acid sequences of SEQ ID NO:109 (CDR1), SEQ ID NO:110 (CDR2) and SEQ ID NO:111 (CDR3) and heavy chain CDRs comprising the amino acid sequences of SEQ ID NO:112 (CDR1), SEQ ID NO:113 (CDR2) and SEQ ID NO:114 (CDR3) (antigen binding unit B7H6 #19);

xx) an antigen binding unit comprising light chain CDRs comprising the amino acid sequences of SEQ ID NO:115 (CDR1), SEQ ID NO:116 (CDR2) and SEQ ID NO:117 (CDR3) and heavy chain CDRs comprising the amino acid sequences of SEQ ID NO:118 (CDR1), SEQ ID NO:119 (CDR2) and SEQ ID NO:120 (CDR3) (antigen binding unit B7H6 #20);

xxi) an antigen binding unit comprising light chain CDRs comprising the amino acid sequences of SEQ ID NO:121 (CDR1), SEQ ID NO:122 (CDR2) and SEQ ID NO:123 (CDR3) and heavy chain CDRs comprising the amino acid sequences of SEQ ID NO:124 (CDR1), SEQ ID NO:125 (CDR2) and SEQ ID NO:126 (CDR3) (antigen binding unit B7H6 #21);

xxii) an antigen binding unit comprising light chain CDRs comprising the amino acid sequences of SEQ ID NO:127 (CDR1), SEQ ID NO:128 (CDR2) and SEQ ID NO:129 (CDR3) and heavy chain CDRs comprising the amino acid sequences of SEQ ID NO:130 (CDR1), SEQ ID NO:131 (CDR2) and SEQ ID NO:132 (CDR3) (antigen binding unit B7H6 #22);

xxiii) an antigen binding unit comprising light chain CDRs comprising the amino acid sequences of SEQ ID NO:133 (CDR1), SEQ ID NO:134 (CDR2) and SEQ ID NO:135 (CDR3) and heavy chain CDRs comprising the amino acid sequences of SEQ ID NO:136 (CDR1), SEQ ID NO:137 (CDR2) and SEQ ID NO:138 (CDR3) (antigen binding unit B7H6 #23); and xxiv) an antigen binding unit comprising light chain CDRs comprising the amino acid sequences of SEQ ID NO:139 (CDR1), SEQ ID NO:140 (CDR2) and SEQ ID NO:141 (CDR3) and heavy chain CDRs comprising the amino acid sequences of SEQ ID NO:142 (CDR1), SEQ ID NO:143 (CDR2) and SEQ ID NO:144 (CDR3) (antigen binding unit B7H6 #24).

In some embodiments of the binding protein of the invention, said second antigen binding unit specifically binding to CD3 is selected from the group consisting of i)-vi):

i) an antigen binding unit comprising light chain CDRs comprising the amino acid sequences of SEQ ID NO:257 (CDR1), SEQ ID NO:258 (CDR2) and SEQ ID NO:259 (CDR3) and heavy chain CDRs comprising the amino acid sequences of SEQ ID NO:260 (CDR1), SEQ ID NO:261 (CDR2) and SEQ ID NO:262 (CDR3) (antigen binding unit CD3 #1);

ii) an antigen binding unit comprising light chain CDRs comprising the amino acid sequences of SEQ ID NO:263 (CDR1), SEQ ID NO:264 (CDR2) and SEQ ID NO:265 (CDR3) and heavy chain CDRs comprising the amino acid sequences of SEQ ID NO:266 (CDR1), SEQ ID NO:267 (CDR2) and SEQ ID NO:268 (CDR3) (antigen binding unit CD3 #2);

iii) an antigen binding unit comprising light chain CDRs comprising the amino acid sequences of SEQ ID NO:269 (CDR1), SEQ ID NO:270 (CDR2) and SEQ ID NO:271 (CDR3) and heavy chain CDRs comprising the amino acid sequences of SEQ ID NO:272 (CDR1), SEQ ID NO:273 (CDR2) and SEQ ID NO:274 (CDR3) (antigen binding unit CD3 #3);

iv) an antigen binding unit comprising light chain CDRs comprising the amino acid sequences of SEQ ID NO:275 (CDR1), SEQ ID NO:276 (CDR2) and SEQ ID NO:277 (CDR3) and heavy chain CDRs comprising the amino acid sequences of SEQ ID NO:278 (CDR1), SEQ ID NO:279 (CDR2) and SEQ ID NO:280 (CDR3) (antigen binding unit CD3 #4);

v) an antigen binding unit comprising light chain CDRs comprising the amino acid sequences of SEQ ID NO:281 (CDR1), SEQ ID NO:282 (CDR2) and SEQ ID NO:283 (CDR3) and heavy chain CDRs comprising the amino acid sequences of SEQ ID NO:284 (CDR1), SEQ ID NO:285 (CDR2) and SEQ ID NO:286 (CDR3) (antigen binding unit CD3 #5); and vi) an antigen binding unit comprising light chain CDRs comprising the amino acid sequences of SEQ ID NO:287 (CDR1), SEQ ID NO:288 (CDR2) and SEQ ID NO:289 (CDR3) and heavy chain CDRs comprising the amino acid sequences of SEQ ID NO:290 (CDR1), SEQ ID NO:291 (CDR2) and SEQ ID NO:292 (CDR3) (antigen binding unit CD3 #6).

The first antigen binding units i) to xxiv) as outlined above are termed B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23, and B7H6 #24, respectively and the second antigen binding units i) to vi) as outlined above are termed CD3 #1, CD3 #2, CD3 #3, CD3 #4, CD3 #5 and CD3 #6, respectively. Provided herein is a sequence table which readily allows identification of individual amino acid sequences to specific antigen binding units and full length binding proteins of the present invention. A summary is provided in Table 1 in Example 2.

The terms "first" and "second" with respect to antigen binding units in general, as used herein, is solely intended to indicate that these units are two different units (as they bind to different target antigens). Thus, these terms shall not be understood to refer to the exact order or sequence of the units within the binding protein of the invention.

In some embodiments, the binding protein of the invention comprises a first antigen binding unit selected from the group consisting of B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23, and B7H6 #24 as defined by the respective CDR sequences shown in Table 1 and a second antigen binding unit selected from the group consisting of CD3 #1, CD3 #2, CD3 #3, CD3 #4, CD3 #5 and CD3 #6 as defined by the respective CDR sequences shown in Table 1.

In some embodiments, the binding protein of the invention comprises a first antigen binding unit selected from the group consisting of B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23, and B7H6 #24 as defined by the respective CDR sequences shown in Table 1 and a second antigen binding unit of CD3 #1 as defined by the respective CDR sequences shown in Table 1. In preferred embodiments, the binding protein of the invention comprises a first antigen binding unit selected from the group consisting of B7H6 #1, B7H6 #2, B7H6 #3, B7H6 #4, B7H6 #5, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23, and B7H6 #24 as defined by the respective CDR sequences shown in Table 1 and a second antigen binding unit of CD3 #1 as defined by the respective CDR sequences shown in Table 1. In preferred embodiments, the binding protein of the invention comprises a first antigen binding unit selected from the group consisting of B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23, and B7H6 #24 as defined by the respective CDR sequences shown in Table 1 and a second antigen binding unit of CD3 #1 as defined by the respective CDR sequences shown in Table 1. In preferred embodiments, the binding protein of the invention comprises a first antigen binding unit selected from the group consisting of B7H6 #12, B7H6 #14, B7H6 #15, B7H6 #16, and B7H6 #23 as defined by the respective CDR sequences shown in Table 1 and a second antigen binding unit of CD3 #1 as defined by the respective CDR sequences shown in Table 1.

In addition to the CDR sequences as set out herein, the antigen binding units of the binding proteins of the invention include immunoglobulin framework region (FR) sequences. These sequences are preferably not immunogenic in humans, and are therefore preferably human, humanized or optimized FR sequences. Suitable human, humanized or optimized FR sequences are known in the art. Specifically preferred FR sequences can be taken from the embodiments shown herein, disclosing the complete antigen binding units and thereby CDR sequences as well as FR sequences. In one preferred embodiment, the binding protein of the invention comprises a first antigen binding unit specifically binding to B7H6, comprising light chain CDRs comprising the amino acid sequences of SEQ ID NO:67 (CDR1), SEQ ID NO:68 (CDR2) and SEQ ID NO:69 (CDR3) and heavy chain CDRs comprising the amino acid sequences of SEQ ID NO:70 (CDR1), SEQ ID NO:71 (CDR2) and SEQ ID NO:72 (CDR3) and a second antigen binding unit specifically binding to CD3, comprising light chain CDRs comprising the amino acid sequences of SEQ ID NO:257 (CDR1), SEQ ID NO:258 (CDR2) and SEQ ID NO:259 (CDR3) and heavy chain CDRs comprising the amino acid sequences of SEQ ID NO:260 (CDR1), SEQ ID NO:261 (CDR2) and SEQ ID NO:262 (CDR3). Such antigen binding protein is referred to herein as B7H6 #14/CD3 #1. In a particularly preferred embodiment, the antigen binding units specifically binding to B7H6 and CD3, respectively, each comprise CDRs as defined above (B7H6 #12/CD3 #1) within a VL/VH domain, e.g. a sequence optimized VL/VH domain. In a particularly preferred embodiment, the antigen binding units specifically binding to B7H6 and CD3, respectively (B7H6 #12/CD3 #1), are each formed by a scFab and are optionally each linked to an Fc domain.

In one preferred embodiment, the binding protein of the invention comprises a first antigen binding unit specifically binding to B7H6, comprising light chain CDRs comprising the amino acid sequences of SEQ ID NO:79 (CDR1), SEQ ID NO:80 (CDR2) and SEQ ID NO:81 (CDR3) and heavy chain CDRs comprising the amino acid sequences of SEQ ID NO:82 (CDR1), SEQ ID NO:83 (CDR2) and SEQ ID NO:84 (CDR3) and a second antigen binding unit specifically binding to CD3, comprising light chain CDRs comprising the amino acid sequences of SEQ ID NO:257 (CDR1), SEQ ID NO:258 (CDR2) and SEQ ID NO:259 (CDR3) and heavy chain CDRs comprising the amino acid sequences of SEQ ID NO:260 (CDR1), SEQ ID NO:261 (CDR2) and SEQ ID NO:262 (CDR3). Such antigen binding protein is referred to herein as B7H6 #14/CD3 #1. In a particularly preferred embodiment, the antigen binding units specifically binding to B7H6 and CD3, respectively, each comprise CDRs as defined above (B7H6 #14/CD #1) within a VL/VH domain, e.g. a sequence optimized VL/VH domain. In a particularly preferred embodiment, the antigen binding units specifically binding to B7H6 and CD3, respectively (B7H6 #14/CD3 #1), are each formed by a scFab and are optionally each linked to an Fc domain.

In one preferred embodiment, the binding protein of the invention comprises a first antigen binding unit specifically binding to B7H6, comprising light chain CDRs comprising the amino acid sequences of SEQ ID NO:85 (CDR1), SEQ ID NO:86 (CDR2) and SEQ ID NO:87 (CDR3) and heavy chain CDRs comprising the amino acid sequences of SEQ ID NO:88 (CDR1), SEQ ID NO:89 (CDR2) and SEQ ID NO:90 (CDR3) and a second antigen binding unit specifically binding to CD3, comprising light chain CDRs comprising the amino acid sequences of SEQ ID NO:257 (CDR1), SEQ ID NO:258 (CDR2) and SEQ ID NO:259 (CDR3) and heavy chain CDRs comprising the amino acid sequences of SEQ ID NO:260 (CDR1), SEQ ID NO:261 (CDR2) and SEQ ID NO:262 (CDR3). Such antigen binding protein is referred to herein as B7H6 #15/CD3 #1. In a particularly preferred embodiment, the antigen binding units specifically binding to B7H6 and CD3, respectively, each comprises CDRs as defined above (B7H6 #15/CD3 #1) within a VL/VH domain, e.g. a sequence optimized VL/VH domain. In a particularly preferred embodiment, the antigen binding units specifically binding to B7H6 and CD3, respectively (B7H6 #15/CD3 #1), are each formed by a scFab and are optionally each linked to an Fc domain.

In one preferred embodiment, the binding protein of the invention comprises a first antigen binding unit specifically binding to B7H6, comprising light chain CDRs comprising the amino acid sequences of SEQ ID NO:91 (CDR1), SEQ ID NO:92 (CDR2) and SEQ ID NO:93 (CDR3) and heavy chain CDRs comprising the amino acid sequences of SEQ ID NO:94 (CDR1), SEQ ID NO:95 (CDR2) and SEQ ID NO:96 (CDR3) and a second antigen binding unit specifically binding to CD3, comprising light chain CDRs comprising the amino acid sequences of SEQ ID NO:257 (CDR1), SEQ ID NO:258 (CDR2) and SEQ ID NO:259 (CDR3) and heavy chain CDRs comprising the amino acid sequences of SEQ ID NO:260 (CDR1), SEQ ID NO:261 (CDR2) and SEQ ID NO:262 (CDR3). Such antigen binding protein is referred to herein as B7H6 #16/CD3 #1. In a particularly preferred embodiment, the antigen binding units specifically binding to B7H6 and CD3, respectively, each comprise CDRs as defined above (B7H6 #16/CD3 #1) within a VL/VH domain, e.g. a sequence optimized VL/VH domain. In a particularly preferred embodiment, the antigen binding units specifically binding to B7H6 and CD3, respectively (B7H6 #16/CD3 #1), are each formed by a scFab and are optionally each linked to an Fc domain.

In one preferred embodiment, the binding protein of the invention comprises a first antigen binding unit specifically binding to B7H6, comprising light chain CDRs comprising the amino acid sequences of SEQ ID NO:133 (CDR1), SEQ ID NO:134 (CDR2) and SEQ ID NO:135 (CDR3) and heavy chain CDRs comprising the amino acid sequences of SEQ ID NO:136 (CDR1), SEQ ID NO:137 (CDR2) and SEQ ID NO:138 (CDR3) and a second antigen binding unit specifically binding to CD3, comprising light chain CDRs comprising the amino acid sequences of SEQ ID NO:257 (CDR1), SEQ ID NO:258 (CDR2) and SEQ ID NO:259 (CDR3) and heavy chain CDRs comprising the amino acid sequences of SEQ ID NO:260 (CDR1), SEQ ID NO:261 (CDR2) and SEQ ID NO:262 (CDR3). Such antigen binding protein is referred to herein as B7H6 #14/CD3 #1. In a particularly preferred embodiment, the antigen binding units specifically binding to B7H6 and CD3, respectively, each comprise CDRs as defined above (B7H6 #23/CD3 #1) within a VL/VH domain, e.g. a sequence optimized VL/VH domain. In a particularly preferred embodiment, the antigen binding units specifically binding to B7H6 and CD3, respectively (B7H6 #23/CD3 #1), are each formed by a scFab and are optionally each linked to an Fc domain.

In preferred embodiments of the binding proteins of the invention, the first and the second binding unit each comprise a light chain variable domain and a heavy chain variable domain said light/heavy chain variable domains defined by the CDR sequences of any one of B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23, or B7H6 #24 for the first antigen binding unit and said light/heavy chain variable domains defined by the CDR sequences of any one of CD3 #1, CD3 #2, CD3 #3, CD3 #4, CD3 #5 or CD3 #6 for the second antigen binding unit. In some embodiments of the binding protein of the invention, the VH and/or VL domain of the antigen binding units of any one of B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23, B7H6 #24, CD3 #1, CD3 #2, CD3 #3, CD3 #4, CD3 #5 or CD3 #6 is a human, humanized or optimized VH and/or VL domain.

In preferred embodiments of the binding protein of the invention, the light/heavy chain variable domains of the first antigen binding unit specifically binding to B7H6 are further defined as follows i) a light chain variable domain comprising the amino acid sequence of SEQ ID NO:145 and heavy chain variable domain comprising the amino acid sequence of SEQ ID NO:146 (antigen binding unit B7H6 #1); or ii) a light chain variable domain comprising the amino acid sequences of SEQ ID NO:147 and heavy chain variable domain comprising the amino acid sequences of SEQ ID NO:148 (antigen binding unit B7H6 #2); or iii) a light chain variable domain comprising the amino acid sequence of SEQ ID NO:149 and heavy chain variable domain comprising the amino acid sequence of SEQ ID NO:150 (antigen binding unit B7H6 #3); or iv) a light chain variable domain comprising the amino acid sequence of SEQ ID NO:151 and heavy chain variable domain comprising the amino acid sequence of SEQ ID NO:152 (antigen binding unit B7H6 #4); or v) a light chain variable domain comprising the amino acid sequence of SEQ ID NO:153 and heavy chain variable domain comprising the amino acid sequence of SEQ ID NO:154 (antigen binding unit B7H6 #5); or vi) a light chain variable domain comprising the amino acid sequence of SEQ ID NO:155 and heavy chain variable domain comprising the amino acid sequence of SEQ ID NO:156 (antigen binding unit B7H6 #6); or vii) a light chain variable domain comprising the amino acid sequence of SEQ ID NO:157 and heavy chain variable domain comprising the amino acid sequence of SEQ ID NO:158 (antigen binding unit B7H6 #7); or viii) a light chain variable domain comprising the amino acid sequence of SEQ ID NO:159 and heavy chain variable domain comprising the amino acid sequence of SEQ ID NO:160 (antigen binding unit B7H6 #8); or ix) a light chain variable domain comprising the amino acid sequence of SEQ ID NO:161 and heavy chain variable domain comprising the amino acid sequence of SEQ ID NO:162 (antigen binding unit B7H6 #9); or x) a light chain variable domain comprising the amino acid sequence of SEQ ID NO:163 and heavy chain variable domain comprising the amino acid sequence of SEQ ID NO:164 (antigen binding unit B7H6 #10); or xi) a light chain variable domain comprising the amino acid sequence of SEQ ID NO:165 and heavy chain variable domain comprising the amino acid sequence of SEQ ID NO:166 (antigen binding unit B7H6 #11); or xii) a light chain variable domain comprising the amino acid sequence of SEQ ID NO:167 and heavy chain variable domain comprising the amino acid sequence of SEQ ID NO:168 (antigen binding unit B7H6 #12); or xiii) a light chain variable domain comprising the amino acid sequence of SEQ ID NO:169 and heavy chain variable domain comprising the amino acid sequence of SEQ ID NO:170 (antigen binding unit B7H6 #13); or xiv) a light chain variable domain comprising the amino acid sequence of SEQ ID NO:171 and heavy chain variable domain comprising the amino acid sequence of SEQ ID NO:172 (antigen binding unit B7H6 #14); or xv) a light chain variable domain comprising the amino acid sequence of SEQ ID NO:173 and heavy chain variable domain comprising the amino acid sequence of SEQ ID NO:174 (antigen binding unit B7H6 #15); or xvi) a light chain variable domain comprising the amino acid sequence of SEQ ID NO:175 and heavy chain variable domain comprising the amino acid sequence of SEQ ID NO:176 (antigen binding unit B7H6 #16); or xvii) a light chain variable domain comprising the amino acid sequence of SEQ ID NO:177 and heavy chain variable domain comprising the amino acid sequence of SEQ ID NO:178 (antigen binding unit B7H6 #17); or xviii) a light chain variable domain comprising the amino acid sequence of SEQ ID NO:179 and heavy chain variable domain comprising the amino acid sequence of SEQ ID NO:180 (antigen binding unit B7H6 #18); or xix) a light chain variable domain comprising the amino acid sequence of SEQ ID NO:181 and heavy chain variable domain comprising the amino acid sequence of SEQ ID NO:182 (antigen binding unit B7H6 #19); or xx) a light chain variable domain comprising the amino acid sequence of SEQ ID NO:183 and heavy chain variable domain comprising the amino acid sequence of SEQ ID NO:184 (antigen binding unit B7H6 #20); or xxi) a light chain variable domain comprising the amino acid sequence of SEQ ID NO:185 and heavy chain variable domain comprising the amino acid sequence of SEQ ID NO:186 (antigen binding unit B7H6 #21); or xxii) a light chain variable domain comprising the amino acid sequence of SEQ ID NO:187 and heavy chain variable domain comprising the amino acid sequence of SEQ ID NO:188 (antigen binding unit B7H6 #22); or xxiii) a light chain variable domain comprising the amino acid sequence of SEQ ID NO:189 and heavy chain variable domain comprising the amino acid sequence of SEQ ID NO:190 (antigen binding unit B7H6 #23); or xxiv) a light chain variable domain comprising the amino acid sequence of SEQ ID NO:191 and heavy chain variable domain comprising the amino acid sequence of SEQ ID NO:192 (antigen binding unit B7H6 #24).

In preferred embodiments of the binding protein of the invention, the light/heavy chain variable domains of the second antigen binding unit specifically binding to CD3 are further defined as follows i) a light chain variable domain comprising the amino acid sequence of SEQ ID NO:293 and a heavy chain variable domain comprising the amino acid sequence of SEQ ID NO:294) (antigen binding unit CD3 #1); or ii) a light chain variable domain comprising the amino acid sequence of SEQ ID NO:295 and a heavy chain variable domain comprising the amino acid sequence of SEQ ID NO:296 (antigen binding unit CD3 #2); or iii) a light chain variable domain comprising the amino acid sequence of SEQ ID NO:297 and a heavy chain variable domain comprising the amino acid sequence of SEQ ID NO:298 (antigen binding unit CD3 #3); or iv) a light chain variable domain comprising the amino acid sequence of SEQ ID NO:299 and a heavy chain variable domain comprising the amino acid sequence of SEQ ID NO:300 (antigen binding unit CD3 #4); or v) a light chain variable domain comprising the amino acid sequence of SEQ ID NO:301 and a heavy chain variable domain comprising the amino acid sequence of SEQ ID NO:302 (antigen binding unit CD3 #5); or vi) a light chain variable domain comprising the amino acid sequence of SEQ ID NO:303 and a heavy chain variable domain comprising the amino acid sequence of SEQ ID NO:304 (antigen binding unit CD3 #6).

In preferred embodiments, the binding protein of the invention comprises a combination of a first and a second antigen binding unit selected from the group consisting of B7H6 #1/CD3 #1, B7H6 #2/CD3 #1, B7H6 #3/CD3 #1, B7H6 #4/CD3 #1, B7H6 #5/CD3 #1, B7H6 #6/CD3 #1, B7H6 #7/CD3 #1, B7H6 #8/CD3 #1, B7H6 #9/CD3 #1, B7H6 #10/CD3 #1, B7H6 #11/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, and B7H6 #24/CD3 #1, the first and second antigen binding unit being defined by the CDR and/or VH and VL sequences of the antigen binding units as shown in Table 1.

In preferred embodiments, the binding protein of the invention comprises a combination of a first and a second antigen binding unit selected from the group consisting of B7H6 #1/CD3 #1, B7H6 #2/CD3 #1, B7H6 #3/CD3 #1, B7H6 #4/CD3 #1, B7H6 #5/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, and B7H6 #24/CD3 #1, the first and second antigen binding unit being defined by the CDR and/or VH and VL sequences of the antigen binding units as shown in Table 1.

In preferred embodiments, the binding protein of the invention comprises a combination of a first and a second antigen binding unit selected from the group consisting of B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, and B7H6 #24/CD3 #1, the first and second antigen binding unit being defined by the CDR and/or VH and VL sequences of the antigen binding units as shown in Table 1.

In preferred embodiments, the binding protein of the invention comprises a combination of a first and a second antigen binding unit selected from the group consisting of B7H6 #12/CD3 #1, B7H6 #14/CD3 #1, B7H6 #15/CD3 #1, B7H6 #16/CD3 #1, and B7H6 #23/CD3 #1, the first and second antigen binding unit being defined by the CDR and/or VH and VL sequences of the antigen binding units as shown in Table 1.

In one preferred embodiment, the binding protein of the invention comprises (i) a first antigen binding unit specifically binding to B7H6 comprising a light chain variable domain comprising the amino acid sequences of SEQ ID NO:167 and a heavy chain variable domain comprising the amino acid sequences of SEQ ID NO:168 and (ii) a second antigen binding unit specifically binding to CD3 comprising a light chain variable domain comprising the amino acid sequence of SEQ ID NO:293 and a heavy chain variable domain comprising the amino acid sequence of SEQ ID NO:294. Such binding protein is referred to herein as B7H6 #12/CD3 #1. In a particularly preferred embodiment, the antigen binding units specifically binding to B7H6 and CD3, respectively, as defined above (B7H6 #12/CD3 #1) are each formed by a scFab, optionally covalently linked to an Fc domain.

In one preferred embodiment, the binding protein of the invention comprises (i) a first antigen binding unit specifically binding to B7H6 comprising a light chain variable domain comprising the amino acid sequences of SEQ ID NO:171 and a heavy chain variable domain comprising the amino acid sequences of SEQ ID NO:172 and (ii) a second antigen binding unit specifically binding to CD3 comprising a light chain variable domain comprising the amino acid sequence of SEQ ID NO:293 and a heavy chain variable domain comprising the amino acid sequence of SEQ ID NO:294. Such binding protein is referred to herein as B7H6 #14/CD3 #1. In a particularly preferred embodiment, the antigen binding units specifically binding to B7H6 and CD3, respectively, as defined above (B7H6 #14/CD3 #1) are each formed by a scFab, optionally covalently linked to an Fc domain.

In one preferred embodiment, the binding protein of the invention comprises (i) a first antigen binding unit specifically binding to B7H6 comprising a light chain variable domain comprising the amino acid sequences of SEQ ID NO:173 and a heavy chain variable domain comprising the amino acid sequences of SEQ ID NO:174 and (ii) a second antigen binding unit specifically binding to CD3 comprising a light chain variable domain comprising the amino acid sequence of SEQ ID NO:293 and a heavy chain variable domain comprising the amino acid sequence of SEQ ID NO:294. Such binding protein is referred to herein as B7H6 #15/CD3 #1. In a particularly preferred embodiment, the antigen binding units specifically binding to B7H6 and CD3, respectively, as defined above (B7H6 #15/CD3 #1) are each formed by a scFab, optionally covalently linked to an Fc domain.

In one preferred embodiment, the binding protein of the invention comprises (i) a first antigen binding unit specifically binding to B7H6 comprising a light chain variable domain comprising the amino acid sequences of SEQ ID NO:175 and a heavy chain variable domain comprising the amino acid sequences of SEQ ID NO:176 and (ii) a second antigen binding unit specifically binding to CD3 comprising a light chain variable domain comprising the amino acid sequence of SEQ ID NO:293 and a heavy chain variable domain comprising the amino acid sequence of SEQ ID NO:294. Such binding protein is referred to herein as B7H6 #16/CD3 #1. In a particularly preferred embodiment, the antigen binding units specifically binding to B7H6 and CD3, respectively, as defined above (B7H6 #16/CD3 #1) are each formed by a scFab, optionally covalently linked to an Fc domain.

In one preferred embodiment, the binding protein of the invention comprises (i) a first antigen binding unit specifically binding to B7H6 comprising a light chain variable domain comprising the amino acid sequences of SEQ ID NO:189 and a heavy chain variable domain comprising the amino acid sequences of SEQ ID NO:190 and (ii) a second antigen binding unit specifically binding to CD3 comprising a light chain variable domain comprising the amino acid sequence of SEQ ID NO:293 and a heavy chain variable domain comprising the amino acid sequence of SEQ ID NO:294. Such binding protein is referred to herein as B7H6 #23/CD3 #1. In a particularly preferred embodiment, the antigen binding units specifically binding to B7H6 and CD3, respectively, as defined above (B7H6 #23/CD3 #1) are each formed by a scFab, optionally covalently linked to an Fc domain.

In some embodiments, the binding protein of the invention comprises i) a first antigen binding unit specifically binding to B7H6 (e.g. any one of B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18 B7H6 #19, B7H6 #20, B7H6 #21, B7H6 #22, B7H6 #23, B7H6 #24 as defined by the respective CDR or VH/VL sequences shown in Table 1) which comprises a first light chain variable domain covalently linked to a first heavy chain variable domain with a first peptide linker and/or ii) a second antigen binding unit specifically binding to CD3 (e.g. any one of CD3 #1, CD3 #2, CD3 #3, CD3 #4, CD3 #5 or CD3 #6 as defined by the respective CDR or VH/VL sequences shown in Table 1) which comprises a second light chain variable domain covalently linked to a second heavy chain variable domain with a second peptide linker. Optionally, the first and the second antigen binding units are covalently linked to each other with a peptide linker.

In some embodiments of the binding proteins of the invention, the first and/or the second antigen binding unit further comprises a CL and a CH1 domain like in a light/heavy Fab fragment of a conventional antibody molecule, thus said first binding unit comprises a) a VL domain (e.g., defined by the light chain CDR (LCCDR) or VL sequences of any one of B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23, or B7H6 #24) covalently linked (preferably directly bound) to a first CL domain and b) a VH domain (e.g., defined by the heavy chain CDR (HCCDR) or VH sequences of any one of B7H6 #1, B7H6 #2, B7H6 #3, B7H6 #4, B7H6 #5, B7H6 #6 B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23, or B7H6 #24) covalently linked (preferably directly bound) to a first CH1 domain and/or said second antigen binding unit comprises a) a VL domain (e.g., defined by the LCCDR or VL sequences of any one of CD3 #1, CD3 #2, CD3 #3, CD3 #4, CD3 #5 or CD3 #6) covalently linked (preferably directly bound) to a second CL domain and b) a VH domain (e.g., defined by HCCDR or VH sequences of any one of CD3 #1, CD3 #2, CD3 #3, CD3 #4, CD3 #5 or CD3 #6) covalently linked (preferably directly bound) to a second CH1 domain.

In the context of the present invention, a CL domain is the constant domain of an antibody light chain, for example either a kappa (κ) or a lambda (λ) light chain. An example of a constant region of a kappa light chain is shown in SEQ ID NO:247. An example of a constant region of a lambda light chain is shown in SEQ ID NO:248. In some embodiments, the first and the second CL domain are the same, e.g. the first and the second CL domain are both a kappa light chain constant domain or the first and the second CL domain are both a lambda light chain constant domain. In preferred embodiments, the first and the second CL domain are different, e.g., the first CL domain is a constant kappa domain and the second CL domain is a constant lambda domain or vice versa.

In the context of the present invention, a CH1 domain is the first constant domain of an antibody heavy chain. An example of a constant CH1 domain is shown in SEQ ID NO:249.

In preferred embodiments of the binding proteins of the invention, the first antigen binding unit specific for B7H6 (e.g., any one of B7H6 #1, B7H6 #2, B7H6 #3, B7H6 #4, B7H6 #5, B7H6 #6 B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23, or B7H6 #24 defined by the CDR and/or VH/VL sequences shown in Table 1) comprises from N- to C-terminus: a first light chain variable domain, a first CL domain, a first linker peptide, a first VH domain and a first CH1 domain, and/or the second binding unit (e.g., CD3 #1, CD3 #2, CD3 #3, CD3 #4, CD3 #5 or CD3 #6 defined by the CDR and/or VH/VL sequences shown in Table 1) of the binding proteins of the invention comprises from N- to C-terminus: a second light chain variable domain, a second CL domain, a second linker peptide, a second VH domain and a second CH1 domain. In these embodiments, the first and/or the second binding unit have the structure of a single chain Fab. For both, the first and/or the second antigen binding unit, when forming a single chain Fab, the order can be reversed such that from N- to C-terminus the antigen binding unit comprises: VH-CH1-[linker peptide]-VL-CL. In some embodiments of the protein of the invention when the first and/or second antigen binding unit comprise a Fab or a single chain Fab, the constant domains can be of the same type (e.g., both CL domains are kappa or lambda light chain constant domains) or of different types (the first CL domain is a kappa and the second CL domain is a lambda light chain constant domain or vice versa), preferably the first and the second CL domain are of different types. In preferred embodiments, the first antigen binding unit consists of a first single chain Fab specific for B7H6 (preferably any one of B7H6 #12, B7H6 #14, B7H6 #15, B7H6 #16 or B7H6 #23 as defined by the CDR and or VH/VL sequences as shown in Table 1) and the second antigen binding unit consists of a second single chain Fab specific for CD3 (e.g., CD3 #1 as defined by the CDR and or VH/VL sequences as shown in Table 1).

The linker sequence of the B7H6/CD3 binding proteins (e.g., B7H6/CD3 scFabs described above) may be a naturally occurring sequence or a non-naturally occurring sequence. If used for therapeutic purposes, the linker is preferably non-immunogenic in the subject to which the binding protein of the invention is administered. Preferably, the linker comprises 26 to 42 amino acids, for example 30 to 40 amino acids. In a further aspect, a linker used in a protein of the present invention comprises 34 to 40 amino acids, for example 36 to 39 amino acids, for example 38 amino acids.

One useful group of linker sequences are linkers derived from the hinge region of heavy chain antibodies as described in WO1996/34103 and WO1994/04678. Other examples are poly-alanine linker sequences such as Ala-Ala-Ala.

Further preferred examples of linker sequences are Gly/Ser linkers of different length such as (glyxsery)z linkers, including e.g. (gly4ser)3 (SEQ ID NO: 341), (gly4ser)5 (SEQ ID NO: 342), (gly4ser)7 (SEQ ID NO: 343), (gly3ser)3 (SEQ ID NO: 344), (gly3ser)5 (SEQ ID NO: 345), (gly3ser)7 (SEQ ID NO: 346), (gly3ser2)3 (SEQ ID NO: 347), (gly3ser2)5 (SEQ ID NO: 348), and (gly3ser2)7 (SEQ ID NO: 349) or a linker of any one of SEQ ID NOs: 250, 251, 252, 253, 254, 255 or 256, preferably SEQ ID NO: 250.

In some embodiments of the binding proteins of the invention, the VL domain of the first antigen binding unit (e.g., defined by the light chain CDR (LCCDR) or VL sequences of any one of B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18 B7H6 #19, B7H6 #20, B7H6 #21, B7H6 #22, B7H6 #23, B7H6 #24 as shown in Table 1) is covalently linked via a first Gly/Ser linker (e.g., Gly/Ser linker of any one of 26 to 42 amino acids, 30 to 40 amino acids, 34 to 40 amino acids, or 36 to 39 amino acids, preferably 38 amino acids) to the VH domain of the first antigen binding unit (e.g., defined by the heavy chain CDR (HCCDR) or VH sequences of any one of B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18 B7H6 #19, B7H6 #20, B7H6 #21, B7H6 #22, B7H6 #23, B7H6 #24 as shown in Table 1); and the VL domain of the second antigen binding unit (e.g., defined by the light chain CDR (LCCDR) or VL sequences of any one of CD3 #1, CD3 #2, CD3 #3, CD3 #4, CD3 #5 or CD3 #6 as shown in Table 1) is covalently linked via a second Gly/Ser linker (e.g., Gly/Ser linker of any one of 26 to 42 amino acids, 30 to 40 amino acids, 34 to 40 amino acids, or 36 to 39 amino acids, preferably 38 amino acids) to the VH domain of the second antigen binding unit (e.g., defined by the heavy chain CDR (HCCDR) or VH sequences of any one of CD3 #1, CD3 #2, CD3 #3, CD3 #4, CD3 #5 or CD3 #6 as shown in Table 1). More preferably, the first and the second linker are the same. Even more preferably, the first and the second linker each comprise the amino acid sequence of SEQ ID NO:250.

In preferred embodiments of the binding proteins of the invention, the first antigen binding unit specifically binding to B7H6 comprises from N to C-terminus i) a VL domain (e.g., defined by the light chain CDR (LCCDR) or VL sequences of any one of B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18 B7H6 #19, B7H6 #20, B7H6 #21, B7H6 #22, B7H6 #23, B7H6 #24 as shown in Table 1), ii) a first CL domain, iii) a via a first Gly/Ser linker (e.g., Gly/Ser linker of any one of 26 to 42 amino acids, 30 to 40 amino acids, 34 to 40 amino acids, or 36 to 39 amino acids, preferably 38 amino acids), iv) a VH domain (e.g., defined by the heavy chain CDR (HCCDR) or VH sequences of any one of B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18 B7H6 #19, B7H6 #20, B7H6 #21, B7H6 #22, B7H6 #23, B7H6 #24 as shown in Table 1), and v) a first CH1 domain and/or the second antigen binding unit specifically binding to CD3 comprises from N to C terminus i) a VL domain (e.g., defined by the light chain CDR (LCCDR) or VL sequences of any one of CD3 #1, CD3 #2, CD3 #3, CD3 #4, CD3 #5 or CD3 #6 as shown in Table 1), ii) a second CL domain, iii) a second Gly/Ser linker (e.g., Gly/Ser linker of any one of 26 to 42 amino acids, 30 to 40 amino acids, 34 to 40 amino acids, or 36 to 39 amino acids, preferably 38 amino acids), iv) a VH domain of the second antigen binding unit (e.g., defined by the heavy chain CDR (HCCDR) or VH sequences of any one of CD3 #1, CD3 #2, CD3 #3, CD3 #4, CD3 #5 or CD3 #6 as shown in Table 1) and v) a second CH1 domain. Preferably, i) to v) are each linked via a direct covalent bond in the order i) to v) from the N to the C terminus of the antigen binding unit (each antigen binding unit thus having the structure of a scFab). More preferably, the first and the second linker are the same. Even more preferably, the first and the second linker each comprise the amino acid sequence of SEQ ID NO:250.

In preferred embodiments, the binding protein of the invention comprises a first single chain Fab forming a first antigen binding unit specific for B7H6 and comprising a sequence selected from the group consisting of SEQ ID NO:193, SEQ ID NO:194, SEQ ID NO:195, SEQ ID NO:196, SEQ ID NO:197, SEQ ID NO:198 SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215 and SEQ ID NO:216 and a second single chain Fab forming a second antigen binding unit specific for CD3 and comprising the sequence of SEQ ID NO:305.

In preferred embodiments, the binding protein of the invention comprises a first single chain Fab forming a first antigen binding unit specific for B7H6 and comprising a sequence selected from the group consisting of SEQ ID NO:193, SEQ ID NO:194, SEQ ID NO:195, SEQ ID NO:196, SEQ ID NO:197, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215 and SEQ ID NO:216 and a second single chain Fab forming a second antigen binding unit specific for CD3 and comprising the sequence of SEQ ID NO:305.

In preferred embodiments, the binding protein of the invention comprises a first single chain Fab forming a first antigen binding unit specific for B7H6 and comprising a sequence selected from the group consisting of SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215 and SEQ ID NO:216 and a second single chain Fab forming a second antigen binding unit specific for CD3 and comprising the sequence of SEQ ID NO:305.

In one preferred embodiment, the binding protein of the invention comprises a first single chain Fab comprising the sequence of SEQ ID NO:204 and a second single chain Fab comprising the sequence of SEQ ID NO:305, optionally each single chain Fab is further linked to an Fc domain and thereby forming a first polypeptide chain (a "B7H6 chain") and a second polypeptide chain (a "CD3 chain") In one preferred embodiment, the binding protein of the invention comprises a first single chain Fab comprising the sequence of SEQ ID NO:206 and a second single chain Fab comprising the sequence of SEQ ID NO:305, optionally each single chain Fab is further linked to an Fc domain and thereby forming a first polypeptide chain (a B7H6 chain) and a second polypeptide chain (a CD3 chain). In one preferred embodiment, the binding protein of the invention comprises a first single chain Fab comprising the sequence of SEQ ID NO:207 and a second single chain Fab comprising the sequence of SEQ ID NO:305, optionally each single chain Fab is further linked to an Fc domain and thereby forming a first polypeptide chain (a B7H6 chain) and a second polypeptide chain (a CD3 chain). In one preferred embodiment, the binding protein of the invention comprises a first single chain Fab comprising the sequence of SEQ ID NO:208 and a second single chain Fab comprising the sequence of SEQ ID NO:305, optionally each single chain Fab is further linked to an Fc domain and thereby forming a first polypeptide chain (a B7H6 chain) and a second polypeptide chain (a CD3 chain). In one preferred embodiment, the binding protein of the invention comprises a first single chain Fab comprising the sequence of SEQ ID NO:215 and a second single chain Fab comprising the sequence of SEQ ID NO:305, optionally each single chain Fab is further linked to an Fc domain and thereby forming a first polypeptide chain (a B7H6 chain) and a second polypeptide chain (a CD3 chain).

In some embodiments, the first antigen binding unit (e.g., any one of B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18 B7H6 #19, B7H6 #20, B7H6 #21, B7H6 #22, B7H6 #23, or B7H6 #24 as defined by the CDR and/or VH/VL sequences shown in Table 1) and/or the second antigen binding unit (e.g., any one of CD3 #1, CD3 #2, CD3 #3, CD3 #4, CD3 #5 or CD3 #6 as defined by the CDR and/or VH/VL sequences shown in Table 1) comprises a VL domain covalently linked (preferably directly bound) to a CL domain and a VH domain linked to a CH1 domain (together forming a Fab fragment), and said CH1 domain is further covalently linked (e.g., directly bound) to an Fc domain thereby forming an arm of a conventional Y shaped antibody molecule with one light and one heavy chain. In some embodiments, the first and the second antigen binding unit each form a Fab fragment, i.e. a first and a second Fab fragment, which is each covalently linked (preferably directly bound) to a first and a second Fc domain, respectively, thereby forming a conventional heterotetrameric bispecific and bivalent (monovalent for B7H6 and CD3, respectively) antibody molecule.

In preferred embodiments, the binding protein of the invention comprises (i) a first antigen binding unit comprising a first single chain Fab specifically binding to B7H6, i.e. an antibody light chain (VL-CL) covalently linked to the VH-CH1 domains of a heavy chain (the VL and VH domain of any one of B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18 B7H6 #19, B7H6 #20, B7H6 #21, B7H6 #22, B7H6 #23, or B7H6 #24 as defined by the CDR and/or VH/VL sequences shown in Table 1) via a peptide linker (e.g., Gly/Ser linker of any one of 26 to 42 amino acids, 30 to 40 amino acids, 34 to 40 amino acids, or 36 to 39 amino acids, preferably 38 amino acids, even more preferably a linker of SEQ ID NO:250), which first antigen binding unit is covalently linked (e.g., directly bound) to a first Fc domain and (ii) a second antigen binding unit comprising a second single chain Fab specifically binding to CD3, i.e. an antibody light chain (VL-CL) covalently linked to the VH-CH1 domains of a heavy chain (the VL and VH domain of any one of CD3 #1 CD3 #2, CD3 #3, CD3 #4, CD3 #5, CD3 #6 as defined by the respective CDR or VH/VL sequences shown in Table 1), which second antigen binding unit is covalently linked (e.g., directly bound) to a second Fc domain. Thus, in preferred embodiments, the binding protein of the invention comprises (i) a first polypeptide chain comprising (a) a first antigen binding unit specific for B7H6, said first antigen binding unit comprising a first single chain Fab specific for B7H6 (preferably any one of B7H6 #12, B7H6 #14, B7H6 #15, B7H6 #16 or B7H6 #23 as defined by the CDR and or VH/VL sequences as shown in Table 1) and (b) a first Fc domain (this first polypeptide chain herein referred to also as "B7H6 chain") and (ii) a second polypeptide chain specific for CD3 comprising (a) a second antigen biding unit comprising a second single chain Fab specific for CD3 (preferably CD3 #1 as defined by the CDR and/or VL/VH sequences shown in Table 1) and (b) a second Fc domain (this second polypeptide chain also herein referred to as "CD3 chain"). Accordingly, the term "polypeptide chain" as used herein comprises at least a scFab and an Fc domain. In some embodiments, the first and the second Fc domain are the same. In preferred embodiments, the first and the second Fc domains are different. The resulting binding proteins of the invention comprise two different polypeptide chains bearing a full Fc and having two independent binding sites, a first antigen binding unit, formed by a first scFab specific for B7H6 and a second binding unit, formed by a second scFab specific for CD3.

In preferred embodiments, the binding protein of the invention comprises two different polypeptide chains, each comprising an antigen binding unit, formed by a scFab, with different specificity each covalently linked to an Fc domain, the polypeptide chains covalently linked to each other, either via disulfide bonds or potentially via a peptide linker. In preferred embodiments, the binding protein of the invention is a bispecific, bivalent (monovalent for B7H6 and CD3, respectively) heterodimeric protein comprising two polypeptide chains, one polypeptide chain (a first polypeptide chain or B7H6 chain) comprising an antigen binding unit formed by a scFab specifically binding to B7H6 (e.g., any one of B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18 B7H6 #19, B7H6 #20, B7H6 #21, B7H6 #22, B7H6 #23, or B7H6 #24 as defined by the CDR and/or VH/VL sequences shown in Table 1) and an Fc domain (preferably an Fc domain of SEQ ID NO:242) and another polypeptide chain (a second polypeptide chain or CD3 chain) comprising an antigen binding unit formed by a scFab specifically binding to CD3 (e.g. any one of CD3 #1, CD3 #2, CD3 #3, CD3 #4, CD3 #5, or CD3 #6) and an Fc domain (preferably an Fc domain of SEQ ID NO:243). In some embodiments, the first antigen binding unit consists of a first single chain Fab and the second antigen binding unit consists of a second single chain Fab. In some embodiments of the binding protein, the first polypeptide chain specific for B7H6 (a B7H6 chain) consists of a) a first antigen binding unit consisting of a scFab ((preferably any one of B7H6 #12, B7H6 #14, B7H6 #15, B7H6 #16 or B7H6 #23 as defined by the CDR, VH/VL and/or scFab sequences as shown in Table 1) and b) a first Fc domain and the second polypeptide chain specific for CD3 (a CD3 chain) consists of a) a second antigen binding unit consisting of a scFab (preferably CD3 #1 as defined by the CDR, VH/VL and/or scFab sequences as shown in Table 1) and b) a second Fc domain. Preferably, the C-terminus of the scFab is linked to the N-terminus of the Fc domain via a direct covalent bond. Preferably, the first and the second polypeptide chain are covalently linked to each other via disulfide bonds, and form an antibody like structure (FIG. 1) similar to a conventional Y-shaped antibody molecule.

In the context of the present invention, an Fc domain is for example derived from the heavy chain of an IgG, for example an $IgG_1$, $IgG_2$ or $IgG_4$. For example, an Fc domain of the present invention is a Fc domain of a heavy chain of an $IgG_1$ or $IgG_4$ and comprises a hinge region and two constant domains ($C_{H2}$ and $C_{H3}$). Examples of Fc domains (including a hinge region) are shown in SEQ ID NOs:241 and 244.

The numbering of the amino acids in the amino acid chains of a protein of the present invention is herein according to the Eu numbering system (Edelman et al, PNAS USA 1969 May, 63(1):78-85; Cunningham et al. PNAS USA 1969, November, 64(3):997-1003), unless otherwise specified. This means that the amino acid numbers indicated herein correspond to the positions in a heavy chain of the corresponding sub-type (e.g. $IgG_1$ or $IgG_4$), according to the Eu numbering system, unless otherwise specified.

In some embodiments, the first Fc domain and the second Fc domain in a protein of the present invention each comprises one or more amino acid changes which reduce the formation of homodimers of the first or second polypeptide chains instead of heterodimers of a first and a second polypeptide chain. Through these changes, a "protrusion" is generated in one of the Fc domains by replacing one or more, small amino acid side chains from the interface of one of the heavy chains with larger side chains (e.g. tyrosine or tryptophan). Compensatory "cavities" of identical or similar size are created on the interface of the other Fc domain by replacing large amino acid side chains with smaller ones (e.g. alanine or threonine). This provides a mechanism for increasing the yield of the heterodimer over other unwanted end-products such as homodimers, in particular homodimers of the Fc domain with the "protrusion" (see for example Ridgway et al. Protein Eng, 1996. 9(7): p. 617-21; Atwell et al, JMB, 1997, 270, 26-35). In some embodiments, such amino acid changes are a tyrosine (Y) at position 366 [T366Y] of the first Fc domain and a threonine (T) at position 407 [Y407T] of the second Fc domain. In some embodiments, the first Fc domain comprises a serine (S) at position 366 [T366S] and the second Fc domain comprises a tryptophan (W) at position 366 [T366W], an alanine (A) at position 368 [L368A] and a valine (V) at position 407 [Y407V]. In preferred embodiments, the first Fc domain comprises a tryptophan (W) at position 366 [T366W] and the second Fc domain comprises a serine (S) at position 366 [T366S], an alanine (A) at position 368 [L368A] and a valine (V) at position 407 [Y407V]. For example, position 366 of the Fc domain according to Eu numbering, corresponding to the amino acid position 146 in the human IgG1 Fc sequence of SEQ ID NO:241, is changed from T at position 146 in SEQ ID NO:241 to W at position 146 in SEQ ID NO:242; and positions 366, 368 and 407 according to Eu numbering, corresponding to the amino acid positions 146, 148 and 187, respectively, in SEQ ID NO:241, are changed from T, L and Y at these positions in SEQ ID NO:241 to S, A and V at these positions in SEQ ID NO:243. In any of these embodiments, the amino acid changes described for the first Fc domain may be located in the second Fc domain and the respective amino acid changes for the second Fc domain may be located in the first Fc domain. In other words, the term "first" and "second" can be exchanged in these embodiments. In some embodiments, such a Fc domain is an Fc domain derived from the heavy chain of an $IgG_1$ or $IgG_4$.

In some embodiments, the first Fc domain comprises a cysteine (C) at position 354 [S354C] in addition to the tryptophan (W) at position 366 [T366W] and the second Fc domain comprises a cysteine (C) at position 349 [Y349C] in addition to the serine (S) at position 366 [T366S], the alanine (A) at position 368 [L368A] and the valine (V) at position 407 [Y407V]. In one aspect, such Fc domain is an Fc domain derived from the heavy chain of an $IgG_4$.

In some embodiments, the first Fc domain or the second Fc domain in a binding protein of the present invention further comprises one or more amino acid changes which reduce the binding of the Fc domain to protein A. In some embodiments, such amino acid changes are an arginine at position 435 [H435R] and a phenylalanine at position 436 [Y436F] of one of the Fc domains. Both changes are derived from the sequence of human IgG3 (IgG3 does not bind to protein A). These two mutations are located in the CH3 domain and are incorporated in one of the Fc domains to reduce binding to Protein A (see for example Jendeberg et al. J Immunol Methods, 1997. 201(1): p. 25-34). These two changes facilitate the removal of homodimers of heavy chains comprising these changes during protein purification.

In some embodiments, in a binding protein of the present invention, the Fc domain, which comprises a threonine (T) at position 407 [Y407T], further comprises an arginine at position 435 [H435R] and a phenylalanine at position 436 [Y436F]. In this case, the other heavy chain comprises a tyrosine (Y) at position 366 [T366Y], but does not include the two changes at positions 435 and 436. Alternatively, in some embodiments, in a protein of the present invention, the Fc domain, which comprises a serine (S) at position 366 [T366S], an alanine (A) at position 368 [L368A] and a valine (V) at position 407 [Y407V], further comprises an arginine at position 435 [H435R] and a phenylalanine at position 436 [Y436F]. In this case, the other Fc domain comprises a tryptophan (W) at position 366 [T366W], but does not include the two changes at positions 435 and 436. Thus, the Fc domain comprising the amino acid change resulting in a “cavity” as described above also comprises the amino acid changes, which reduce binding to Protein A. Homodimers comprising this Fc domain are removed through reduced binding to Protein A. The production of homodimers of the other Fc domain, which comprises the “protrusion”, is reduced by the presence of the “protrusion”.

In some embodiments, the Fc domain of a protein of the present invention may or may not further comprises YTE mutations (M252Y/S254T/T256E, Eu numbering (Dall’Acqua et al. J. Biol. Chem. 2006, 281(33):23514-24). These mutations have been shown to improve the pharmacokinetic properties of Fc domains through preferential enhancement of binding affinity for neonatal FcRn receptor at pH 6.0.

In some embodiments, the first and/or the second Fc domain of the present invention derived from an IgG1 also includes the “KO” mutations (L234A, L235A) (Xu et al, Cellular Immunology 2000 Feb. 25, 200(1):16-26). In a further aspect, the first and/or the second Fc domain of the present invention derived from an IgG4 also includes the Pro hinge mutation (S228P) (Angal et al, Molecular Immunology 1993, 30(1):105-108; Labrijn et al, Nature Biotechnology 2009, 27:767-771).

In preferred embodiments of the binding protein of the invention, the first Fc domain comprises an amino acid sequence of SEQ ID NO:242 and the second Fc domain comprises an amino acid sequence of SEQ ID NO:243.

In preferred embodiments of the invention, the binding protein comprises i) a first polypeptide chain comprising the amino acid sequence of SEQ ID NO:217 and a second polypeptide chain comprising the amino acid sequence of SEQ ID NO:311 (B7H6 #1/CD3 #1), or ii) a first polypeptide chain comprising the amino acid sequence of SEQ ID NO:218 and a second polypeptide chain comprising the amino acid sequence of SEQ ID NO:311 (B7H6 #2/CD3 #1), or iii) a first polypeptide chain comprising the amino acid sequence of SEQ ID NO:219 and a second polypeptide chain comprising the amino acid sequence of SEQ ID NO:311 (B7H6 #3/CD3 #1), or iv) a first polypeptide chain comprising the amino acid sequence of SEQ ID NO:220 and a second polypeptide chain comprising the amino acid sequence of SEQ ID NO:311 (B7H6 #4/CD3 #1), or v) a first polypeptide chain comprising the amino acid sequence of SEQ ID NO:221 and a second polypeptide chain comprising the amino acid sequence of SEQ ID NO:311 (B7H6 #5/CD3 #1), or vi) a first polypeptide chain comprising the amino acid sequence of SEQ ID NO:222 and a second polypeptide chain comprising the amino acid sequence of SEQ ID NO:311 (B7H6 #6/CD3 #1); or vii) a first polypeptide chain comprising the amino acid sequence of SEQ ID NO:223 and a second polypeptide chain comprising the amino acid sequence of SEQ ID NO:311 (B7H6 #7/CD3 #1); or viii) a first polypeptide chain comprising the amino acid sequence of SEQ ID NO:224 and a second polypeptide chain comprising the amino acid sequence of SEQ ID NO:311 (B7H6 #8/CD3 #1); or ix) a first polypeptide chain comprising the amino acid sequence of SEQ ID NO:225 and a second polypeptide chain comprising the amino acid sequence of SEQ ID NO:311 (B7H6 #9/CD3 #1); or x) a first polypeptide chain comprising the amino acid sequence of SEQ ID NO:226 and a second polypeptide chain comprising the amino acid sequence of SEQ ID NO:311 (B7H6 #10/CD3 #1); or xi) a first polypeptide chain comprising the amino acid sequence of SEQ ID NO:227 and a second polypeptide chain comprising the amino acid sequence of SEQ ID NO:311 (B7H6 #11/CD3 #1); or xii) a first polypeptide chain comprising the amino acid sequence of SEQ ID NO:228 and a second polypeptide chain comprising the amino acid sequence of SEQ ID NO:311 (B7H6 #12/CD3 #1); or xiii) a first polypeptide chain comprising the amino acid sequence of SEQ ID NO:229 and a second polypeptide chain comprising the amino acid sequence of SEQ ID NO:311 (B7H6 #13/CD3 #1); or xiv) a first polypeptide chain comprising the amino acid sequence of SEQ ID NO:230 and a second polypeptide chain comprising the amino acid sequence of SEQ ID NO:311 (B7H6 #14/CD3 #1); or xv) a first polypeptide chain comprising the amino acid sequence of SEQ ID NO:231 and a second polypeptide chain comprising the amino acid sequence of SEQ ID NO:311 (B7H6 #15/CD3 #1), or xvi) a first polypeptide chain comprising the amino acid sequence of SEQ ID NO:232 and a second polypeptide chain comprising the amino acid sequence of SEQ ID NO:311 (B7H6 #16/CD3 #1); or xvii) a first polypeptide chain comprising the amino acid sequence of SEQ ID NO:233 and a second polypeptide chain comprising the amino acid sequence of SEQ ID NO:311 (B7H6 #17/CD3 #1); or xviii) a first polypeptide chain comprising the amino acid sequence of SEQ ID NO:234 and a second polypeptide chain comprising the amino acid sequence of SEQ ID NO:311 (B7H6 #18/CD3 #1); or xix) a first polypeptide chain comprising the amino acid sequence of SEQ ID NO:235 and a second polypeptide chain comprising the amino acid sequence of SEQ ID NO:311 (B7H6 #19/CD3 #1); or xx) a first polypeptide chain comprising the amino acid sequence of SEQ ID NO:236 and a second polypeptide chain comprising the amino acid sequence of SEQ ID NO:311 (B7H6 #20/CD3 #1); or xxi) a first polypeptide chain comprising the amino acid sequence of SEQ ID NO:237 and a second polypeptide chain comprising the amino acid sequence of SEQ ID NO:311 (B7H6 #21/CD3 #1); or xxii) a first polypeptide chain comprising the amino acid sequence of SEQ ID NO:238 and a second polypeptide chain comprising the amino acid sequence of SEQ ID NO:311 (B7H6 #22/CD3

#1); or xxiii) a first polypeptide chain comprising the amino acid sequence of SEQ ID NO:239 and a second polypeptide chain comprising the amino acid sequence of SEQ ID NO:311 (B7H6 #23/CD3 #1); or xxiv) a first polypeptide chain comprising the amino acid sequence of SEQ ID NO:240 and a second polypeptide chain comprising the amino acid sequence of SEQ ID NO:311 (B7H6 #24/CD3 #1). Preferably, the first and second polypeptide chain are linked via one or more disulfide bonds and form an antibody like structure (FIG. 1) similar to a conventional Y-shaped antibody molecule.

In preferred embodiments, the first polypeptide chain comprises an amino acid sequence from the group consisting of any one of SEQ ID NOs:217, 218, 219, 220, 221, 228, 229, 230, 231, 232, 233, 234, 235, 236, 237, 238, 239, and 240 and the second polypeptide chain comprises the amino acid sequence of SEQ ID NO:311. Even more preferably, the first polypeptide chain comprises an amino acid sequence of any one of SEQ ID NOs: 228, 229, 230, 231, 232, 233, 234, 235, 236, 237, 238, 239, and 240 and the second polypeptide chain comprises the amino acid sequence of SEQ ID NO:311, the first and second polypeptide chain are linked via one or more disulfide bonds and form an antibody like structure (FIG. 1) similar to a conventional Y-shaped antibody molecule.

In one preferred embodiment, the binding protein comprises a first polypeptide chain specific for B7H6 comprising an amino acid sequence of SEQ ID NO:228 and a second polypeptide chain specific for CD3 comprising the amino acid sequence of SEQ ID NO:311.

In one preferred embodiment, the binding protein comprises a first polypeptide chain specific for B7H6 comprising an amino acid sequence of SEQ ID NO:230 and a second polypeptide chain specific for CD3 comprising the amino acid sequence of SEQ ID NO:311.

In one preferred embodiment, the binding protein comprises a first polypeptide chain specific for B7H6 comprising an amino acid sequence of SEQ ID NO:231 and a second polypeptide chain specific for CD3 comprising the amino acid sequence of SEQ ID NO:311.

In one preferred embodiment, the binding protein comprises a first polypeptide chain specific for B7H6 comprising an amino acid sequence of SEQ ID NO:232 and a second polypeptide chain specific for CD3 comprising the amino acid sequence of SEQ ID NO:311.

In one preferred embodiment, the binding protein comprises a first polypeptide chain specific for B7H6 comprising an amino acid sequence of SEQ ID NO:239 and a second polypeptide chain specific for CD3 comprising the amino acid sequence of SEQ ID NO:311.

For all of the embodiments described herein it shall be understood that, by using the term "comprising", it is intended to also include an embodiment in which the respective protein, molecule, antigen binding unit or polypeptide chain "consists of" the amino acid sequence as indicated:

In one preferred embodiment, the binding protein comprises a first polypeptide chain specific for B7H6 consisting of an amino acid sequence of SEQ ID NO:228 and a second polypeptide chain specific for CD3 consisting of the amino acid sequence of SEQ ID NO:311. Preferably, the first and second polypeptide chain are linked via one or more disulfide bonds and form an antibody like structure (FIG. 1) similar to a conventional Y-shaped antibody molecule.

In one preferred embodiment, the binding protein comprises a first polypeptide chain specific for B7H6 consisting of an amino acid sequence of SEQ ID NO:230 and a second polypeptide chain specific for CD3 consisting of the amino acid sequence of SEQ ID NO:311. Preferably, the first and second polypeptide chain are linked via one or more disulfide bonds and form an antibody like structure (FIG. 1) similar to a conventional Y-shaped antibody molecule.

In one preferred embodiment, the binding protein comprises a first polypeptide chain specific for B7H6 consisting of an amino acid sequence of SEQ ID NO:231 and a second polypeptide chain specific for CD3 consisting of the amino acid sequence of SEQ ID NO:311. Preferably, the first and second polypeptide chain are linked via one or more disulfide bonds and form an antibody like structure (FIG. 1) similar to a conventional Y-shaped antibody molecule.

In one preferred embodiment, the binding protein comprises a first polypeptide chain specific for B7H6 consisting of an amino acid sequence of SEQ ID NO:232 and a second polypeptide chain specific for CD3 consisting of the amino acid sequence of SEQ ID NO:311. Preferably, the first and second polypeptide chain are linked via one or more disulfide bonds and form an antibody like structure (FIG. 1) similar to a conventional Y-shaped antibody molecule.

In one preferred embodiment, the binding protein comprises a first polypeptide chain specific for B7H6 consisting of an amino acid sequence of SEQ ID NO:239 and a second polypeptide chain specific for CD3 consisting of the amino acid sequence of SEQ ID NO:311. Preferably, the first and second polypeptide chain are linked via one or more disulfide bonds and form an antibody like structure (FIG. 1) similar to a conventional Y-shaped antibody molecule.

In a further aspect, the present invention provides a binding protein comprising a first polypeptide chain specifically binding to B7H6 (a B7H6 chain) and a second polypeptide chain specifically binding to CD3 (a CD3 chain), wherein the first polypeptide chain specifically binding to B7H6 comprises a first light chain covalently linked (preferably directly bound) to a first linker, which is itself covalently linked (e.g., directly bound) to a first heavy chain, and wherein the second polypeptide chain specifically binding to CD3 comprises a second light chain covalently linked (preferably directly bound) to a second linker, which is itself covalently linked (e.g., directly bound) to a second heavy chain.

All definitions and preferred embodiments provided herein above with regard to the binding protein of the invention having the specifically recited antigen-binding units apply mutatis mutandis also to this binding proteins of the invention comprising a first and second polypeptide chain, unless otherwise defined herein.

In some embodiments, the first polypeptide chain (also referred to herein as B7H6 chain), starting from its N-terminus, comprises a first light chain variable domain specifically binding to B7H6, a first light chain constant domain, a first linker, a first heavy chain variable domain specific for B7H6 and a first heavy chain constant region. In some embodiments, the second polypeptide chain (also referred to herein as CD3 chain) starting from its N-terminus, comprises a second light chain variable domain specifically binding to CD3, a second light chain constant domain, a second linker, a second heavy chain variable domain specific for CD3 and a second heavy chain constant domain.

The resulting proteins bear a full Fc, and is larger than an IgG (due to the presence of the linker between the light chain and the heavy chain) and has two independent binding sites (e.g., each binding site being monovalent for the respective antigen), a first binding site for B7H6 and a second binding site for CD3. Preferably, the first and second polypeptide chain are linked via one or more disulfide bonds. As such, the proteins of the invention are antibody-like structures, having the Y shaped structure of a conventional full length antibody (see FIG. 1), comprising two polypeptide chains, each comprising a scFab and a Fc domain. In preferred embodiments, the proteins of the invention comprise (i) a first polypeptide chain specific for B7H6 (a B7H6 chain) consisting of a first scFab specific for B7H6 and a first Fc domain and (ii) a second polypeptide chain specific for CD3 (a CD3 chain) consisting of a second single chain Fab specific for CD3 and a second Fc domain.

Preferably, the first scFab is linked to the first Fc domain via a direct covalent bond and the second scFab is linked to the second Fc domain via a direct covalent bond. This bispecific format greatly reduces heterogeneity after expression and purification (e.g. by avoiding mispairing of light and heavy variable domains with different binding specificities), while maintaining the functional properties of the binding moieties within a structure less likely to generate unwanted immunogenic reactions. This also enables good expression of heterodimeric proteins, e.g. in mammalian cells.

In preferred embodiments of the protein of the invention, the first polypeptide chain specifically binding to B7H6 (B7H6 chain) comprises a first light chain variable domain and a first heavy chain variable domain, which comprise CDR sequences selected from the group consisting of i) to xxiv):

i) light chain CDRs comprising the amino acid sequences of SEQ ID NO:1 (CDR1), SEQ ID NO:2 (CDR2) and SEQ ID NO:3 (CDR3) and heavy chain CDRs comprising the amino acid sequences of SEQ ID NO:4 (CDR1), SEQ ID NO:5 (CDR2) and SEQ ID NO:6 (CDR3);

ii) light chain CDRs comprising the amino acid sequences of SEQ ID NO:7 (CDR1), SEQ ID NO:8 (CDR2) and SEQ ID NO:9 (CDR3) and heavy chain CDRs comprising the amino acid sequences of SEQ ID NO:10 (CDR1), SEQ ID NO:11 (CDR2) and SEQ ID NO:12 (CDR3);

iii) light chain CDRs comprising the amino acid sequences of SEQ ID NO:13 (CDR1), SEQ ID NO:14 (CDR2) and SEQ ID NO:15 (CDR3) and heavy chain CDRs comprising the amino acid sequences of SEQ ID NO:16 (CDR1), SEQ ID NO:17 (CDR2) and SEQ ID NO:18 (CDR3);

iv) light chain CDRs comprising the amino acid sequences of SEQ ID NO:19 (CDR1), SEQ ID NO:20 (CDR2) and SEQ ID NO:21 (CDR3) and heavy chain CDRs comprising the amino acid sequences of SEQ ID NO:22 (CDR1), SEQ ID NO:23 (CDR2) and SEQ ID NO:24 (CDR3);

v) light chain CDRs comprising the amino acid sequences of SEQ ID NO:25 (CDR1), SEQ ID NO:26 (CDR2) and SEQ ID NO:27 (CDR3) and heavy chain CDRs comprising the amino acid sequences of SEQ ID NO:28 (CDR1), SEQ ID NO:29 (CDR2) and SEQ ID NO:30 (CDR3);

vi) light chain CDRs comprising the amino acid sequences of SEQ ID NO:31 (CDR1), SEQ ID NO:32 (CDR2) and SEQ ID NO:33 (CDR3) and heavy chain CDRs comprising the amino acid sequences of SEQ ID NO:34 (CDR1), SEQ ID NO:35 (CDR2) and SEQ ID NO:36 (CDR3);

vii) light chain CDRs comprising the amino acid sequences of SEQ ID NO:37 (CDR1), SEQ ID NO:38 (CDR2) and SEQ ID NO:39 (CDR3) and heavy chain CDRs comprising the amino acid sequences of SEQ ID NO:40 (CDR1), SEQ ID NO:41 (CDR2) and SEQ ID NO:42 (CDR3);

viii) light chain CDRs comprising the amino acid sequences of SEQ ID NO:43 (CDR1), SEQ ID NO:44 (CDR2) and SEQ ID NO:45 (CDR3) and heavy chain CDRs comprising the amino acid sequences of SEQ ID NO:46 (CDR1), SEQ ID NO:47 (CDR2) and SEQ ID NO:48 (CDR3);

ix) light chain CDRs comprising the amino acid sequences of SEQ ID NO:49 (CDR1), SEQ ID NO:50 (CDR2) and SEQ ID NO:51 (CDR3) and heavy chain CDRs comprising the amino acid sequences of SEQ ID NO:52 (CDR1), SEQ ID NO:53 (CDR2) and SEQ ID NO:54 (CDR3);

x) light chain CDRs comprising the amino acid sequences of SEQ ID NO:55 (CDR1), SEQ ID NO:56 (CDR2) and SEQ ID NO:57 (CDR3) and heavy chain CDRs comprising the amino acid sequences of SEQ ID NO:58 (CDR1), SEQ ID NO:59 (CDR2) and SEQ ID NO:60 (CDR3);

xi) light chain CDRs comprising the amino acid sequences of SEQ ID NO:61 (CDR1), SEQ ID NO:62 (CDR2) and SEQ ID NO:63 (CDR3) and heavy chain CDRs comprising the amino acid sequences of SEQ ID NO:64 (CDR1), SEQ ID NO:65 (CDR2) and SEQ ID NO:66 (CDR3);

xii) light chain CDRs comprising the amino acid sequences of SEQ ID NO:67 (CDR1), SEQ ID NO:68 (CDR2) and SEQ ID NO:69 (CDR3) and heavy chain CDRs comprising the amino acid sequences of SEQ ID NO:70 (CDR1), SEQ ID NO:71 (CDR2) and SEQ ID NO:72 (CDR3);

xiii) light chain CDRs comprising the amino acid sequences of SEQ ID NO:73 (CDR1), SEQ ID NO:74 (CDR2) and SEQ ID NO:75 (CDR3) and heavy chain CDRs comprising the amino acid sequences of SEQ ID NO:76 (CDR1), SEQ ID NO:77 (CDR2) and SEQ ID NO:78 (CDR3);

xiv) light chain CDRs comprising the amino acid sequences of SEQ ID NO:79 (CDR1), SEQ ID NO:80 (CDR2) and SEQ ID NO:81 (CDR3) and heavy chain CDRs comprising the amino acid sequences of SEQ ID NO:82 (CDR1), SEQ ID NO:83 (CDR2) and SEQ ID NO:84 (CDR3);

xv) light chain CDRs comprising the amino acid sequences of SEQ ID NO:85 (CDR1), SEQ ID NO:86 (CDR2) and SEQ ID NO:87 (CDR3) and heavy chain CDRs comprising the amino acid sequences of SEQ ID NO:88 (CDR1), SEQ ID NO:89 (CDR2) and SEQ ID NO:90 (CDR3);

xvi) light chain CDRs comprising the amino acid sequences of SEQ ID NO:91 (CDR1), SEQ ID NO:92 (CDR2) and SEQ ID NO:93 (CDR3) and heavy chain CDRs comprising the amino acid sequences of SEQ ID NO:94 (CDR1), SEQ ID NO:95 (CDR2) and SEQ ID NO:96 (CDR3);

xvii) light chain CDRs comprising the amino acid sequences of SEQ ID NO:97 (CDR1), SEQ ID NO:98 (CDR2) and SEQ ID NO:99 (CDR3) and heavy chain CDRs comprising the amino acid sequences of SEQ ID NO:100 (CDR1), SEQ ID NO:101 (CDR2) and SEQ ID NO:102 (CDR3);

xviii) light chain CDRs comprising the amino acid sequences of SEQ ID NO:103 (CDR1), SEQ ID NO:104 (CDR2) and SEQ ID NO:105 (CDR3) and heavy chain CDRs comprising the amino acid sequences of SEQ ID NO:106 (CDR1), SEQ ID NO:107 (CDR2) and SEQ ID NO:108 (CDR3);

xix) light chain CDRs comprising the amino acid sequences of SEQ ID NO:109 (CDR1), SEQ ID NO:110 (CDR2) and SEQ ID NO:111 (CDR3) and heavy chain CDRs comprising the amino acid sequences of SEQ ID NO:112 (CDR1), SEQ ID NO:113 (CDR2) and SEQ ID NO:114 (CDR3);

xx) light chain CDRs comprising the amino acid sequences of SEQ ID NO:115 (CDR1), SEQ ID NO:116 (CDR2) and SEQ ID NO:117 (CDR3) and heavy chain CDRs comprising the amino acid sequences of SEQ ID NO:118 (CDR1), SEQ ID NO:119 (CDR2) and SEQ ID NO:120 (CDR3);

xxi) light chain CDRs comprising the amino acid sequences of SEQ ID NO:121 (CDR1), SEQ ID NO:122 (CDR2) and SEQ ID NO:123 (CDR3) and heavy chain CDRs comprising the amino acid sequences of SEQ ID NO:124 (CDR1), SEQ ID NO:125 (CDR2) and SEQ ID NO:126 (CDR3);

xxii) light chain CDRs comprising the amino acid sequences of SEQ ID NO:127 (CDR1), SEQ ID NO:128 (CDR2) and SEQ ID NO:129 (CDR3) and heavy chain CDRs comprising the amino acid sequences of SEQ ID NO:130 (CDR1), SEQ ID NO:131 (CDR2) and SEQ ID NO:132 (CDR3);

xxiii) light chain CDRs comprising the amino acid sequences of SEQ ID NO:133 (CDR1), SEQ ID NO:134 (CDR2) and SEQ ID NO:135 (CDR3) and heavy chain CDRs comprising the amino acid sequences of SEQ ID NO:136 (CDR1), SEQ ID NO:137 (CDR2) and SEQ ID NO:138 (CDR3); and xxiv) light chain CDRs comprising the amino acid sequences of SEQ ID NO:139 (CDR1), SEQ ID NO:140 (CDR2) and SEQ ID NO:141 (CDR3) and heavy chain CDRs comprising the amino acid sequences of SEQ ID NO:142 (CDR1), SEQ ID NO:143 (CDR2) and SEQ ID NO:144 (CDR3).

The respective light/heavy chain variable domains defined by these CDR sequences are termed B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23 and B7H6 #24, respectively.

In preferred embodiments of the binding protein of the invention, said second polypeptide chain specifically binding to CD3 (CD3 chain) comprises a second light chain variable domain and second heavy chain variable domain, which comprises CDR sequences selected from the group consisting of:

i) light chain CDRs comprising the amino acid sequences of SEQ ID NO:257 (CDR1), SEQ ID NO:258 (CDR2) and SEQ ID NO:259 (CDR3) and heavy chain CDRs comprising the amino acid sequences of SEQ ID NO:260 (CDR1), SEQ ID NO:261 (CDR2) and SEQ ID NO:262 (CDR3);

ii) light chain CDRs comprising the amino acid sequences of SEQ ID NO:263 (CDR1), SEQ ID NO:264 (CDR2) and SEQ ID NO:265 (CDR3) and heavy chain CDRs comprising the amino acid sequences of SEQ ID NO:266 (CDR1), SEQ ID NO:267 (CDR2) and SEQ ID NO:268 (CDR3);

iii) light chain CDRs comprising the amino acid sequences of SEQ ID NO:269 (CDR1), SEQ ID NO:270 (CDR2) and SEQ ID NO:271 (CDR3) and heavy chain CDRs comprising the amino acid sequences of SEQ ID NO:272 (CDR1), SEQ ID NO:273 (CDR2) and SEQ ID NO:274 (CDR3);

iv) light chain CDRs comprising the amino acid sequences of SEQ ID NO:275 (CDR1), SEQ ID NO:276 (CDR2) and SEQ ID NO:277 (CDR3) and heavy chain CDRs comprising the amino acid sequences of SEQ ID NO:278 (CDR1), SEQ ID NO:279 (CDR2) and SEQ ID NO:280 (CDR3);

v) light chain CDRs comprising the amino acid sequences of SEQ ID NO:281 (CDR1), SEQ ID NO:282 (CDR2) and SEQ ID NO:283 (CDR3) and heavy chain CDRs comprising the amino acid sequences of SEQ ID NO:284 (CDR1), SEQ ID NO:285 (CDR2) and SEQ ID NO:286 (CDR3); and vi) light chain CDRs comprising the amino acid sequences of SEQ ID NO:287 (CDR1), SEQ ID NO:288 (CDR2) and SEQ ID NO:289 (CDR3) and heavy chain CDRs comprising the amino acid sequences of SEQ ID NO:290 (CDR1), SEQ ID NO:291 (CDR2) and SEQ ID NO:292 (CDR3).

The respective light/heavy chain variable domains defined by these CDR sequences are termed CD3 #1, CD3 #2, CD3 #3, CD3 #4, CD3 #5 and CD3 #6, respectively.

Preferably, the light chain and heavy chain CDR sequences are selected from the group consisting of B7H6 #1, B7H6 #2, B7H6 #, B7H6 #4, B7H6 #5, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23 and B7H6 #24 as defined above.

In one preferred embodiment, the binding protein of the invention comprises (i) a first polypeptide chain specifically binding to B7H6 (B7H6 chain), comprising a first light chain variable domain with light chain CDRs comprising the amino acid sequences of SEQ ID NO:67 (CDR1), SEQ ID NO:68 (CDR2) and SEQ ID NO:69 (CDR3) and a first heavy chain variable domain with heavy chain CDRs comprising the amino acid sequences of SEQ ID NO:70 (CDR1), SEQ ID NO:71 (CDR2) and SEQ ID NO:72 (CDR3); and (ii) a second polypeptide chain specifically binding to CD3, comprising a second light chain variable domain with light chain CDRs comprising the amino acid sequences of SEQ ID NO:257 (CDR1), SEQ ID NO:258 (CDR2) and SEQ ID NO:259 (CDR3) and a second heavy chain variable domain with heavy chain CDRs comprising the amino acid sequences of SEQ ID NO:260 (CDR1), SEQ ID NO:261 (CDR2) and SEQ ID NO:262 (CDR3).

In one preferred embodiment, the binding protein of the invention comprises (i) a first polypeptide chain specifically binding to B7H6 (B7H6 chain), comprising a first light chain variable domain with light chain CDRs comprising the amino acid sequences of SEQ ID NO:79 (CDR1), SEQ ID NO:80 (CDR2) and SEQ ID NO:81 (CDR3) and a first heavy chain variable domain with heavy chain CDRs comprising the amino acid sequences of SEQ ID NO:82 (CDR1), SEQ ID NO:83 (CDR2) and SEQ ID NO:84 (CDR3); and (ii) a second polypeptide chain specifically binding to CD3, comprising a second light chain variable domain with light chain CDRs comprising the amino acid sequences of SEQ ID NO:257 (CDR1), SEQ ID NO:258 (CDR2) and SEQ ID NO:259 (CDR3) and a second heavy chain variable domain with heavy chain CDRs comprising the amino acid sequences of SEQ ID NO:260 (CDR1), SEQ ID NO:261 (CDR2) and SEQ ID NO:262 (CDR3).

In one preferred embodiment, the binding protein of the invention comprises (i) a first polypeptide chain specifically binding to B7H6, comprising a first light chain variable domain with light chain CDRs comprising the amino acid sequences of SEQ ID NO:85 (CDR1), SEQ ID NO:86 (CDR2) and SEQ ID NO:87 (CDR3) and a first heavy chain variable domain with heavy chain CDRs comprising the amino acid sequences of SEQ ID NO:88 (CDR1), SEQ ID NO:89 (CDR2) and SEQ ID NO:90 (CDR3); and (ii) a second polypeptide chain specifically binding to CD3, comprising a second light chain variable domain with light chain CDRs comprising the amino acid sequences of SEQ ID NO:257 (CDR1), SEQ ID NO:258 (CDR2) and SEQ ID NO:259 (CDR3) and a second heavy chain variable domain with heavy chain CDRs comprising the amino acid sequences of SEQ ID NO:260 (CDR1), SEQ ID NO:261 (CDR2) and SEQ ID NO:262 (CDR3).

In one preferred embodiment, the binding protein of the invention comprises (i) a first polypeptide chain specifically binding to B7H6, comprising a first light chain variable domain with light chain CDRs comprising the amino acid sequences of SEQ ID NO:91 (CDR1), SEQ ID NO:92 (CDR2) and SEQ ID NO:93 (CDR3) and a first heavy chain variable domain with heavy chain CDRs comprising the amino acid sequences of SEQ ID NO:94 (CDR1), SEQ ID NO:95 (CDR2) and SEQ ID NO:96 (CDR3); and (ii) a second polypeptide chain specifically binding to CD3, comprising a second light chain variable domain with light chain CDRs comprising the amino acid sequences of SEQ ID NO:257 (CDR1), SEQ ID NO:258 (CDR2) and SEQ ID NO:259 (CDR3) and a second heavy chain variable domain with heavy chain CDRs comprising the amino acid sequences of SEQ ID NO:260 (CDR1), SEQ ID NO:261 (CDR2) and SEQ ID NO:262 (CDR3).

In one preferred embodiment, the binding protein of the invention comprises (i) a first polypeptide chain specifically binding to B7H6, comprising a first light chain variable domain with light chain CDRs comprising the amino acid sequences of SEQ ID NO:133 (CDR1), SEQ ID NO:134 (CDR2) and SEQ ID NO:135 (CDR3) and a first heavy chain variable domain with heavy chain CDRs comprising the amino acid sequences of SEQ ID NO:136 (CDR1), SEQ ID NO:137 (CDR2) and SEQ ID NO:138 (CDR3); and (ii) a second polypeptide chain specifically binding to CD3, comprising a second light chain variable domain with light chain CDRs comprising the amino acid sequences of SEQ ID NO:257 (CDR1), SEQ ID NO:258 (CDR2) and SEQ ID NO:259 (CDR3) and a second heavy chain variable domain with heavy chain CDRs comprising the amino acid sequences of SEQ ID NO:260 (CDR1), SEQ ID NO:261 (CDR2) and SEQ ID NO:262 (CDR3).

In preferred embodiments of the protein of the invention, said first polypeptide chain specifically binding to B7H6 (B7H6 chain) comprises a light chain variable domain (a first light chain variable domain) and a heavy chain variable domain (a first heavy chain variable domain) selected from the group consisting of i) to xiv):

i) a light chain variable domain comprising the amino acid sequences of SEQ ID NO:145 and heavy chain variable domain comprising the amino acid sequences of SEQ ID NO:146 (B7H6 #1);

ii) a light chain variable domain comprising the amino acid sequences of SEQ ID NO:147 and heavy chain variable domain comprising the amino acid sequences of SEQ ID NO:148 (B7H6 #2);

iii) a light chain variable domain comprising the amino acid sequences of SEQ ID NO:149 and heavy chain variable domain comprising the amino acid sequences of SEQ ID NO:150 (B7H6 #3);

iv) a light chain variable domain comprising the amino acid sequences of SEQ ID NO:151 and heavy chain variable domain comprising the amino acid sequences of SEQ ID NO:152 (B7H6 #4);

v) a light chain variable domain comprising the amino acid sequences of SEQ ID NO:153 and heavy chain variable domain comprising the amino acid sequences of SEQ ID NO:154 (B7H6 #5);

vi) a light chain variable domain comprising the amino acid sequences of SEQ ID NO:155 and heavy chain variable domain comprising the amino acid sequences of SEQ ID NO:156 (B7H6 #6);

vii) a light chain variable domain comprising the amino acid sequence of SEQ ID NO:157 and heavy chain variable domain comprising the amino acid sequence of SEQ ID NO:158 (B7H6 #7);

viii) a light chain variable domain comprising the amino acid sequence of SEQ ID NO:159 and heavy chain variable domain comprising the amino acid sequence of SEQ ID NO:160 (B7H6 #8);

ix) a light chain variable domain comprising the amino acid sequence of SEQ ID NO:161 and heavy chain variable domain comprising the amino acid sequence of SEQ ID NO:162 (B7H6 #9);

x) a light chain variable domain comprising the amino acid sequence of SEQ ID NO:163 and heavy chain variable domain comprising the amino acid sequence of SEQ ID NO:164 (B7H6 #10);

xi) a light chain variable domain comprising the amino acid sequence of SEQ ID NO:165 and heavy chain variable domain comprising the amino acid sequence of SEQ ID NO:166 (B7H6 #11);

xii) a light chain variable domain comprising the amino acid sequence of SEQ ID NO:167 and heavy chain variable domain comprising the amino acid sequence of SEQ ID NO:168 (B7H6 #12);

xiii) a light chain variable domain comprising the amino acid sequence of SEQ ID NO:169 and heavy chain variable domain comprising the amino acid sequence of SEQ ID NO:170 (B7H6 #13);

xiv) a light chain variable domain comprising the amino acid sequence of SEQ ID NO:171 and heavy chain variable domain comprising the amino acid sequence of SEQ ID NO:172 (B7H6 #14);

xv) a light chain variable domain comprising the amino acid sequence of SEQ ID NO:173 and heavy chain variable domain comprising the amino acid sequence of SEQ ID NO:174 (B7H6 #15);

xvi) a light chain variable domain comprising the amino acid sequence of SEQ ID NO:175 and heavy chain variable domain comprising the amino acid sequence of SEQ ID NO:176 (B7H6 #16);

xvii) a light chain variable domain comprising the amino acid sequence of SEQ ID NO:177 and heavy chain variable domain comprising the amino acid sequence of SEQ ID NO:178 (B7H6 #17);

xviii) a light chain variable domain comprising the amino acid sequence of SEQ ID NO:179 and heavy chain variable domain comprising the amino acid sequence of SEQ ID NO:180 (B7H6 #18);

xix) a light chain variable domain comprising the amino acid sequence of SEQ ID NO:181 and heavy chain variable domain comprising the amino acid sequence of SEQ ID NO:182 (B7H6 #19);

xx) a light chain variable domain comprising the amino acid sequence of SEQ ID NO:183 and heavy chain variable domain comprising the amino acid sequence of SEQ ID NO:184 (B7H6 #20);

xxi) a light chain variable domain comprising the amino acid sequence of SEQ ID NO:185 and heavy chain variable domain comprising the amino acid sequence of SEQ ID NO:186 (B7H6 #21);

xxii) a light chain variable domain comprising the amino acid sequence of SEQ ID NO:187 and heavy chain variable domain comprising the amino acid sequence of SEQ ID NO:188 (B7H6 #22);

xxiii) a light chain variable domain comprising the amino acid sequence of SEQ ID NO:189 and heavy chain variable domain comprising the amino acid sequence of SEQ ID NO:190 (B7H6 #23); and xxiv) a light chain variable domain comprising the amino acid sequence of SEQ ID NO:191 and heavy chain variable domain comprising the amino acid sequence of SEQ ID NO:192 (B7H6 #24).

Preferably, the light chain variable and heavy chain variable domain sequences are selected from the group consisting of B7H6 #1, B7H6 #2, B7H6 #, B7H6 #4, B7H6 #5, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23 and B7H6 #24 as defined above.

In preferred embodiments of the protein of the invention, said second polypeptide chain specifically binding to CD3 (CD3 chain) comprises a light chain variable domain (a second light chain variable domain) and a heavy chain variable domain (a second heavy chain variable domain) selected from the group consisting of:

i) a light chain variable domain comprising the amino acid sequence of SEQ ID NO:293 and a heavy chain variable domain comprising the amino acid sequence of SEQ ID NO:294 (CD3 #1);

ii) a light chain variable domain comprising the amino acid sequence of SEQ ID NO:295 and a heavy chain variable domain comprising the amino acid sequence of SEQ ID NO:296 (CD3 #2);

iii) a light chain variable domain comprising the amino acid sequence of SEQ ID NO:297 and a heavy chain variable domain comprising the amino acid sequence of SEQ ID NO:298 (CD3 #3)

iv) a light chain variable domain comprising the amino acid sequence of SEQ ID NO:299 and a heavy chain variable domain comprising the amino acid sequence of SEQ ID NO:300 (CD3 #4)

v) a light chain variable domain comprising the amino acid sequence of SEQ ID NO:301 and a heavy chain variable domain comprising the amino acid sequence of SEQ ID NO:302 (CD3 #5)

vi) a light chain variable domain comprising the amino acid sequence of SEQ ID NO:303 and a heavy chain variable domain comprising the amino acid sequence of SEQ ID NO:304 (CD3 #6).

In some embodiments, the binding protein of the invention comprises a first and a second polypeptide chain comprising CDR and/or VH and VL sequences of the light/heavy chain variable domains selected from the list consisting of B7H6 #1/CD3 #1, B7H6 #2/CD3 #1, B7H6 #3/CD3 #1, B7H6 #4/CD3 #1, B7H6 #5/CD3 #1, B7H6 #6/CD3 #1, B7H6 #7/CD3 #1, B7H6 #8/CD3 #1, B7H6 #9/CD3 #1, B7H6 #10/CD3 #1, B7H6 #11/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1, In preferred embodiments, the binding protein of the invention comprises a first and a second polypeptide chain comprising CDR and/or VH and VL sequences of the light/heavy chain variable domains selected from the list consisting of B7H6 #12/CD3 #1, B7H6 #14/CD3 #1, B7H6 #15/CD3 #1, B7H6 #16/CD3 #1, B7H6 #23/CD3 #1. Even more preferably, the first polypeptide chain comprises an Fc domain comprising an amino acid sequence of SEQ ID NO:242 and said second polypeptide chain comprises an Fc domain comprising an amino acid sequence of SEQ ID NO:243.

In one preferred embodiment, the binding protein of the invention comprises (i) a first polypeptide chain specifically binding to B7H6 (B7H6 chain) comprising a light chain variable domain of SEQ ID NO:167 and heavy chain variable domain of SEQ ID NO:168; and (ii) a second polypeptide chain specifically binding to CD3 (CD3 chain), comprising a light chain variable domain of SEQ ID NO:293 and a heavy chain variable domain of SEQ ID NO:294.

In one preferred embodiment, the binding protein of the invention comprises (i) a first polypeptide chain specifically binding to B7H6 (B7H6 chain), comprising a light chain variable domain of SEQ ID NO:171 and heavy chain variable domain of SEQ ID NO:172; and (ii) a second polypeptide chain specifically binding to CD3 (CD3 chain), comprising a light chain variable domain of SEQ ID NO:293 and a heavy chain variable domain of SEQ ID NO:294.

In one preferred embodiment, the binding protein of the invention comprises (i) a first polypeptide chain specifically binding to B7H6 (B7H6 chain), comprising a light chain variable domain of SEQ ID NO:173 and heavy chain variable domain of SEQ ID NO:174; and (ii) a second polypeptide chain specifically binding to CD3 (CD3 chain), comprising a light chain variable domain of SEQ ID NO:293 and a heavy chain variable domain of SEQ ID NO:294.

In one preferred embodiment, the binding protein of the invention comprises (i) a first polypeptide chain specifically binding to B7H6 (B7H6 chain), comprising a light chain variable domain of SEQ ID NO:175 and heavy chain variable domain of SEQ ID NO:176; and (ii) a second polypeptide chain specifically binding to CD3 (CD3 chain), comprising a light chain variable domain of SEQ ID NO:293 and a heavy chain variable domain of SEQ ID NO:294.

In one preferred embodiment, the binding protein of the invention comprises (i) a first polypeptide chain specifically binding to B7H6 (B7H6 chain), comprising a light chain variable domain of SEQ ID NO:189 and heavy chain variable domain of SEQ ID NO:190; and (ii) a second polypeptide chain specifically binding to CD3 (CD3 chain), comprising a light chain variable domain of SEQ ID NO:293 and a heavy chain variable domain of SEQ ID NO:294.

In preferred embodiments, the first polypeptide chain specific for B7H6 comprises a single chain Fab with the amino acid sequence of any one of SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215 or SEQ ID NO:216 and the second polypeptide chain specific for CD3 comprises a single chain Fab with the amino acid sequence of SEQ ID NO:305.

Preferably, the first polypeptide chain comprises a single chain Fab comprising an amino acid sequence selected from the group consisting of SEQ ID NO:193, SEQ ID NO:194, SEQ ID NO:195, SEQ ID NO:196, SEQ ID NO:197, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215 and SEQ ID NO:216, more preferably an amino acid sequence selected from the group consisting of SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215 and SEQ ID NO:216, and the second polypeptide chain comprises a single chain Fab comprising an amino acid sequence of SEQ ID NO.305.

In one preferred embodiment, the first polypeptide chain specific for B7H6 (B7H6 chain) comprises a single chain Fab comprising the amino acid sequence of SEQ ID NO:204 and the second polypeptide chain specific for CD3 (CD3 chain) comprises a single chain Fab comprising the amino acid sequence of SEQ ID NO:305.

In one preferred embodiment, the first polypeptide chain specific for B7H6 (B7H6 chain) comprises a single chain Fab comprising the amino acid sequence of SEQ ID NO:206 and the second polypeptide chain specific for CD3 (CD3 chain) comprises a single chain Fab comprising the amino acid sequence of SEQ ID NO:305.

In one preferred embodiment, the first polypeptide chain specific for B7H6 (B7H6 chain) comprises a single chain Fab comprising the amino acid sequence of SEQ ID NO:207 and the second polypeptide chain specific for CD3 (CD3 chain) comprises a single chain Fab comprising the amino acid sequence of SEQ ID NO:305.

In one preferred embodiment, the first polypeptide chain specific for B7H6 (B7H6 chain) comprises a single chain Fab comprising the amino acid sequence of SEQ ID NO:208 and the second polypeptide chain specific for CD3 (CD3 chain) comprises a single chain Fab comprising the amino acid sequence of SEQ ID NO:305.

In one preferred embodiment, the first polypeptide chain specific for B7H6 (B7H6 chain) comprises a single chain Fab comprising the amino acid sequence of SEQ ID NO:215 and the second polypeptide chain specific for CD3 (CD3 chain) comprises a single chain Fab comprising the amino acid sequence of SEQ ID NO:305.

Also with regard to this specific embodiment directed to scFabs, it is intented that the term comprising also includes "consisting of" the amino acid sequence as defined herein above in more general terms.

In some embodiments of binding protein of the invention, the first and second polypeptide chain comprises an Fc domain derived from the heavy chain of an IgG, for example an IgG1, IgG2 or IgG4. For example, an Fc domain of the present invention is a Fc domain of a heavy chain of an IgG1 or IgG4 and comprises a hinge region and two constant domains (CH2 and CH3). Examples of Fc domains of human IgGs are shown in SEQ ID NO:241 and SEQ ID NO:244.

In some embodiments of the binding protein of the invention, the heavy chain comprises one or more amino acid changes. For example, such amino acid changes are a tyrosine (Y) at position 366 [T366Y] of the first heavy chain and a threonine (T) at position 407 [Y407T] of the second heavy chain. In some embodiments, the first heavy chain comprises a serine (S) at position 366 [T366S] and the second heavy chain comprises a tryptophan (W) at position 366 [T366W], an alanine (A) at position 368 [L368A] and a valine (V) at position 407 [Y407V]. In preferred embodiments, the first heavy chain comprises a tryptophan (W) at position 366 [T366W] and the second heavy chain comprises a serine (S) at position 366 [T366S], an alanine (A) at position 368 [L368A] and a valine (V) at position 407 [Y407V]. For example, position 366 of the Fc domain according to Eu numbering, corresponding to the amino acid position 146 in the human IgG1 Fc sequence of SEQ ID NO:241, is changed from T at position 146 in SEQ ID NO:241 to W at position 146 in SEQ ID NO:242; and positions 366, 368 and 407 according to Eu numbering, corresponding to the amino acid positions 146, 148 and 187, respectively, in SEQ ID NO:241, are changed from T, L and Y at these positions in SEQ ID NO:241 to S, A and V at these positions in SEQ ID NO:243. In any of these embodiments, the amino acid changes described for the first heavy chain may be located in the second heavy chain and the respective amino acid changes for the second heavy chain may be located in the first heavy chain. In other words, the term "first" and "second" can be exchanged in these embodiments. In some embodiments, the heavy chain is derived from the heavy chain of an $IgG_1$ or $IgG_4$.

In some embodiments, the first heavy chain or the second heavy chain in a protein of the present invention further comprises one or more amino acid changes which reduce the binding of the heavy chain to protein A. In some embodiments, such amino acid changes are an arginine at position 435 [H435R] and a phenylalanine at position 436 [Y436F] of one of the heavy chains.

In some embodiments, in a protein of the present invention, the heavy chain, which comprises a threonine (T) at position 407 [Y407T], further comprises an arginine at position 435 [H435R] and a phenylalanine at position 436 [Y436F]. In this case, the other heavy chain comprises a tyrosine (Y) at position 366 [T366Y], but does not include the two changes at positions 435 and 436. Alternatively, in some embodiments, in a protein of the present invention, the heavy chain, which comprises a serine (S) at position 366 [T366S], an alanine (A) at position 368 [L368A] and a valine (V) at position 407 [Y407V], further comprises an arginine at position 435 [H435R] and a phenylalanine at position 436 [Y436F]. In this case, the other heavy chain comprises a tryptophan (W) at position 366 [T366W], but does not include the two changes at positions 435 and 436. Thus, the heavy chain comprising the amino acid change resulting in a "cavity" as described above also comprises the amino acid changes, which reduce binding to Protein A. Homodimers comprising these heavy chains are removed through reduced binding to Protein A. The production of homodimers of the other heavy chain, which comprises the "protrusion", is reduced by the presence of the "protrusion".

In some embodiments, the heavy chain of a protein of the present invention may or may not further comprise YTE mutations (M252Y/S254T/T256E, Eu numbering (Dall'Acqua et al., J. Biol. Chem. 2006, 281(33):23514-24)). These mutations have been shown to improve the pharmacokinetic properties of heavy chain through preferential enhancement of binding affinity for neonatal FcRn receptor at pH 6.0.

In some embodiments, the first and/or the second heavy chain of the present invention derived from an IgG1 also includes the "KO" mutations (L234A, L235A) (Xu et al, Cellular Immunology 2000 Feb. 25, 200(1):16-26). In a further aspect, the first and/or the second heavy chain of the present invention derived from an IgG4 also includes the Pro hinge mutation (S228P) (Angal et al, Molecular Immunology 1993, 30(1):105-108; Labrijn et al, Nature Biotechnology 2009, 27:767-771).

In preferred embodiments of the binding protein of the invention, the first polypeptide chain comprises an Fc domain comprising an amino acid sequence of SEQ ID NO:242 and the second polypeptide chain comprises an Fc domain comprising an amino acid sequence of SEQ ID NO:243.

In preferred embodiments of the invention, the binding protein comprises i) a first polypeptide chain comprising the amino acid sequence of SEQ ID NO:217 and a second polypeptide chain comprising the amino acid sequence of SEQ ID NO:311 (B7H6 #1/CD3 #1), or ii) a first polypeptide chain comprising the amino acid sequence of SEQ ID NO:218 and a second polypeptide chain comprising the amino acid sequence of SEQ ID NO:311 (B7H6 #2/CD3 #1), or iii) a first polypeptide chain comprising the amino acid sequence of SEQ ID NO:219 and a second polypeptide chain comprising the amino acid sequence of SEQ ID NO:311 (B7H6 #3/CD3 #1), or iv) a first polypeptide chain comprising the amino acid sequence of SEQ ID NO:220 and a second polypeptide chain comprising the amino acid sequence of SEQ ID NO:311 (B7H6 #4/CD3 #1), or v) a first polypeptide chain comprising the amino acid sequence of SEQ ID NO:221 and a second polypeptide chain comprising the amino acid sequence of SEQ ID NO:311 (B7H6 #5/CD3 #1), or vi) a first polypeptide chain comprising the amino acid sequence of SEQ ID NO:222 and a second polypeptide chain comprising the amino acid sequence of SEQ ID NO:311 (B7H6 #6/CD3 #1); or vii) a first polypeptide chain comprising the amino acid sequence of SEQ ID NO:223 and a second polypeptide chain comprising the amino acid sequence of SEQ ID NO:311 (B7H6 #7/CD3 #1); or viii) a first polypeptide chain comprising the amino acid sequence of SEQ ID NO:224 and a second polypeptide chain comprising the amino acid sequence of SEQ ID NO:311 (B7H6 #8/CD3 #1); or ix) a first polypeptide chain comprising the amino acid sequence of SEQ ID NO:225 and a second polypeptide chain comprising the amino acid sequence of SEQ ID NO:311 (B7H6 #9/CD3 #1); or x) a first polypeptide chain comprising the amino acid sequence of SEQ ID NO:226 and a second polypeptide chain comprising the amino acid sequence of SEQ ID NO:311 (B7H6 #10/CD3 #1); or xi) a first polypeptide chain comprising the amino acid sequence of SEQ ID NO:227 and a second polypeptide chain comprising the amino acid sequence of SEQ ID NO:311 (B7H6 #11/CD3 #1); or xii) a first polypeptide chain comprising the amino acid sequence of SEQ ID NO:228 and a second polypeptide chain comprising the amino acid sequence of SEQ ID NO:311 (B7H6 #12/CD3 #1); or xiii) a first polypeptide chain comprising the amino acid sequence of SEQ ID NO:229 and a second polypeptide chain comprising the amino acid sequence of SEQ ID NO:311 (B7H6 #13/CD3 #1); or xiv) a first polypeptide chain comprising the amino acid sequence of SEQ ID NO:230 and a second polypeptide chain comprising the amino acid sequence of SEQ ID NO:311 (B7H6 #14/CD3 #1); or xv) a first polypeptide chain comprising the amino acid sequence of SEQ ID NO:231 and a second polypeptide chain comprising the amino acid sequence of SEQ ID NO:311 (B7H6 #15/CD3 #1), or xvi) a first polypeptide chain comprising the amino acid sequence of SEQ ID NO:232 and a second polypeptide chain comprising the amino acid sequence of SEQ ID NO:311 (B7H6 #16/CD3 #1); or xvii) a first polypeptide chain comprising the amino acid sequence of SEQ ID NO:233 and a second polypeptide chain comprising the amino acid sequence of SEQ ID NO:311 (B7H6 #17/CD3 #1); or xviii) a first polypeptide chain comprising the amino acid sequence of SEQ ID NO:234 and a second polypeptide chain comprising the amino acid sequence of SEQ ID NO:311 (B7H6 #18/CD3 #1); or xix) a first polypeptide chain comprising the amino acid sequence of SEQ ID NO:235 and a second polypeptide chain comprising the amino acid sequence of SEQ ID NO:311 (B7H6 #19/CD3 #1); or xx) a first polypeptide chain comprising the amino acid sequence of SEQ ID NO:236 and a second polypeptide chain comprising the amino acid sequence of SEQ ID NO:311 (B7H6 #20/CD3 #1); or xxi) a first polypeptide chain comprising the amino acid sequence of SEQ ID NO:237 and a second polypeptide chain comprising the amino acid sequence of SEQ ID NO:311 (B7H6 #21/CD3 #1); or xxii) a first polypeptide chain comprising the amino acid sequence of SEQ ID NO:238 and a second polypeptide chain comprising the amino acid sequence of SEQ ID NO:311 (B7H6 #22/CD3 #1); or xxiii) a first polypeptide chain comprising the amino acid sequence of SEQ ID NO:239 and a second polypeptide chain comprising the amino acid sequence of SEQ ID NO:311 (B7H6 #23/CD3 #1); or xxiv) a first polypeptide chain comprising the amino acid sequence of SEQ ID NO:240 and a second polypeptide chain comprising the amino acid sequence of SEQ ID NO:311 (B7H6 #24/CD3 #1). Preferably, the first and second polypeptide chain are linked via one or more disulfide bonds and form an antibody like structure (FIG. 1) similar to a conventional Y-shaped antibody molecule.

In one preferred embodiment, the binding protein comprises a first polypeptide chain specific for B7H6 comprising an amino acid sequence of SEQ ID NO:228 and a second polypeptide chain specific for CD3 comprising the amino acid sequence of SEQ ID NO:311. Preferably, the first and second polypeptide chain are linked via one or more disulfide bonds and form an antibody like structure (FIG. 1) similar to a conventional Y-shaped antibody molecule.

In one preferred embodiment, the binding protein comprises a first polypeptide chain specific for B7H6 comprising an amino acid sequence of SEQ ID NO:230 and a second polypeptide chain specific for CD3 comprising the amino acid sequence of SEQ ID NO:311. Preferably, the first and second polypeptide chain are linked via one or more disulfide bonds and form an antibody like structure (FIG. 1) similar to a conventional Y-shaped antibody molecule.

In one preferred embodiment, the binding protein comprises a first polypeptide chain specific for B7H6 comprising an amino acid sequence of SEQ ID NO:231 and a second polypeptide chain specific for CD3 comprising of the amino acid sequence of SEQ ID NO:311. Preferably, the first and second polypeptide chain are linked via one or more disulfide bonds and form an antibody like structure (FIG. 1) similar to a conventional Y-shaped antibody molecule.

In one preferred embodiment, the binding protein comprises a first polypeptide chain specific for B7H6 comprising an amino acid sequence of SEQ ID NO:232 and a second polypeptide chain specific for CD3 comprising the amino acid sequence of SEQ ID NO:311. Preferably, the first and second polypeptide chain are linked via one or more disulfide bonds and form an antibody like structure (FIG. 1) similar to a conventional Y-shaped antibody molecule.

In a further aspect, the proteins of the invention comprise a first antigen binding unit or polypeptide chain specific for B7H6 with an affinity of preferably ≤10 nM, more preferably ≤1 nM, even more preferable ≤0.1 nM, to human and cynomolgus monkey B7H6. The affinity can be measured in a SPR (BIAcore® SPR system (GE Healthcare Life Sciences)) assay using recombinant B7H6-protein, as described, e.g. in the examples or other methods that are well known for the skilled person. The proteins comprise a second antigen binding unit or polypeptide chain with an affinity of preferably ≤500 nM, more preferably ≤100 nM, even more preferably ≤10 nM to human and cynomolgus monkey CD3εγ complex.

In a further aspect, the B7H6/CD3 binding proteins of the invention do not bind to B7H6-negative cells and do not cross-react with B7H1 (see e.g. example 10 and example 4, respectively).

In preferred embodiments, the B7H6/CD3 binding proteins of the present invention (e.g. any one of B7H6 #1/CD3 #1, B7H6 #2/CD3 #1, B7H6 #3/CD3 #1, B7H6 #4/CD3 #1, B7H6 #5/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1) do not inhibit activation of natural killer cells. Notably, B7H6/CD3 binding proteins of the invention, which do not inhibit activation of natural killer cells in vitro, bind to B7H6 in which the NKp30 interaction sites were substituted with alanine.

B7H6 on the cell surface binds to NKp30 on the cell surface of NK cells, which triggers NKp30-mediated activation of NK cells, NK cell cytotoxicity and cytokine secretion (Brandt et al, J. Exp. Med. 2009, 206(7):1495-503). This situation can be mimicked in vitro by cultivation of NK cell lines (e.g. NK92MI) or primary NK cells on plates coated with recombinant B7H6 extracellular domain protein with subsequent analysis of upregulation of activation markers such as CD25 or CD69 or cytokine secretion by NK cells. This assay setting was used to assess whether our B7H6/CD3 binding proteins inhibit the interaction of B7H6 and NKp30 resulting in inhibition of IFNγ secretion (Example 11).

Figure 4:
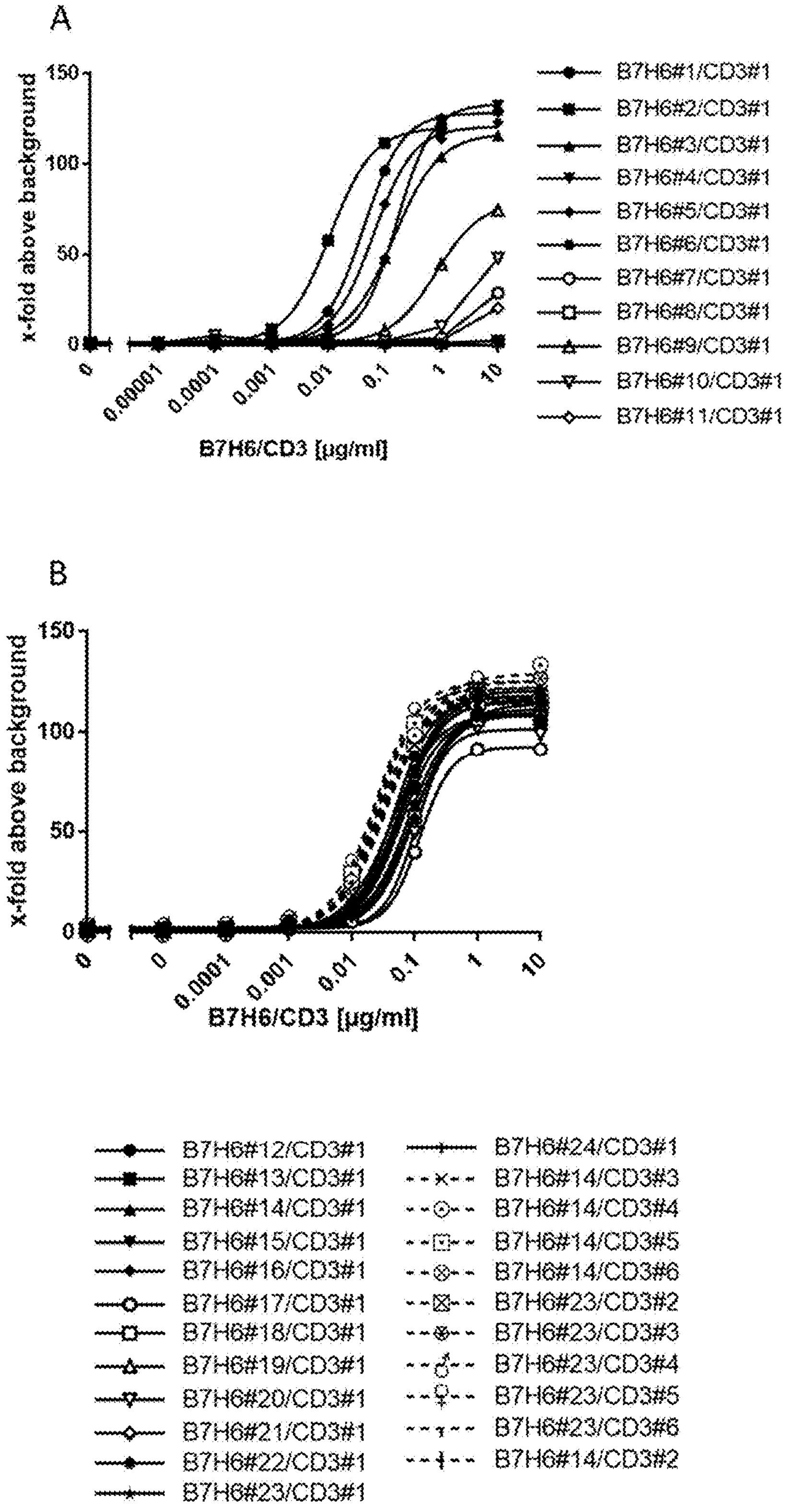
FIG. 4: Binding of 34 exemplary B7H6/CD3 binding proteins to recombinant human Alanine-mutated B7H6 extracellular protein.
Figure 9:
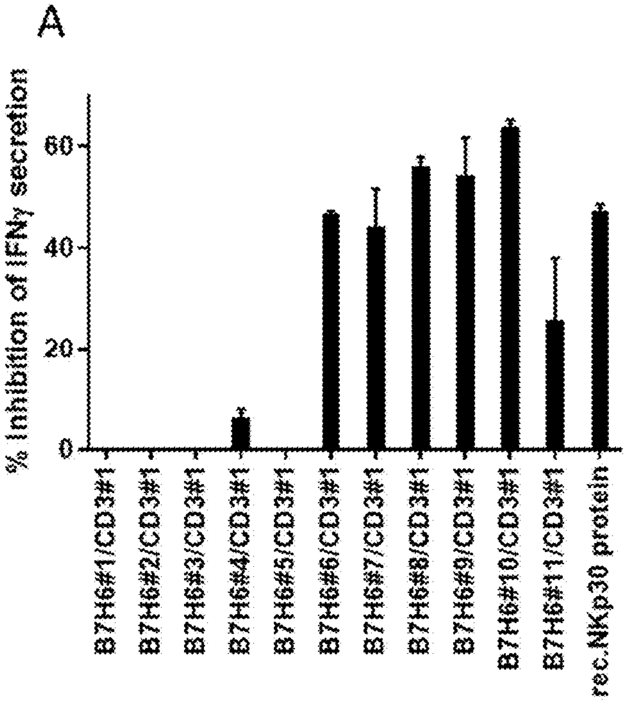
FIG. 9: Inhibitory activity of 17 exemplary B7H6/CD3 binding proteins of B7H6-dependent IFNγ secretion by NK-92MI cells.
Figure 9:
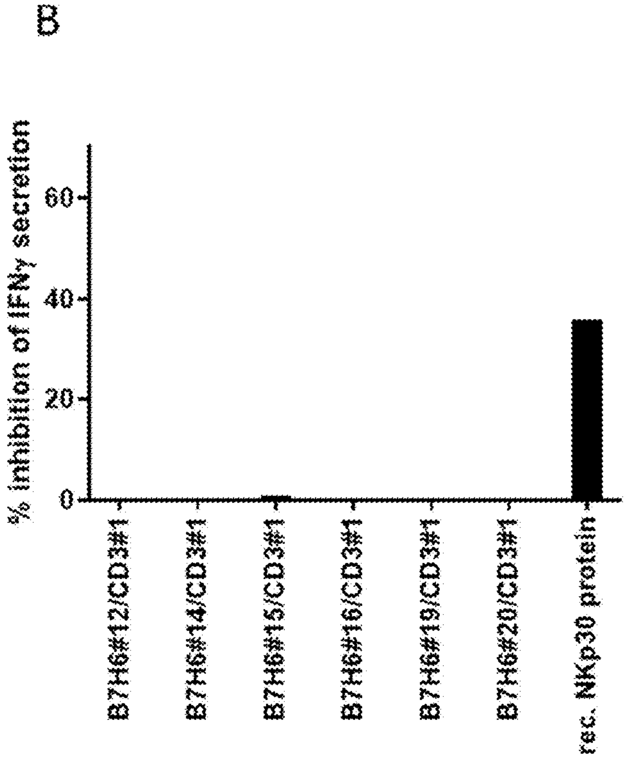

Using recombinant Ala-mutated B7H6 extracellular proteins; in which the NKp30 interaction sites were substituted with alanine, it was seen that there are two groups of binding proteins: 1) binding proteins that potently bind to wild-type B7H6 but which do not or only weakly bind to recombinant Ala-mutated B7H6 extracellular proteins were found to inhibit the B7H6 dependent secretion of IFNγ by NK cells in vitro ("inhibitors of B7H6 dependent NK cell activation") and 2) binding proteins that potently bind to wild-type B7H6 and maintain the ability to bind also to the recombinant Ala-mutated B7H6 extracellular proteins were found to not inhibit the B7H6 dependent activation of NK cells and associated IFNγ secretion in vitro ("non-inhibitors of B7H6 dependent NK cell activation") (See examples 6 and 11, FIGS. 4 and 9). Surprisingly binding proteins of the invention which are non-inhibitors of B7H6 dependent NK cell activation are more potent in T cell redirected lysis of B7H6 expressing tumor cells (see example 12, FIGS. 10 and 11). Without being bound by theory, it is likely that non-inhibitors of B7H6 dependent NK cell activation allow B7H6 NKp30 interaction without impacting the natural role of B7H6 in mediating innate immunity.

Figure 10:
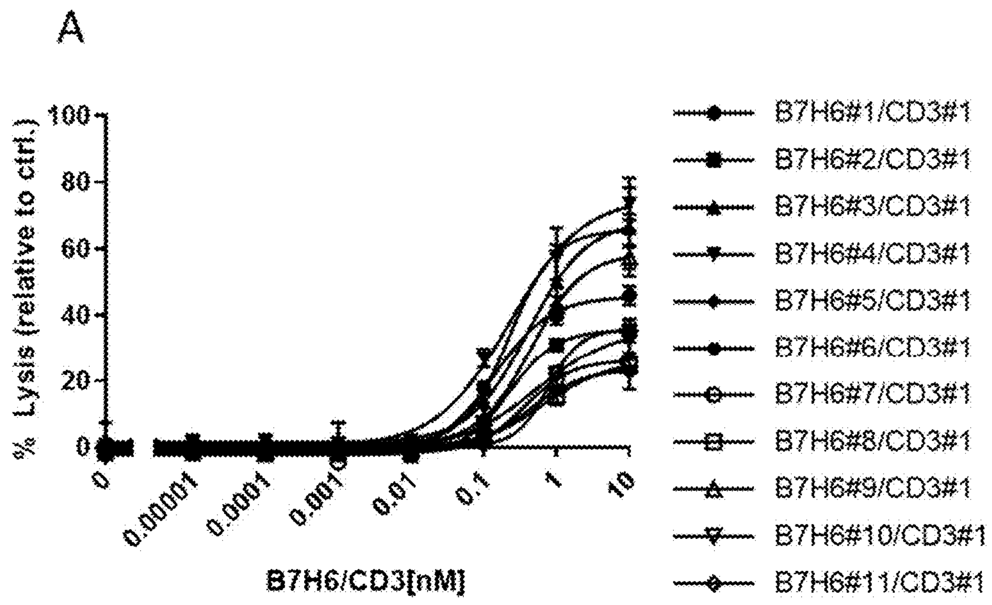
FIG. 10: Potency in lysing target cells of 11 exemplary B7H6/CD3 binding proteins redirecting non-stimulated T-cells towards human HCT-15 cells.
Figure 10:
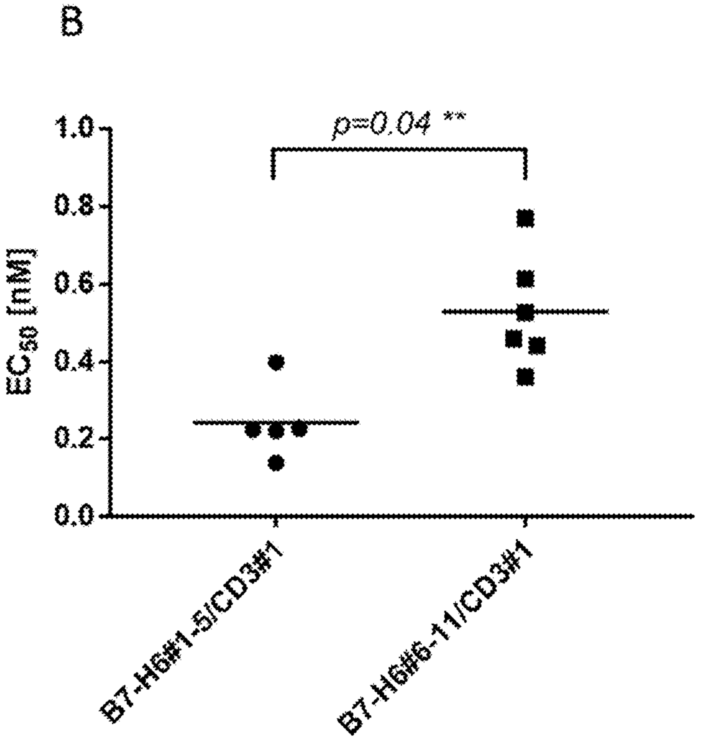
Figure 11:
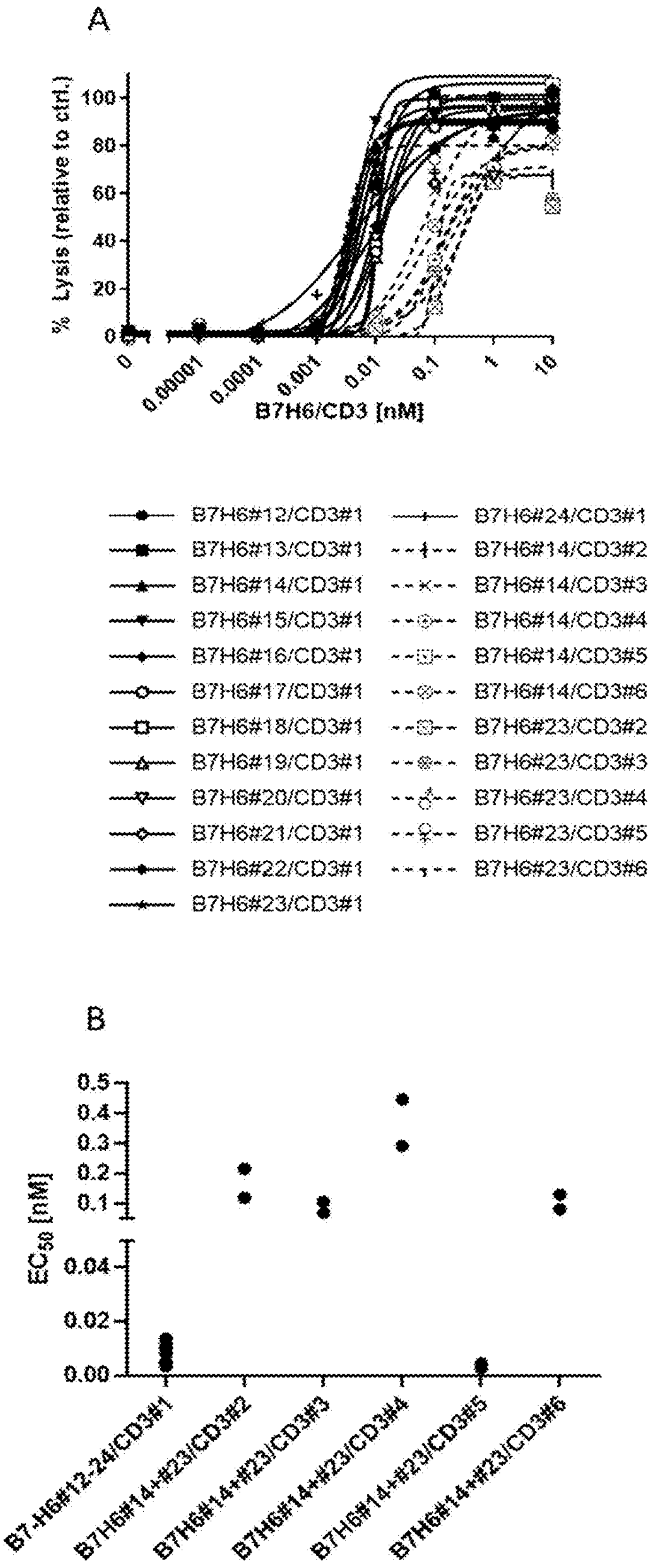
FIG. 11: Potency in lysing target cells of 23 exemplary B7H6/CD3 binding proteins redirecting non-stimulated T-cells towards human HCT-15 cells.
Figure 20:
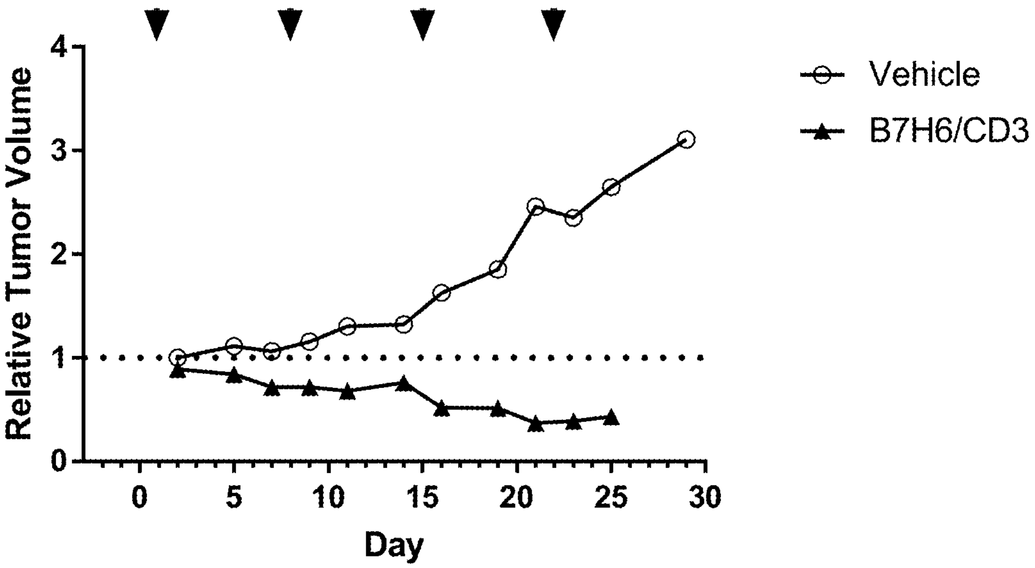
FIG. 20: Anti-tumor activity of one exemplary B7H6/CD3 binding protein in a T-cell engrafted mouse xenograft model.
Figure 23:
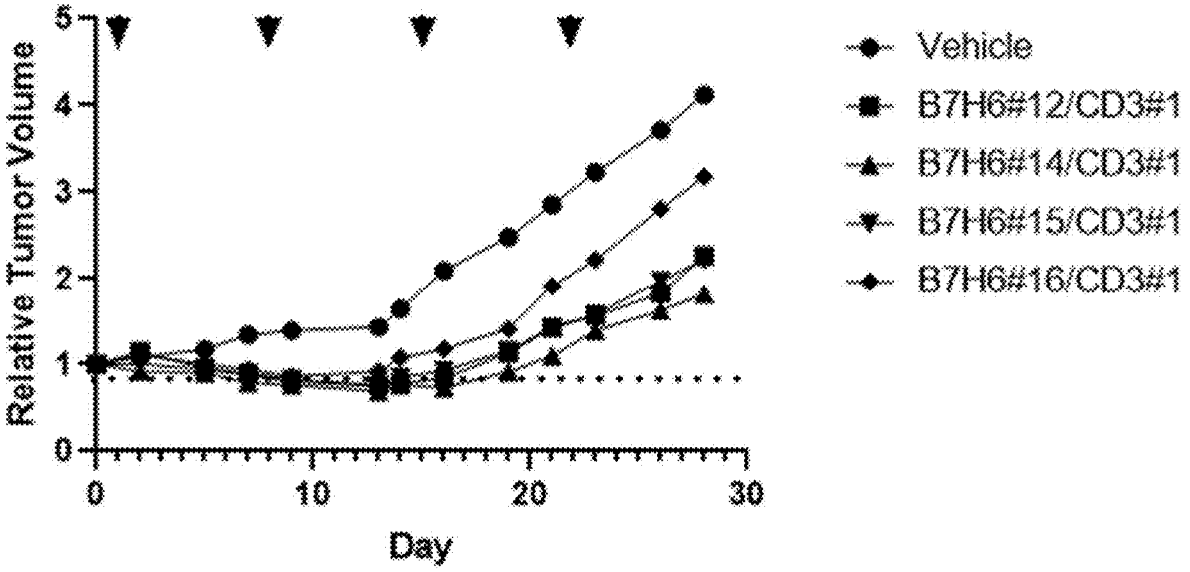
FIG. 23: Anti-tumor activity of four exemplary B7H6/CD3 binding proteins in a T-cell engrafted mouse xenograft model.

In a further aspect, the B7H6/CD3 binding proteins of the present invention are capable of mediating T cell redirected cytotoxicity against tumor cells independent of NK cell activity (as shown in the mouse xenograft model where no NK cells are present, see Example 19, FIGS. 20 and 23, as well as in the cell lysis assay in the absence of NK cells, see Example 12, FIGS. 10 and 11).

Various methods can be used to measure the cytotoxicity mediated by the B7H6/CD3 binding proteins of the present invention. For example, cytotoxicity can be measured using the method described in example 12. Effector cells can be e.g. stimulated or unstimulated (human or cynomolgus monkey) T cells or their subsets (e.g. CD4, CD8) or unstimulated (human or cynomolgus monkey) peripheral blood mononuclear cells (PBMCs). The target cells should express at least the extracellular domain of (human or cynomolgus monkey) B7H6 and can be cells with endogenous (natural) B7H6 expression, such as human small cell lung carcinoma cell lines SHP77, NCI-H82, alternatively also recombinant cells that express either the full-length B7H6 or the extracellular domain of B7H6. The effector to target cell ratio (E:T) is usually about 10:1 but can vary. Cytotoxic activity of B7H6/CD3 binding molecules can be determined e.g. in a LDH-release assay after 48 or 72 hours of incubation. Modifications in incubation time and read-out used for determination of cytotoxicity are possible and known to the skilled person. Read-out systems for cytotoxicity can comprise MTT/MTS assays, ATP-based assays, FACS-based assays, 51-Chromium release assays, sulforhodamine B (SRB) assays, colorimetric (WST) assays, clonogenic assays, ECIS technology and bioluminescent assays.

The cytotoxic activity mediated by B7H6/CD3 binding proteins of the present invention is preferably measured in a cell-based cytotoxicity assay. The cytotoxicity is represented by the $EC_{90}$ values measured in the cytotoxicity assay. The skilled person is aware that an $EC_{90}$ can be expected to be lower when purified T cells are used as effector cells, compared with PBMCs, the skilled person is also aware that the $EC_{90}$ can be even lower when stimulated T cells are used. It can furthermore expected that the $EC_{90}$ values are lower when the target cells express a high number of B7H6 on the cell surface compared to cell expressing a low number of B7H6 molecules on the cell surface. The $EC_{90}$ of the B7H6/CD3 binding protein is preferably ≤10 nM, more preferably ≤5 nM and even more preferably ≤1 nM.

Preferably, the multi-specific binding proteins of the invention do not induce/mediate lysis of B7H6 negative cells. The term "do not induce/mediate lysis" of B7H6-negative cells means that an B7H6/CD3 binding molecule does not induce or mediate lysis of more than 30%, preferably not more than 20%, more preferably not more than 10% and particular not more than 5% or B7H6-negative cells, whereas lysis of the B7H6-positive colorectal cell line is set to be 100%. This usually applies for concentrations of the binding protein of up to 1000 nM.

Furthermore, the B7H6/CD3 binding proteins of the invention are shown to reach a monomer content of above 95% in a two-step purification process (see example 20), have favorable pharmacokinetic properties and good downstream manufacturability and are further expected to have good bio-distribution (see e.g., example 18). The proteins of the present invention furthermore have a favorable immunogenicity profile (see example 22) and have good stability in-vitro and in-vivo (see e.g., examples 21 and 18). Furthermore, the B7H6/CD3 binding proteins of the invention show favorable efficacy in a humanized in vivo xenograft mouse model. B7H6/CD3 binding proteins induced strong tumor regression starting already after the first dose of B7H6/CD3 binding proteins (see e.g., examples 19).

Furthermore the B7H6/CD3 binding proteins of the invention induce tumor regression at very low doses of 0.05 mg/kg administered once weekly (q7d), further supporting their therapeutic applicability. In particular, the B7H6/CD3 binding proteins of the invention induce selective T cell proliferation, T cell activation, T cell degranulation and cytokine secretion (see examples 16, 14, 15, 17, respectively) only in the presence of B7H6-positive target cells and not in the presence of B7H6-negative target cells, and further significantly increase T cell infiltration into tumor tissue (see example 24).

A further aspect of the present invention provides isolated nucleic acid molecules encoding the first and/or the second antigen binding unit (any one of the antigen binding units B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23, and B7H6 #24 and/or any one of the antigen binding units CD3 #1, CD3 #2, CD3 #3, CD3 #4, CD3 #5, and CD3 #6 as defined by CDR, VH/VL or scFab sequences as shown in Table 1, respectively) of a multi-specific binding protein of the invention. In some embodiments, the nucleic acid molecules further encode a first and/or a second Fc domain as described herein, the first and/or second Fc domain linked to the 3' end of the nucleic acid molecule encoding the first and/or second antigen binding unit, respectively. In some embodiments, the nucleic acid molecule encodes i) a first polypeptide chain comprising a first single chain Fab specific for B7H6 (e.g., any one of B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23, and B7H6 #24), and a first Fc domain and/or ii) a second polypeptide chain comprising a second single chain Fab specific for CD3 (e.g., any one of CD3 #1, CD3 #2, CD3 #3, CD3 #4, CD3 #5, and CD3 #6, preferably CD3 #1) and a second Fc domain.

Preferably the nucleic acid molecule comprises a nucleotide sequence encoding a first single chain Fab specific for B7H6 of any one of SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215 or SEQ ID NO:216 and/or a second single chain Fab of SEQ ID NO:305. In preferred embodiments, the nucleic acid molecule comprises the nucleotide sequence encoding a first scFab specific for B7H6 of any one of SEQ ID NO:204, SEQ ID NO:206, SEQ ID NO:207, SEQ ID NO:208, or SEQ ID NO:215, and/or the nucleotide sequence encoding a second scFab specific for CD3 comprising the amino acid sequence of SEQ ID NO:305.

A further aspect of the invention provides an expression vector containing a DNA molecule comprising the nucleotide sequence encoding the first and/or second antigen binding domain (e.g. a first and/or second single chain Fab of the invention). Preferably the expression vector comprises, in addition, a nucleic acid molecule, preferably a DNA molecule, encoding a first and/or second Fc domain, linked to the nucleic acid molecule, preferably the DNA molecule, encoding the first and/or second antigen binding domain (e.g. first and/or second single chain Fab) respectively. As such, the expression vector comprises a nucleotide sequence encoding a polypeptide chain comprising a first single chain Fab linked to a first Fc domain and/or a nucleotide sequence encoding a polypeptide chain comprising a second single chain Fab linked to a second Fc domain.

In a preferred embodiment, the expression vector contains a DNA molecule comprising the nucleotide sequence encoding the first polypeptide chain specific for B7H6 and/or the second polypeptide chain specific for CD3 of the invention. In a preferred embodiment, the expression vector comprises the nucleotide sequence encoding a first polypeptide chain of any one of SEQ ID NO:217, SEQ ID NO:218, SEQ ID NO:219, SEQ ID NO:220, SEQ ID NO:221, SEQ ID NO:222, SEQ ID NO:223, SEQ ID NO; 224, SEQ ID NO:225, SEQ ID NO:226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239 or SEQ ID NO: 240 and/or the nucleotide sequence encoding a second polypeptide chain comprising SEQ ID NO:311.

In further preferred embodiments, the expression vector comprises the nucleotide sequence encoding a first polypeptide chain of any one of SEQ ID NO:228, SEQ ID NO:230, SEQ ID NO:231, SEQ ID NO:232, and SEQ ID NO:239 and/or the nucleotide sequence encoding a second polypeptide chain comprising SEQ ID NO:311.

In a specifically preferred embodiment, two expression vectors may be used, one of them for expression of the first polypeptide chain specific for B7H6, the other one for expression of the second polypeptide chain specific for CD3, which two expression vectors may then both be transfected into a host cell for recombinant protein expression.

Preferably, the expression vector will be a vector comprising said nucleic acid molecule or molecules, operably linked to at least one regulatory sequence, wherein such regulatory sequence may be a promoter, enhancer, or terminator sequence, and most preferably a heterologous promotor, enhancer, or terminator sequence.

In another aspect, the invention relates to a host cell having an expression vector encoding a first polypeptide chain specific for B7H6 of the invention and an expression vector encoding a second polypeptide chain specific for CD3 of the invention.

According to a particularly preferred embodiment, said host cells are eukaryotic cells such as mammalian cells. In another embodiment, such host cells are bacterial cells. Other useful cells are yeast cells or other fungal cells.

Suitable mammalian cells include for example CHO cells, BHK cells, HeLa cells, COS cells, and the like. However, amphibian cells, insect cells, plant cells, and any other cells used in the art for the expression of heterologous proteins can be used as well.

Anti-B7H6 Antibodies

A further aspect of the invention provides anti-B7H6 antibody molecules comprising i) light chain CDRs comprising the amino acid sequences of SEQ ID NO:1 (CDR1), SEQ ID NO:2 (CDR2) and SEQ ID NO:3 (CDR3) and heavy chain CDRs comprising the amino acid sequences of SEQ ID NO:4 (CDR1), SEQ ID NO:5 (CDR2) and SEQ ID NO:6 (CDR3); or ii) light chain CDRs comprising the amino acid sequences of SEQ ID NO:7 (CDR1), SEQ ID NO:8 (CDR2) and SEQ ID NO:9 (CDR3) and heavy chain CDRs comprising the amino acid sequences of SEQ ID NO:10 (CDR1), SEQ ID NO:11 (CDR2) and SEQ ID NO:12 (CDR3); or iii) light chain CDRs comprising the amino acid sequences of SEQ ID NO:13 (CDR1), SEQ ID NO:14 (CDR2) and SEQ ID NO:15 (CDR3) and heavy chain CDRs comprising the amino acid sequences of SEQ ID NO:16 (CDR1), SEQ ID NO:17 (CDR2) and SEQ ID NO:18 (CDR3); or iv) light chain CDRs comprising the amino acid sequences of SEQ ID NO:19 (CDR1), SEQ ID NO:20 (CDR2) and SEQ ID NO:21 (CDR3) and heavy chain CDRs comprising the amino acid sequences of SEQ ID NO:22 (CDR1), SEQ ID NO:23 (CDR2) and SEQ ID NO:24 (CDR3); or v) light chain CDRs comprising the amino acid sequences of SEQ ID NO:25 (CDR1), SEQ ID NO:26 (CDR2) and SEQ ID NO:27 (CDR3) and heavy chain CDRs comprising the amino acid sequences of SEQ ID NO:28 (CDR1), SEQ ID NO:29 (CDR2) and SEQ ID NO:30 (CDR3); or vi) light chain CDRs comprising the amino acid sequences of SEQ ID NO:31 (CDR1), SEQ ID NO:32 (CDR2) and SEQ ID NO:33 (CDR3) and heavy chain CDRs comprising the amino acid sequences of SEQ ID NO:34 (CDR1), SEQ ID NO:35 (CDR2) and SEQ ID NO:36 (CDR3); or vii) light chain CDRs comprising the amino acid sequences of SEQ ID NO:37 (CDR1), SEQ ID NO:38 (CDR2) and SEQ ID NO:39 (CDR3) and heavy chain CDRs comprising the amino acid sequences of SEQ ID NO:40 (CDR1), SEQ ID NO:41 (CDR2) and SEQ ID NO:42 (CDR3); or viii) light chain CDRs comprising the amino acid sequences of SEQ ID NO:43 (CDR1), SEQ ID NO:44 (CDR2) and SEQ ID NO:45 (CDR3) and heavy chain CDRs comprising the amino acid sequences of SEQ ID NO:46 (CDR1), SEQ ID NO:47 (CDR2) and SEQ ID NO:48 (CDR3); or ix) light chain CDRs comprising the amino acid sequences of SEQ ID NO:49 (CDR1), SEQ ID NO:50 (CDR2) and SEQ ID NO:51 (CDR3) and heavy chain CDRs comprising the amino acid sequences of SEQ ID NO:52 (CDR1), SEQ ID NO:53 (CDR2) and SEQ ID NO:54 (CDR3); or x) light chain CDRs comprising the amino acid sequences of SEQ ID NO:55 (CDR1), SEQ ID NO:56 (CDR2) and SEQ ID NO:57 (CDR3) and heavy chain CDRs comprising the amino acid sequences of SEQ ID NO:58 (CDR1), SEQ ID NO:59 (CDR2) and SEQ ID NO:60 (CDR3); or xi) light chain CDRs comprising the amino acid sequences of SEQ ID NO:61 (CDR1), SEQ ID NO:62 (CDR2) and SEQ ID NO:63 (CDR3) and heavy chain CDRs comprising the amino acid sequences of SEQ ID NO:64 (CDR1), SEQ ID NO:65 (CDR2) and SEQ ID NO:66 (CDR3); or xii) light chain CDRs comprising the amino acid sequences of SEQ ID NO:67 (CDR1), SEQ ID NO:68 (CDR2) and SEQ ID NO:69 (CDR3) and heavy chain CDRs comprising the amino acid sequences of SEQ ID NO:70 (CDR1), SEQ ID NO:71 (CDR2) and SEQ ID NO:72 (CDR3); or xiii) light chain CDRs comprising the amino acid sequences of SEQ ID NO:73 (CDR1), SEQ ID NO:74 (CDR2) and SEQ ID NO:75 (CDR3) and heavy chain CDRs comprising the amino acid sequences of SEQ ID NO:76 (CDR1), SEQ ID NO:77 (CDR2) and SEQ ID NO:78 (CDR3); or xiv) comprising light chain CDRs comprising the amino acid sequences of SEQ ID NO:79 (CDR1), SEQ ID NO:80 (CDR2) and SEQ ID NO:81 (CDR3) and heavy chain CDRs comprising the amino acid sequences of SEQ ID NO:82 (CDR1), SEQ ID NO:83 (CDR2) and SEQ ID NO:84 (CDR3); or xv) light chain CDRs comprising the amino acid sequences of SEQ ID NO:85 (CDR1), SEQ ID NO:86 (CDR2) and SEQ ID NO:87 (CDR3) and heavy chain CDRs comprising the amino acid sequences of SEQ ID NO:88 (CDR1), SEQ ID NO:89 (CDR2) and SEQ ID NO:90 (CDR3); or xvi) light chain CDRs comprising the amino acid sequences of SEQ ID NO:91 (CDR1), SEQ ID NO:92 (CDR2) and SEQ ID NO:93 (CDR3) and heavy chain CDRs comprising the amino acid sequences of SEQ ID NO:94 (CDR1), SEQ ID NO:95 (CDR2) and SEQ ID NO:96 (CDR3); or xvii) light chain CDRs comprising the amino acid sequences of SEQ ID NO:97 (CDR1), SEQ ID NO:98 (CDR2) and SEQ ID NO:99 (CDR3) and heavy chain CDRs comprising the amino acid sequences of SEQ ID NO:100 (CDR1), SEQ ID NO:101 (CDR2) and SEQ ID NO:102 (CDR3); or xviii) light chain CDRs comprising the amino acid sequences of SEQ ID NO:103 (CDR1), SEQ ID NO:104 (CDR2) and SEQ ID NO:105 (CDR3) and heavy chain CDRs comprising the amino acid sequences of SEQ ID NO:106 (CDR1), SEQ ID NO:107 (CDR2) and SEQ ID NO:108 (CDR3); or xix) light chain CDRs comprising the amino acid sequences of SEQ ID NO:109 (CDR1), SEQ ID NO:110 (CDR2) and SEQ ID NO:111 (CDR3) and heavy chain CDRs comprising the amino acid sequences of SEQ ID NO:112 (CDR1), SEQ ID NO:113 (CDR2) and SEQ ID NO:114 (CDR3); or xx) light chain CDRs comprising the amino acid sequences of SEQ ID NO:115 (CDR1), SEQ ID NO:116 (CDR2) and SEQ ID NO:117 (CDR3) and heavy chain CDRs comprising the amino acid sequences of SEQ ID NO:118 (CDR1), SEQ ID NO:119 (CDR2) and SEQ ID NO:120 (CDR3); or xxi) light chain CDRs comprising the amino acid sequences of SEQ ID NO:121 (CDR1), SEQ ID NO:122 (CDR2) and SEQ ID NO:123 (CDR3) and heavy chain CDRs comprising the amino acid sequences of SEQ ID NO:124 (CDR1), SEQ ID NO:125 (CDR2) and SEQ ID NO:126 (CDR3); or xxii) light chain CDRs comprising the amino acid sequences of SEQ ID NO:127 (CDR1), SEQ ID NO:128 (CDR2) and SEQ ID NO:129 (CDR3) and heavy chain CDRs comprising the amino acid sequences of SEQ ID NO:130 (CDR1), SEQ ID NO:131 (CDR2) and SEQ ID NO:132 (CDR3); or xxiii) light chain CDRs comprising the amino acid sequences of SEQ ID NO:133 (CDR1), SEQ ID NO:134 (CDR2) and SEQ ID NO:135 (CDR3) and heavy chain CDRs comprising the amino acid sequences of SEQ ID NO:136 (CDR1), SEQ ID NO:137 (CDR2) and SEQ ID NO:138 (CDR3); or xxiv) light chain CDRs comprising the amino acid sequences of SEQ ID NO:139 (CDR1), SEQ ID NO:140 (CDR2) and SEQ ID NO:141 (CDR3) and heavy chain CDRs comprising the amino acid sequences of SEQ ID NO:142 (CDR1), SEQ ID NO:143 (CDR2) and SEQ ID NO:144 (CDR3).

The antibodies i) to xxiv) as outlined above are termed B7H6 #1, B7H6 #2, B7H6 #3, B7H6 #4, B7H6 #5, B7H6 #6, B7H6 #7, B7H6 #8, B7H6 #9, B7H6 #10, B7H6 #11, B7H6 #12, B7H6 #13, B7H6 #14, B7H6 #15, B7H6 #16, B7H6 #17, B7H6 #18, B7H6 #19, B7H6 #20, B7H6 #21, B7H6 #22, B7H6 #23, and B7H6 #24, respectively. Provided herein is a sequence table which readily allows identification of individual amino acid sequences to specific antibodies of the present invention.

In some embodiments, the anti-B7H6 antibody of the invention is a chimeric, a humanized a human or an optimized antibody molecule. In some embodiments, the antibody molecule is a monoclonal antibody Fab, F(ab)2, Fv or scFv. In some embodiments, the anti-B7H6 antibody molecule of the invention comprises a heavy chain constant region selected from the group consisting of IgG1, IgG2, IgG3, IgG4, IgM, IgA and IgE constant regions. In some embodiments, the light chain constant region of the anti-B7H6 antibody molecule of the invention is kappa or lambda.

In some embodiments, the anti-B7H6 antibody of the invention has a heavy chain variable domain comprising an amino acid sequence at least 85% identical to any one of SEQ ID NOs:146, 148, 150, 152, 154, 156, 158, 160, 162, 164, 166, 168, 170, 172, 174, 176, 178, 180, 182, 184, 186, 188, 190, and 192. Preferably, the antibody molecule has a heavy chain variable domain comprising an amino acid sequence of SEQ ID NOs: 146, 148, 150, 152, 154, 156, 158, 160, 162, 164, 166, 168, 170, 172, 174, 176, 178, 180, 182, 184, 186, 188, 190 or 192.

In some embodiments, the anti-B7H6 antibody molecule has a light chain variable domain comprising an amino acid sequence at least 85% identical to any one of SEQ ID NOs: 145, 147, 149, 151, 153, 155, 157, 159, 161, 163, 165, 167, 169, 171, 173, 175, 177, 179, 181, 183, 185, 187, 189, and 191. Preferably, the antibody molecule has a light chain variable domain comprising an amino acid sequence of SEQ ID NOs: 145, 147, 149, 151, 153, 155, 157, 159, 161, 163, 165, 167, 169, 171, 173, 175, 177, 179, 181, 183, 185, 187, 189, and 191.

Methods of calculating amino acid sequence identities are well known in the art and further discussed herein in the Definitions section of the specification.

In some embodiments, the anti-B7H6 antibody molecule has i) a heavy chain variable domain comprising the amino acid sequence of SEQ ID NO:146 and a light chain variable domain comprising the amino acid sequence of SEQ ID NO:145 (B7H6 #1), or ii) a heavy chain variable domain comprising the amino acid sequence of SEQ ID NO: 148 and a light chain variable domain comprising the amino acid sequence of SEQ ID NO: 147 (B7H6 #2); or iii) a heavy chain variable domain comprising the amino acid sequence of SEQ ID NO:150 and a light chain variable domain comprising the amino acid sequence of SEQ ID NO:149 (B7H6 #3), or iv) a heavy chain variable domain comprising the amino acid sequence of SEQ ID NO:152 and a light chain variable domain comprising the amino acid sequence of SEQ ID NO:151 (B7H6 #4); or v) a heavy chain variable domain comprising the amino acid sequence of SEQ ID NO:154 and a light chain variable domain comprising the amino acid sequence of SEQ ID NO:153 (B7H6 #5); or vi) a heavy chain variable domain comprising the amino acid sequence of SEQ ID NO:156 and a light chain variable domain comprising the amino acid sequence of SEQ ID NO:155 (B7H6 #6); or vii) a heavy chain variable domain comprising the amino acid sequence of SEQ ID NO:158 and light chain variable domain comprising the amino acid sequence of SEQ ID NO:157 (B7H6 #7); or viii) a heavy chain variable domain comprising the amino acid sequence of SEQ ID NO:160 and light chain variable domain comprising the amino acid sequence of SEQ ID NO:159 (B7H6 #8); or ix) a heavy chain variable domain comprising the amino acid sequence of SEQ ID NO:162 and light chain variable domain comprising the amino acid sequence of SEQ ID NO:161 (B7H6 #9); or x) a heavy chain variable domain comprising the amino acid sequence of SEQ ID NO:164 and light chain variable domain comprising the amino acid sequence of SEQ ID NO:163 (B7H6 #10); or xi) a heavy chain variable domain comprising the amino acid sequence of SEQ ID NO:166 and light chain variable domain comprising the amino acid sequence of SEQ ID NO:165 (B7H6 #11); or xii) a heavy chain variable domain comprising the amino acid sequence of SEQ ID NO:168 and light chain variable domain comprising the amino acid sequence of SEQ ID NO:167 (B7H6 #12); or xiii) a heavy chain variable domain comprising the amino acid sequence of SEQ ID NO:170 and light chain variable domain comprising the amino acid sequence of SEQ ID NO:169 (B7H6 #13); or xiv) a heavy chain variable domain comprising the amino acid sequence of SEQ ID NO:172 and light chain variable domain comprising the amino acid sequence of SEQ ID NO:171 (B7H6 #14); or xv) a heavy chain variable domain comprising the amino acid sequence of SEQ ID NO:174 and light chain variable domain comprising the amino acid sequence of SEQ ID NO:173 (B7H6 #15); or xvi) a heavy chain variable domain comprising the amino acid sequence of SEQ ID NO:176 and light chain variable domain comprising the amino acid sequence of SEQ ID NO:175 (B7H6 #16); or xvii) a heavy chain variable domain comprising the amino acid sequence of SEQ ID NO:178 and light chain variable domain comprising the amino acid sequence of SEQ ID NO:177 (B7H6 #17); or xviii) a heavy chain variable domain comprising the amino acid sequence of SEQ ID NO:180 and light chain variable domain comprising the amino acid sequence of SEQ ID NO:179 (B7H6 #18); or xix) a heavy chain variable domain comprising the amino acid sequence of SEQ ID NO:182 and light chain variable domain comprising the amino acid sequence of SEQ ID NO:181 (B7H6 #19); or xx) a heavy chain variable domain comprising the amino acid sequence of SEQ ID NO:184 and light chain variable domain comprising the amino acid sequence of SEQ ID NO:183 (B7H6 #20); or xxi) a heavy chain variable domain comprising the amino acid sequence of SEQ ID NO:186 and light chain variable domain comprising the amino acid sequence of SEQ ID NO:185 (B7H6 #21); or xxii) a heavy chain variable domain comprising the amino acid sequence of SEQ ID NO:188 and light chain variable domain comprising the amino acid sequence of SEQ ID NO:187 (B7H6 #22); or xxiii) a heavy chain variable domain comprising the amino acid sequence of SEQ ID NO:190 and light chain variable domain comprising the amino acid sequence of SEQ ID NO:189 (B7H6 #23); or xxiv) a heavy chain variable domain comprising the amino acid sequence of SEQ ID NO:192 and light chain variable domain comprising the amino acid sequence of SEQ ID NO:191 (B7H6 #24).

In some embodiments, the anti-B7H6 antibody of the invention is a mouse monoclonal antibody. In the context of this invention a mouse monoclonal antibody includes an antibody where the VH and VL are obtained from immunization of mice with human B7H6 protein, subsequent selection of suitable VH and VL sequences binding with certain affinity to human B7H6, and then further joining such VH and VL sequences to constant domains which are derived from mouse (e.g., from mouse IgG2a) by recombinant techniques; and which are produced by recombinant expression in host cells. Further encompassed by the invention are chimeric antibodies, e.g., comprising variable and constant regions from different species. In some embodiments, the antibody molecule of the invention is a chimeric antibody comprising VH and VL domains derived from mouse as described above and further comprising constant domains derived from another species such as human, rabbit, rat, goat, donkey. In some embodiments, the chimeric antibody comprises VH and VL domains derived from mouse and further humanized or sequence optimized as defined above and further comprises constant domains derived from another species. In some embodiments, the chimeric antibody comprises VH and VL domains derived from a transgenic animal (e.g. a mouse) comprising human IgG sequences, thus comprises human VH and VL sequences, and further comprises constant domains derived from another species. In any of the embodiments of chimeric antibodies as outlined above, the heavy chain constant region is a mouse, human, rabbit, rat, goat or donkey heavy chain region.

In some embodiments, the anti-B7H6 antibody molecule of the invention has a constant domain selected from the group consisting of IgG1, IgG2, IgG3, IgG4, IgM, IgA and IgE constant domains. In a preferred embodiment, the anti-B7H6 antibody has a constant domain of IgG2a. In some embodiments, the anti-B7H6 antibody molecule has a light chain constant domain which is kappa or lambda, preferably the light chain constant domain is a kappa light chain constant domain, preferably comprising the sequence of SEQ ID NO:247.

The B7H6 specific antibodies provided herein may be used for labelling, localizing, identifying or targeting cells expressing B7H6 (e.g. in ELISA assays, FACS analysis, immunohistology or the like) by attaching a dye, a drug or another molecule with binding specificity for a different antigen.

Another aspect of the present invention provides isolated nucleic acid molecules encoding the heavy chain variable domain and/or the light chain variable domain of an anti-B7H6 antibody molecule of the invention.

Preferably the nucleic acid molecule comprises a nucleotide sequence encoding the heavy chain variable domain of any one of SEQ ID NOs: 146, 148, 150, 152, 154, 156, 158, 160, 162, 164, 166, 168, 170, 172, 174, 176, 178, 180, 182, 184, 186, 188, 190, or 192. Preferably the nucleic acid molecule comprises a nucleotide sequence encoding the light chain variable domain of any one of SEQ ID NOs: 145, 147, 149, 151, 153, 155, 157, 159, 161, 163, 165, 167, 169, 171, 173, 175, 177, 179, 181, 183, 185, 187, 189, or 191.

A further aspect of the invention provides an expression vector containing a DNA molecule comprising the nucleotide sequence encoding the heavy chain variable domain and/or the light chain variable domain of an anti-B7H6 antibody molecule of the invention.

Preferably the expression vector comprises, in addition, a nucleic acid molecule, preferably a DNA molecule, encoding the constant domains of a heavy chain and/or the constant domain of a light chain, respectively, linked to the nucleic acid molecule, preferably the DNA molecule, encoding the heavy chain variable domain and/or the light chain variable domain, respectively.

In a specifically preferred embodiment, two expression vectors may be used, one of them for expression of the heavy chain, the other one for expression of the light chain, which two expression vectors may then both be transfected into a host cell for recombinant protein expression.

Preferably, the expression vector will be a vector comprising said nucleic acid molecule or molecules, operably linked to at least one regulatory sequence, wherein such regulatory sequence may be a promoter, enhancer, or terminator sequence, and most preferably a heterologous promotor, enhancer, or terminator sequence.

In another aspect, the invention relates to a host cell having an expression vector encoding a heavy chain of an anti-B7H6 antibody molecule of the invention and an expression vector encoding a light chain of an anti-B7H6 antibody molecule of the invention.

According to a particularly preferred embodiment, said host cells are eukaryotic cells such as mammalian cells. In another embodiment, such host cells are bacterial cells. Other useful cells are yeast cells or other fungal cells.

Suitable mammalian cells include for example CHO cells, BHK cells, HeLa cells, COS cells, and the like. However, amphibian cells, insect cells, plant cells, and any other cells used in the art for the expression of heterologous proteins can be used as well.

Methods of Manufacture and Purification

The invention further provides methods of manufacturing a multi-specific binding protein of the invention, such methods generally comprising the steps of:

culturing host cells comprising an expression vector comprising a nucleic acid encoding a binding protein of the invention under conditions that allow formation of the binding protein of the invention; and, recovering the binding protein expressed by the host cells from the culture; and optionally further purifying and/or modifying and/or formulating the binding protein of the invention.

The invention further provides methods of manufacturing an anti-B7H6 antibody of the invention, such methods generally comprising the steps of:

culturing host cells comprising an expression vector comprising a nucleic acid encoding an antibody molecule of the invention under conditions that allow formation of the antibody molecule; and, recovering the antibody molecule expressed by the host cells from the culture; and optionally further purifying and/or modifying and/or formulating the antibody molecule of the invention.

A nucleic acid of the invention can e.g. be a DNA molecule comprising coding sequences as well as regulatory sequences and optionally natural or artificial introns, or can be a cDNA molecule. It may have its original codons or may have an optimized codon usage that has been specifically adapted for expression in the intended host cell or host organism.

According to one embodiment of the invention, the nucleic acid of the invention is in essentially isolated form, as defined above.

The nucleic acids of the invention may be prepared or obtained in a manner known per se (e.g. by automated DNA synthesis and/or recombinant DNA technology), based on the information on the amino acid sequences for the proteins of the invention given herein.

The nucleic acid of the invention will typically be incorporated into an expression vector, i.e. a vector that can provide for expression of the protein when transfected into a suitable host cell or other expression system.

For manufacturing the binding proteins or antibodies of the invention, the skilled artisan may choose from a great variety of expression systems well known in the art, e.g. those reviewed by Kipriyanow and Le Gall, 2004.

Expression vectors include plasmids, retroviruses, cosmids, EBV derived episomes, and the like. The expression vector and expression control sequences are selected to be compatible with the host cell. The nucleotide sequence encoding the first antigen binding unit (e.g. the B7H6 specific single chain Fab or the full length B7H6 chain of the binding protein of the invention) and the nucleotide sequence encoding the second antigen binding unit (e.g. CD3 specific single chain Fab or the full length CD3 chain of the binding protein of the invention) of the B7H6/CD3 binding protein can be inserted into separate vectors. In certain embodiments, both DNA sequences are inserted into the same expression vector. The nucleotide sequence encoding the light chain of a B7H6 antibody and the nucleotide sequence encoding the heavy chain of a B7H6 antibody can be inserted into separate vectors. In certain embodiments, both DNA sequences are inserted into the same expression vector.

Convenient vectors are those that encode a functionally complete human CH (constant heavy) immunoglobulin sequence, with appropriate restriction sites engineered so that any antigen binding unit such as a single chain Fab sequence or any heavy/light chain variable domain can be easily inserted and expressed, as described above. For the antibody heavy chain, it can be, without limitation, any IgG isotype (IgG1, IgG2, IgG3, IgG4) or other immunoglobulins, including allelic variants.

The recombinant expression vector may also encode a signal peptide that facilitates secretion of the full length CD3 or B7H6 chain from a host cell or of the light/heavy chain of an anti-B7H6 antibody. The DNA encoding the protein chain may be cloned into the vector such that the signal peptide is linked in-frame to the amino terminus of the mature full length chain DNA. The signal peptide may be an immunoglobulin signal peptide or a heterologous peptide from a non-immunoglobulin protein. Alternatively, the DNA sequence encoding the full length chains of the protein of the invention may already contain a signal peptide sequence.

In addition to the B7H6/CD3 chain encoding DNA sequences or the heavy/light chain of a B7H6 antibody encoding DNA sequences, the recombinant expression vectors typically carries regulatory sequences, optionally heterologous regulatory sequences, including promoters, enhancers, termination and polyadenylation signals and other expression control elements that control the expression of the protein chains in a host cell. Examples for promoter sequences (exemplified for expression in mammalian cells) are promoters and/or enhancers derived from CMV (such as the CMV Simian Virus 40 (SV40) promoter/enhancer), adenovirus, (e.g., the adenovirus major late promoter (AdMLP)), polyoma and strong mammalian promoters such as native immunoglobulin and actin promoters. Examples for polyadenylation signals are BGH polyA, SV40 late or early polyA; alternatively, 3'UTRs of immunoglobulin genes etc. can be used.

The recombinant expression vectors may also carry sequences that regulate replication of the vector in host cells (e.g. origins of replication) and selectable marker genes. Nucleic acid molecules encoding the full length chain with the first antigen binding unit (single chain Fab and Fc domain) or an antigen-binding portion thereof and/or the full length chain with the second antigen binding unit (single chain Fab and Fc domain) or an antigen-binding portion thereof, and vectors comprising these DNA molecules can be introduced into host cells, e.g. bacterial cells or higher eukaryotic cells, e.g. mammalian cells, according to transfection methods well known in the art, including liposome-mediated transfection, polycation-mediated transfection, protoplast fusion, microinjections, calcium phosphate precipitation, electroporation or transfer by viral vectors.

Preferably, the DNA molecules encoding the B7H6 and CD3 chain of the protein of the invention are present on two expression vectors which are co-transfected into the host cell, preferably a mammalian cell.

Mammalian cell lines available as hosts for expression are well known in the art and include, inter alia, Chinese hamster ovary (CHO) cells, NS0, SP2/0 cells, HeLa cells, baby hamster kidney (BHK) cells, monkey kidney cells (COS), human carcinoma cells (e.g., Hep G2 and A-549 cells), 3T3 cells or the derivatives/progenies of any such cell line. Other mammalian cells, including but not limited to human, mice, rat, monkey and rodent cells lines, or other eukaryotic cells, including but not limited to yeast, insect and plant cells, or prokaryotic cells such as bacteria may be used.

The proteins of the invention are produced by culturing the host cells for a period of time sufficient to allow for expression of the protein in the host cells. Protein molecules are preferably recovered from the culture medium as a secreted polypeptide or it can be recovered from host cell lysates if for example expressed without a secretory signal. It is necessary to purify the protein molecules using standard protein purification methods used for recombinant proteins and host cell proteins in a way that substantially homogenous preparations of the protein are obtained. By way of example, state-of-the art purification methods useful for obtaining protein molecules of the invention include, as a first step, removal of cells and/or particulate cell debris from the culture medium or lysate. The protein is then purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin. As a final step in the process for obtaining a protein molecule preparation, the purified protein molecule may be dried, e.g. lyophilized, as described below for therapeutic applications.

The present invention relates to binding proteins that have binding specificities for at least two different targets. In relation to the present invention, the binding molecules are derived from antibodies. Techniques for making binding molecules include, but are not limited to, recombinant co-expression of two immunoglobulin chains having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168; Atwell et al, JMB, 1997, 270, 26-35). Binding proteins of the invention may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific proteins (see, e.g., Kostelny et al., Immunol., 148(5): 1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., Immunol., 152:5368 (1994)); and preparing trispecific antibodies as described, e.g., in Tutt et al. Immunol. 147: 60 (1991).

The compositions (e.g., multi-specific binding proteins and anti-B7H6 antibodies) and methods disclosed herein encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid sequence that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain have at least about 85%, 90%, 91%, 92%, 93%, 94%, 95%, 96%, 97%, 98% or 99% identity to a reference sequence, e.g., a sequence provided herein. In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity, for example, nucleotide sequences having at least about 85%, 90%, 91%, 92%, 93%, 94%, 95%, 96%, 97%, 98% or 99% identity to a reference sequence.

The nucleic acid molecules of the invention include, but are not limited to, the DNA molecules encoding the polypeptide sequences shown in the sequence listing. Also, the present invention also relates to nucleic acid molecules that hybridize to the DNA molecules encoding the polypeptide sequences shown in the sequence listing under high stringency binding and washing conditions, as defined in WO 2007/042309. Preferred molecules (from an mRNA perspective) are those that have at least 75% or 80% (preferably at least 85%, more preferably at least 90% and most preferably at least 95%) homology or sequence identity with one of the DNA molecules described herein. By way of example, in view of expressing the antibodies in eukaryotic cells, the DNA sequences shown in the sequence listing have been designed to match codon usage in eukaryotic cells. If it is desired to express the antibodies in *E. coli*, these sequences can be changed to match *E. coli* codon usage. Variants of DNA molecules of the invention can be constructed in several different ways, as described e.g. in WO 2007/042309.

The proteins of the invention may have a modified N-terminal sequence, e.g. a deletion of one or more of the N-terminal amino acids, or an exchange of e.g. the first, N-terminal amino acid (e.g. glutamate to alanine), to optimize the molecule for being expressed by using certain expression systems (such as specific vectors or host cells), or for being expressed as inclusion bodies or in soluble form, or for being secreted into the medium or the periplasmic space or for being contained within the cell, or for yielding a more homogenous product. The polypeptides of the invention may have a modified C-terminal sequence, such as an additional alanine, and/or further amino acid exchanges in the C-terminal part or at other defined positions within any of the framework regions, as explained e.g. in WO2012/175741, WO2011/075861, or WO2013/024059, in order to e.g. further enhance stability or reduce immunogenicity of such polypeptides.

For the avoidance of doubt, all of the embodiments relating to pharmaceutical compositions, kits, treatment methods, medical uses, combinations, methods of administration and dosages as described herein are contemplated for any of the multi-specific binding proteins described herein, either alone or in combination with further therapeutic agents (as specified in more detail below).

Pharmaceutical Compositions, Methods of Administration, Dosages

The invention further relates to pharmaceutical compositions for the treatment of a disease (as specified in more detail below), wherein such compositions comprise at least one multi-specific binding protein of the invention. The invention further encompasses methods of treating a disease (as specified in more detail below) using at least one multi-specific binding protein of the invention or pharmaceutical composition as set out below, and further encompasses the preparation of a medicament for the treatment of such disease by using such binding protein of the invention or pharmaceutical composition.

The binding proteins of the invention (e.g., any one of B7H6 #1/CD3 #1, B7H6 #2/CD3 #1, B7H6 #3/CD3 #1, B7H6 #4/CD3 #1, B7H6 #5/CD3 #1, B7H6 #6/CD3 #1, B7H6 #7/CD3 #1, B7H6 #8/CD3 #1, B7H6 #9/CD3 #1, B7H6 #10/CD3 #1, B7H6 #11/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1 as defined by the sequences shown in Table 1) and/or the compositions comprising the same can be administered to a patient in need thereof in any suitable manner, depending on the specific pharmaceutical formulation or composition to be used. Thus, the binding proteins of the invention and/or the compositions comprising the same can for example be administered intravenously (i.v.), subcutaneously (s.c.), intramuscularly (i.m.), intraperitoneally (i.p.), transdermally, orally, sublingually (e.g. in the form of a sublingual tablet, spray or drop placed under the tongue and adsorbed through the mucus membranes into the capillary network under the tongue), (intra-)nasally (e.g. in the form of a nasal spray and/or as an aerosol), topically, by means of a suppository, by inhalation, or any other suitable manner in an effective amount or dose. The binding protein can be administered by infusion, bolus or injection. In preferred embodiments, the administration is by intravenous infusion or subcutaneous injection.

The binding proteins of the invention and/or the compositions comprising the same are administered according to a regimen of treatment that is suitable for treating and/or alleviating the disease, disorder or condition to be treated or alleviated. The clinician will generally be able to determine a suitable treatment regimen, depending on factors such as the disease, disorder or condition to be treated or alleviated, the severity of the disease, the severity of the symptoms thereof, the specific binding protein of the invention to be used, the specific route of administration and pharmaceutical formulation or composition to be used, the age, gender, weight, diet, general condition of the patient, and similar factors well known to the clinician. Generally, the treatment regimen will comprise the administration of one or more binding proteins of the invention, or of one or more compositions comprising the same, in therapeutically effective amounts or doses.

Generally, for the treatment and/or alleviation of the diseases, disorders and conditions mentioned herein and depending on the specific disease, disorder or condition to be treated, the potency of the specific binding protein of the invention to be used, the specific route of administration and the specific pharmaceutical formulation or composition used, the binding proteins of the invention will generally be administered in an amount between 0.005 and 20.0 mg per kilogram of body weight and dose, preferably between 0.05 and 10.0 mg/kg/dose, either continuously (e.g. by infusion) or more preferably as single doses (such as e.g. twice a week, weekly, once every two or three weeks or monthly doses; cf. below), but can significantly vary, especially, depending on the before-mentioned parameters. Thus, in some cases it may be sufficient to use less than the minimum dose given above, whereas in other cases the upper limit may have to be exceeded. When administering large amounts it may be advisable to divide them up into a number of smaller doses spread over a certain period, e.g. two or more days.

Depending on the specific binding protein of the invention and its specific pharmacokinetic and other properties, it may be administered daily, every second, third, fourth, fifth or sixth day, weekly, once every two or three weeks, monthly, and the like. An administration regimen could include long-term treatment. By "long-term" is meant at least two weeks and preferably months, or years of duration.

The efficacy of the multi-specific binding protein of the invention, and of compositions comprising the same, can be tested using any suitable in vitro assay, cell-based assay, in vivo assay and/or animal model known per se, or any combination thereof, depending on the specific disease involved. Suitable assays and animal models will be clear to the skilled person, and for example include the assays and animal models used in the Examples below.

Formulations

For pharmaceutical use, the binding proteins of the invention may be formulated as a pharmaceutical preparation comprising (i) at least one binding protein of the invention (e.g., any one of B7H6 #1/CD3 #1, B7H6 #2/CD3 #1, B7H6 #3/CD3 #1, B7H6 #4/CD3 #1, B7H6 #5/CD3 #1, B7H6 #6/CD3 #1, B7H6 #7/CD3 #1, B7H6 #8/CD3 #1, B7H6 #9/CD3 #1, B7H6 #10/CD3 #1, B7H6 #11/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1) and (ii) at least one pharmaceutically acceptable carrier, diluent, excipient, adjuvant, and/or stabilizer, and (iii) optionally one or more further pharmacologically active polypeptides and/or compounds.

By "pharmaceutically acceptable" is meant that the respective material does not show any biological or otherwise undesirable effects when administered to an individual and does not interact in a deleterious manner with any of the other components of the pharmaceutical composition (such as e.g. the pharmaceutically active ingredient) in which it is contained. Specific examples can be found in standard handbooks, such as e.g. Remington's Pharmaceutical Sciences, 18th Ed., Mack Publishing Company, USA (1990). For example, the binding proteins of the invention may be formulated and administered in any manner known per se for conventional antibodies and antibody fragments and other pharmaceutically active proteins. Thus, according to a further embodiment, the invention relates to a pharmaceutical composition or preparation that contains at least one binding protein of the invention and at least one pharmaceutically acceptable carrier, diluent, excipient, adjuvant and/or stabilizer, and optionally one or more further pharmacologically active substances, in the form of lyophilized or otherwise dried formulations or aqueous or non-aqueous solutions or suspensions.

Pharmaceutical preparations for parenteral administration, such as intravenous, intramuscular, subcutaneous injection or intravenous infusion may for example be sterile solutions, suspensions, dispersions, emulsions, or powders which comprise the active ingredient and which are suitable, optionally after a further dissolution or dilution step, for infusion or injection. Suitable carriers or diluents for such preparations for example include, without limitation, sterile water and pharmaceutically acceptable aqueous buffers and solutions such as physiological phosphate-buffered saline, Ringer's solutions, dextrose solution, and Hank's solution; water oils; glycerol; ethanol; glycols such as propylene glycol, as well as mineral oils, animal oils and vegetable oils, for example peanut oil, soybean oil, as well as suitable mixtures thereof.

Solutions of the binding proteins of the invention may also contain a preservative to prevent the growth of microorganisms, such as antibacterial and antifungal agents, for example, p-hydroxybenzoates, parabens, chlorobutanol, phenol, sorbic acid, thiomersal, (alkali metal salts of) ethylenediamine tetraacetic acid, and the like. In many cases, it will be preferable to include isotonic agents, for example, sugars, buffers or sodium chloride. Optionally, emulsifiers and/or dispersants may be used. The proper fluidity can be maintained, for example, by the formation of liposomes, by the maintenance of the required particle size in the case of dispersions or by the use of surfactants. Other agents delaying absorption, for example, aluminum monostearate and gelatin, may also be added. The solutions may be filled into injection vials, ampoules, infusion bottles, and the like.

In all cases, the ultimate dosage form must be sterile, fluid and stable under the conditions of manufacture and storage. Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Usually, aqueous solutions or suspensions will be preferred. Generally, suitable formulations for therapeutic proteins such as the binding proteins of the invention are buffered solutions, such as solutions including the protein in a suitable concentration (such as from 0.001 to 400 mg/ml, preferably from 0.005 to 200 mg/ml, more preferably 0.01 to 200 mg/ml, more preferably 1.0-100 mg/ml, such as 1.0 mg/ml (i.v. administration) or 100 mg/ml (s c administration) and an aqueous buffer such as:

phosphate buffered saline, pH 7.4,
other phosphate buffers, pH 6.2 to 8.2,
acetate buffers, pH 3.2 to 7.5, preferably pH 4.8 to 5.5
histidine buffers, pH 5.5 to 7.0,
succinate buffers, pH 3.2 to 6.6, and
citrate buffers, pH 2.1 to 6.2, and, optionally, salts (e.g. NaCl) and/or sugars (such as e.g. sucrose and trehalose) and/or other polyalcohols (such as e g mannitol and glycerol) for providing isotonicity of the solution.

In addition, other agents such as a detergent, e.g. 0.02% TWEEN™ 20 or TWEEN™-80, may be included in such solutions. Formulations for subcutaneous application may include significantly higher concentrations of the antibody of the invention, such as up to 100 mg/ml or even above 100 mg/ml. However, it will be clear to the person skilled in the art that the ingredients and the amounts thereof as given above do only represent one, preferred option. Alternatives and variations thereof will be immediately apparent to the skilled person, or can easily be conceived starting from the above disclosure. The above described formulations can optionally be provided as lyophilized formulation that is to be reconstituted in a solution, e.g. in water for injection (WFI).

According to a further aspect of the invention, a binding protein of the invention may be used in combination with a device useful for the administration of protein, such as a syringe, injector pen, micropump, or other device.

Method of Treatment

A further aspect of the invention provides a method of treating cancer comprising administering to a patient in need thereof a therapeutically effective amount of the binding protein of the invention.

A further aspect of the invention provides a binding protein of the invention for use in a method of treating cancer.

A further aspect of the invention is the use of the binding protein of the invention for preparing a pharmaceutical composition for treating cancer.

For the avoidance of doubt, the medical use aspects of the invention may comprise any of the specific binding proteins of the invention as described above (e.g., any one of B7H6 #1/CD3 #1, B7H6 #2/CD3 #1, B7H6 #3/CD3 #1, B7H6 #4/CD3 #1, B7H6 #5/CD3 #1, B7H6 #6/CD3 #1, B7H6

#7/CD3 #1, B7H6 #8/CD3 #1, B7H6 #9/CD3 #1, B7H6 #10/CD3 #1, B7H6 #11/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1).

As used herein, the term "cancer" is meant to include all types of cancerous growths or oncogenic processes, metastatic tissues or malignantly transformed cells, tissues, or organs, irrespective of histopathologic type or stage of invasiveness.

Exemplary cancers whose growth can be inhibited using the multi-specific binding proteins described herein are any B7H6 expressing tumors, preferably colorectal cancer (e.g. metastatic colorectal cancer, mCRC), non-small cell lung cancer (NSCLC), head and neck squamous cell carcinoma (HNSCC).

Cancers whose growth can be inhibited using the multi-specific binding proteins described herein are any B7H6 expressing tumors including but not limited to T cell lymphoma, myeloid leukemia, breast cancer; ovarian cancer, oral squamous carcinoma and gastro-intestinal cancers. Gastro-intestinal cancers include but are not limited to esophageal cancer (e.g., gastroesophageal junction cancer), stomach (gastric) cancer, hepatocellularcarcinoma, biliary tract cancer (e.g., cholangiocarcinoma), gallbladder cancer, pancreatic cancer or colorectal cancer (CRC).

In some embodiments, the following cancers, tumors, and other proliferative diseases may be treated with multi-specific binding proteins of the invention: head and neck cancer, preferably HNSCC; lung cancer; preferably NSCLC; breast cancer; thyroid cancer; cervical cancer; ovarian cancer; endometrial cancer; liver cancer (hepatoblastoma or hepatocellular carcinoma); pancreatic cancer; prostate cancer; gastric sarcoma; gastrointestinal stromal tumor, esophageal cancer; colon cancer; colorectal cancer; renal cancer; skin cancer; brain tumor; glioblastoma; Non-Hodgkin lymphomas (T or B cell lymphoma); leukemia (chronic or acute myeloid leukemias, nonlymphocytic leukemia), or multiple myeloma.

In a preferred embodiment of the invention the cancer is mCRC.

All cancers, tumors, neoplasms, etc., mentioned above which are characterized by their specific location/origin in the body are meant to include both the primary tumors and the metastatic tumors derived therefrom.

It is possible that a patient is more likely to respond to treatment with a binding protein of the invention (as described herein) if that patient has a cancer which is characterized by having a high expression of B7H6. Thus, in some embodiments, the cancer to be treated with the binding proteins of the invention is a cancer with high expression of B7H6, e.g., B7H6 expression is higher than the average expression in cancer cells of a population of patients suffering from the same type of a B7H6 expressing cancer.

The binding proteins of the invention may be used in therapeutic regimens in the context of first line, second line, or any further line treatments and maintenance treatment.

The binding proteins of the invention may be used for the prevention, short-term or long-term treatment of the above-mentioned diseases, optionally also in combination with radiotherapy, one or more additional therapeutic agents and/or surgery.

In preferred embodiments, the protein of the invention is used for the treatment of cancer in combination with a PD-1 antagonist, such as an anti-PD-1 antibody or an anti-PDL-1 antibody. Preferably said anti-PD-1 antibody is selected from the group consisting of pembrolizumab, nivolumab, pidilizumab, PD1-1, PD1-2, PD1-3, PD1-4, and PD1-5 as described herein (as defined by the sequences in Table A below) and in WO2017/198741 (incorporated herein by reference). Preferably said anti-PDL-1 antibody is selected from the group consisting of atezolizumab, avelumab and durvalumab. In particular preferred embodiments, the binding protein of the invention (preferably any one of B7H6 #1/CD3 #1, B7H6 #2/CD3 #1, B7H6 #3/CD3 #1, B7H6 #4/CD3 #1, B7H6 #5/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1) is used for the treatment of cancer in combination with PD1-1. In particular preferred embodiments, the binding protein of the invention (preferably any one of B7H6 #1/CD3 #1, B7H6 #2/CD3 #1, B7H6 #3/CD3 #1, B7H6 #4/CD3 #1, B7H6 #5/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1) is used for the treatment of cancer in combination with PD1-2. In particular preferred embodiments, the binding protein of the invention (preferably any one of B7H6 #1/CD3 #1, B7H6 #2/CD3 #1, B7H6 #3/CD3 #1, B7H6 #4/CD3 #1, B7H6 #5/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1) is used for the treatment of cancer in combination with PD1-3. In particular preferred embodiments, the binding protein of the invention (preferably any one of B7H6 #1/CD3 #1, B7H6 #2/CD3 #1, B7H6 #3/CD3 #1, B7H6 #4/CD3 #1, B7H6 #5/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1) is used for the treatment of cancer in combination with PD1-4. In particular preferred embodiments, the binding protein of the invention (preferably any one of B7H6 #1/CD3 #1, B7H6 #2/CD3 #1, B7H6 #3/CD3 #1, B7H6 #4/CD3 #1, B7H6 #5/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1).

TABLE A

Amino acid sequences and SEQ ID NOs of heavy chain and light chain sequences of anti-PD1 antibodies PD1-1, PD1-2, PD1-3, PD1-4, PD1-5.

| SEQ ID Number: | Brief description of sequence | Sequence |
|---|---|---|
| SEQ ID NO: 331 | PD1-1 HC | EVMLVESGGGLVQPGGSLRLSCTASGFTFSASAMSWVRQAPGKGLEWV AYISGGGGDTYYSSSVKGRFTISRDNAKNSLYLQMNSLRAEDTAVYYC ARHSNVNYYAMDYWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLG |
| SEQ ID NO: 332 | PD1-1 LC | EIVLTQSPATLSLSPGERATMSCRASENIDTSGISFMNWYQQKPGQAP KLLIYVASNQGSGIPARFSGSGSGTDFTLTISRLEPEDFAVYYCQQSK EVPWTFGQGTKLEIKRTVAAPSVFIFPPSDEQLKSGTASVVCLLNNFY PREAKVQWKVDNALQSGNSQESVTEQDSKDSTYSLSSTLTLSKADYEK HKVYACEVTHQGLSSPVTKSFNRGEC |
| SEQ ID NO: 333 | PD1-2 HC | EVMLVESGGGLVQPGGSLRLSCTASGFTFSASAMSWVRQAPGKGLEWV AYISGGGGDTYYSSSVKGRFTISRDNAKNSLYLQMNSLRAEDTAVYYC ARHSNPNYYAMDYWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLG |
| SEQ ID NO: 334 | PD1-2 LC | EIVLTQSPATLSLSPGERATMSCRASENIDTSGISFMNWYQQKPGQAP KLLIYVASNQGSGIPARFSGSGSGTDFTLTISRLEPEDFAVYYCQQSK EVPWTFGQGTKLEIKRTVAAPSVFIFPPSDEQLKSGTASVVCLLNNFY PREAKVQWKVDNALQSGNSQESVTEQDSKDSTYSLSSTLTLSKADYEK HKVYACEVTHQGLSSPVTKSFNRGEC |
| SEQ ID NO: 335 | PD1-3 HC | EVMLVESGGGLVQPGGSLRLSCTASGFTFSKSAMSWVRQAPGKGLEWV AYISGGGGDTYYSSSVKGRFTISRDNAKNSLYLQMNSLRAEDTAVYYC ARHSNVNYYAMDYWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLG |
| SEQ ID NO: 336 | PD1-3 LC | EIVLTQSPATLSLSPGERATMSCRASENIDVSGISFMNWYQQKPGQAP KLLIYVASNQGSGIPARFSGSGSGTDFTLTISRLEPEDFAVYYCQQSK EVPWTFGQGTKLEIKRTVAAPSVFIFPPSDEQLKSGTASVVCLLNNFY PREAKVQWKVDNALQSGNSQESVTEQDSKDSTYSLSSTLTLSKADYEK HKVYACEVTHQGLSSPVTKSFNRGEC |
| SEQ ID NO: 337 | PD1-4 HC | EVMLVESGGGLVQPGGSLRLSCTASGFTFSKSAMSWVRQAPGKGLEWV AYISGGGGDTYYSSSVKGRFTISRDNAKNSLYLQMNSLRAEDTAVYYC ARHSNVNYYAMDYWGQGTLVTVSSASTKGPSVFPLAPCSRSTSESTAA LGCLVKDYFPEPVTVSWNSGALTSGVHTFPAVLQSSGLYSLSSVVTVP SSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEAL HNHYTQKSLSLSLG |
| SEQ ID NO: 338 | PD1-4 LC | EIVLTQSPATLSLSPGERATMSCRASENIDVSGISFMNWYQQKPGQAP KLLIYVASNQGSGIPARFSGSGSGTDFTLTISRLEPEDFAVYYCQQSK EVPWTFGQGTKLEIKRTVAAPSVFIFPPSDEQLKSGTASVVCLLNNFY PREAKVQWKVDNALQSGNSQESVTEQDSKDSTYSLSSTLTLSKADYEK HKVYACEVTHQGLSSPVTKSFNRGEC |
| SEQ ID NO: 339 | PD1-5 HC | EVMLVESGGGLVQPGGSLRLSCTASGFTFSKSAMSWVRQAPGKGLEWV AYISGGGGDTYYSSSVKGRFTISRDNAKNSLYLQMNSLRAEDTAVYYC ARHSNVNYYAMDYWGQGTLVTVSSASTKGPSVFPLAPCSRSTSESTAA |

TABLE A-continued

Amino acid sequences and SEQ ID NOs of heavy chain and light chain sequences of anti-PD1 antibodies PD1-1, PD1-2, PD1-3, PD1-4, PD1-5.

| SEQ ID Number: | Brief description of sequence | Sequence |
|---|---|---|
| | | LGCLVKDYFPEPVTVSWNSGALTSGVHTFPAVLQSSGLYSLSSVVTVP<br>SSSLGTKTYTCNVDHKPSNTKVDKRVESKYGPPCPPCPAPEFLGGPSV<br>FLFPPKPKDTLMISRTPEVTCVVVDVSQEDPEVQFNWYVDGVEVHNAK<br>TKPREEQFNSTYRVVSVLTVLHQDWLNGKEYKCKVSNKGLPSSIEKTI<br>SKAKGQPREPQVYTLPPSQEEMTKNQVSLTCLVKGFYPSDIAVEWESN<br>GQPENNYKTTPPVLDSDGSFFLYSRLTVDKSRWQEGNVFSCSVMHEAL<br>HNHYTQKSLSLSLG |
| SEQ ID NO: 340 | PD1-5 LC | EIVLTQSPATLSLSPGERATMSCRASENIDVSGISFMNWYQQKPGQAP<br>KLLIYVASNQGSGIPARFSGSGSGTDFTLTISRLEPEDFAVYYCQQSK<br>EVPWTFGQGTKLEIKRTVAAPSVFIFPPSDEQLKSGTASVVCLLNNFY<br>PREAKVQWKVDNALQSGNSQESVTEQDSKDSTYSLSSTLTLSKADYEK<br>HKVYACEVTHQGLSSPVTKSFNRGEC |

According to these preferred embodiments and any other of the aspects of the present invention, antibodies PD1-1, PD1-2, PD1-3, PD1-4 and PD1-5 are antibody molecules as disclosed in WO2017/198741, and are defined by the sequences as shown in Table A above.

Accordingly, PD1-1 has a heavy chain comprising the amino acid sequence of SEQ ID NO:331 and a light chain comprising the amino acid sequence of SEQ ID NO:332;

PD1-2 has a heavy chain comprising the amino acid sequence of SEQ ID NO:333 and a light chain comprising the amino acid sequence of SEQ ID NO:334;

PD1-3 has a heavy chain comprising the amino acid sequence of SEQ ID NO:335 and a light chain comprising the amino acid sequence of SEQ ID NO:336;

PD1-4 has a heavy chain comprising the amino acid sequence of SEQ ID NO:337 and a light chain comprising the amino acid sequence of SEQ ID NO:338; and PD1-5 has a heavy chain comprising the amino acid sequence of SEQ ID NO:339 and a light chain comprising the amino acid sequence of SEQ ID NO:340.

The above also includes the use of the binding proteins of the invention in various methods of treating the above diseases by administering a therapeutically effective dose to a patient in need thereof, as well as the use of these binding proteins for the manufacture of medicaments for the treatment of such diseases, as well as pharmaceutical compositions including such binding proteins of the invention, as well as the preparation and/or manufacture of medicaments including such binding proteins of the invention, and the like.

Combinations with Other Active Substances or Treatments

A binding protein of the invention (e.g., any one of B7H6 #1/CD3 #1, B7H6 #2/CD3 #1, B7H6 #3/CD3 #1, B7H6 #4/CD3 #1, B7H6 #5/CD3 #1, B7H6 #6/CD3 #1, B7H6 #7/CD3 #1, B7H6 #8/CD3 #1, B7H6 #9/CD3 #1, B7H6 #10/CD3 #1, B7H6 #11/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1) may be used on its own or in combination with other cancer therapies, e.g. surgery, radiotherapy, chemotherapy, targeted therapies, immunotherapies or combinations thereof. For example, a binding protein of the invention may be used for the treatment of cancer in combination with one or more additional therapeutic agents, in particular in combination with a cytotoxic or cytostatic chemotherapeutic agent, a therapeutically active compound that inhibits angiogenesis, a signal transduction pathway inhibitor, e.g., an EGFR inhibitor, an immune modulator, an immune checkpoint inhibitor, a mitotic checkpoint inhibitor or a hormonal therapy agent.

The additional therapeutic agent may be administered simultaneously with, optionally as a component of the same pharmaceutical preparation, or before or after administration of the B7H6/CD3 binding protein.

Cytostatic and/or cytotoxic active substances which may be administered in combination with binding molecules of the invention include, without being restricted thereto, hormones, hormone analogues and antihormones, aromatase inhibitors, LHRH agonists and antagonists, inhibitors of growth factors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF)), inhibitors are for example (anti-)growth factor antibodies, (anti-)growth factor receptor antibodies and tyrosine kinase inhibitors, such as for example cetuximab, gefitinib, afatinib, nintedanib, imatinib, lapatinib, bosutinib and trastuzumab; antimetabolites (e.g. antifolates such as methotrexate, raltitrexed, pyrimidine analogues such as 5-fluorouracil (5-FU), FOLFOX (combination regimen of folinic acid, 5-FU and oxaliplatin), FOLFIRI (combination regimen of folinic acid, 5-FU and irinotecan), gemcitabine, irinotecan, doxorubicin, TAS-102, capecitabine and gemcitabine, purine and adenosine analogues such as mercaptopurine, thioguanine, cladribine and pentostatin, cytarabine (ara C), fludarabine); antitumor antibiotics (e.g. anthracyclins); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. *Vinca* alkaloids such as for example vinblastine, vindesin, vinorelbin and vincristine; and taxanes such as paclitaxel, docetaxel); angiogenesis inhibitors, including bevacizumab, ramucirumab and aflibercept, tubuline inhibitors; DNA synthesis inhibitors, PARP inhibitors, topoisomerase inhibitors (e.g.

epipodophyllotoxins such as for example etoposide and etopophos, teniposide, amsacrin, topotecan, irinotecan, mitoxantrone), serine/threonine kinase inhibitors (e.g. PDK1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK33 inhibitors, AKT inhibitors, PLK1 inhibitors (such as volasertib), inhibitors of CDKs, including CDK9 inhibitors, Aurora kinase inhibitors), tyrosine kinase inhibitors (e.g. PTK2/FAK inhibitors), protein protein interaction inhibitors, MEK inhibitors, ERK inhibitors, FLT3 inhibitors, BRD4 inhibitors, IGF-1R inhibitors, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, immunotherapeutic agents such as immune checkpoint inhibitors (e.g. CTLA4, PD1, PD-L1, LAG3, and TIM3 binding molecules/immunoglobulins, such as ipilimumab, nivolumab, pembrolizumab) and various chemotherapeutic agents such as amifostin, anagrelid, clodronat, filgrastin, interferon, interferon alpha, leucovorin, rituximab, procarbazine, levamisole, mesna, mitotane, pamidronate and porfimer; proteasome inhibitors (such as Bortezomib); Smac and BH3 mimetics; agents restoring p53 functionality including mdm2-p53 antagonist; inhibitors of the Wnt/beta-catenin signaling pathway; and/or cyclin-dependent kinase 9 inhibitors.

Particularly preferred are treatments with the binding molecules of the invention in combination with one or more immunotherapeutic agents, including anti-PD-1 and anti-PD-L1 agents and anti LAGS agents: Exemplary anti-PD1 agents include but are not limited to anti-PD-1 antibody PDR-001, pembrolizumab, nivolumab, pidilizumab and PD1-1, PD1-2, PD1-3, PD1-4 and PD1-5 as disclosed herein (Table A) and in WO2017/198741. Exemplary anti-PDL-1 agents include but are not limited to atezolizumab, avelumab and durvalumab. In preferred embodiments, the binding molecule of the invention (preferably any one of B7H6 #1/CD3 #1, B7H6 #2/CD3 #1, B7H6 #3/CD3 #1, B7H6 #4/CD3 #1, B7H6 #5/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1) is combined with PD1-1. In preferred embodiments, the binding molecule of the invention (preferably any one of B7H6 #1/CD3 #1, B7H6 #2/CD3 #1, B7H6 #3/CD3 #1, B7H6 #4/CD3 #1, B7H6 #5/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1) is combined with PD1-2. In preferred embodiments, the binding molecule of the invention (preferably any one of B7H6 #1/CD3 #1, B7H6 #2/CD3 #1, B7H6 #3/CD3 #1, B7H6 #4/CD3 #1, B7H6 #5/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1) is combined with PD1-3. In preferred embodiments, the binding molecule of the invention (preferably any one of B7H6 #1/CD3 #1, B7H6 #2/CD3 #1, B7H6 #3/CD3 #1, B7H6 #4/CD3 #1, B7H6 #5/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1) is combined with PD1-4. In preferred embodiments, the binding molecule of the invention (preferably any one of B7H6 #1/CD3 #1, B7H6 #2/CD3 #1, B7H6 #3/CD3 #1, B7H6 #4/CD3 #1, B7H6 #5/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1)) is combined with PD1-5.

In certain embodiments, the additional therapeutic agent may be a further immunotherapeutic agent, such as modulators of: TIM-1, TIM-3, TIM-4, PD-L2, LAG3, CTLA-4, Galectin 9, Galectin-1, CD69, CD113, GPR56, CD48, GARP, CAECAM-1, BTLA, TIGIT, CD160, LAIR1, 2B4, CEACAM, CD39, TGFβ, IL-10, Fas ligand, ICOS, B7 family (B7-1, B7-2, B7-H1 (PDL-1), B7-DC (PD-L2), B7-H2 (ICOS-L), B7-H3, B7-H4, B7-H5 (VISTA)), gp49B, PIR-B, KIR family receptors, SIRPalpha (CD47), ILT-2, ILT-4, IDO, CD39, arginase, CD73 HHLA2, butyrophilins, or A2aR.

In some embodiments, the additional immunotherapeutic agent is a member of the TNF family of molecules that bind to cognate TNF receptor family members, which include CD40 and CD40L, OX-40, OX-40L, CD70, CD27L, CD30, CD30L, 4-1BBL, CD137, CD137/FAP, GITR, TRAIL/Apo2-L, TRAILR1/DR4, TRAILR2/DR5, TRAILR3, TRAILR4, OPG, RANK, RANKL, TWEAKR/Fn14, TWEAK, BAH-R, EDAR, XEDAR, TACI, APRIL, BCMA, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR. Preferably, the additional immunotherapeutic agent is CD137/FAP.

In some embodiments, the additional immunotherapeutic agent is selected from (i) antagonists of cytokines that inhibit T cell activation (e.g., IL-6, IL-10, TGF-B, VEGF; "immunosuppressive cytokines") and/or (ii) agonists of cytokines that stimulate T cell activation and/or cytokines such as IL2, for stimulating an immune response, e.g., for treating proliferative diseases, such as cancer.

In some embodiments, the additional immunotherapeutic agent is an agonist of a protein that stimulates T cell activation, such as CD28, GITRL, OX40L, CD27, and CD28H or a STING agonist.

In some embodiments, the additional therapeutic agent is an oncolytic virus including but not limited to an oncolytic virus derived from vaccinia virus, adenovirus, (AdV), herpes simplex virus (HSV1 or HSV2), reovirus, myxoma virus (MYXV), poliovirus, vesicular stomatitis virus (VSV), Maraba virus, varicella virus, measles virus (MV), or Newcastle disease virus (NDV).

Kits

The invention also encompasses kits comprising at least a multi-specific binding protein of the invention (e.g., any one any one of B7H6 #1/CD3 #1, B7H6 #2/CD3 #1, B7H6 #3/CD3 #1, B7H6 #4/CD3 #1, B7H6 #5/CD3 #1, B7H6 #6/CD3 #1, B7H6 #7/CD3 #1, B7H6 #8/CD3 #1, B7H6 #9/CD3 #1, B7H6 #10/CD3 #1, B7H6 #11/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1) and optionally one or more other components selected from the group consisting of other drugs used for the treatment of the diseases and disorders as described above.

In one embodiment, the kit includes a composition containing an effective amount of a binding protein of the invention in unit dosage form.

The invention also encompasses kits comprising at least a multi-specific binding protein of the invention, and one or more other components selected from the group consisting of other drugs used for the treatment of the diseases and disorders as described above.

In one embodiment, the kit includes a composition containing an effective amount of a multi-specific binding protein of the invention in unit dosage form (preferably any one of any one of B7H6 #1/CD3 #1, B7H6 #2/CD3 #1, B7H6 #3/CD3 #1, B7H6 #4/CD3 #1, B7H6 #5/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1). In a further embodiment the kit includes both a composition containing an effective amount of a multi-specific binding protein of the invention in unit dosage form (preferably any one of any one of B7H6 #1/CD3 #1, B7H6 #2/CD3 #1, B7H6 #3/CD3 #1, B7H6 #4/CD3 #1, B7H6 #5/CD3 #1, B7H6 #12/CD3 #1, B7H6 #13/CD3 #1, B7H6 #14/CD3 #1, B7H6 #15/CD3 #1, B7H6 #16/CD3 #1, B7H6 #17/CD3 #1, B7H6 #18/CD3 #1, B7H6 #19/CD3 #1, B7H6 #20/CD3 #1, B7H6 #21/CD3 #1, B7H6 #22/CD3 #1, B7H6 #23/CD3 #1, B7H6 #24/CD3 #1) and a composition containing an effective amount of a PD-1 antagonist in unit dosage form, such as an anti PD-1 antibody, most preferably PD1-1, PD1-2, PD1-3, PD1-4, and PD1-5 as described herein (e.g. Table A) and in WO2017/198741.

In some embodiments, the kit comprises a sterile container which contains such a composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments. Further, the kit may comprise the pharmaceutical composition in a first container with the binding protein of the invention in lyophilized form and a second container with a pharmaceutically acceptable diluent (e.g., sterile water) for injection. The pharmaceutically acceptable diluent can be used for reconstitution or dilution of the binding protein.

If desired, a multi-specific binding protein of the invention, is provided together with instructions for administering the multi-specific binding proteins to a subject having cancer. The instructions will generally include information about the use of the composition for the treatment or prevention of a cancer. In other embodiments, the instructions include at least one of the following: description of the therapeutic agent; dosage schedule and administration for treatment or prevention of cancer or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

As amenable, these suggested kit components may be packaged in a manner customary for use by those of skill in the art. For example, these suggested kit components may be provided in solution or as a liquid dispersion or the like.

EXAMPLES

The following examples illustrate the invention. These examples should not be construed as to limit the scope of this invention.

Example 1: Design and Construction of B7H6/CD3 Binding Proteins

The present inventors have developed multi-specific binding proteins that bind B7H6 and CD3 and that induce T-cell activation leading to lysis of B7H6-expressing tumor cells. The molecular design used has an IgG antibody scaffold and an IgG-like structure. It features knob-in-hole technology in the Fc for hetero-dimerization of the Knob and Hole arms. In addition, the binding protein has flexible peptide sequences between the light and the corresponding heavy chain in each arm. Thus, the binding protein comprises two arms, one binding to CD3, the other one binding to B7H6, each arm comprising a single chain Fab and an Fc region (see FIG. 1).

Preferably the binding molecule is bispecific and bivalent (monovalent for each of the two targets).

Preparation of Binding Domains that Recognize B7H6 and CD3 Using High Throughput V Gene Recovery from Hybridomas and Cultured Single B Cells.

To obtain anti-B7H6 binders, hybridomas or single B cells derived from B7H6 immunized wild-type and ALIVAMAB™ humanized mice (Ablexis, San Francisco, Calif., USA: ALIVAMAB MOUSE™ transgenic mouse platform with human immunoglobulin loci) were cultured in vitro. Supernatants were screened for binding to recombinant human B7H6, by ALPHALISA® Immunoassay kit (PerkinElmer, Waltham, Mass., USA), to NCI-H716 cells (ATCC®, CCL-251™) expressing human B7H6, and also binding to recombinantly expressed cynomolgus B7-H6 on CHO cells, by Flow Cytometry.

Immunoglobulin (Ig) VH and VL genes were then amplified from identified positive clones. To isolate RNA from hybridomas, about $2\times10^6$ cells from single clones were pelleted and used as source material. For single B cells, 100 to 500 cells expanded from singularly isolated B cells were used as source material. RNA was isolated using RNeasy® Plus mini RNA extraction kit (Qiagen, Hilden, Germany). cDNA was then synthesized using SMARTer® cDNA synthesis kit (Clontech, Mountain View, Calif.) according to manufacturer's instructions. To facilitate cDNA synthesis, oligodT was used to prime reverse transcription of all messenger RNAs followed by "5' capping" with a SMARTer IIA oligonucleotide. Subsequent amplification of the VH and VL fragments was performed using a 2-step PCR amplification using 5' primers targeting the SMARTer IIA cap and 3' primers targeting consensus regions in CH1. Briefly, each 50 µl PCR reaction consists of 20 µM of forward and reverse primer mixes, 25 µl of PrimeSTAR® Max DNA polymerase premix (Clontech), 2 µl of unpurified cDNA, and 21 µl of double-distilled H2O. The cycling program starts at 94° C. for 3 min, followed by 35 cycles (94° C. for 30 Sec, 50° C. for 1 min, 68° C. for 1 min), and ends at 72° C. for 7 min. The second round PCR was performed with VL and VH 2nd round primers containing 15 bp complementary extensions that "overlap" respective regions in their respective pTT5 mother vector (VH and VL). A second round PCR was performed with the same PCR cycling program.

In-Fusion® HD Cloning Kit (Clontech, U.S.A.) was used for directional cloning of VL gene into a pTT5 huIgK vector and VH gene into a pTT5 huIgG1KO vector. To facilitate In-Fusion® HD Cloning, PCR products were purified and treated with Cloning Enhancer before In-Fusion HD Cloning. Cloning and transformation were performed according to manufacturer's protocol (Clontech, U.S.A.). Mini-prep DNAs were subjected to Sanger sequencing to confirm that complete V-gene fragments were obtained.

Using this methodology, pairs of Ig VH and VL genes encoding binding domains with specificity for B7H6 were prepared. Recombinant antibodies were produced by transient transfection of CHO-E37 cells with the corresponding heavy and light chain-encoding plasmids.

To obtain additional anti-CD3 binders, immunization of WT mice was carried out using a huCD3ε peptide1-27 construct. Hybridoma supernatants were screened for binding to recombinant huCD3E+G-Fc protein and to recombinant cyCD3E+G-Fc protein, as well as for binding to huCD3-positive and cyCD3-positive cells. The variable regions of positive clones were recovered and cloned as IgG or IgG-like bispecific construct for further evaluation.

Humanization/Optimization of B7H6 and CD3 Binders

Sequences of B7H6 or CD3 binders as described above as well as CD3 binders described in the literature (Pessano et al., EMBO J. 1985 February; 4(2): 337-44; Salmerón A et al., J Immunol. 1991 Nov. 1; 147(9):3047-52) were humanized and/or optimized. Sequence optimization/humanization of antibodies is a methodology to engineer antibodies raised in non-human species (against a specific antigen/epitope) for use as therapeutics that resemble antibodies produced in humans and thereby eliminating potential adverse effects such as immunogenicity while retaining the specificity. The sequence optimization/humanization approach utilized here was as described by Singh et al, 2015 (Singh S et al., mAbs 2015: 7(4):778-91). In brief, closely matching human germlines were identified in silico, and optimization/humanization variants were evaluated using a phage screening method. Final lead candidate sequences were selected based on binding, percent human score and EpiVax® (in silico predictive tool for potential immunogenicity) score.

Construction of Bispecific Proteins Binding B7H6 and CD3

The variable regions of the B7H6 and CD3 binders were cloned into the expression vector pTT5 (National Research Council, Canada), using common molecular biology techniques to form bispecific binding proteins with one B7H6 specific binding arm comprising a single chain Fab binding to B7H6 and an Fc region (such binding unit also referred to herein as "B7H6 arm" or "B7H6 chain") and a CD3 specific binding arm comprising a single chain Fab binding to CD3 and an Fc region (such binding unit also referred to herein as "CD3 arm" or "CD3 chain). The Fc regions of the B7H6 and CD3 arms include either "W" or "SAY" mutations (Atwell et al, JMB, 1997, 270, 26-35) and the respective chains are referred to as W or SAV chains. For multi-fragment DNA assembly, a Gibson-assembly and NEBuilder® HiFi DNA Assembly approaches were used, following manufacturer's protocols (New England Biolabs, Ipswich, Mass., USA). DNA mini-preps were sequenced.

Each expression vector contains eukaryotic promoter elements for the chain-encoding gene (B7H6 or CD3 arm/chain), i.e., the gene encoding the signal sequence and the light and heavy chain, an expression cassette for a prokaryotic selection marker gene such as ampicillin, and an origin of replication. These DNA plasmids were propagated in ampicillin resistant *E. coli* colonies and cultures and were purified.

Example 2: Expression and Purification of Bispecific Binding Proteins Binding B7H6 and CD3

Bispecific molecules binding B7H6 and CD3 were produced by transient transfection of CHO-E cells with the pTT5 vectors carrying the B7H6/CD3-chain-encoding genes (one chain as W chain and the other as SAV chain). Briefly, transfected CHO-E cells growing in suspension in serum-free media were cultivated in shake flasks under agitation at 140 rpm, 37° C. and 5% $CO_2$ and kept at conditions of exponential growth. On the day of transfection, cells were chemically transfected with W-chain plasmid and SAV-chain plasmid in 1:3 mass ratio, using Minis Bio TransIT Pro® transfection reagent. Cells were then seeded at 1 to 2×10^6 cells/ml in 1 L of Gibco® FreeStyle™ CHO expression medium (LifeTechnologies, NY, US). Cells were then incubated under orbital shaking for 10 days with one-time feed at day? with 200 ml commercial feed solution to optimize expression of the proteins. Antibody titers in the cell culture supernatants were determined using an Octet® instrument (Pall ForteBio, Calif., US) and protA biosensor tips according to manufacturer's instructions.

Recombinant B7H6/CD3 binding proteins were purified from culture supernatant in a two-step process, using a GE Healthcare Life Sciences ÄKTA™ Pure protein purification system. First, the sample was captured from the harvested cell culture fluid by Protein-A affinity chromatography using MabSelect™ column (GE Healthcare). Protein binds to Protein A at neutral pH and was washed with high salt (1M NaCl) to remove cell culture media components and any proteins or components which non-specifically bind to Protein A. The antibody or antibody-like construct sample was eluted in an isocratic mode using 30 mM sodium acetate, pH 3.5. Eluted sample was neutralized to pH 5.0 using 1% solution of 3M sodium acetate, pH 9.0. Neutralized protein was sterile filtered with 0.22 μm filtration system. The concentration was measured by UV280 by nanodrop 8000 spectrophotometer. In a second purification, Cation exchange chromatography was applied using a POROS™50 HS cation exchange resin column (Applied Biosystems, Carlsbad, Calif., USA) or Size-exclusion chromatography using a HiLoad® 26/600 Superdex® 200 pg column (GE Healthcare). The two-step purified material was stored in final buffer of 50 mM Sodium Acetate and 100 mM NaCl, pH 5.0 Purity and degree of heterogeneity of the samples were assessed by analytical size-exclusion chromatography, mass spectrometry and analytical ultracentrifugation. Samples that were advanced for functional testing comprised two-step purified material, with about 95 to 99% monomer content.

TABLE 1

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 1 | B7H6#1 LCCDR1 | KSSQSLFYSSNQKNYLA |
| SEQ ID NO: 2 | B7H6#1 LCCDR2 | WASTRES |
| SEQ ID NO: 3 | B7H6#1 LCCDR3 | QQYYNYPRT |
| SEQ ID NO: 4 | B7H6#1 HCCDR1 | GYTFTDYYMN |
| SEQ ID NO: 5 | B7H6#1 HCCDR2 | YIYPKTGGNGYNQKFKD |
| SEQ ID NO: 6 | B7H6#1 HCCDR3 | ENWDGYTMAY |
| SEQ ID NO: 7 | B7H6#2 LCCDR1 | RATSSLYSMH |
| SEQ ID NO: 8 | B7H6#2 LCCDR2 | ATFNLAS |
| SEQ ID NO: 9 | B7H6#2 LCCDR3 | QQWSTNPPKLT |
| SEQ ID NO: 10 | B7H6#2 HCCDR1 | GFNIKNTFIH |
| SEQ ID NO: 11 | B7H6#2 HCCDR2 | RIDPANGNTIYASKFQG |
| SEQ ID NO: 12 | B7H6#2 HCCDR3 | TYGGTNYFDY |
| SEQ ID NO: 13 | B7H6#3 LCCDR1 | KASHNVGVYVA |
| SEQ ID NO: 14 | B7H6#3 LCCDR2 | SASNRYS |
| SEQ ID NO: 15 | B7H6#3 LCCDR3 | QQYNSYPLT |
| SEQ ID NO: 16 | B7H6#3 HCCDR1 | GFTFSDYYMT |
| SEQ ID NO: 17 | B7H6#3 HCCDR2 | NIDYDGSRIYYLDSLKS |
| SEQ ID NO: 18 | B7H6#3 HCCDR3 | DDPAWLAY |
| SEQ ID NO: 19 | B7H6#4 LCCDR1 | KASQNVGKYVA |
| SEQ ID NO: 20 | B7H6#4 LCCDR2 | SASNRYD |
| SEQ ID NO: 21 | B7H6#4 LCCDR3 | QQYISYPLT |
| SEQ ID NO: 22 | B7H6#4 HCCDR1 | GYTFTNYWMN |
| SEQ ID NO: 23 | B7H6#4 HCCDR2 | GIYLNGDSTDYNEKFKG |
| SEQ ID NO: 24 | B7H6#4 HCCDR3 | RGDYFGDF |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 25 | B7H6#5 LCCDR1 | RASQDIRNDLG |
| SEQ ID NO: 26 | B7H6#5 LCCDR2 | AASSLES |
| SEQ ID NO: 27 | B7H6#5 LCCDR3 | LQYYNHPLT |
| SEQ ID NO: 28 | B7H6#5 HCCDR1 | GYTFTGYYIH |
| SEQ ID NO: 29 | B7H6#5 HCCDR2 | WINPHSGATNYAQNFQG |
| SEQ ID NO: 30 | B7H6#5 HCCDR3 | ERWGSGTFNI |
| SEQ ID NO: 31 | B7H6#6 LCCDR1 | KASQSVSNDVV |
| SEQ ID NO: 32 | B7H6#6 LCCDR2 | STSNRYI |
| SEQ ID NO: 33 | B7H6#6 LCCDR3 | QQDYSSPYT |
| SEQ ID NO: 34 | B7H6#6 HCCDR1 | GYTFTDYTMH |
| SEQ ID NO: 35 | B7H6#6 HCCDR2 | GINPNYDNTGYSEKFKD |
| SEQ ID NO: 36 | B7H6#6 HCCDR3 | SGSRRSFYFDY |
| SEQ ID NO: 37 | B7H6#7 LCCDR1 | RASQGISSWLA |
| SEQ ID NO: 38 | B7H6#7 LCCDR2 | AASSLQS |
| SEQ ID NO: 39 | B7H6#7 LCCDR3 | QQANSFPRT |
| SEQ ID NO: 40 | B7H6#7 HCCDR1 | GGSISYNYWS |
| SEQ ID NO: 41 | B7H6#7 HCCDR2 | HIYYSGSTNYNPSLKS |
| SEQ ID NO: 42 | B7H6#7 HCCDR3 | VGTWGSFDD |
| SEQ ID NO: 43 | B7H6#8 LCCDR1 | RSSQSLLYNNRYNYLD |
| SEQ ID NO: 44 | B7H6#8 LCCDR2 | LGSNRAS |
| SEQ ID NO: 45 | B7H6#8 LCCDR3 | MQTLQIPIT |
| SEQ ID NO: 46 | B7H6#8 HCCDR1 | GDTLNSYGIS |
| SEQ ID NO: 47 | B7H6#8 HCCDR2 | GIIPIFDTTKYAQKFQG |
| SEQ ID NO: 48 | B7H6#8 HCCDR3 | ERGYRFSEDYYFYYGMDV |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 49 | B7H6#9 LCCDR1 | RASESVDNFGVSFMN |
| SEQ ID NO: 50 | B7H6#9 LCCDR2 | AASNQGS |
| SEQ ID NO: 51 | B7H6#9 LCCDR3 | QQSKEVPWT |
| SEQ ID NO: 52 | B7H6#9 HCCDR1 | DYTFTHYWIH |
| SEQ ID NO: 53 | B7H6#9 HCCDR2 | IIGPSDNEIHYNQDFKD |
| SEQ ID NO: 54 | B7H6#9 HCCDR3 | QIISMVVGTEYFDV |
| SEQ ID NO: 55 | B7H6#10 LCCDR1 | RASQGISSWLA |
| SEQ ID NO: 56 | B7H6#10 LCCDR2 | VASSLQR |
| SEQ ID NO: 57 | B7H6#10 LCCDR3 | QQANSFPRT |
| SEQ ID NO: 58 | B7H6#10 HCCDR1 | GDSISSYYWS |
| SEQ ID NO: 59 | B7H6#10 HCCDR2 | HIYTSEKNNYNPSLKS |
| SEQ ID NO: 60 | B7H6#10 HCCDR3 | VGNWGSHDA |
| SEQ ID NO: 61 | B7H6#11 LCCDR1 | RSSQSLLHSNGYNYLD |
| SEQ ID NO: 62 | B7H6#11 LCCDR2 | LGSNRAS |
| SEQ ID NO: 63 | B7H6#11 LCCDR3 | MQALQTPLT |
| SEQ ID NO: 64 | B7H6#11 HCCDR1 | GITFSYYTMN |
| SEQ ID NO: 65 | B7H6#11 HCCDR2 | SISSRSSYIYYADSVKG |
| SEQ ID NO: 66 | B7H6#11 HCCDR3 | DKGDYSKDIYYYYGMDV |
| SEQ ID NO: 67 | B7H6#12 LCCDR1 | KASQNVGKYVA |
| SEQ ID NO: 68 | B7H6#12 LCCDR2 | SASNRYD |
| SEQ ID NO: 69 | B7H6#12 LCCDR3 | QQYISYPLT |
| SEQ ID NO: 70 | B7H6#12 HCCDR1 | GYTFTNYWMN |
| SEQ ID NO: 71 | B7H6#12 HCCDR2 | GIYLNGDSTDYNEKFKG |
| SEQ ID NO: 72 | B7H6#12 HCCDR3 | RGDYFGDF |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 73 | B7H6#13 LCCDR1 | KASQNVGKYVA |
| SEQ ID NO: 74 | B7H6#13 LCCDR2 | SASNRYD |
| SEQ ID NO: 75 | B7H6#13 LCCDR3 | QQYISYPLT |
| SEQ ID NO: 76 | B7H6#13 HCCDR1 | GYTFTSYWMN |
| SEQ ID NO: 77 | B7H6#13 HCCDR2 | GIYLNGDSTDYNEKFKG |
| SEQ ID NO: 78 | B7H6#13 HCCDR3 | RGDYFGDF |
| SEQ ID NO: 79 | B7H6#14 LCCDR1 | KASQNVGKYVA |
| SEQ ID NO: 80 | B7H6#14 LCCDR2 | SASNRYD |
| SEQ ID NO: 81 | B7H6#14 LCCDR3 | QQYISYPLT |
| SEQ ID NO: 82 | B7H6#14 HCCDR1 | GYTFTNYWMN |
| SEQ ID NO: 83 | B7H6#14 HCCDR2 | GIYLNGDSTDYNEKFKG |
| SEQ ID NO: 84 | B7H6#14 HCCDR3 | RGDYFGDF |
| SEQ ID NO: 85 | B7H6#15 LCCDR1 | KASQNVGKYVA |
| SEQ ID NO: 86 | B7H6#15 LCCDR2 | SASNRYD |
| SEQ ID NO: 87 | B7H6#15 LCCDR3 | QQYISYPLT |
| SEQ ID NO: 88 | B7H6#15 HCCDR1 | GYTFTNYWMN |
| SEQ ID NO: 89 | B7H6#15 HCCDR2 | GIYLSGDSTDYNEKFKG |
| SEQ ID NO: 90 | B7H6#15 HCCDR3 | RGDYFGDF |
| SEQ ID NO: 91 | B7H6#16 LCCDR1 | KASQNVGKYVA |
| SEQ ID NO: 92 | B7H6#16 LCCDR2 | SASNRYD |
| SEQ ID NO: 93 | B7H6#16 LCCDR3 | QQYISYPLT |
| SEQ ID NO: 94 | B7H6#16 HCCDR1 | GYTFTSYWMN |
| SEQ ID NO: 95 | B7H6#16 HCCDR2 | GIYLSGESTDYNEKFKG |
| SEQ ID NO: 96 | B7H6#16 HCCDR3 | RGDYFGDF |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 97 | B7H6#17 LCCDR1 | KASQNVGKYVA |
| SEQ ID NO: 98 | B7H6#17 LCCDR2 | SASNRYD |
| SEQ ID NO: 99 | B7H6#17 LCCDR3 | QQYISYPLT |
| SEQ ID NO: 100 | B7H6#17 HCCDR1 | GYTFTSYWMN |
| SEQ ID NO: 101 | B7H6#17 HCCDR2 | GIYLSGDSTDYNEKFKG |
| SEQ ID NO: 102 | B7H6#17 HCCDR3 | RGDYFGDF |
| SEQ ID NO: 103 | B7H6#18 LCCDR1 | KASQNVGKYVA |
| SEQ ID NO: 104 | B7H6#18 LCCDR2 | SASNRYD |
| SEQ ID NO: 105 | B7H6#18 LCCDR3 | QQYISYPLT |
| SEQ ID NO: 106 | B7H6#18 HCCDR1 | GYTFTSYWMN |
| SEQ ID NO: 107 | B7H6#18 HCCDR2 | GIYLSGDSTDYNEKFKG |
| SEQ ID NO: 108 | B7H6#18 HCCDR3 | RGDYFGDF |
| SEQ ID NO: 109 | B7H6#19 LCCDR1 | KASQNVGKYVA |
| SEQ ID NO: 110 | B7H6#19 LCCDR2 | SASNRYD |
| SEQ ID NO: 111 | B7H6#19 LCCDR3 | QQYISYPLT |
| SEQ ID NO: 112 | B7H6#19 HCCDR1 | GYTFTSYWMN |
| SEQ ID NO: 113 | B7H6#19 HCCDR2 | GIYLSGESTDYNEKFKG |
| SEQ ID NO: 114 | B7H6#19 HCCDR3 | RGDYFGDF |
| SEQ ID NO: 115 | B7H6#20 LCCDR1 | KASQNVGKYVA |
| SEQ ID NO: 116 | B7H6#20 LCCDR2 | SASNRYD |
| SEQ ID NO: 117 | B7H6#20 LCCDR3 | QQYISYPLT |
| SEQ ID NO: 118 | B7H6#20 HCCDR1 | GYTFTSYWMN |
| SEQ ID NO: 119 | B7H6#20 HCCDR2 | GIYLSGDSTDYNEKFKG |
| SEQ ID NO: 120 | B7H6#20 HCCDR3 | RGDYFGDF |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 121 | B7H6#21 LCCDR1 | KASQNVGKYVA |
| SEQ ID NO: 122 | B7H6#21 LCCDR2 | SASNRYD |
| SEQ ID NO: 123 | B7H6#21 LCCDR3 | QQYISYPLT |
| SEQ ID NO: 124 | B7H6#21 HCCDR1 | GYTFTSYWMN |
| SEQ ID NO: 125 | B7H6#21 HCCDR2 | GIYLSGESTDYNEKFKG |
| SEQ ID NO: 126 | B7H6#21 HCCDR3 | RGDYFGDF |
| SEQ ID NO: 127 | B7H6#22 LCCDR1 | KASQNVGKYVA |
| SEQ ID NO: 128 | B7H6#22 LCCDR2 | SASNRYD |
| SEQ ID NO: 129 | B7H6#22 LCCDR3 | QQYISYPLT |
| SEQ ID NO: 130 | B7H6#22 HCCDR1 | GYTFTSYWMN |
| SEQ ID NO: 131 | B7H6#22 HCCDR2 | GIYLSGDSTDYNEKFKG |
| SEQ ID NO: 132 | B7H6#22 HCCDR3 | RGDYFGDF |
| SEQ ID NO: 133 | B7H6#23 LCCDR1 | KASQNVGKYVA |
| SEQ ID NO: 134 | B7H6#23 LCCDR2 | SASNRYD |
| SEQ ID NO: 135 | B7H6#23 LCCDR3 | QQYISYPLT |
| SEQ ID NO: 136 | B7H6#23 HCCDR1 | GYTFTSYWMN |
| SEQ ID NO: 137 | B7H6#23 HCCDR2 | GIYLSGESTDYNEKFKG |
| SEQ ID NO: 138 | B7H6#23 HCCDR3 | RGDYFGDF |
| SEQ ID NO: 139 | B7H6#24 LCCDR1 | KASQNVGKYVA |
| SEQ ID NO: 140 | B7H6#24 LCCDR2 | SASNRYD |
| SEQ ID NO: 141 | B7H6#24 LCCDR3 | QQYISYPLT |
| SEQ ID NO: 142 | B7H6#24 HCCDR1 | GYTFTNYWMN |
| SEQ ID NO: 143 | B7H6#24 HCCDR2 | GIYLSGDSTDYNEKFKG |
| SEQ ID NO: 144 | B7H6#24 HCCDR3 | RGDYFGDF |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 145 | B7H6#1 VL | DIVMSQSPSSLAVSVGEKVTMNCKSSQSLFYSSNQKNYLAWYQQKPGQSPKLLIYWASTRESGVPDRFTGSGSGTDFTLTISSVKAEDLAVYYCQQYYNYPRTFGGGTKLEIK |
| SEQ ID NO: 146 | B7H6#1 VH | EVQLQQSGPELVKPGTSVKMSCKASGYTFTDYYMNWVKQSQGKNLEWIAYIYPKTGGNGYNQKFKDKATLTVDKSSNTAYMELRSLTSDDSAVYYCGRENWDGYTMAYWGQGTSVTVSS |
| SEQ ID NO: 147 | B7H6#2 VL | EIVLTQSPDFLSASPGEKVTMTCRATSSLYSMHWYQQKPGSSPKPWIYATFNLASGVPARFSGSGSGTSYSLTITRVEAEDAATYYCQQWSTNPPKLTFGAGTKLELK |
| SEQ ID NO: 148 | B7H6#2 VH | EVQLQQSGAELVRPGASVKLSCTASGFNIKNTFIHWVNQRPEQGLEWIGRIDPANGNTIYASKFQGRATITTDTSSNTAYMHLSSLTSGDTAVYYCARTYGGTNYFDYWGQGTTLTVSS |
| SEQ ID NO: 149 | B7H6#3 VL | DIVMTQSQKLLSTSVGDRISVTCKASHNVGVYVAWYQQKPGHSPKALIHSASNRYSGVPDRFTGSGSGTDFTLTITNVQSEDLAEYFCQQYNSYPLTFGAGTKLELI |
| SEQ ID NO: 150 | B7H6#3 VH | EVKLVESEGGLVQPGSSMKLSCTASGFTFSDYYMTWVRQVPEKGLEWVGNIDYDGSRIYYLDSLKSRFIISRDNAKNILYLQMNSLKSEDTATYYCARDDPAWLAYWGQGTLVTVSS |
| SEQ ID NO: 151 | B7H6#4 VL | DIVMTQSQKFMSTSVGDRVSVTCKASQNVGKYVAWYQQKPGQSPKALIYSASNRYDGVPDRFTGSGSGTDFTLTITNVQSEDLTEYFCQQYISYPLTFGAGTKLELK |
| SEQ ID NO: 152 | B7H6#4 VH | QVQLQQPGSVLVRPGASVRLSCKASGYTFTNYWMNWMKQRPGQGLEWIGGIYLNGDSTDYNEKFKGKATLTVDTSSSTTYMDLSSLTYEDSAVYYCTTRGDYFGDFWGQGTTLTVSS |
| SEQ ID NO: 153 | B7H6#5 VL | AIQMTQSPSSLSASVGDRVTITCRASQDIRNDLGWFQQRPGKAPNLLIYAASSLESGVPSRFSGRGSGTDFTLTISSLQPEDFATYYCLQYYNHPLTFGGGTKVEIK |
| SEQ ID NO: 154 | B7H6#5 VH | QVQLVQSGAEVKKPGASVKVSCKASGYTFTGYYIHWVRQAPGQGLEWMGWINPHSGATNYAQNFQGRVTMTRDTSISTAYMELSRLRSDDAAVYYCARERWGSGTFNIWGQGTMVTVSS |
| SEQ ID NO: 155 | B7H6#6 VL | DIVMTQSPDSLPVSAGDRVTITCKASQSVSNDVVWYQQKPGQSPKLLMYSTSNRYIGVPDRFTGSGYGTDFTFTISTVQAEDLAVYFCQQDYSSPYTFGGGTKLEIK |
| SEQ ID NO: 156 | B7H6#6 VH | EVQLQQSGPELLKPGASVKISCKTSGYTFTDYTMHWVKQSHGKSLEWIGGINPNYDNTGYSEKFKDKATLTVDKSSSTAYMELRSLTSEDSAVYYCTRSGSRRSFYFDYWGQGTTLTVSS |
| SEQ ID NO: 157 | B7H6#7 VL | DIQMTQSPSSVSASVGDRVTITCRASQGISSWLAWYQQKPGKAPNLLIYAASSLQSGVPSRFSGSGSGTDFTLTISSLQPEDFATYYCQQANSFPRTFGQGTKVEIK |
| SEQ ID NO: 158 | B7H6#7 VH | QVQLQESGPGLVKPSETLSLTYTVSGGSISYNYWSWIRQPPEKGLEWIGHIYYSGSTNYNPSLKSRVTISVDTSKNQFSLKLNSVTAADTAVYYCARVGTWGSFDDWGQGTLVTVSS |
| SEQ ID NO: 159 | B7H6#8 VL | DIVMTQSPLSLPVTPGEPASISCRSSQSLLYNNRYNYLDWYLQKPGQSPEVLIYLGSNRASGVPDRFSGSGSGTDFTLKISRVEAEDFGVYYCMQTLQIPITFGQGTRLEIK |
| SEQ ID NO: 160 | B7H6#8 VH | QVQVVQSGAEVKKPGSSVKVSCKGSGDTLNSYGISWMRQAPGQGLEWMGGIIPIFDTTKYAQKFQGRVTITADKSTTTVYMELSSLRFEDTAVYYCARERGYRFSEDYYFYYGMDVWGQGTTVTVSS |
| SEQ ID NO: 161 | B7H6#9 VL | DIVLTQSPVSLAVSLGQRATISCRASESVDNFGVSFMNWFQQKPGQPPKLLIYAASNQGSGVPARFSGSGSGTDFSLNIHPLEEDDTAMYFCQQSKEVPWTFGGGTRLEIK |
| SEQ ID NO: 162 | B7H6#9 VH | QVQLQQPGAEMVRPGSSVKLSCKASDYTFTHYWIHWVKQRPLEGLEWIGIIGPSDNEIHYNQDFKDKATLTVDKSSNTAYLHLNSLTSEDSAVYYCARQIISMVVGTEYFDVWGTGTTVTVSS |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 163 | B7H6#10 VL | DIQMTQSPSSVSASVGDRVTITCRASQGISSWLAWYQQKPGKAPKLLIYVASSLQRGVPSRFSGSGSGTDFTLTISNLQPEDFATYYCQQANSFPRTFGQGTKVEIK |
| SEQ ID NO: 164 | B7H6#10 VH | QVHLQESGPGLVKPSETLSLTCTVSGDSISSYYWSWIRQPAGKGLEWIGHIYTSEKNNYNPSLKSRVIMSVDTSKNQFSLNLSSVTAADTAVYYCARVGNWGSHDAWGQGTLVTVSS |
| SEQ ID NO: 165 | B7H6#11 VL | DIVMTQSPLSLPVTPGEPASISCRSSQSLLHSNGYNYLDWYLQKPGQSPQVLIYLGSNRASGVPDRFSGSGSGTDFTLKISRVEAEDVGVYYCMQALQTPLTFGGGTKVEIK |
| SEQ ID NO: 166 | B7H6#11 VH | ELQLVNSGGGLVKSGGSLRLSCAASGITFSYYTMNWVRQAPGKGLEWVSSISSRSSYIYYADSVKGRFTISRDNAENSLYLQMNSLRAEDTAVYYCARDKGDYSKDIYYYYGMDVWGQGTTVTVSS |
| SEQ ID NO: 167 | B7H6#12 VL | DIQMTQSPSSLSASVGDRVTITCKASQNVGKYVAWYQQKPGKAPKSLIYSASNRYDGVPSRFSGSGSGTDFTLTISSLQPEDFTTYYCQQYISYPLTFGAGTKLEIK |
| SEQ ID NO: 168 | B7H6#12 VH | QVQLVQSGAEVKKPGASVKVSCKASGYTFTNYWMNWVKQAPGQGLEWMGGIYLNGDSTDYNEKFKGKATMTVDTSTSTVYMELSSLRSEDTAVYYCTRRGDYFGDFWGQGTLVTVSS |
| SEQ ID NO: 169 | B7H6#13 VL | DIQMTQSPSSLSASVGDRVTITCKASQNVGKYVAWYQQKPGKAPKSLIYSASNRYDGVPSRFSGSGSGTDFTLTISSLQPEDFTTYYCQQYISYPLTFGAGTKLEIK |
| SEQ ID NO: 170 | B7H6#13 VH | QVQLVQSGAEVKKPGASVKVSCKASGYTFTSYWMNWMKQAPGQGLEWMGGIYLNGDSTDYNEKFKGRVTMTVDTSTSTVYMELSSLRSEDTAVYYCTRRGDYFGDFWGQGTLVTVSS |
| SEQ ID NO: 171 | B7H6#14 VL | DIQMTQSPSSLSASVGDRVTITCKASQNVGKYVAWYQQKPGKAPKSLIYSASNRYDGVPSRFSGSGSGTDFTLTISSLQPEDFATYFCQQYISYPLTFGAGTKLEIK |
| SEQ ID NO: 172 | B7H6#14 VH | QVQLVQSGAEVKKPGASVKVSCKASGYTFTNYWMNWMKQAPGQGLEWIGGIYLNGDSTDYNEKFKGKVTMTVDTSTSTVYMELSSLRSEDTAVYYCTRRGDYFGDFWGQGTLVTVSS |
| SEQ ID NO: 173 | B7H6#15 VL | DIQMTQSPSSLSASVGDRVTITCKASQNVGKYVAWYQQKPGKAPKSLIYSASNRYDGVPSRFSGSGSGTDFTLTISSLQPEDFTTYYCQQYISYPLTFGAGTKLEIK |
| SEQ ID NO: 174 | B7H6#15 VH | QVQLVQSGAEVKKPGASVKVSCKASGYTFTNYWMNWMRQAPGQGLEWMGGIYLSGDSTDYNEKFKGRVTMTVDTSTSTVYMELSSLRSEDTAVYYCTRRGDYFGDFWGQGTLVTVSS |
| SEQ ID NO: 175 | B7H6#16 VL | DIQMTQSPSSLSASVGDRVTITCKASQNVGKYVAWYQQKPGKAPKSLIYSASNRYDGVPSRFSGSGSGTDFTLTISSLQPEDFTTYYCQQYISYPLTFGAGTKLEIK |
| SEQ ID NO: 176 | B7H6#16 VH | QVQLVQSGAEVKKPGASVKVSCKASGYTFTSYWMNWMRQAPGQGLEWMGGIYLSGESTDYNEKFKGRVTMTVDTSTSTVYMELSSLRSEDTAVYYCTRRGDYFGDFWGQGTLVTVSS |
| SEQ ID NO: 177 | B7H6#17 VL | DIQMTQSPSSLSASVGDRVTITCKASQNVGKYVAWYQQKPGKAPKSLIYSASNRYDGVPSRFSGSGSGTDFTLTISSLQPEDFTTYYCQQYISYPLTFGAGTKLEIK |
| SEQ ID NO: 178 | B7H6#17 VH | QVQLVQSGAEVKKPGASVKVSCKASGYTFTSYWMNWMRQAPGQGLEWMGGIYLSGDSTDYNEKFKGRVTMTVDTSTSTVYMELSSLRSEDTAVYYCTRRGDYFGDFWGQGTLVTVSS |
| SEQ ID NO: 179 | B7H6#18 VL | DIQMTQSPSSLSASVGDRVTITCKASQNVGKYVAWYQQKPGKAPKSLIYSASNRYDAVPSRFSGSGSGTDFTLTISSLQPEDFTTYYCQQYISYPLTFGAGTKLEIK |
| SEQ ID NO: 180 | B7H6#18 VH | QVQLVQSGAEVKKPGASVKVSCKASGYTFTSYWMNWMRQAPGQGLEWMGGIYLSGDSTDYNEKFKGRVTMTVDTSTSTVYMELSSLRSEDTAVYYCTRRGDYFGDFWGQGTLVTVSS |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 181 | B7H6#19 VL | DIQMTQSPSSLSASVGDRVTITCKASQNVGKYVAWYQQKPGK APKSLIYSASNRYDGVPSRFSGSGSGTDFTLTISSLQPEDFTTYYC QQYISYPLTFGAGTKLEIK |
| SEQ ID NO: 182 | B7H6#19 VH | QVQLVQSGAEVKKPGASVKVSCKASGYTFTSYWMNWVKQA PGQGLEWMGGIYLSGESTDYNEKFKGKATMTVDTSTSTVYM ELSSLRSEDTAVYYCTRRGDYFGDFWGQGTLVTVSS |
| SEQ ID NO: 183 | B7H6#20 VL | DIQMTQSPSSLSASVGDRVTITCKASQNVGKYVAWYQQKPGK APKSLIYSASNRYDAVPSRFSGSGSGTDFTLTISSLQPEDFTTYYC QQYISYPLTFGAGTKLEIK |
| SEQ ID NO: 184 | B7H6#20 VH | QVQLVQSGAEVKKPGASVKVSCKASGYTFTSYWMNWVKQA PGQGLEWMGGIYLSGDSTDYNEKFKGKATMTVDTSTSTVYM ELSSLRSEDTAVYYCTRRGDYFGDFWGQGTLVTVSS |
| SEQ ID NO: 185 | B7H6#21 VL | DIQMTQSPSSLSASVGDRVTITCKASQNVGKYVAWYQQKPGK APKSLIYSASNRYDGVPSRFSGSGSGTDFTLTISSLQPEDFATYFC QQYISYPLTFGAGTKLEIK |
| SEQ ID NO: 186 | B7H6#21 VH | QVQLVQSGAEVKKPGASVKVSCKASGYTFTSYWMNWMKQA PGQGLEWIGGIYLSGESTDYNEKFKGKVTMTVDTSTSTVYM ELSSLRSEDTAVYYCTRRGDYFGDFWGQGTLVTVSS |
| SEQ ID NO: 187 | B7H6#22 VL | DIQMTQSPSSLSASVGDRVTITCKASQNVGKYVAWYQQKPGK APKSLIYSASNRYDAVPSRFSGSGSGTDFTLTISSLQPEDFATYFC QQYISYPLTFGAGTKLEIK |
| SEQ ID NO: 188 | B7H6#22 VH | QVQLVQSGAEVKKPGASVKVSCKASGYTFTSYWMNWMKQA PGQGLEWIGGIYLSGDSTDYNEKFKGKVTMTVDTSTSTVYM ELSSLRSEDTAVYYCTRRGDYFGDFWGQGTLVTVSS |
| SEQ ID NO: 189 | B7H6#23 VL | DIQMTQSPSSLSASVGDRVTITCKASQNVGKYVAWYQQKPGK APKSLIYSASNRYDAVPSRFSGSGSGTDFTLTISSLQPEDFATYFC QQYISYPLTFGAGTKLEIK |
| SEQ ID NO: 190 | B7H6#23 VH | QVQLVQSGAEVKKPGASVKVSCKASGYTFTSYWMNWMKQA PGQGLEWIGGIYLSGESTDYNEKFKGKVTMTVDTSTSTVYM ELSSLRSEDTAVYYCTRRGDYFGDFWGQGTLVTVSS |
| SEQ ID NO: 191 | B7H6#24 VL | DIQMTQSPSSLSASVGDRVTITCKASQNVGKYVAWYQQKPGK APKSLIYSASNRYDAVPSRFSGSGSGTDFTLTISSLQPEDFTTYYC QQYISYPLTFGAGTKLEIK |
| SEQ ID NO: 192 | B7H6#24 VH | QVQLVQSGAEVKKPGASVKVSCKASGYTFTNYWMNWMRQA PGQGLEWMGGIYLSGDSTDYNEKFKGRVTMTVDTSTSTVYM ELSSLRSEDTAVYYCTRRGDYFGDFWGQGTLVTVSS |
| SEQ ID NO: 193 | B7H6#1 scFab | DIVMSQSPSSLAVSVGEKVTMNCKSSQSLFYSSNQKNYLAWY QQKPGQSPKLLIYWASTRESGVPDRFTGSGSGTDFTLTISSVKA EDLAVYYCQQYYNYPRTFGGGTKLEIKRTVAAPSVFIFPPSDEQ LKSGTASVVCLLNNFYPREAKVQWKVDNALQSGNSQESVTEQ DSKDSTYSLSSTLTLSKADYEKHKVYACEVTHQGLSSPVTKSFNR GECGGGGSEGKSSGSGSESKSTEGKSSGSGSESKSTGGGGSEV QLQQSGPELVKPGTSVKMSCKASGYTFTDYYMNWVKQSQGK NLEWIAYIYPKTGGNGYNQKFKDKATLTVDKSSNTAYMELRSL TSDDSAVYYCGRENWDGYTMAYWGQGTSVTVSSASTKGPSV FPLAPSSKSTSGGTAALGCLVKDYFPEPVTVSWNSGALTSGVH TFPAVLQSSGLYSLSSVVTVPSSSLGTQTYICNVNHKPSNTKVDK RVEPKSC |
| SEQ ID NO: 194 | B7H6#2 scFab | EIVLTQSPDFLSASPGEKVTMTCRATSSLYSMHWYQQKPGSSP KPWIYATFNLASGVPARFSGSGSGTSYSLTITRVEAEDAATYYC QQWSTNPPKLTFGAGTKLELKRTVAAPSVFIFPPSDEQLKSGTA SVVCLLNNFYPREAKVQWKVDNALQSGNSQESVTEQDSKDST YSLSSTLTLSKADYEKHKVYACEVTHQGLSSPVTKSFNRGECGG GGSEGKSSGSGSESKSTEGKSSGSGSESKSTGGGGSEVQLQQS GAELVRPGASVKLSCTASGFNIKNTFIHWVNQRPEQGLEWIGR IDPANGNTIYASKFQGRATITTDTSSNTAYMHLSSLTSGDTAVY YCARTYGGTNYFDYWGQGTTLTVSSASTKGPSVFPLAPSSKSTS GGTAALGCLVKDYFPEPVTVSWNSGALTSGVHTFPAVLQSSGL YSLSSVVTVPSSSLGTQTYICNVNHKPSNTKVDKRVEPKSC |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 195 | B7H6#3 scFab | DIVMTQSQKLLSTSVGDRISVTCKASHNVGVYVAWYQQKPGH SPKALIHSASNRYSGVPDRFTGSGSGTDFTLTITNVQSEDLAEYF CQQYNSYPLTFGAGTKLELIRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGECGGGG SEGKSSGSGSESKSTEGKSSGSGSESKSTGGGGSEVKLVESEGG LVQPGSSMKLSCTASGFTFSDYYMTWVRQVPEKGLEWVGNI DYDGSRIYYLDSLKSRFIISRDNAKNILYLQMNSLKSEDTATYYCA RDDPAWLAYWGQGTLVTVSSASTKGPSVFPLAPSSKSTSGGT AALGCLVKDYFPEPVTVSWNSGALTSGVHTFPAVLQSSGLYSLS SVVTVPSSSLGTQTYICNVNHKPSNTKVDKRVEPKSC |
| SEQ ID NO: 196 | B7H6#4 scFab | DIVMTQSQKFMSTSVGDRVSVTCKASQNVGKYVAWYQQKP GQSPKALIYSASNRYDGVPDRFTGSGSGTDFTLTITNVQSEDLT EYFCQQYISYPLTFGAGTKLELKRTVAAPSVFIFPPSDEQLKSGT ASVVCLLNNFYPREAKVQWKVDNALQSGNSQESVTEQDSKDS TYSLSSTLTLSKADYEKHKVYACEVTHQGLSSPVTKSFNRGECG GGGSEGKSSGSGSESKSTEGKSSGSGSESKSTGGGGSQVQLQQ PGSVLVRPGASVRLSCKASGYTFTNYWMNWMKQRPGQGLE WIGGIYLNGDSTDYNEKFKGKATLTVDTSSSTTYMDLSSLTYED SAVYYCTTRGDYFGDFWGQGTTLTVSSASTKGPSVFPLAPSSKS TSGGTAALGCLVKDYFPEPVTVSWNSGALTSGVHTFPAVLQSS GLYSLSSVVTVPSSSLGTQTYICNVNHKPSNTKVDKRVEPKSC |
| SEQ ID NO: 197 | B7H6#5 scFab | AIQMTQSPSSLSASVGDRVTITCRASQDIRNDLGWFQQRPGK APNLLIYAASSLESGVPSRFSGRGSGTDFTLTISSLQPEDFATYYC LQYYNHPLTFGGGTKVEIKRIVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGECGGGG SEGKSSGSGSESKSTEGKSSGSGSESKSTGGGGSQVQLVQSGA EVKKPGASVKVSCKASGYTFTGYYIHWVRQAPGQGLEWMG WINPHSGATNYAQNFQGRVTMTRDTSISTAYMELSRLRSDDA AVYYCARERWGSGTFNIWGQGTMVTVSSASTKGPSVFPLAPS SKSTSGGTAALGCLVKDYFPEPVTVSWNSGALTSGVHTFPAVL QSSGLYSLSSVVTVPSSSLGTQTYICNVNHKPSNTKVDKRVEPK SC |
| SEQ ID NO: 198 | B7H6#6 scFab | DIVMTQSPDSLPVSAGDRVTITCKASQSVSNDVVWYQQKPGQ SPKLLMYSTSNRYIGVPDRFTGSGYGTDFTFTISTVQAEDLAVYF CQQDYSSPYTFGGGTKLEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGECGGGG SEGKSSGSGSESKSTEGKSSGSGSESKSTGGGGSEVQLQQSGPE LLKPGASVKISCKTSGYTFTDYTMHWVKQSHGKSLEWIGGINP NYDNTGYSEKFKDKATLTVDKSSSTAYMELRSLTSEDSAVYYCT RSGSRRSFYFDYWGQGTTLTVSSASTKGPSVFPLAPSSKSTSGG TAALGCLVKDYFPEPVTVSWNSGALTSGVHTFPAVLQSSGLYSL SSVVTVPSSSLGTQTYICNVNHKPSNTKVDKRVEPKSC |
| SEQ ID NO: 199 | B7H6#7 scFab | DIQMTQSPSSVSASVGDRVTITCRASQGISSWLAWYQQKPGK APNLLIYAASSLQSGVPSRFSGSGSGTDFTLTISSLQPEDFATYYC QQANSFPRTFGQGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGECGGGG SEGKSSGSGSESKSTEGKSSGSGSESKSTGGGGSQVQLQESGP GLVKPSETLSLTYTVSGGSISYNYWSWIRQPPEKGLEWIGHIYYS GSTNYNPSLKSRVTISVDTSKNQFSLKLNSVTAADTAVYYCARV GTWGSFDDWGQGTLVTVSSASTKGPSVFPLAPSSKSTSGGTA ALGCLVKDYFPEPVTVSWNSGALTSGVHTFPAVLQSSGLYSLSS VVTVPSSSLGTQTYICNVNHKPSNTKVDKRVEPKSC |
| SEQ ID NO: 200 | B7H6#8 scFab | DIVMTQSPLSLPVTPGEPASISCRSSQSLLYNNRYNYLDWYLQK PGQSPEVLIYLGSNRASGVPDRFSGSGSGTDFTLKISRVEAEDF GVYYCMQTLQIPITFGQGTRLEIKRTVAAPSVFIFPPSDEQLKSG TASVVCLLNNFYPREAKVQWKVDNALQSGNSQESVTEQDSKD STYSLSSTLTLSKADYEKHKVYACEVTHQGLSSPVTKSFNRGECG GGGSEGKSSGSGSESKSTEGKSSGSGSESKSTGGGGSQVQVVQ SGAEVKKPGSSVKVSCKGSGDTLNSYGISWMRQAPGQGLEW MGGIIPIFDTTKYAQKFQGRVTITADKSTTTVYMELSSLRFEDTA VYYCARERGYRFSEDYYFYYGMDVWGQGTTVTVSSASTKGPS VFPLAPSSKSTSGGTAALGCLVKDYFPEPVTVSWNSGALTSGV |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| | | HTFPAVLQSSGLYSLSSVVTVPSSSLGTQTYICNVNHKPSNTKVDKRVEPKSC |
| SEQ ID NO: 201 | B7H6#9 scFab | DIVLTQSPVSLAVSLGQRATISCRASESVDNFGVSFMNWFQQKPGQPPKLLIYAASNQGSGVPARFSGSGSGTDFSLNIHPLEEDDTAMYFCQQSKEVPWTFGGGTRLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSEGKSSGSGSESKSTEGKSSGSGSESKSTGGGGSQVQLQQPGAEMVRPGSSVKLSCKASDYTFTHYWIHWVKQRPLEGLEWIGIIGPSDNEIHYNQDFKDKATLTVDKSSNTAYLHLNSLTSEDSAVYYCARQIISMVVGTEYFDVWGTGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSC |
| SEQ ID NO: 202 | B7H6#10 scFab | DIQMTQSPSSVSASVGDRVTITCRASQGISSWLAWYQQKPGKAPKLLIYVASSLQRGVPSRFSGSGSGTDFTLTISNLQPEDFATYYCQQANSFPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSEGKSSGSGSESKSTEGKSSGSGSESKSTGGGGSQVHLQESGPGLVKPSETLSLTCTVSGDSISSYYWSWIRQPAGKGLEWIGHIYTSEKNNYNPSLKSRVIMSVDTSKNQFSLNLSSVTAADTAVYYCARVGNWGSHDAWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSC |
| SEQ ID NO: 203 | B7H6#11 scFab | DIVMTQSPLSLPVTPGEPASISCRSSQSLLHSNGYNYLDWYLQKPGQSPQVLIYLGSNRASGVPDRFSGSGSGTDFTLKISRVEAEDVGVYYCMQALQTPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSEGKSSGSGSESKSTEGKSSGSGSESKSTGGGGSELQLVNSGGGLVKSGGSLRLSCAASGITFSYYTMNWVRQAPGKGLEWVSSISSRSSYIYYADSVKGRFTISRDNAENSLYLQMNSLRAEDTAVYYCARDKGDYSKDIYYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSC |
| SEQ ID NO: 204 | B7H6#12 scFab | DIQMTQSPSSLSASVGDRVTITCKASQNVGKYVAWYQQKPGKAPKSLIYSASNRYDGVPSRFSGSGSGTDFTLTISSLQPEDFTTYYCQQYISYPLTFGAGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSEGKSSGSGSESKSTEGKSSGSGSESKSTGGGGSQVQLVQSGAEVKKPGASVKVSCKASGYTFTNYWMNWVKQAPGQGLEWMGGIYLNGDSTDYNEKFKGKATMTVDTSTSTVYMELSSLRSEDTAVYYCTRRGDYFGDFWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSC |
| SEQ ID NO: 205 | B7H6#13 scFab | DIQMTQSPSSLSASVGDRVTITCKASQNVGKYVAWYQQKPGKAPKSLIYSASNRYDGVPSRFSGSGSGTDFTLTISSLQPEDFTTYYCQQYISYPLTFGAGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSEGKSSGSGSESKSTEGKSSGSGSESKSTGGGGSQVQLVQSGAEVKKPGASVKVSCKASGYTFTSYWMNWMKQAPGQGLEWMGGIYLNGDSTDYNEKFKGRVTMTVDTSTSTVYMELSSLRSEDTAVYYCTRRGDYFGDFWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSC |
| SEQ ID NO: 206 | B7H6#14 scFab | DIQMTQSPSSLSASVGDRVTITCKASQNVGKYVAWYQQKPGKAPKSLIYSASNRYDGVPSRFSGSGSGTDFTLTISSLQPEDFATYFCQQYISYPLTFGAGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSEGKSSGSGSESKSTEGKSSGSGSESKSTGGGGSQVQLVQSGAEVKKPGASVKVSCKASGYTFTNYWMNWMKQAPGQGLEWIG |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| | | GIYLNGDSTDYNEKFKGKVTMTVDTSTSTVYMELSSLRSEDTA VYYCTRRGDYFGDFWGQGTLVTVSSASTKGPSVFPLAPSSKST SGGTAALGCLVKDYFPEPVTVSWNSGALTSGVHTFPAVLQSSG LYSLSSVVTVPSSSLGTQTYICNVNHKPSNTKVDKRVEPKSC |
| SEQ ID NO: 207 | B7H6#15 scFab | DIQMTQSPSSLSASVGDRVTITCKASQNVGKYVAWYQQKPGK APKSLIYSASNRYDGVPSRFSGSGSGTDFTLTISSLQPEDFTTYYC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTNYWMNWMRQAPGQGLEWMG GIYLSGDSTDYNEKFKGRVTMTVDTSTSTVYMELSSLRSEDTA VYYCTRRGDYFGDFWGQGTLVTVSSASTKGPSVFPLAPSSKST SGGTAALGCLVKDYFPEPVTVSWNSGALTSGVHTFPAVLQSSG LYSLSSVVTVPSSSLGTQTYICNVNHKPSNTKVDKRVEPKSC |
| SEQ ID NO: 208 | B7H6#16 scFab | DIQMTQSPSSLSASVGDRVTITCKASQNVGKYVAWYQQKPGK APKSLIYSASNRYDGVPSRFSGSGSGTDFTLTISSLQPEDFTTYYC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTSYWMNWMRQAPGQGLEWMG GIYLSGESTDYNEKFKGRVTMTVDTSTSTVYMELSSLRSEDTA VYYCTRRGDYFGDFWGQGTLVTVSSASTKGPSVFPLAPSSKST SGGTAALGCLVKDYFPEPVTVSWNSGALTSGVHTFPAVLQSSG LYSLSSVVTVPSSSLGTQTYICNVNHKPSNTKVDKRVEPKSC |
| SEQ ID NO: 209 | B7H6#17 scFab | DIQMTQSPSSLSASVGDRVTITCKASQNVGKYVAWYQQKPGK APKSLIYSASNRYDGVPSRFSGSGSGTDFTLTISSLQPEDFTTYYC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTSYWMNWMRQAPGQGLEWMG GIYLSGDSTDYNEKFKGRVTMTVDTSTSTVYMELSSLRSEDTA VYYCTRRGDYFGDFWGQGTLVTVSSASTKGPSVFPLAPSSKST SGGTAALGCLVKDYFPEPVTVSWNSGALTSGVHTFPAVLQSSG LYSLSSVVTVPSSSLGTQTYICNVNHKPSNTKVDKRVEPKSC |
| SEQ ID NO: 210 | B7H6#18 scFab | DIQMTQSPSSLSASVGDRVTITCKASQNVGKYVAWYQQKPGK APKSLIYSASNRYDAVPSRFSGSGSGTDFTLTISSLQPEDFTTYYC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTSYWMNWMRQAPGQGLEWMG GIYLSGDSTDYNEKFKGRVTMTVDTSTSTVYMELSSLRSEDTA VYYCTRRGDYFGDFWGQGTLVTVSSASTKGPSVFPLAPSSKST SGGTAALGCLVKDYFPEPVTVSWNSGALTSGVHTFPAVLQSSG LYSLSSVVTVPSSSLGTQTYICNVNHKPSNTKVDKRVEPKSC |
| SEQ ID NO: 211 | B7H6#19 scFab | DIQMTQSPSSLSASVGDRVTITCKASQNVGKYVAWYQQKPGK APKSLIYSASNRYDGVPSRFSGSGSGTDFTLTISSLQPEDFTTYYC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTSYWMNWVKQAPGQGLEWMG GIYLSGESTDYNEKFKGKATMTVDTSTSTVYMELSSLRSEDTA VYYCTRRGDYFGDFWGQGTLVTVSSASTKGPSVFPLAPSSKST SGGTAALGCLVKDYFPEPVTVSWNSGALTSGVHTFPAVLQSSG LYSLSSVVTVPSSSLGTQTYICNVNHKPSNTKVDKRVEPKSC |
| SEQ ID NO: 212 | B7H6#20 scFab | DIQMTQSPSSLSASVGDRVTITCKASQNVGKYVAWYQQKPGK APKSLIYSASNRYDAVPSRFSGSGSGTDFTLTISSLQPEDFTTYYC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTSYWMNWVKQAPGQGLEWMG |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| | | GIYLSGDSTDYNEKFKGKATMTVDTSTSTVYMELSSLRSEDTA VYYCTRRGDYFGDFWGQGTLVTVSSASTKGPSVFPLAPSSKST SGGTAALGCLVKDYFPEPVTVSWNSGALTSGVHTFPAVLQSSG LYSLSSVVTVPSSSLGTQTYICNVNHKPSNTKVDKRVEPKSC |
| SEQ ID NO: 213 | B7H6#21 scFab | DIQMTQSPSSLSASVGDRVTITCKASQNVGKYVAWYQQKPGK APKSLIYSASNRYDGVPSRFSGSGSGTDFTLTISSLQPEDFATYFC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTSYWMNWMKQAPGQGLEWIG GIYLSGESTDYNEKFKGKVTMTVDTSTSTVYMELSSLRSEDTA VYYCTRRGDYFGDFWGQGTLVTVSSASTKGPSVFPLAPSSKST SGGTAALGCLVKDYFPEPVTVSWNSGALTSGVHTFPAVLQSSG LYSLSSVVTVPSSSLGTQTYICNVNHKPSNTKVDKRVEPKSC |
| SEQ ID NO: 214 | B7H6#22 scFab | DIQMTQSPSSLSASVGDRVTITCKASQNVGKYVAWYQQKPGK APKSLIYSASNRYDAVPSRFSGSGSGTDFTLTISSLQPEDFATYFC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTSYWMNWMKQAPGQGLEWIG GIYLSGDSTDYNEKFKGKVTMTVDTSTSTVYMELSSLRSEDTA VYYCTRRGDYFGDFWGQGTLVTVSSASTKGPSVFPLAPSSKST SGGTAALGCLVKDYFPEPVTVSWNSGALTSGVHTFPAVLQSSG LYSLSSVVTVPSSSLGTQTYICNVNHKPSNTKVDKRVEPKSC |
| SEQ ID NO: 215 | B7H6#23 scFab | DIQMTQSPSSLSASVGDRVTITCKASQNVGKYVAWYQQKPGK APKSLIYSASNRYDAVPSRFSGSGSGTDFTLTISSLQPEDFATYFC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTSYWMNWMKQAPGQGLEWIG GIYLSGESTDYNEKFKGKVTMTVDTSTSTVYMELSSLRSEDTA VYYCTRRGDYFGDFWGQGTLVTVSSASTKGPSVFPLAPSSKST SGGTAALGCLVKDYFPEPVTVSWNSGALTSGVHTFPAVLQSSG LYSLSSVVTVPSSSLGTQTYICNVNHKPSNTKVDKRVEPKSC |
| SEQ ID NO: 216 | B7H6#24 scFab | DIQMTQSPSSLSASVGDRVTITCKASQNVGKYVAWYQQKPGK APKSLIYSASNRYDAVPSRFSGSGSGTDFTLTISSLQPEDFTTYYC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTNYWMNWMRQAPGQGLEWMG GIYLSGDSTDYNEKFKGRVTMTVDTSTSTVYMELSSLRSEDTA VYYCTRRGDYFGDFWGQGTLVTVSSASTKGPSVFPLAPSSKST SGGTAALGCLVKDYFPEPVTVSWNSGALTSGVHTFPAVLQSSG LYSLSSVVTVPSSSLGTQTYICNVNHKPSNTKVDKRVEPKSC |
| SEQ ID NO: 217 | B7H6#1 chain | DIVMSQSPSSLAVSVGEKVTMNCKSSQSLFYSSNQKNYLAWY QQKPGQSPKLLIYWASTRESGVPDRFTGSGSGTDFTLTISSVKA EDLAVYYCQQYYNYPRTFGGGTKLEIKRTVAAPSVFIFPPSDEQ LKSGTASVVCLLNNFYPREAKVQWKVDNALQSGNSQESVTEQ DSKDSTYSLSSTLTLSKADYEKHKVYACEVTHQGLSSPVTKSFNR GECGGGGSEGKSSGSGSESKSTEGKSSGSGSESKSTGGGGSEV QLQQSGPELVKPGTSVKMSCKASGYTFTDYYMNWVKQSQGK NLEWIAYIYPKTGGNGYNQKFKDKATLTVDKSSNTAYMELRSL TSDDSAVYYCGRENWDGYTMAYWGQGTSVTVSSASTKGPSV FPLAPSSKSTSGGTAALGCLVKDYFPEPVTVSWNSGALTSGVH TFPAVLQSSGLYSLSSVVTVPSSSLGTQTYICNVNHKPSNTKVDK RVEPKSCDKTHTCPPCPAPEAAGGPSVFLFPPKPKDTLMISRTP EVTCVVVDVSHEDPEVKFNWYVDGVEVHNAKTKPREEQYNST YRVVSVLTVLHQDWLNGKEYKCKVSNKALPAPIEKTISKAKGQP REPQVYTLPPSREEMTKNQVSLWCLVKGFYPSDIAVEWESNG QPENNYKTTPPVLDSDGSFFLYSKLTVDKSRWQQGNVFSCSV MHEALHNHYTQKSLSLSPG |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 218 | B7H6#2 chain | EIVLTQSPDFLSASPGEKVTMTCRATSSLYSMHWYQQKPGSSP<br>KPWIYATFNLASGVPARFSGSGSGTSYSLTITRVEAEDAATYYC<br>QQWSTNPPKLTFGAGTKLELKRTVAAPSVFIFPPSDEQLKSGTA<br>SVVCLLNNFYPREAKVQWKVDNALQSGNSQESVTEQDSKDST<br>YSLSSTLTLSKADYEKHKVYACEVTHQGLSSPVTKSFNRGECGG<br>GGSEGKSSGSGSESKSTEGKSSGSGSESKSTGGGGSEVQLQQS<br>GAELVRPGASVKLSCTASGFNIKNTFIHWVNQRPEQGLEWIGR<br>IDPANGNTIYASKFQGRATITTDTSSNTAYMHLSSLTSGDTAVY<br>YCARTYGGTNYFDYWGQGTTLTVSSASTKGPSVFPLAPSSKSTS<br>GGTAALGCLVKDYFPEPVTVSWNSGALTSGVHTFPAVLQSSGL<br>YSLSSVVTVPSSSLGTQTYICNVNHKPSNTKVDKRVEPKSCDKT<br>HTCPPCPAPEAAGGPSVFLFPPKPKDTLMISRTPEVTCVVVDVS<br>HEDPEVKFNWYVDGVEVHNAKTKPREEQYNSTYRVVSVLTVL<br>HQDWLNGKEYKCKVSNKALPAPIEKTISKAKGQPREPQVYTLP<br>PSREEMTKNQVSLWCLVKGFYPSDIAVEWESNGQPENNYKTT<br>PPVLDSDGSFFLYSKLTVDKSRWQQGNVFSCSVMHEALHNHY<br>TQKSLSLSPG |
| SEQ ID NO: 219 | B7H6#3 chain | DIVMTQSQKLLSTSVGDRISVTCKASHNVGVYVAWYQQKPGH<br>SPKALIHSASNRYSGVPDRFTGSGSGTDFTLTITNVQSEDLAEYF<br>CQQYNSYPLTFGAGTKLELIRTVAAPSVFIFPPSDEQLKSGTASV<br>VCLLNNFYPREAKVQWKVDNALQSGNSQESVTEQDSKDSTYS<br>LSSTLTLSKADYEKHKVYACEVTHQGLSSPVTKSFNRGECGGGG<br>SEGKSSGSGSESKSTEGKSSGSGSESKSTGGGGSEVKLVESEGG<br>LVQPGSSMKLSCTASGFTFSDYYMTWVRQVPEKGLEWVGNI<br>DYDGSRIYYLDSLKSRFIISRDNAKNILYLQMNSLKSEDTATYYCA<br>RDDPAWLAYWGQGTLVTVSSASTKGPSVFPLAPSSKSTSGGT<br>AALGCLVKDYFPEPVTVSWNSGALTSGVHTFPAVLQSSGLYSLS<br>SVVTVPSSSLGTQTYICNVNHKPSNTKVDKRVEPKSCDKTHTCP<br>PCPAPEAAGGPSVFLFPPKPKDTLMISRTPEVTCVVVDVSHEDP<br>EVKFNWYVDGVEVHNAKTKPREEQYNSTYRVVSVLTVLHQD<br>WLNGKEYKCKVSNKALPAPIEKTISKAKGQPREPQVYTLPPSRE<br>EMTKNQVSLWCLVKGFYPSDIAVEWESNGQPENNYKTTPPVL<br>DSDGSFFLYSKLTVDKSRWQQGNVFSCSVMHEALHNHYTQKS<br>LSLSPG |
| SEQ ID NO: 220 | B7H6#4 chain | DIVMTQSQKFMSTSVGDRVSVTCKASQNVGKYVAWYQQKP<br>GQSPKALIYSASNRYDGVPDRFTGSGSGTDFTLTITNVQSEDLT<br>EYFCQQYISYPLTFGAGTKLELKRTVAAPSVFIFPPSDEQLKSGT<br>ASVVCLLNNFYPREAKVQWKVDNALQSGNSQESVTEQDSKDS<br>TYSLSSTLTLSKADYEKHKVYACEVTHQGLSSPVTKSFNRGECG<br>GGGSEGKSSGSGSESKSTEGKSSGSGSESKSTGGGGSQVQLQQ<br>PGSVLVRPGASVRLSCKASGYTFTNYWMNWMKQRPGQGLE<br>WIGGIYLNGDSTDYNEKFKGKATLTVDTSSSTTYMDLSSLTYED<br>SAVYYCTTRGDYFGDFWGQGTTLTVSSASTKGPSVFPLAPSSKS<br>TSGGTAALGCLVKDYFPEPVTVSWNSGALTSGVHTFPAVLQSS<br>GLYSLSSVVTVPSSSLGTQTYICNVNHKPSNTKVDKRVEPKSCD<br>KTHTCPPCPAPEAAGGPSVFLFPPKPKDTLMISRTPEVTCVVVD<br>VSHEDPEVKFNWYVDGVEVHNAKTKPREEQYNSTYRVVSVLT<br>VLHQDWLNGKEYKCKVSNKALPAPIEKTISKAKGQPREPQVYT<br>LPPSREEMTKNQVSLWCLVKGFYPSDIAVEWESNGQPENNYK<br>TTPPVLDSDGSFFLYSKLTVDKSRWQQGNVFSCSVMHEALHN<br>HYTQKSLSLSPG |
| SEQ ID NO: 221 | B7H6#5 chain | AIQMTQSPSSLSASVGDRVTITCRASQDIRNDLGWFQQRPGK<br>APNLLIYAASSLESGVPSRFSGRGSGTDFTLTISSLQPEDFATYYC<br>LQYYNHPLTFGGGTKVEIKRIVAAPSVFIFPPSDEQLKSGTASV<br>VCLLNNFYPREAKVQWKVDNALQSGNSQESVTEQDSKDSTYS<br>LSSTLTLSKADYEKHKVYACEVTHQGLSSPVTKSFNRGECGGGG<br>SEGKSSGSGSESKSTEGKSSGSGSESKSTGGGGSQVQLVQSGA<br>EVKKPGASVKVSCKASGYTFTGYYIHWVRQAPGQGLEWMG<br>WINPHSGATNYAQNFQGRVTMTRDTSISTAYMELSRLRSDDA<br>AVYYCARERWGSGTFNIWGQGTMVTVSSASTKGPSVFPLAPS<br>SKSTSGGTAALGCLVKDYFPEPVTVSWNSGALTSGVHTFPAVL<br>QSSGLYSLSSVVTVPSSSLGTQTYICNVNHKPSNTKVDKRVEPK<br>SCDKTHTCPPCPAPEAAGGPSVFLFPPKPKDTLMISRTPEVTCV<br>VVDVSHEDPEVKFNWYVDGVEVHNAKTKPREEQYNSTYRVVS<br>VLTVLHQDWLNGKEYKCKVSNKALPAPIEKTISKAKGQPREPQ<br>VYTLPPSREEMTKNQVSLWCLVKGFYPSDIAVEWESNGQPEN<br>NYKTTPPVLDSDGSFFLYSKLIVDKSRWQQGNVFSCSVMHEAL<br>HNHYTQKSLSLSPG |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 222 | B7H6#6 chain | DIVMTQSPDSLPVSAGDRVTITCKASQSVSNDVVWYQQKPGQ<br>SPKLLMYSTSNRYIGVPDRFTGSGYGTDFTFTISTVQAEDLAVYF<br>CQQDYSSPYTFGGGTKLEIKRTVAAPSVFIFPPSDEQLKSGTASV<br>VCLLNNFYPREAKVQWKVDNALQSGNSQESVTEQDSKDSTYS<br>LSSTLTLSKADYEKHKVYACEVTHQGLSSPVTKSFNRGECGGGG<br>SEGKSSGSGSESKSTEGKSSGSGSESKSTGGGGSEVQLQQSGPE<br>LLKPGASVKISCKTSGYTFTDYTMHWVKQSHGKSLEWIGGINP<br>NYDNTGYSEKFKDKATLTVDKSSSTAYMELRSLTSEDSAVYYCT<br>RSGSRRSFYFDYWGQGTTLTVSSASTKGPSVFPLAPSSKSTSGG<br>TAALGCLVKDYFPEPVTVSWNSGALTSGVHTFPAVLQSSGLYSL<br>SSVVTVPSSSLGTQTYICNVNHKPSNTKVDKRVEPKSCDKTHTC<br>PPCPAPEAAGGPSVFLFPPKPKDTLMISRTPEVTCVVVDVSHED<br>PEVKFNWYVDGVEVHNAKTKPREEQYNSTYRVVSVLTVLHQD<br>WLNGKEYKCKVSNKALPAPIEKTISKAKGQPREPQVYTLPPSRE<br>EMTKNQVSLWCLVKGFYPSDIAVEWESNGQPENNYKTTPPVL<br>DSDGSFFLYSKLTVDKSRWQQGNVFSCSVMHEALHNHYTQKS<br>LSLSPG |
| SEQ ID NO: 223 | B7H6#7 chain | DIQMTQSPSSVSASVGDRVTITCRASQGISSWLAWYQQKPGK<br>APNLLIYAASSLQSGVPSRFSGSGSGTDFTLTISSLQPEDFATYYC<br>QQANSFPRTFGQGTKVEIKRTVAAPSVFIFPPSDEQLKSGTASV<br>VCLLNNFYPREAKVQWKVDNALQSGNSQESVTEQDSKDSTYS<br>LSSTLTLSKADYEKHKVYACEVTHQGLSSPVTKSFNRGECGGGG<br>SEGKSSGSGSESKSTEGKSSGSGSESKSTGGGGSQVQLQESGP<br>GLVKPSETLSLTYTVSGGSISYNYWSWIRQPPEKGLEWIGHIYYS<br>GSTNYNPSLKSRVTISVDTSKNQFSLKLNSVTAADTAVYYCARV<br>GTWGSFDDWGQGTLVTVSSASTKGPSVFPLAPSSKSTSGGTA<br>ALGCLVKDYFPEPVTVSWNSGALTSGVHTFPAVLQSSGLYSLSS<br>VVTVPSSSLGTQTYICNVNHKPSNTKVDKRVEPKSCDKTHTCPP<br>CPAPEAAGGPSVFLFPPKPKDTLMISRTPEVTCVVVDVSHEDPE<br>VKFNWYVDGVEVHNAKTKPREEQYNSTYRVVSVLTVLHQDW<br>LNGKEYKCKVSNKALPAPIEKTISKAKGQPREPQVYTLPPSREE<br>MTKNQVSLWCLVKGFYPSDIAVEWESNGQPENNYKTTPPVLD<br>SDGSFFLYSKLTVDKSRWQQGNVFSCSVMHEALHNHYTQKSL<br>SLSPG |
| SEQ ID NO: 224 | B7H6#8 chain | DIVMTQSPLSLPVTPGEPASISCRSSQSLLYNNRYNYLDWYLQK<br>PGQSPEVLIYLGSNRASGVPDRFSGSGSGTDFTLKISRVEAEDF<br>GVYYCMQTLQIPITFGQGTRLEIKRTVAAPSVFIFPPSDEQLKSG<br>TASVVCLLNNFYPREAKVQWKVDNALQSGNSQESVTEQDSKD<br>STYSLSSTLTLSKADYEKHKVYACEVTHQGLSSPVTKSFNRGECG<br>GGGSEGKSSGSGSESKSTEGKSSGSGSESKSTGGGGSQVQVVQ<br>SGAEVKKPGSSVKVSCKGSGDTLNSYGISWMRQAPGQGLEW<br>MGGIIPIFDTTKYAQKFQGRVTITADKSTTTVYMELSSLRFEDTA<br>VYYCARERGYRFSEDYYFYYGMDVWGQGTTVTVSSASTKGPS<br>VFPLAPSSKSTSGGTAALGCLVKDYFPEPVTVSWNSGALTSGV<br>HTFPAVLQSSGLYSLSSVVTVPSSSLGTQTYICNVNHKPSNTKV<br>DKRVEPKSCDKTHTCPPCPAPEAAGGPSVFLFPPKPKDTLMISR<br>TPEVTCVVVDVSHEDPEVKFNWYVDGVEVHNAKTKPREEQY<br>NSTYRVVSVLTVLHQDWLNGKEYKCKVSNKALPAPIEKTISKAK<br>GQPREPQVYTLPPSREEMTKNQVSLWCLVKGFYPSDIAVEWE<br>SNGQPENNYKTTPPVLDSDGSFFLYSKLTVDKSRWQQGNVFS<br>CSVMHEALHNHYTQKSLSLSPG |
| SEQ ID NO: 225 | B7H6#9 chain | DIVLTQSPVSLAVSLGQRATISCRASESVDNFGVSFMNWFQQK<br>PGQPPKLLIYAASNQGSGVPARFSGSGSGTDFSLNIHPLEEDDT<br>AMYFCQQSKEVPWTFGGGTRLEIKRTVAAPSVFIFPPSDEQLK<br>SGTASVVCLLNNFYPREAKVQWKVDNALQSGNSQESVTEQDS<br>KDSTYSLSSTLTLSKADYEKHKVYACEVTHQGLSSPVTKSFNRGE<br>CGGGGSEGKSSGSGSESKSTEGKSSGSGSESKSTGGGGSQVQL<br>QQPGAEMVRPGSSVKLSCKASDYTFTHYWIHWVKQRPLEGLE<br>WIGIIGPSDNEIHYNQDFKDKATLTVDKSSNTAYLHLNSLTSEDS<br>AVYYCARQIISMVVGTEYFDVWGTGTTVTVSSASTKGPSVFPL<br>APSSKSTSGGTAALGCLVKDYFPEPVTVSWNSGALTSGVHTFP<br>AVLQSSGLYSLSSVVTVPSSSLGTQTYICNVNHKPSNTKVDKRV<br>EPKSCDKTHTCPPCPAPEAAGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPRE<br>PQVYTLPPSREEMTKNQVSLWCLVKGFYPSDIAVEWESNGQP<br>ENNYKTTPPVLDSDGSFFLYSKLTVDKSRWQQGNVFSCSVMH<br>EALHNHYTQKSLSLSPG |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 226 | B7H6#10 chain | DIQMTQSPSSVSASVGDRVTITCRASQGISSWLAWYQQKPGK APKLLIYVASSLQRGVPSRFSGSGSGTDFTLTISNLQPEDFATYY CQQANSFPRTFGQGTKVEIKRTVAAPSVFIFPPSDEQLKSGTAS VVCLLNNFYPREAKVQWKVDNALQSGNSQESVTEQDSKDSTY SLSSTLTLSKADYEKHKVYACEVTHQGLSSPVTKSFNRGECGGG GSEGKSSGSGSESKSTEGKSSGSGSESKSTGGGGSQVHLQESG PGLVKPSETLSLTCTVSGDSISSYYWSWIRQPAGKGLEWIGHIY TSEKNNYNPSLKSRVIMSVDTSKNQFSLNLSSVTAADTAVYYCA RVGNWGSHDAWGQGTLVTVSSASTKGPSVFPLAPSSKSTSGG TAALGCLVKDYFPEPVTVSWNSGALTSGVHTFPAVLQSSGLYSL SSVVTVPSSSLGTQTYICNVNHKPSNTKVDKRVEPKSCDKTHTC PPCPAPEAAGGPSVFLFPPKPKDTLMISRTPEVTCVVVDVSHED PEVKFNWYVDGVEVHNAKTKPREEQYNSTYRVVSVLTVLHQD WLNGKEYKCKVSNKALPAPIEKTISKAKGQPREPQVYTLPPSRE EMTKNQVSLWCLVKGFYPSDIAVEWESNGQPENNYKTTPPVL DSDGSFFLYSKLTVDKSRWQQGNVFSCSVMHEALHNHYTQKS LSLSPG |
| SEQ ID NO: 227 | B7H6#11 chain | DIVMTQSPLSLPVTPGEPASISCRSSQSLLHSNGYNYLDWYLQK PGQSPQVLIYLGSNRASGVPDRFSGSGSGTDFTLKISRVEAEDV GVYYCMQALQTPLTFGGGTKVEIKRTVAAPSVFIFPPSDEQLKS GTASVVCLLNNFYPREAKVQWKVDNALQSGNSQESVTEQDSK DSTYSLSSTLTLSKADYEKHKVYACEVTHQGLSSPVTKSFNRGEC GGGGSEGKSSGSGSESKSTEGKSSGSGSESKSTGGGGSELQLV NSGGGLVKSGGSLRLSCAASGITFSYYTMNWVRQAPGKGLEW VSSISSRSSYIYYADSVKGRFTISRDNAENSLYLQMNSLRAEDTA VYYCARDKGDYSKDIYYYYGMDVWGQGTTVTVSSASTKGPSV TFPAVLQSSGLYSLSSVVTVPSSSLGTQTYICNVNHKPSNTKVDK RVEPKSCDKTHTCPPCPAPEAAGGPSVFLFPPKPKDTLMISRTP EVTCVVVDVSHEDPEVKFNWYVDGVEVHNAKTKPREEQYNST YRVVSVLTVLHQDWLNGKEYKCKVSNKALPAPIEKTISKAKGQP REPQVYTLPPSREEMTKNQVSLWCLVKGFYPSDIAVEWESNG QPENNYKTTPPVLDSDGSFFLYSKLTVDKSRWQQGNVFSCSV MHEALHNHYTQKSLSLSPG |
| SEQ ID NO: 228 | B7H6#12 chain | DIQMTQSPSSLSASVGDRVTITCKASQNVGKYVAWYQQKPGK APKSLIYSASNRYDGVPSRFSGSGSGTDFTLTISSLQPEDFTTYYC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTNYWMNWVKQAPGQGLEWMG GIYLNGDSTDYNEKFKGKATMTVDTSTSTVYMELSSLRSEDTA VYYCTRRGDYFGDFWGQGTLVTVSSASTKGPSVFPLAPSSKST SGGTAALGCLVKDYFPEPVTVSWNSGALTSGVHTFPAVLQSSG LYSLSSVVTVPSSSLGTQTYICNVNHKPSNTKVDKRVEPKSCDKT HTCPPCPAPEAAGGPSVFLFPPKPKDTLMISRTPEVTCVVVDVS HEDPEVKFNWYVDGVEVHNAKTKPREEQYNSTYRVVSVLTVL HQDWLNGKEYKCKVSNKALPAPIEKTISKAKGQPREPQVYTLP PSREEMTKNQVSLWCLVKGFYPSDIAVEWESNGQPENNYKTT PPVLDSDGSFFLYSKLTVDKSRWQQGNVFSCSVMHEALHNHY TQKSLSLSPG |
| SEQ ID NO: 229 | B7H6#13 chain | DIQMTQSPSSLSASVGDRVTITCKASQNVGKYVAWYQQKPGK APKSLIYSASNRYDGVPSRFSGSGSGTDFTLTISSLQPEDFTTYYC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTSYWMNWMKQAPGQGLEWMG GIYLNGDSTDYNEKFKGRVTMTVDTSTSTVYMELSSLRSEDTA VYYCTRRGDYFGDFWGQGTLVTVSSASTKGPSVFPLAPSSKST SGGTAALGCLVKDYFPEPVTVSWNSGALTSGVHTFPAVLQSSG LYSLSSVVTVPSSSLGTQTYICNVNHKPSNTKVDKRVEPKSCDKT HTCPPCPAPEAAGGPSVFLFPPKPKDTLMISRTPEVTCVVVDVS HEDPEVKFNWYVDGVEVHNAKTKPREEQYNSTYRVVSVLTVL HQDWLNGKEYKCKVSNKALPAPIEKTISKAKGQPREPQVYTLP PSREEMTKNQVSLWCLVKGFYPSDIAVEWESNGQPENNYKTT PPVLDSDGSFFLYSKLTVDKSRWQQGNVFSCSVMHEALHNHY TQKSLSLSPG |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 230 | B7H6#14 chain | DIQMTQSPSSLSASVGDRVTITCKASQNVGKYVAWYQQKPGK APKSLIYSASNRYDGVPSRFSGSGSGTDFTLTISSLQPEDFATYFC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTNYWMNWMKQAPGQGLEWIG GIYLNGDSTDYNEKFKGKVTMTVDTSTSTVYMELSSLRSEDTAV YYCTRRGDYFGDFWGQGTLVTVSSASTKGPSVFPLAPSSKSTSG GTAALGCLVKDYFPEPVTVSWNSGALTSGVHTFPAVLQSSGLY SLSSVVTVPSSSLGTQTYICNVNHKPSNTKVDKRVEPKSCDKTH TCPPCPAPEAAGGPSVFLFPPKPKDTLMISRTPEVTCVVVDVSH EDPEVKFNWYVDGVEVHNAKTKPREEQYNSTYRVVSVLTVLH QDWLNGKEYKCKVSNKALPAPIEKTISKAKGQPREPQVYTLPPS REEMTKNQVSLWCLVKGFYPSDIAVEWESNGQPENNYKTTPP VLDSDGSFFLYSKLTVDKSRWQQGNVFSCSVMHEALHNHYTQ KSLSLSPG |
| SEQ ID NO: 231 | B7H6#15 chain | DIQMTQSPSSLSASVGDRVTITCKASQNVGKYVAWYQQKPGK APKSLIYSASNRYDGVPSRFSGSGSGTDFTLTISSLQPEDFTTYYC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTNYWMNWMRQAPGQGLEWMG GIYLSGDSTDYNEKFKGRVTMTVDTSTSTVYMELSSLRSEDTAV YYCTRRGDYFGDFWGQGTLVTVSSASTKGPSVFPLAPSSKSTSG GTAALGCLVKDYFPEPVTVSWNSGALTSGVHTFPAVLQSSGLY SLSSVVTVPSSSLGTQTYICNVNHKPSNTKVDKRVEPKSCDKTH TCPPCPAPEAAGGPSVFLFPPKPKDTLMISRTPEVTCVVVDVSH EDPEVKFNWYVDGVEVHNAKTKPREEQYNSTYRVVSVLTVLH QDWLNGKEYKCKVSNKALPAPIEKTISKAKGQPREPQVYTLPPS REEMTKNQVSLWCLVKGFYPSDIAVEWESNGQPENNYKTTPP VLDSDGSFFLYSKLTVDKSRWQQGNVFSCSVMHEALHNHYTQ KSLSLSPG |
| SEQ ID NO: 232 | B7H6#16 chain | DIQMTQSPSSLSASVGDRVTITCKASQNVGKYVAWYQQKPGK APKSLIYSASNRYDGVPSRFSGSGSGTDFTLTISSLQPEDFTTYYC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTSYWMNWMRQAPGQGLEWMG GIYLSGESTDYNEKFKGRVTMTVDTSTSTVYMELSSLRSEDTAV YYCTRRGDYFGDFWGQGTLVTVSSASTKGPSVFPLAPSSKSTSG GTAALGCLVKDYFPEPVTVSWNSGALTSGVHTFPAVLQSSGLY SLSSVVTVPSSSLGTQTYICNVNHKPSNTKVDKRVEPKSCDKTH TCPPCPAPEAAGGPSVFLFPPKPKDTLMISRTPEVTCVVVDVSH EDPEVKFNWYVDGVEVHNAKTKPREEQYNSTYRVVSVLTVLH QDWLNGKEYKCKVSNKALPAPIEKTISKAKGQPREPQVYTLPPS REEMTKNQVSLWCLVKGFYPSDIAVEWESNGQPENNYKTTPP VLDSDGSFFLYSKLTVDKSRWQQGNVFSCSVMHEALHNHYTQ KSLSLSPG |
| SEQ ID NO: 233 | B7H6#17 chain | DIQMTQSPSSLSASVGDRVTITCKASQNVGKYVAWYQQKPGK APKSLIYSASNRYDGVPSRFSGSGSGTDFTLTISSLQPEDFTTYYC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTSYWMNWMRQAPGQGLEWMG GIYLSGDSTDYNEKFKGRVTMTVDTSTSTVYMELSSLRSEDTAV YYCTRRGDYFGDFWGQGTLVTVSSASTKGPSVFPLAPSSKSTSG GTAALGCLVKDYFPEPVTVSWNSGALTSGVHTFPAVLQSSGLY SLSSVVTVPSSSLGTQTYICNVNHKPSNTKVDKRVEPKSCDKTH TCPPCPAPEAAGGPSVFLFPPKPKDTLMISRTPEVTCVVVDVSH EDPEVKFNWYVDGVEVHNAKTKPREEQYNSTYRVVSVLTVLH QDWLNGKEYKCKVSNKALPAPIEKTISKAKGQPREPQVYTLPPS REEMTKNQVSLWCLVKGFYPSDIAVEWESNGQPENNYKTTPP VLDSDGSFFLYSKLTVDKSRWQQGNVFSCSVMHEALHNHYTQ KSLSLSPG |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 234 | B7H6#18 chain | DIQMTQSPSSLSASVGDRVTITCKASQNVGKYVAWYQQKPGK APKSLIYSASNRYDAVPSRFSGSGSGTDFTLTISSLQPEDFTTYYC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTSYWMNWMRQAPGQGLEWMG GIYLSGDSTDYNEKFKGRVTMTVDTSTSTVYMELSSLRSEDTAV YYCTRRGDYFGDFWGQGTLVTVSSASTKGPSVFPLAPSSKSTSG GTAALGCLVKDYFPEPVTVSWNSGALTSGVHTFPAVLQSSGLY SLSSVVTVPSSSLGTQTYICNVNHKPSNTKVDKRVEPKSCDKTH TCPPCPAPEAAGGPSVFLFPPKPKDTLMISRTPEVTCVVVDVSH EDPEVKFNWYVDGVEVHNAKTKPREEQYNSTYRVVSVLTVLH QDWLNGKEYKCKVSNKALPAPIEKTISKAKGQPREPQVYTLPPS REEMTKNQVSLWCLVKGFYPSDIAVEWESNGQPENNYKTTPP VLDSDGSFFLYSKLTVDKSRWQQGNVFSCSVMHEALHNHYTQ KSLSLSPG |
| SEQ ID NO: 235 | B7H6#19 chain | DIQMTQSPSSLSASVGDRVTITCKASQNVGKYVAWYQQKPGK APKSLIYSASNRYDGVPSRFSGSGSGTDFTLTISSLQPEDFTTYYC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTSYWMNWVKQAPGQGLEWMG GIYLSGESTDYNEKFKGKATMTVDTSTSTVYMELSSLRSEDTAV YYCTRRGDYFGDFWGQGTLVTVSSASTKGPSVFPLAPSSKSTSG GTAALGCLVKDYFPEPVTVSWNSGALTSGVHTFPAVLQSSGLY SLSSVVTVPSSSLGTQTYICNVNHKPSNTKVDKRVEPKSCDKTH TCPPCPAPEAAGGPSVFLFPPKPKDTLMISRTPEVTCVVVDVSH EDPEVKFNWYVDGVEVHNAKTKPREEQYNSTYRVVSVLTVLH QDWLNGKEYKCKVSNKALPAPIEKTISKAKGQPREPQVYTLPPS REEMTKNQVSLWCLVKGFYPSDIAVEWESNGQPENNYKTTPP VLDSDGSFFLYSKLTVDKSRWQQGNVFSCSVMHEALHNHYTQ KSLSLSPG |
| SEQ ID NO: 236 | B7H6#20 chain | DIQMTQSPSSLSASVGDRVTITCKASQNVGKYVAWYQQKPGK APKSLIYSASNRYDAVPSRFSGSGSGTDFTLTISSLQPEDFTTYYC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTSYWMNWVKQAPGQGLEWMG GIYLSGDSTDYNEKFKGKATMTVDTSTSTVYMELSSLRSEDTAV YYCTRRGDYFGDFWGQGTLVTVSSASTKGPSVFPLAPSSKSTSG GTAALGCLVKDYFPEPVTVSWNSGALTSGVHTFPAVLQSSGLY SLSSVVTVPSSSLGTQTYICNVNHKPSNTKVDKRVEPKSCDKTH TCPPCPAPEAAGGPSVFLFPPKPKDTLMISRTPEVTCVVVDVSH EDPEVKFNWYVDGVEVHNAKTKPREEQYNSTYRVVSVLTVLH QDWLNGKEYKCKVSNKALPAPIEKTISKAKGQPREPQVYTLPPS REEMTKNQVSLWCLVKGFYPSDIAVEWESNGQPENNYKTTPP VLDSDGSFFLYSKLTVDKSRWQQGNVFSCSVMHEALHNHYTQ KSLSLSPG |
| SEQ ID NO: 237 | B7H6#21 chain | DIQMTQSPSSLSASVGDRVTITCKASQNVGKYVAWYQQKPGK APKSLIYSASNRYDGVPSRFSGSGSGTDFTLTISSLQPEDFATYFC QQYISYPLTFGAGTKLEIKRTVAAPSVFIFPPSDEQLKSGTASVV CLLNNFYPREAKVQWKVDNALQSGNSQESVTEQDSKDSTYSL SSTLTLSKADYEKHKVYACEVTHQGLSSPVTKSFNRGECGGGGS EGKSSGSGSESKSTEGKSSGSGSESKSTGGGGSQVQLVQSGAE VKKPGASVKVSCKASGYTFTSYWMNWMKQAPGQGLEWIG GIYLSGESTDYNEKFKGKVTMTVDTSTSTVYMELSSLRSEDTAV YYCTRRGDYFGDFWGQGTLVTVSSASTKGPSVFPLAPSSKSTSG GTAALGCLVKDYFPEPVTVSWNSGALTSGVHTFPAVLQSSGLY SLSSVVTVPSSSLGTQTYICNVNHKPSNTKVDKRVEPKSCDKTH TCPPCPAPEAAGGPSVFLFPPKPKDTLMISRTPEVTCVVVDVSH EDPEVKFNWYVDGVEVHNAKTKPREEQYNSTYRVVSVLTVLH QDWLNGKEYKCKVSNKALPAPIEKTISKAKGQPREPQVYTLPPS REEMTKNQVSLWCLVKGFYPSDIAVEWESNGQPENNYKTTPP VLDSDGSFFLYSKLTVDKSRWQQGNVFSCSVMHEALHNHYTQ KSLSLSPG |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 238 | B7H6#22 chain | DIQMTQSPSSLSASVGDRVTITCKASQNVGKYVAWYQQKPGK<br>APKSLIYSASNRYDAVPSRFSGSGSGTDFTLTISSLQPEDFATYFC<br>QQYISYPLTFGAGTKLEIKRTVAAPSVFIFPPSDEQLKSGTASVV<br>CLLNNFYPREAKVQWKVDNALQSGNSQESVTEQDSKDSTYSL<br>SSTLTLSKADYEKHKVYACEVTHQGLSSPVTKSFNRGECGGGGS<br>EGKSSGSGSESKSTEGKSSGSGSESKSTGGGGSQVQLVQSGAE<br>VKKPGASVKVSCKASGYTFTSYWMNWMKQAPGQGLEWIG<br>GIYLSGDSTDYNEKFKGKVTMTVDTSTSTVYMELSSLRSEDTAV<br>YYCTRRGDYFGDFWGQGTLVTVSSASTKGPSVFPLAPSSKSTSG<br>GTAALGCLVKDYFPEPVTVSWNSGALTSGVHTFPAVLQSSGLY<br>SLSSVVTVPSSSLGTQTYICNVNHKPSNTKVDKRVEPKSCDKTH<br>TCPPCPAPEAAGGPSVFLFPPKPKDTLMISRTPEVTCVVVDVSH<br>EDPEVKFNWYVDGVEVHNAKTKPREEQYNSTYRVVSVLTVLH<br>QDWLNGKEYKCKVSNKALPAPIEKTISKAKGQPREPQVYTLPPS<br>REEMTKNQVSLWCLVKGFYPSDIAVEWESNGQPENNYKTTPP<br>VLDSDGSFFLYSKLTVDKSRWQQGNVFSCSVMHEALHNHYTQ<br>KSLSLSPG |
| SEQ ID NO: 239 | B7H6#23 chain | DIQMTQSPSSLSASVGDRVTITCKASQNVGKYVAWYQQKPGK<br>APKSLIYSASNRYDAVPSRFSGSGSGTDFTLTISSLQPEDFATYFC<br>QQYISYPLTFGAGTKLEIKRTVAAPSVFIFPPSDEQLKSGTASVV<br>CLLNNFYPREAKVQWKVDNALQSGNSQESVTEQDSKDSTYSL<br>SSTLTLSKADYEKHKVYACEVTHQGLSSPVTKSFNRGECGGGGS<br>EGKSSGSGSESKSTEGKSSGSGSESKSTGGGGSQVQLVQSGAE<br>VKKPGASVKVSCKASGYTFTSYWMNWMKQAPGQGLEWIG<br>GIYLSGESTDYNEKFKGKVTMTVDTSTSTVYMELSSLRSEDTAV<br>YYCTRRGDYFGDFWGQGTLVTVSSASTKGPSVFPLAPSSKSTSG<br>GTAALGCLVKDYFPEPVTVSWNSGALTSGVHTFPAVLQSSGLY<br>SLSSVVTVPSSSLGTQTYICNVNHKPSNTKVDKRVEPKSCDKTH<br>TCPPCPAPEAAGGPSVFLFPPKPKDTLMISRTPEVTCVVVDVSH<br>EDPEVKFNWYVDGVEVHNAKTKPREEQYNSTYRVVSVLTVLH<br>QDWLNGKEYKCKVSNKALPAPIEKTISKAKGQPREPQVYTLPPS<br>REEMTKNQVSLWCLVKGFYPSDIAVEWESNGQPENNYKTTPP<br>VLDSDGSFFLYSKLTVDKSRWQQGNVFSCSVMHEALHNHYTQ<br>KSLSLSPG |
| SEQ ID NO: 240 | B7H6#24 chain | DIQMTQSPSSLSASVGDRVTITCKASQNVGKYVAWYQQKPGK<br>APKSLIYSASNRYDAVPSRFSGSGSGTDFTLTISSLQPEDFTTYYC<br>QQYISYPLTFGAGTKLEIKRTVAAPSVFIFPPSDEQLKSGTASVV<br>CLLNNFYPREAKVQWKVDNALQSGNSQESVTEQDSKDSTYSL<br>SSTLTLSKADYEKHKVYACEVTHQGLSSPVTKSFNRGECGGGGS<br>EGKSSGSGSESKSTEGKSSGSGSESKSTGGGGSQVQLVQSGAE<br>VKKPGASVKVSCKASGYTFTNYWMNWMRQAPGQGLEWMG<br>GIYLSGDSTDYNEKFKGRVTMTVDTSTSTVYMELSSLRSEDTAV<br>YYCTRRGDYFGDFWGQGTLVTVSSASTKGPSVFPLAPSSKSTSG<br>GTAALGCLVKDYFPEPVTVSWNSGALTSGVHTFPAVLQSSGLY<br>SLSSVVTVPSSSLGTQTYICNVNHKPSNTKVDKRVEPKSCDKTH<br>TCPPCPAPEAAGGPSVFLFPPKPKDTLMISRTPEVTCVVVDVSH<br>EDPEVKFNWYVDGVEVHNAKTKPREEQYNSTYRVVSVLTVLH<br>QDWLNGKEYKCKVSNKALPAPIEKTISKAKGQPREPQVYTLPPS<br>REEMTKNQVSLWCLVKGFYPSDIAVEWESNGQPENNYKTTPP<br>VLDSDGSFFLYSKLTVDKSRWQQGNVFSCSVMHEALHNHYTQ<br>KSLSLSPG |
| SEQ ID NO: 241 | Fc domain* (IgG1) | DKTHTCPPCPAPELLGGPSVFLFPPKPKDTLMISRTPEVTCVVV<br>DVSHEDPEVKFNWYVDGVEVHNAKTKPREEQYNSTYRVVSVL<br>TVLHQDWLNGKEYKCKVSNKALPAPIEKTISKAKGQPREPQVY<br>TLPPSREEMTKNQVSLTCLVKGFYPSDIAVEWESNGQPENNYK<br>TTPPVLDSDGSFFLYSKLTVDKSRWQQGNVFSCSVMHEALHN<br>HYTQKSLSLSPG |
| SEQ ID NO: 242 | Fc W domain (IgG1, LALA) | DKTHTCPPCPAPEAAGGPSVFLFPPKPKDTLMISRTPEVTCVVV<br>DVSHEDPEVKFNWYVDGVEVHNAKTKPREEQYNSTYRVVSVL<br>TVLHQDWLNGKEYKCKVSNKALPAPIEKTISKAKGQPREPQVY<br>TLPPSREEMTKNQVSLWCLVKGFYPSDIAVEWESNGQPENNYK<br>TTPPVLDSDGSFFLYSKLTVDKSRWQQGNVFSCSVMHEALHN<br>HYTQKSLSLSPG |
| SEQ ID NO: 243 | Fc, SAV domain (IgG1, RF/LALA) | DKTHTCPPCPAPEAAGGPSVFLFPPKPKDTLMISRTPEVTCVVV<br>DVSHEDPEVKFNWYVDGVEVHNAKTKPREEQYNSTYRVVSVL<br>TVLHQDWLNGKEYKCKVSNKALPAPIEKTISKAKGQPREPQVY<br>TLPPSREEMTKNQVSLSCAVKGFYPSDIAVEWESNGQPENNYK |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| | | TTPPVLDSDGSFFLVSKLTVDKSRWQQGNVFSCSVMHEALHN RFTQKSLSLSPG |
| SEQ ID NO: 244 | Fc domain (IgG4Pro) | ESKYGPPCPPCPAPEFLGGPSVFLFPPKPKDTLMISRTPEVTCVV VDVSQEDPEVQFNWYVDGVEVHNAKTKPREEQFNSTYRVVS VLTVLHQDWLNGKEYKCKVSNKGLPSSIEKTISKAKGQPREPQ VYTLPPSQEEMTKNQVSLTCLVKGFYPSDIAVEWESNGQPEN NYKTTPPVLDSDGSFFLYSRLTVDKSRWQEGNVFSCSVMHEAL HNHYTQKSLSLSLG |
| SEQ ID NO: 245 | Fc W domain (IgG4Pro) | ESKYGPPCPPCPAPEFLGGPSVFLFPPKPKDTLMISRTPEVTCVV VDVSQEDPEVQFNWYVDGVEVHNAKTKPREEQFNSTYRVVS VLTVLHQDWLNGKEYKCKVSNKGLPSSIEKTISKAKGQPREPQ VYTLPPSQEEMTKNQVSLWCLVKGFYPSDIAVEWESNGQPEN NYKTTPPVLDSDGSFFLYSRLTVDKSRWQEGNVFSCSVMHEAL HNHYTQKSLSLSLG |
| SEQ ID NO: 246 | Fc SAV domain (IgG4Pro, RF) | ESKYGPPCPPCPAPEFLGGPSVFLFPPKPKDTLMISRTPEVTCVV VDVSQEDPEVQFNWYVDGVEVHNAKTKPREEQFNSTYRVVS VLTVLHQDWLNGKEYKCKVSNKGLPSSIEKTISKAKGQPREPQ VYTLPPSQEEMTKNQVSLSCAVKGFYPSDIAVEWESNGQPEN NYKTTPPVLDSDGSFFLVSRLTVDKSRWQEGNVFSCSVMHEAL HNRFTQKSLSLSLG |
| SEQ ID NO: 247 | constant region of a kappa light chain | RTVAAPSVFIFPPSDEQLKSGTASVVCLLNNFYPREAKVQWKV DNALQSGNSQESVTEQDSKDSTYSLSSTLTLSKADYEKHKVYAC EVTHQGLSSPVTKSFNRGEC |
| SEQ ID NO: 248 | constant region of a lambda light chain | GQPKAAPSVTLFPPSSEELQANKATLVCLISDFYPGAVKVAWK ADGSPVNTGVETTTPSKQSNNKYAASSYLSLTPEQWKSHRSYS CQVTHEGSTVEKTVAPAECS |
| SEQ ID NO: 249 | Constant region of heavy chain CH1 | ASTKGPSVFPLAPSSKSTSGGTAALGCLVKDYFPEPVTVSWNSG ALTSGVHTFPAVLQSSGLYSLSSVVTVPSSSLGTQTYICNVNHKP SNTKVDKRVEPKSC |
| SEQ ID NO: 250 | Linker | GGGGSEGKSSGSGSESKSTEGKSSGSGSESKSTGGGGS |
| SEQ ID NO: 251 | Linker | GGGGSGGGGSGGSGGSGGGGGS |
| SEQ ID NO: 252 | Linker | GGGGSGGGGSGGGGSGGGGSGGGGGS |
| SEQ ID NO: 253 | Linker | GGGGSGGGGGGSGGGGGGSGGGGSGGGGGS |
| SEQ ID NO: 254 | Linker | GGGGSGGGGSGGGSGGGSGGGGSGGGGSGGGGGS |
| SEQ ID NO: 255 | Linker | GGGGSGGGGSGGGSGGGSGGGSGGGGSGGGGSGGGGGS |
| SEQ ID NO: 256 | Linker | GGGGSGGGGSGGGSGGGSGGGSGGGGSGGGGGSGGGSGG GGS |
| SEQ ID NO: 257 | CD3#1 LCCDR1 | RSSTGAVTTSNYAN |
| SEQ ID NO: 258 | CD3#1 LCCDR2 | GTNKRAP |
| SEQ ID NO: 259 | CD3#1 LCCDR3 | ALWYSNLWV |
| SEQ ID NO: 260 | CD3#1 HCCDR1 | GFTFNTYAMN |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 261 | CD3#1 HCCDR2 | RIRSKYNNYATYYADSVKD |
| SEQ ID NO: 262 | CD3#1 HCCDR3 | HGNFGNSYVSWFAY |
| SEQ ID NO: 263 | CD3#2 LCCDR1 | KSSQSLLNSRTRKNYLA |
| SEQ ID NO: 264 | CD3#2 LCCDR2 | WASTRES |
| SEQ ID NO: 265 | CD3#2 LCCDR3 | KQSFILRT |
| SEQ ID NO: 266 | CD3#2 HCCDR1 | GYSFTDYYVH |
| SEQ ID NO: 267 | CD3#2 HCCDR2 | WIYPGNGNIKYNERFRG |
| SEQ ID NO: 268 | CD3#2 HCCDR3 | DNYSAYYFAY |
| SEQ ID NO: 269 | CD3#3 LCCDR1 | KSSQSLLNSRTRKVYLA |
| SEQ ID NO: 270 | CD3#3 LCCDR2 | WASTRES |
| SEQ ID NO: 271 | CD3#3 LCCDR3 | KQSFILRT |
| SEQ ID NO: 272 | CD3#3 HCCDR1 | GYTFTSYYVH |
| SEQ ID NO: 273 | CD3#3 HCCDR2 | WIYPGGGNIKYAQKFQG |
| SEQ ID NO: 274 | CD3#3 HCCDR3 | DQYSAYYFAY |
| SEQ ID NO: 275 | CD3#4 LCCDR1 | KSSQSLLNSRTRKVYLA |
| SEQ ID NO: 276 | CD3#4 LCCDR2 | WASTRES |
| SEQ ID NO: 277 | CD3#4 LCCDR3 | KQSFILRT |
| SEQ ID NO: 278 | CD3#4 HCCDR1 | GYSFTSYYVH |
| SEQ ID NO: 279 | CD3#4 HCCDR2 | WIYPGGGNIKYNQKFQG |
| SEQ ID NO: 280 | CD3#4 HCCDR3 | DHYSAYYFAY |
| SEQ ID NO: 281 | CD3#5 LCCDR1 | KSSQSLLNSRTRKTYLA |
| SEQ ID NO: 282 | CD3#5 LCCDR2 | WASTRES |
| SEQ ID NO: 283 | CD3#5 LCCDR3 | KQSFILRT |
| SEQ ID NO: 284 | CD3#5 HCCDR1 | GYTFTGYYVH |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 285 | CD3#5 HCCDR2 | WIYPGGGSTKYAQKFQG |
| SEQ ID NO: 286 | CD3#5 HCCDR3 | DQYSAYYFAY |
| SEQ ID NO: 287 | CD3#6 LCCDR1 | KSSQSLLNSRTRKTYLA |
| SEQ ID NO: 288 | CD3#6 LCCDR2 | WASTRES |
| SEQ ID NO: 289 | CD3#6 LCCDR3 | KQSFILRT |
| SEQ ID NO: 290 | CD3#6 HCCDR1 | GYTFTSYYVH |
| SEQ ID NO: 291 | CD3#6 HCCDR2 | WIYPGGGNIKYAQKFQG |
| SEQ ID NO: 292 | CD3#6 HCCDR3 | DQYSAYYFAY |
| SEQ ID NO: 293 | CD3#1 VL | EAVVTQEPSLTVSPGGTVTLTCRSSTGAVTTSNYANWVQEKPG QLPRGLIGGTNKRAPWVPARFSGSLLGGKAALTLSGAQPEDEA EYFCALWYSNLWVFGGGTKLTVL |
| SEQ ID NO: 294 | CD3#1 VH | EVQLVESGGGLVQPGGSLKLSCAASGFTFNTYAMNWVRQAP GKGLEWVARIRSKYNNYATYYADSVKDRFTISRDDSKNTAYLQ MNNLKTEDTAVYYCVRHGNFGNSYVSWFAYWGQGTLVTVSA |
| SEQ ID NO: 295 | CD3#2 VL | DIVMTQSPDSLAVSLGERATINCKSSQSLLNSRTRKNYLAWYQ QKPGQPPKLLIYWASTRESGVPDRFSGSGSGTDFTLTISSLQAE DVAVYYCKQSFILRTFGQGTKLEIK |
| SEQ ID NO: 296 | CD3#2 VH | QVQLVQSGAEVKKPGASVKVSCKASGYSFTDYYVHWVRQAP GQGLEWMGWIYPGNGNIKYNERFRGRVTMTRDTSTSTVYME LSSLRSEDTAVYYCARDNYSAYYFAYWGQGTTVTVSS |
| SEQ ID NO: 297 | CD3#3 VL | DIVMTQSPDSLAVSLGERATINCKSSQSLLNSRTRKVYLAWYQ QKPGQPPKLLIYWASTRESGVPDRFSGSGSGTDFTLTISSLQAE DVAVYYCKQSFILRTFGQGTKLEIK |
| SEQ ID NO: 298 | CD3#3 VH | QVQLVQSGAEVKKPGASVKVSCKASGYTFTSYYVHWVRQAP GQGLEWIGWIYPGGGNIKYAQKFQGRVTMTRDTSTSTVYME LSSLRSEDTAVYYCARDQYSAYYFAYWGQGTTVTVSS |
| SEQ ID NO: 299 | CD3#4 VL | DIVMTQSPDSLAVSLGERATINCKSSQSLLNSRTRKVYLAWYQ QKPGQPPKLLIYWASTRESGVPDRFSGSGSGTDFTLTISSLQAE DVAVYYCKQSFILRTFGQGTKLEIK |
| SEQ ID NO: 300 | CD3#4 VH | QVQLVQSGAEVKKPGASVKVSCKASGYSFTSYYVHWVRQAP GQGLEWIGWIYPGGGNIKYNQKFQGRVTMTRDTSTSTVYME LSSLRSEDTAVYYCARDHYSAYYFAYWGQGTTVTVSS |
| SEQ ID NO: 301 | CD3#5 VL | DIVMTQSPDSLAVSLGERATISCKSSQSLLNSRTRKTYLAWYQ QKPGQPPKLLIYWASTRESGVPDRFSGSGSGTDFTLTISSLQAE DVAVYYCKQSFILRTFGQGTKLEIK |
| SEQ ID NO: 302 | CD3#5 VH | QVQLVQSGAEVKKPGASVKVSCKASGYTFTGYYVHWVRQAP GQGLEWMGWIYPGGGSTKYAQKFQGRVTMTRDTSTSTVYME LSSLRSEDTAVYYCARDQYSAYYFAYWGQGTTVTVSS |
| SEQ ID NO: 303 | CD3#6 VL | DIVMTQSPDSLAVSLGERATISCKSSQSLLNSRTRKTYLAWYQ QKPGQPPKLLIYWASTRESGVPDRFSGSGSGTDFTLTISSLQAE DVAVYYCKQSFILRTFGQGTKLEIK |
| SEQ ID NO: 304 | CD3#6 VH | QVQLVQSGAEVKKPGASVKVSCKASGYTFTSYYVHWVRQAP GQGLEWIGWIYPGGGNIKYAQKFQGRVTMTRDTSTSTVYME LSSLRSEDTAVYYCARDQYSAYYFAYWGQGTTVTVSS |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| SEQ ID NO: 305 | CD3#1 scFab | EAVVTQEPSLTVSPGGTVTLTCRSSTGAVTTSNYANWVQEKPGQLPRGLIGGTNKRAPWVPARFSGSLLGGKAALTLSGAQPEDEAEYFCALWYSNLWVFGGGTKLTVLGQPKAAPSVTLFPPSSEELQANKATLVCLISDFYPGAVKVAWKADGSPVNTGVETTTPSKQSNNKYAASSYLSLTPEQWKSHRSYSCQVTHEGSTVEKTVAPAECSGGGGSEGKSSGSGSESKSTEGKSSGSGSESKSTGGGGSEVQLVESGGGLVQPGGSLKLSCAASGFTFNTYAMNWVRQAPGKGLEWVARIRSKYNNYATYYADSVKDRFTISRDDSKNTAYLQMNNLKTEDTAVYYCVRHGNFGNSYVSWFAYWGQGTLVTVSAASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSC |
| SEQ ID NO: 306 | CD3#2 scFab | DIVMTQSPDSLAVSLGERATINCKSSQSLLNSRTRKNYLAWYQQKPGQPPKLLIYWASTRESGVPDRFSGSGSGTDFTLTISSLQAEDVAVYYCKQSFILRTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSEGKSSGSGSESKSTEGKSSGSGSESKSTGGGGSQVQLVQSGAEVKKPGASVKVSCKASGYSFTDYYVHWVRQAPGQGLEWMGWIYPGNGNIKYNERFRGRVTMTRDTSTSTVYMELSSLRSEDTAVYYCARDNYSAYYFAYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSC |
| SEQ ID NO: 307 | CD3#3 scFab | DIVMTQSPDSLAVSLGERATINCKSSQSLLNSRTRKVYLAWYQQKPGQPPKLLIYWASTRESGVPDRFSGSGSGTDFTLTISSLQAEDVAVYYCKQSFILRTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSEGKSSGSGSESKSTEGKSSGSGSESKSTGGGGSQVQLVQSGAEVKKPGASVKVSCKASGYTFTSYYVHWVRQAPGQGLEWIGWIYPGGGNIKYAQKFQGRVTMTRDTSTSTVYMELSSLRSEDTAVYYCARDQYSAYYFAYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSC |
| SEQ ID NO: 308 | CD3#4 scFab | DIVMTQSPDSLAVSLGERATINCKSSQSLLNSRTRKVYLAWYQQKPGQPPKLLIYWASTRESGVPDRFSGSGSGTDFTLTISSLQAEDVAVYYCKQSFILRTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSEGKSSGSGSESKSTEGKSSGSGSESKSTGGGGSQVQLVQSGAEVKKPGASVKVSCKASGYSFTSYYVHWVRQAPGQGLEWIGWIYPGGGNIKYNQKFQGRVTMTRDTSTSTVYMELSSLRSEDTAVYYCARDHYSAYYFAYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSC |
| SEQ ID NO: 309 | CD3#5 scFab | DIVMTQSPDSLAVSLGERATISCKSSQSLLNSRTRKTYLAWYQQKPGQPPKLLIYWASTRESGVPDRFSGSGSGTDFTLTISSLQAEDVAVYYCKQSFILRTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSEGKSSGSGSESKSTEGKSSGSGSESKSTGGGGSQVQLVQSGAEVKKPGASVKVSCKASGYTFTGYYVHWVRQAPGQGLEWMGWIYPGGGSTKYAQKFQGRVTMTRDTSTSTVYMELSSLRSEDTAVYYCARDQYSAYYFAYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSC |
| SEQ ID NO: 310 | CD3#6 scFab | DIVMTQSPDSLAVSLGERATISCKSSQSLLNSRTRKTYLAWYQQKPGQPPKLLIYWASTRESGVPDRFSGSGSGTDFTLTISSLQAEDVAVYYCKQSFILRTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSEGKSSGSGSESKSTEGKSSGSGSESKSTGGGGSQVQLVQSGAEVKKPGASVKVSCKASGYTFTSYYVHWVRQAPGQGLE |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
|---|---|---|
| | | WIGWIYPGGGNIKYAQKFQGRVTMTRDTSTSTVYMELSSLRS EDTAVYYCARDQYSAYYFAYWGQGTTVTVSSASTKGPSVFPLA PSSKSTSGGTAALGCLVKDYFPEPVTVSWNSGALTSGVHTFPA VLQSSGLYSLSSVVTVPSSSLGTQTYICNVNHKPSNTKVDKRVE PKSC |
| SEQ ID NO: 311 | CD3#1 chain | EAVVTQEPSLTVSPGGTVTLTCRSSTGAVTTSNYANWVQEKPG QLPRGLIGGTNKRAPWVPARFSGSLLGGKAALTLSGAQPEDEA EYFCALWYSNLWVFGGGTKLTVLGQPKAAPSVTLFPPSSEELQ ANKATLVCLISDFYPGAVKVAWKADGSPVNTGVETTTPSKQSN NKYAASSYLSLTPEQWKSHRSYSCQVTHEGSTVEKTVAPAECS GGGGSEGKSSGSGSESKSTEGKSSGSGSESKSTGGGGSEVQLV ESGGGLVQPGGSLKLSCAASGFTFNTYAMNWVRQAPGKGLE WVARIRSKYNNYATYYADSVKDRFTISRDDSKNTAYLQMNNLK TEDTAVYYCVRHGNFGNSYVSWFAYWGQGTLVTVSAASTKG PSVFPLAPSSKSTSGGTAALGCLVKDYFPEPVTVSWNSGALTSG VHTFPAVLQSSGLYSLSSVVTVPSSSLGTQTYICNVNHKPSNTK VDKRVEPKSCDKTHTCPPCPAPEAAGGPSVFLFPPKPKDTLMIS RTPEVTCVVVDVSHEDPEVKFNWYVDGVEVHNAKTKPREEQY NSTYRVVSVLTVLHQDWLNGKEYKCKVSNKALPAPIEKTISKAK GQPREPQVYTLPPSREEMTKNQVSLSCAVKGFYPSDIAVEWES NGQPENNYKTTPPVLDSDGSFFLVSKLTVDKSRWQQGNVFSC SVMHEALHNRFTQKSLSLSPG |
| SEQ ID NO: 312 | CD3#2 chain | DIVMTQSPDSLAVSLGERATINCKSSQSLLNSRTRKNYLAWYQ QKPGQPPKLLIYWASTRESGVPDRFSGSGSGTDFTLTISSLQAE DVAVYYCKQSFILRTFGQGTKLEIKRTVAAPSVFIFPPSDEQLKS GTASVVCLLNNFYPREAKVQWKVDNALQSGNSQESVTEQDSK DSTYSLSSTLTLSKADYEKHKVYACEVTHQGLSSPVTKSFNRGEC GGGGSEGKSSGSGSESKSTEGKSSGSGSESKSTGGGGSQVQLV QSGAEVKKPGASVKVSCKASGYSFTDYYVHWVRQAPGQGLE WMGWIYPGNGNIKYNERFRGRVTMTRDTSTSTVYMELSSLRS EDTAVYYCARDNYSAYYFAYWGQGTTVTVSSASTKGPSVFPLA PSSKSTSGGTAALGCLVKDYFPEPVTVSWNSGALTSGVHTFPA VLQSSGLYSLSSVVTVPSSSLGTQTYICNVNHKPSNTKVDKRVE PKSCDKTHTCPPCPAPEAAGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQPRE PQVYTLPPSREEMTKNQVSLSCAVKGFYPSDIAVEWESNGQPE NNYKTTPPVLDSDGSFFLVSKLTVDKSRWQQGNVFSCSVMHE ALHNRFTQKSLSLSPG |
| SEQ ID NO: 313 | CD3#3 chain | DIVMTQSPDSLAVSLGERATINCKSSQSLLNSRTRKVYLAWYQ QKPGQPPKLLIYWASTRESGVPDRFSGSGSGTDFTLTISSLQAE DVAVYYCKQSFILRTFGQGTKLEIKRTVAAPSVFIFPPSDEQLKS GTASVVCLLNNFYPREAKVQWKVDNALQSGNSQESVTEQDSK DSTYSLSSTLTLSKADYEKHKVYACEVTHQGLSSPVTKSFNRGEC GGGGSEGKSSGSGSESKSTEGKSSGSGSESKSTGGGGSQVQLV QSGAEVKKPGASVKVSCKASGYTFTSYYVHWVRQAPGQGLE WIGWIYPGGGNIKYAQKFQGRVTMTRDTSTSTVYMELSSLRS EDTAVYYCARDQYSAYYFAYWGQGTTVTVSSASTKGPSVFPLA PSSKSTSGGTAALGCLVKDYFPEPVTVSWNSGALTSGVHTFPA VLQSSGLYSLSSVVTVPSSSLGTQTYICNVNHKPSNTKVDKRVE PKSCDKTHTCPPCPAPEAAGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQPRE PQVYTLPPSREEMTKNQVSLSCAVKGFYPSDIAVEWESNGQPE NNYKTTPPVLDSDGSFFLVSKLTVDKSRWQQGNVFSCSVMHE ALHNRFTQKSLSLSPG |
| SEQ ID NO: 314 | CD3#4 chain | DIVMTQSPDSLAVSLGERATINCKSSQSLLNSRTRKVYLAWYQ QKPGQPPKLLIYWASTRESGVPDRFSGSGSGTDFTLTISSLQAE DVAVYYCKQSFILRTFGQGTKLEIKRTVAAPSVFIFPPSDEQLKS GTASVVCLLNNFYPREAKVQWKVDNALQSGNSQESVTEQDSK DSTYSLSSTLTLSKADYEKHKVYACEVTHQGLSSPVTKSFNRGEC GGGGSEGKSSGSGSESKSTEGKSSGSGSESKSTGGGGSQVQLV QSGAEVKKPGASVKVSCKASGYSFTSYYVHWVRQAPGQGLE WIGWIYPGGGNIKYNQKFQGRVTMTRDTSTSTVYMELSSLRS EDTAVYYCARDHYSAYYFAYWGQGTTVTVSSASTKGPSVFPLA PSSKSTSGGTAALGCLVKDYFPEPVTVSWNSGALTSGVHTFPA VLQSSGLYSLSSVVTVPSSSLGTQTYICNVNHKPSNTKVDKRVE PKSCDKTHTCPPCPAPEAAGGPSVFLFPPKPKDTLMISRTPEVT |

TABLE 1-continued

Amino acid sequences and SEQ ID NOs of CDRs, VH, VL, scFabs, B7H6-arm and CD3-arm sequences of the proteins/antibody constructs described herein:

| SEQ ID Number | Brief description of sequence | Sequence |
| --- | --- | --- |
| | | CVVVDVSHEDPEVKFNWYVDGVEVHNAKTKPREEQYNSTYR VVSVLTVLHQDWLNGKEYKCKVSNKALPAPIEKTISKAKGQPRE PQVYTLPPSREEMTKNQVSLSCAVKGFYPSDIAVEWESNGQPE NNYKTTPPVLDSDGSFFLVSKLTVDKSRWQQGNVFSCSVMHE ALHNRFTQKSLSLSPG |
| SEQ ID NO: 315 | CD3#5 chain | DIVMTQSPDSLAVSLGERATISCKSSQSLLNSRTRKTYLAWYQ QKPGQPPKLLIYWASTRESGVPDRFSGSGSGTDFTLTISSLQAE DVAVYYCKQSFILRTFGQGTKLEIKRTVAAPSVFIFPPSDEQLKS GTASVVCLLNNFYPREAKVQWKVDNALQSGNSQESVTEQDSK DSTYSLSSTLTLSKADYEKHKVYACEVTHQGLSSPVTKSFNRGEC GGGGSEGKSSGSGSESKSTEGKSSGSGSESKSTGGGGSQVQLV QSGAEVKKPGASVKVSCKASGYTFTGYYVHWVRQAPGQGLE WMGWIYPGGGSTKYAQKFQGRVTMTRDTSTSTVYMELSSLRS EDTAVYYCARDQYSAYYFAYWGQGTTVTVSSASTKGPSVFPLA PSSKSTSGGTAALGCLVKDYFPEPVTVSWNSGALTSGVHTFPA VLQSSGLYSLSSVVTVPSSSLGTQTYICNVNHKPSNTKVDKRVE PKSCDKTHTCPPCPAPEAAGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQPRE PQVYTLPPSREEMTKNQVSLSCAVKGFYPSDIAVEWESNGQPE NNYKTTPPVLDSDGSFFLVSKLTVDKSRWQQGNVFSCSVMHE ALHNRFTQKSLSLSPG |
| SEQ ID NO: 316 | CD3#6 chain | DIVMTQSPDSLAVSLGERATISCKSSQSLLNSRTRKTYLAWYQ QKPGQPPKLLIYWASTRESGVPDRFSGSGSGTDFTLTISSLQAE DVAVYYCKQSFILRTFGQGTKLEIKRTVAAPSVFIFPPSDEQLKS GTASVVCLLNNFYPREAKVQWKVDNALQSGNSQESVTEQDSK DSTYSLSSTLTLSKADYEKHKVYACEVTHQGLSSPVTKSFNRGEC GGGGSEGKSSGSGSESKSTEGKSSGSGSESKSTGGGGSQVQLV QSGAEVKKPGASVKVSCKASGYTFTSYYVHWVRQAPGQGLE WIGWIYPGGGNIKYAQKFQGRVTMTRDTSTSTVYMELSSLRS EDTAVYYCARDQYSAYYFAYWGQGTTVTVSSASTKGPSVFPLA PSSKSTSGGTAALGCLVKDYFPEPVTVSWNSGALTSGVHTFPA VLQSSGLYSLSSVVTVPSSSLGTQTYICNVNHKPSNTKVDKRVE PKSCDKTHTCPPCPAPEAAGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQPRE PQVYTLPPSREEMTKNQVSLSCAVKGFYPSDIAVEWESNGQPE NNYKTTPPVLDSDGSFFLVSKLTVDKSRWQQGNVFSCSVMHE ALHNRFTQKSLSLSPG |

Example 3: Generation of Recombinant Proteins

Human B7H6-His

The full extracellular domain of Human-B7H6 was expressed with a His6-tag (SEQ ID NO: 350) using a pTT vector (encoding human B7H6-His, SEQ ID NO: 317) by transient transfection using the Lenti-X™ Lentiviral System (Clontech). HEK 293F cells (Thermo Fisher) were used at 1.6×106 cells/ml at time of transfection, in Gibco™ Freestyle™ F17 expression medium (Thermo Fisher Scientific). The DNA:PEI complex at 1:3 ratio and 1 mg/L of DNA was pre-incubated for 5 minutes, filtered, and pre-incubated at room temperature for another 15 minutes before adding to the cells. The cells were incubated at 37° C., 5% CO2, and shaking at 140 rpm. Tryptone N1 was added to the cells 24 hours after transfection to a final concentration of 0.5%. The cells were fed again 48 hours after transfection with 2 mM glutamine and 2 g/L glucose. At the same time the temperature was lowered to 33° C. The final fed was added 120 hours after transfection with 2 mM glutamine and 1 g/L glucose. The cells were harvested 144 hours after transfection by centrifuging at 6000 rpm for 15 minutes. The supernatant was clarified using a G4 filter. Protein purification was performed in two steps. First, a Ni-NTA column was used for affinity chromatography with Wash Buffer 1×PBS, pH 7.2+10 mM Imidazole for 10 CV, then Wash Buffer 1×PBS, pH 7.2+20 mM Imidazole for 10 CV, and elution gradient 4-60% of 1×PBS, pH 7.2 supplemented with 0.5M Imidazole. Fractions were collected and analyzed by SDS-PAGE prior to pooling, and concentrating. Second, a Superdex® 200, 16/600, 120 ml column was used for Gel Filtration chromatography (GE Healthcare Life Sciences). The concentrated pool after affinity chromatography, 5 ml, was loaded on the column with flow rate of 0.5 ml/min. The formulation buffer was 20 mM HEPES, 100 mM NaCl, 5% sucrose, pH 7.4. Fractions were collected and analyzed by SDS-PAGE prior to pooling, and then sterilized using a 0.2 um filter.

Cyno B7H6-His

The full extracellular domain of Cyno-B7H6 was expressed with a His6-tag (SEQ ID NO: 350) using a pTT vector (encoding cyno B7H6-His, SEQ ID NO: 320) by transient transfection using the Lenti-X™ Lentiviral System (Clontech). HEK 293F cells (Thermo Fisher) were used at 1.6×106 cells/ml at time of transfection, in Gibco™ Freestyle™ F17 expression medium (Thermo Fisher Scientific).

The DNA:PEI complex at 1:3 ratio and 1 mg/L of DNA was pre-incubated for 5 minutes, filtered, and pre-incubated at room temperature for another 15 minutes before adding to the cells. The cells were incubated at 37° C., 5% CO2, and shaking at 140 rpm. Tryptone N1 was added to the cells 24 hours after transfection to a final concentration of 0.5%. The cells were fed again 48 hours after transfection with 2 mM glutamine and 2 g/L glucose. At the same time the temperature was lowered to 33° C. The final fed was added 120 hours after transfection with 2 mM glutamine and 1 g/L glucose. The cells were harvested 144 hours after transfection by centrifuging at 6000 rpm for 15 minutes. The supernatant was clarified using a G4 filter. Protein purification was performed in two steps. First, a Ni-NTA column was used for affinity chromatography with Wash Buffer 1×PBS, 0.2 M sucrose, 0.01% CHAPS, 5% glycerol, pH 7.2, +10 mM Imidazole for 10 CV, then Wash Buffer 1×PBS, pH 7.2+20 mM Imidazole for 10 CV, and elution gradient 4-60% of 1×PBS, 0.2 M sucrose, 0.01% CHAPS, 5% glycerol, pH 7.2 supplemented with 0.5M Imidazole. Fractions were collected and analyzed by SDS-PAGE prior to pooling, and concentrating. Second, a Superdex® 200, 16/600, was used for Gel Filtration chromatography (GE Healthcare Life Sciences). The concentrated pool after affinity chromatography, 10 ml, was loaded on the column with flow rate of 1.0 ml/min. The formulation buffer was 1×PBS, 0.2M sucrose, 0.01% CHAPS, 5% glycerol, pH 7.2. Fractions were collected and analyzed by SDS-PAGE prior to pooling, and then sterilized using a 0.2 um filter.

Human CD3 E+G HuFc-6×His ("6×His" disclosed as SEQ ID NO: 350) (E+G indicates εγ subunits)

A cell line to produce Human CD3 E+G HuFc-6×His ("6×His" disclosed as SEQ ID NO: 350) was generated using HEK-293 cells (Thermo Fisher), the Lenti-X™ Lentiviral System (Clontech), and plasmid encoding Human CD3 E+G HuFc-6×His ("6×His" disclosed as SEQ ID NO: 350) (human CD3E Accession No: P07766; human CD3E+G-HuFc-His: SEQ ID NO:322). For expression, cells were cultured and expanded in Freestyle™ 293 media (Thermo Fisher Scientific), at 37 C, humidified 8% CO2 environment, and shaking at 135 rpm. The conditioned culture supernatant was harvested at Day 6 by centrifugation for 30 minutes at 9300×g. Expression was monitored by SDS-PAGE and Western Blotting. The conditioned culture supernatant was adjusted with 0.2M Sucrose, 5% glycerol, 0.01% CHAPS, and 10 mM Imidazole. The pH was then adjusted to 7.2. Purification was carried out in a two-step process: affinity purification using Ni/NTA resin (overnight incubation at 4 C, and elution with 250 mM Imidazole); followed by size-exclusion chromatography on a Superdex® 200 column (GE Healthcare Life Sciences) in destination buffer PBS with 0.2M Sucrose, 5% glycerol, 0.01% CHAPS, 1 mM TCEP, pH7.2. The pooled material was concentrated using a 10K MWCO PES membrane Vivacell® 100 centrifugation device prior to final analysis and storage. The purified material was qualified by mass spectrometry and analytical ultra-centrifugation.

Cyno CD3 E+G HuFc-6×his ("6×His" Disclosed as SEQ ID NO: 350) (E+G Indicates εγ Subunits)

A cell line to produce Cyno CD3 E+G HuFc-6×His ("6×His" disclosed as SEQ ID NO: 350) was generated using HEK-293 cells (Thermo Fisher), the Lenti-X™ Lentiviral System (Clontech), and plasmid encoding Cyno CD3 E+G HuFc-6×His ("6×His" disclosed as SEQ ID NO: 350) (Cynomolgus CD3E Accession No: Q95LI5<, cyno CD3 E+G huFc-His: SEQ ID NO:323). For expression, cells were cultured and expanded in Freestyle™ 293 media (Thermo Fisher Scientific), at 37 C, humidified 8% CO2 environment, and shaking at 135 rpm. The conditioned culture supernatant was harvested at Day 6 by centrifugation for 30 minutes at 9300×g. Expression was monitored by SDS-PAGE and Western Blotting. The conditioned culture supernatant was adjusted with 0.2M Sucrose, 5% glycerol, 0.01% CHAPS, and 10 mM Imidazole. The pH was then adjusted to 7.2. Purification was carried out in a two-step process: affinity purification using Ni/NTA resin (overnight incubation at 4 C, and elution with 250 mM Imidazole); followed by size-exclusion chromatography on a Superdex® 200 column (GE Healthcare Life Sciences) in destination buffer PBS with 0.2M Sucrose, 5% glycerol, 0.01% CHAPS, 1 mM TCEP, pH7.2. The pooled material was concentrated using a 10K MWCO PES membrane Vivacell® 100 centrifugation device prior to final analysis and storage. The purified material was qualified by mass spectrometry and analytical ultra-centrifugation.

Fc-His-Tagged Human B7H6 ECD

In this construct, the huB7H6 ECD is followed by a GS linker, then by huIgG1-Fc domain and a C-terminal His6 tag (SEQ ID NO: 350) (SEQ ID NO:318). The construct was expressed by transient transfection using HEK293-6E cells, with DNA:PEI ratio of 1:3 and 1 mg DNA per L culture. The PEI reagent was linear PEI MAX [Mw 40,000] (Polysciences: Cat #24765-2). Transfected cells were incubated at 37° C. with 5% $CO_2$ and 130 rpm. 24-hr post transfection tryptone N1 (Organotechnie; Cat #19553) and glucose were added to a final concentration of 0.5% and 1 g/L respectively. Cells were harvested after 5 days. After centrifugation, the supernatant was filtered through 0.2 μm membrane filter. The huB7H6-ECD-Fc-His protein was purified in a two-step purification: first by affinity on Ni NTA Agarose matrix, and second by gel filtration using Superdex® 200, 26/600 column (GE Healthcare Life Sciences). The pooled fractions were filtered and stored in 1×PBS, 0.2 M sucrose, 5% glycerol, 0.01% CHAPS, pH-7.2 formulation buffer.

Fc-His-Tagged Human Ala-Mutated B7H6 ECD (NKp30 Interaction Sites aa35-38 and aa102-105 Substituted by Ala).

This construct (SEQ ID NO:319) has huB7H6 with Ala substitutions at positions 35-38 and 102-105, so it does not bind NKp30. The huB7H6-Ala-ECD is followed by a GS linker, then by huIgG1Fc domain and a C-terminal His6 tag (SEQ ID NO: 350). This construct was expressed in HEK293-6E cells by transient transfection, purified in a two-step purification process, and stored as described above for the Fc-His-tagged huB7H6-ECD construct.

Human B7H1-Fc

This construct (SEQ ID NO:324) contains huB7H1 with a cMyc tag, a Thrombin cleavage site and a huFc domain. The construct was expressed by transient transfection using HEK293f cells, DNA:PEI ratio of 1:1.5, and 1 mg of DNA per L culture. The flasks were incubated at 37° C. in a humidified 8% CO2 environment with shaking at 135 rpm. The cells were harvested after 3 days. After centrifugation of the cells, the protein was purified from the supernatant. First, affinity purification was performed using nProtein A Sepharose® 4 Fast Flow medium (GE Healthcare, #17-5280-03), and the eluate was dialyzed in 20 mM Tris, 100 mM NaCl, 10% glycerol, 1 mM TCEP, 3 mM $CaCl_2$, pH 8.0. Second, the sample was incubated with Thrombin CleanCleave™ resin (1 mL, Sigma). Third, the pool from the previous step was bound again to nProtein A Sepharose® 4 Fast Flow medium. The non-bound material was saved, further polished by gel filtration on Superdex® 75 (GE Healthcare) column equilibrated in PBS, 1 mM TCEP, pH 7.2 buffer, and concentrated.

Example 4: SPR Based Determination of Affinities to Recombinant B7H6 and CD3 εγ Subunits and Interspecies Cross-Reactivity To determine the affinity of human and cyno B7H6 and human B7H1 to B7H6/CD3 binding proteins, the experiment was performed on a Biacore™ 8K instrument (GE Healthcare Life Sciences). Briefly, the B7H6/CD3 binding protein was captured via Protein A/G. The running buffer for this experiment and all serial dilutions were prepared in HBS-EP+. The CM5 sensor chip was activated with an equal mixture of EDC/NHS across both flow cells for 420 s at a flow rate of 10 μL/min and immobilized with recombinant Protein A/G (50 μg/ml in 10 mM NaOAc, pH 4.5) across all flow cells for 420 s at a flow rate of 10 μL/min resulting in about 2500 RU of Protein A/G on the surface. The sensor chip was deactivated with 1M ethanolamine-HCl across all flow cells for 420 s at a flow rate of 10 μL/min.

About 700 RU of the B7H6/CD3 binding protein was captured on flow cell 2 of the Protein A/G surface for 60 s at a flow rate of 10 μL/min. The analytes HuB7H6, CyB7H6 and HuB7H1 were injected across both flow cells over captured B7H6/CD3 binding protein for 300 s at a flow rate of 30 μL/min with a dissociation of 1200 s. The concentrations of HuB7H6 and CyB7H6 were 0 nM, 6.25 nM, 12.5 nM, 25 nM, 50 nM and 100 nM. The concentrations of HuB7H1 were 0 nM and 1 μM. The surface was regenerated by injecting 10 mM glycine-HCl, pH 1.5 for 20 s at a flow rate of 30 μL/min across both flow cells.

The reference flow cell 1 (interactions with sensor surface) and blank (HBS-EP+ or 0 nM analyte) were subtracted from the raw data. Using the Biacore™ 8K Evaluation Software, sensorgrams were fit globally to 1:1 Langmuir binding to provide association rate constant (ka), dissociation rate constant (kd), and equilibrium dissociation constant (KD) values.

To determine the affinity of the B7H6/CD3 binding protein to human and cyno CD3E+G-hFc, the experiment was performed on a Bio-Rad ProteOn™ XPR36 instrument. Briefly, HuCD3E+G-hFc and CyCD3E+G were amine-coupled on a ProteOn™ GLM sensor chip (Bio-Rad) and the B7H6/CD3 binding protein was flowed over the immobilized surface. The running buffer for this experiment and all serial dilutions were prepared in HBS-EP+. The GLM sensor chip was normalized according to Bio-Rad's recommendations. The sensor chip was activated with an equal mixture of EDC/s-NHS in the horizontal direction for 300 s at a flow rate of 30 μL/min HuCD3E+G-hFc was immobilized in the vertical direction at 0.4 μg/mL, 0.2 μg/mL and 0.1 μg/mL in 10 mM acetate pH 4.5 to L1, L2 and L3, respectively, for 300 s at a flow rate of 30 μL/min resulting in about 100 RU of HuCD3E+G-hFc on L1, 40 RU of HuCD3E+G-hFc on L2 and 0 RU of HuCD3E+G-hFc on L3. CyCD3E+G-hFc was immobilized in the vertical direction at 0.4 μg/mL, 0.2 μg/mL and 0.1 μg/mL in 10 mM acetate pH 4.5 to L4, L5 and L6, respectively, for 300 s at a flow rate of 30 μL/min resulting in about 385 RU of HuCD3E+G-hFc on L4, 170 RU of CyCD3E+G-hFc on L5 and 50 RU of CyCD3E+G-hFc on L6. The sensor chip was deactivated with 1M ethanolamine-HCl in the horizontal direction for 300 s at a flow rate of 30 μL/min. The sensor chip was regenerated with 18 s of 0.85% phosphoric acid at a flow rate of 100 μL/min 2 times horizontally and 2 times vertically.

The B7H6/CD3 binding protein analyte was injected horizontally over the immobilized surface for 300 s at a flow rate of 30 μL/min with a dissociation of 600 s. The concentrations of the B7H6/CD3 binding protein used were 0 nM, 1.2 nM, 3.7 nM, 11.1 nM, 33.3 nM and 100 nM. The surface was regenerated by injecting 0.85% phosphoric acid for 18 s at a flow rate of 100 μL/min 2 times horizontally.

The interspot (interactions with sensor surface) and blank (HBS-EP+ or 0 nM analyte) were subtracted from the raw data. Using the Bio-Rad ProteOn™ Manager software, sensorgrams were fit globally to 1:1 Langmuir binding to provide association rate constant (ka), dissociation rate constant (kd), and equilibrium dissociation constant (KD) values.

Affinities determined as described above are shown for exemplary B7H6/CD3 binding proteins (B7H6/CD3 binding proteins comprising a B7H6 chain of SEQ ID NO: 228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and a CD3 chain of SEQ ID NO:311, and B7H6 binding proteins comprising a B7H6 chain of SEQ ID NO:230 or SEQ ID NO:239 and a CD3 chain of SEQ ID NO:312, SEQ ID NO:313, SEQ ID NO:314, SEQ ID NO:315, or SEQ ID NO:316, respectively) in Table 2.

TABLE 2

Affinities (KD) of B7H6/CD3 binding proteins to humanB7H6, cynoB7H6, humanCD3 εγ subunit, cynoCD3 εγ subunit, and humanB7H1, as determined by SPR analysis. No detectable binding is denoted by 'nb'.

| B7H6 binder | CD3 binder | huB7-H6 [nM] | cyB7-H6 [nM] | cy/hu B7-H6 | huCD3 [nM] | cyCD3 [nM] | cy/hu CD3 | huB7-H1 |
|---|---|---|---|---|---|---|---|---|
| B7H6#12 | CD3#1 | 1.1 | 2.3 | 2.1 | 3.6 | 2.5 | 0.7 | nb at 1 μM |
| B7H6#13 | CD3#1 | 3.0 | 4.6 | 1.5 | 4.1 | 2.8 | 0.7 | nb at 1 μM |
| B7H6#14 | CD3#1 | 0.1 | 0.6 | 5.9 | 4.2 | 2.7 | 0.6 | nb at 1 μM |
| B7H6#15 | CD3#1 | 0.8 | 2.2 | 2.8 | 3.8 | 2.6 | 0.7 | nb at 1 μM |
| B7H6#16 | CD3#1 | 3.1 | 7.2 | 2.3 | 3.7 | 2.6 | 0.7 | nb at 1 μM |
| B7H6#17 | CD3#1 | 8.7 | 8.4 | 1.0 | 13.5 | 3.7 | 0.3 | nb at 1 μM |
| B7H6#18 | CD3#1 | 1.4 | 3.3 | 2.3 | 3.9 | 2.8 | 0.7 | nb at 1 μM |
| B7H6#19 | CD3#1 | 1.6 | 5.1 | 3.1 | 4.0 | 2.4 | 0.6 | nb at 1 μM |
| B7H6#20 | CD3#1 | 1.1 | 4.9 | 4.6 | 4.0 | 2.6 | 0.7 | nb at 1 μM |

TABLE 2-continued

Affinities (KD) of B7H6/CD3 binding proteins to humanB7H6, cynoB7H6, humanCD3 εγ subunit, cynoCD3 εγ subunit, and humanB7H1, as determined by SPR analysis. No detectable binding is denoted by 'nb'.

| B7H6 binder | CD3 binder | huB7-H6 [nM] | cyB7-H6 [nM] | cy/hu B7-H6 | huCD3 [nM] | cyCD3 [nM] | cy/hu CD3 | huB7-H1 |
|---|---|---|---|---|---|---|---|---|
| B7H6#21 | CD3#1 | 3.3 | 1.4 | 0.4 | 4.4 | 2.7 | 0.6 | nb at 1 μM |
| B7H6#22 | CD3#1 | 1.5 | 1.4 | 1.0 | 5.1 | 2.8 | 0.5 | nb at 1 μM |
| B7H6#23 | CD3#1 | 1.3 | 1.2 | 0.9 | 5.5 | 2.7 | 0.5 | nb at 1 μM |
| B7H6#24 | CD3#1 | 1.8 | 3.1 | 1.7 | 7.8 | 3.3 | 0.4 | nb at 1 μM |
| B7H6#14 | CD3#2 | 1.2 | 1.0 | 0.9 | 16.9 | 17.7 | 1.0 | nb at 1 μM |
| B7H6#14 | CD3#3 | 1.1 | 1.1 | 0.9 | 4.8 | 7.1 | 1.5 | nb at 1 μM |
| B7H6#14 | CD3#4 | 1.3 | 1.1 | 0.8 | 7.6 | 8.5 | 1.1 | nb at 1 μM |
| B7H6#14 | CD3#5 | 0.9 | 1.0 | 1.1 | 4.3 | 5.2 | 1.2 | nb at 1 μM |
| B7H6#14 | CD3#6 | 0.4 | 0.9 | 2.1 | 4.1 | 5.7 | 1.4 | nb at 1 μM |
| B7H6#23 | CD3#2 | 1.9 | 2.0 | 1.1 | 10.4 | 10.0 | 1.0 | nb at 1 μM |
| B7H6#23 | CD3#3 | 2.2 | 1.9 | 0.9 | 13.8 | 11.9 | 0.9 | nb at 1 μM |
| B7H6#23 | CD3#4 | 1.7 | 1.7 | 1.0 | 3.8 | 3.6 | 0.9 | nb at 1 μM |
| B7H6#23 | CD3#5 | 2.2 | 1.9 | 0.9 | 2.8 | 3.7 | 1.3 | nb at 1 μM |
| B7H6#23 | CD3#6 | 1.9 | 2.0 | 1.1 | 3.4 | 3.9 | 1.2 | nb at 1 μM |

nb: no binding

Figure 2:
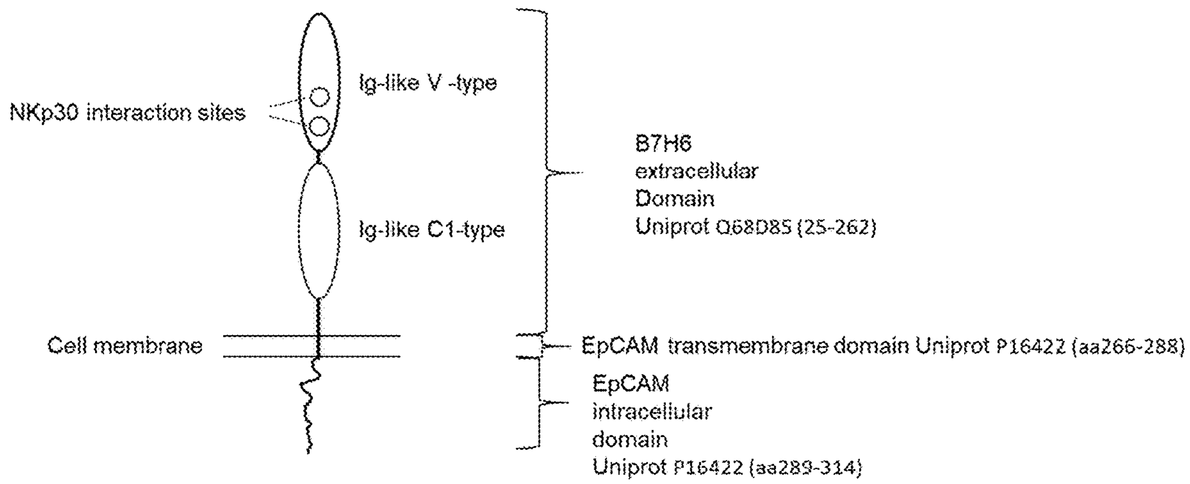
FIG. 2: Schematic representation of the extracellular B7H6 protein expressed on the cell surface of CHO-K1 cells.

Example 5: Generation of Recombinant CHO-K1 Cell Lines Expressing Cynomolgus Monkey B7H6 Extracellular Domain on the Cell Surface For generation of stable CHO-K1 cells expressing the extracellular domain of cynomolgus monkey B7H6 (NCBI: XP_005578557) on the cell surface, the respective coding sequence (aa 25 to 262 of XP_005578557.1) was cloned into pcDNA3.1 (Thermo Fisher Scientific). The construct contains an N-terminal mouse IgG Vk-leading sequence, followed by a 6-His-myc-tag ("6-His" disclosed as SEQ ID NO: 350) and the cynomolgus monkey B7H6 extracellular domain (aa25-262 of NCBI XP_005578557.1). To ensure cell surface localization of the B7H6 extracellular domain, the construct was followed by a linker, and the transmembrane and intracellular domains of EpCAM (Uniprot P16422). The expression of the B7H6 domain on the cell surface was verified by flow cytometry using a mouse monoclonal anti-myc antibody (AbD Serotec). The used sequences are listed in Table 3, a schematic representation of the constructs is shown in FIG. 2.

TABLE 3

Amino acid sequences of B7H6 subdomains expressed on CHO-K1 cells

| Name | Sequence |
|---|---|
| Vk leader | METDTLLLWVLLLWVP<br>GSTGD<br>(SEQ ID NO: 325) |
| 6-His-myc tag | HHHHHHEQKLISEEDL<br>(SEQ ID NO: 326) |
| Cynomolgus B7-H6 extracellular domain (NCBI XP_005578557.1, aa25-262) | DLKVEMMARGIQATRL<br>NDSVTISCKVIYSQPL<br>NITSMGITWFRKSLTL<br>DKEVKVFEFFGDHQKA<br>FRPGANVSLWRLKSGD<br>ASLKLPGVQLEEAGEY<br>RCEVVVTPLKAQGTVQ<br>LKVVASPTSRLFQDQA<br>VVKENEGKYMCESSRF<br>YPKDINITWEKWTQKS<br>PHHVVISENVITGPTI<br>KNMDGTFNITSYLKLN<br>SSQEDPGTVYRCVIRH<br>ESLHTPVSIDFILTAP<br>QQSLSEPEKTDIFS<br>(SEQ ID NO: 327) |
| Linker | SGGGGS<br>(SEQ ID NO: 328) |
| Human EpCAM transmembrane domain (Uniprot P16422, aa266-288) | AGVIAVIVVVVIAVVA<br>GIVVLVI<br>(SEQ ID NO: 329) |
| Human EpCAM intracellular domain (Uniprot P16422, aa289-314) | SRKKRMAKYEKAEIKE<br>MGEMHRELNA<br>(SEQ ID NO: 330) |

Figure 3:
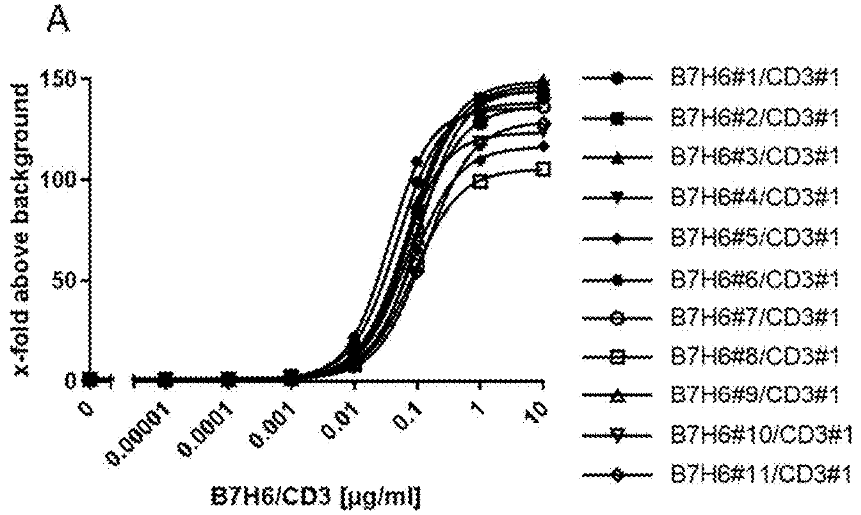
FIG. 3: Binding of 34 exemplary B7H6/CD3 binding proteins to recombinant human B7H6 extracellular protein.
Figure 3:
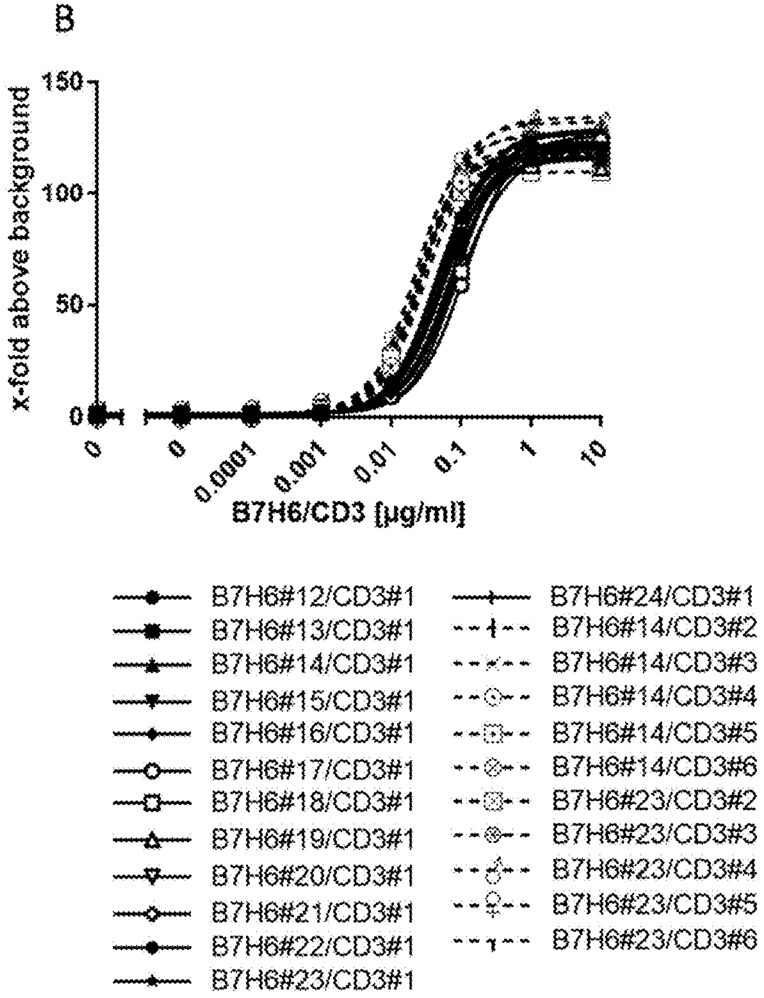

Example 6: Binding of Exemplary B7H6 Binding Proteins to Recombinant Human B7H6 Extracellular Domain Proteins To assess binding of B7H6/CD3 binding proteins to recombinant human Fc-His-tagged B7H6 ECD and human Fc-His-tagged Ala-mutated B7H6 extracellular proteins as described in Example 3, MediSorp™ plates (Nunc, 467320) were coated with 2 μl/ml recombinant proteins overnight at 4° C. The next day, plates were blocked with 0.5% bovine serum albumin (BSA) in phosphate buffered saline (PBS) for 1 hour at room temperature (RT). Subsequently plates were washed with OBS containing 0.05% TWEEN®20 viscous liquid and B7H6/CD3 binding proteins were incubated at concentrations ranging from 0.00001 to 10 μg/ml. After an additional washing step, bound B7H6/CD3 binding proteins were detected by a peroxidase conjugated goat anti-human IgG F(ab')$_2$-specific secondary antibody (Jackson Immunoresearch) and visualized by TMB substrate solution (Bender Med Systems). FIGS. 3A+B and 4A+B show binding of exemplary B7H6/CD3 binding proteins (B7H6/CD3 binding proteins comprising a B7H6 chain of SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and a CD3 chain of SEQ ID NO:311, and B7H6 binding proteins comprising a B7H6 chain of SEQ ID NO:230 or SEQ ID NO:239 and a CD3 chain of SEQ ID NO:312, SEQ ID NO:313, SEQ ID NO:314, SEQ ID NO:315, or SEQ ID NO:316, respectively) to recombinant human B7H6 ECD (FIG. 3A+B) and human Ala-mutated B7H6 ECD (FIG. 4A+B) proteins.

All tested exemplary B7H6/CD3 binding proteins show comparable binding to recombinant human B7H6 ECD (FIG. 3A+B), whereas only B7H6/CD3 binding proteins comprising a B7H6 chain of SEQ ID NO:217, SEQ ID NO:218, SEQ ID NO:219, SEQ ID NO:220, SEQ ID NO:221, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and a CD3 chain of SEQ ID NO:311, and B7H6 binding proteins comprising a B7H6 chain of SEQ ID NO:230 or SEQ ID NO:239 and a CD3 chain of SEQ ID NO:312, SEQ ID NO:313, SEQ ID NO:314, SEQ ID NO:315, or SEQ ID NO:316, respectively, show strong binding to human Fc-His-tagged Ala-mutated B7H6 extracellular protein, in which the NKp30 binding sites were mutated to Alanins B7H6/CD3 binding proteins comprising a B7H6 chain or SEQ ID NO:222, SEQ ID NO:223, SEQ ID NO:224, SEQ ID NO:225, SEQ ID NO:226, SEQ ID NO:227, and a CD3 chain of SEQ ID NO:311 show only weak binding at high concentrations or no binding to Fc-His-tagged Ala-mutated B7H6 extracellular protein.

Example 7: Binding to B7H6-Positive HCT Cells

Figure 5:
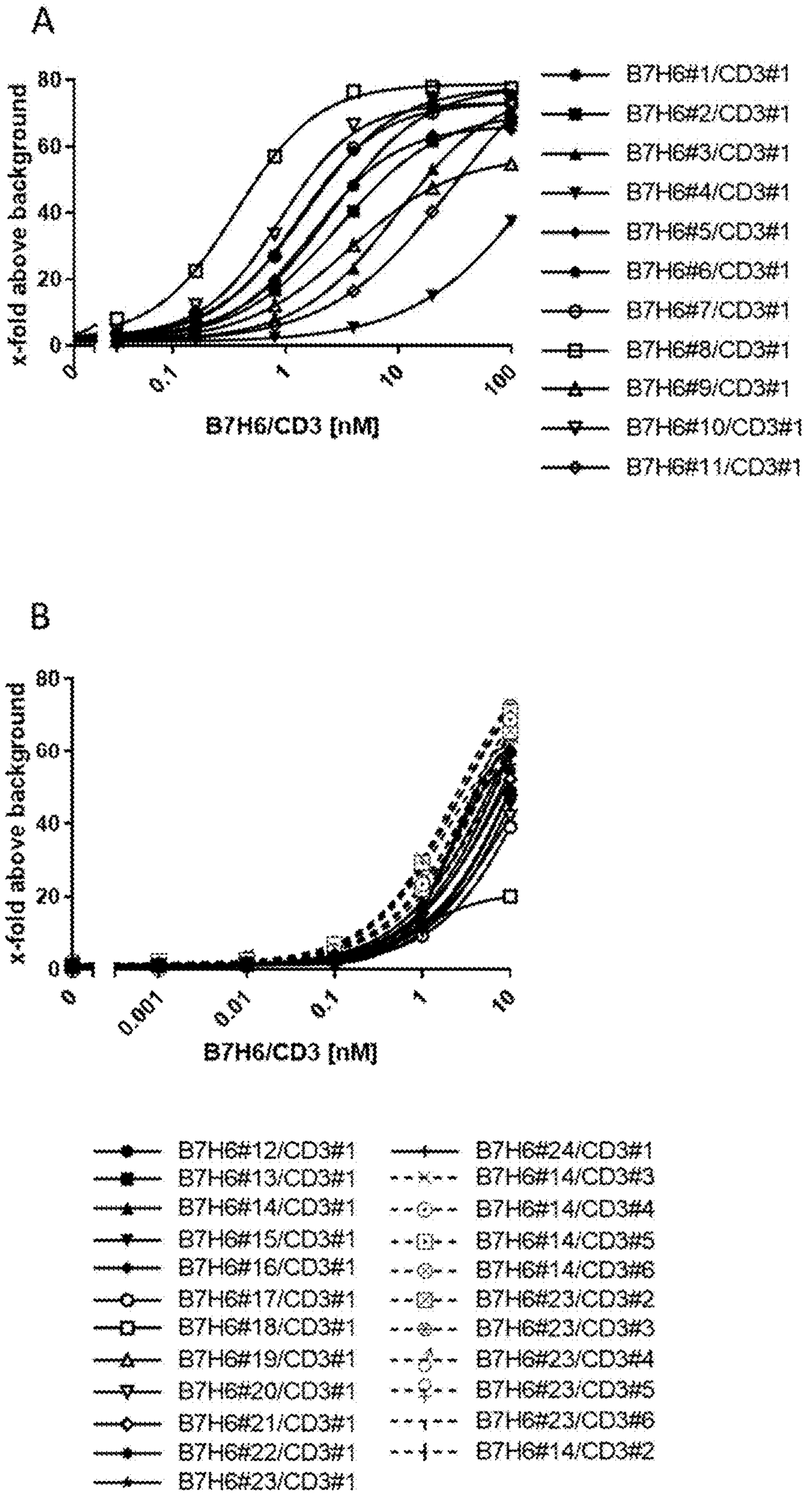
FIG. 5: Binding of 34 exemplary B7H6/CD3 binding proteins to HCT-15 cells expressing endogenous human B7H6.

Binding of B7H6/CD3 binding proteins to HCT-15, a human (colo-rectal cancer) CRC cell line was tested by flow cytometry. In a previous experiment, it has been confirmed that HCT-15 cells expresses B7-H6 on the RNA levels as well as the protein level with approximately 8,000 B7-H6 receptors on the cell surface (data not shown). B7H6/CD3 binding proteins were produced, as described in Example 2. HCT-15 cells were stained with increasing concentrations of two-step purified B7H6/CD3 binding proteins in FACS buffer (PBS/0.5% BSA/0.05% sodium azide). Bound molecules were detected with PE-conjugated anti-human secondary antibody (Sigma-Aldrich, #P8047). FIGS. 5A+B show binding of exemplary B7H6/CD3 binding proteins (B7H6/CD3 binding proteins comprising a B7H6 chain of SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and a CD3 chain of SEQ ID NO:311, and B7H6 binding proteins comprising a B7H6 chain of SEQ ID NO:230 or SEQ ID NO:239 and a CD3 chain of SEQ ID NO:312, SEQ ID NO:313, SEQ ID NO:314, SEQ ID NO:315, or SEQ ID NO:316, respectively) to human HCT-15 cells.

Example 8: Cross-Reactivity to Cynomolgus Monkey B7H6

Figure 6:
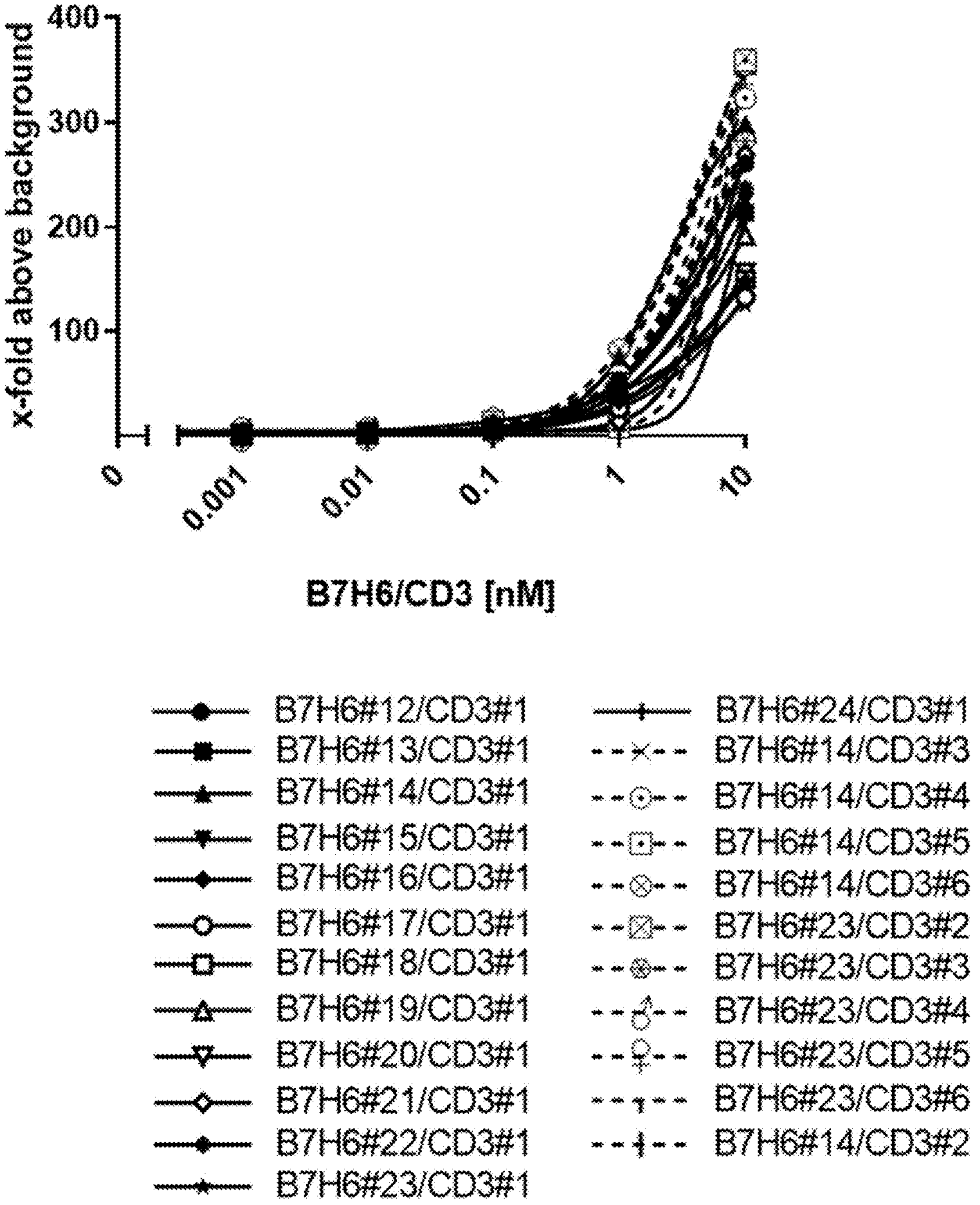
FIG. 6: Binding of 23 exemplary B7H6/CD3 binding proteins to recombinant CHO-K1 cells expressing cynomolgus monkey B7H6.

Binding of B7H6/CD3 binding proteins to recombinant CHO-K1 cells expressing cynomolgus B7H6 was tested by flow cytometry. B7H6/CD3 binding proteins were produced, as described in Example 2. Recombinant cynomolgus B7H6-expressing cell lines were generated as described in Example 5. Cells were stained with increasing concentrations of two-step purified B7H6/CD3 binding proteins in FACS buffer (PBS/0.5% BSA/0.05% sodium azide). Bound molecules were detected with PE-conjugated anti-human secondary antibody (Sigma-Aldrich, #P8047). FIG. 6 shows binding of exemplary B7H6/CD3 binding proteins (B7H6/CD3 binding proteins comprising a B7H6 chain of SEQ ID NO: 228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and a CD3 chain of SEQ ID NO:311, and B7H6 binding proteins comprising a B7H6 chain of SEQ ID NO:230 or SEQ ID NO:239 and a CD3 chain of SEQ ID NO:312, SEQ ID NO:313, SEQ ID NO:314, SEQ ID NO:315, or SEQ ID NO:316, respectively) to recombinant cynomolgus monkey B7H6-expressing cells.

Example 9: Binding to Human T-Cells

Binding of B7H6/CD3 binding proteins to purified human T-cells was tested by flow cytometry. B7H6/CD3 binding proteins were produced, as described in Example 2. T-cells were isolated from buffy coats obtained from the Austrian Red Cross. Informed consent in accordance with the Declaration of Helsinki and with approval of the cantonal ethical committee in Austria was obtained for all buffy coats.

Human peripheral blood mononuclear cells (PBMCs) were prepared using Ficoll® Paque density gradient medium (GE Healthcare Lifesciences) followed by centrifugation.

Human peripheral blood mononuclear cells (PBMCs) were derived from enriched lymphocyte preparations (buffy coats), a side product of blood banks collecting blood for transfusions. Therefore, mononuclear cells were isolated by Ficoll® density gradient centrifugation (35 min without brake at 1400 rpm) and extensive washes with PBS. Remaining erythrocytes were removed by incubating for 3 minutes in ACK lysis buffer (Thermo Fisher Scientific, A1049201), followed by washing in PBS, before suspension in assay medium containing RPMI 1640 GlutaMAX™ supplement (Gibco #61870-010), 5% human AB serum AB (Gemini, GemCell cat #100-512 LOT #H56500I)+1% MEM-NEAA (Gibco #11140-035), 10 mM HEPES (Affymetrix #7365-49-9), 10 μM beta-(Gibco #21985-023) and sodium pyruvat (Gibco #11360-039).

T-cells were isolated by negative selection using the Pan T Cell Isolation Kit II (Miltenyi Biotec #130-091-156). In brief, cells were resuspended in 40 μl buffer PBS/0.5% BSA (Gibco ref #041-94553 M)/2 mM EDTA (Invitrogen ref #15575-038) per 10 Mio cells and incubated with 10 μl of Biotin-Antibody cocktail per 10 Mio cells for 5 min at 4° C. Subsequently, 30 μl buffer and 20 μl anti-biotin MACS® MicroBeds/10 million cells were added and incubated for 10 min at 4° C. Subsequently the mixture was placed in a pre-rinsed 25LS column (Miltenyi Biotec #130-042-401) in the magnetic field of suitable MACS® microbeads separator (Miltenyi Biotec). Flow-through was collected and washed in assay medium.

Figure 7:
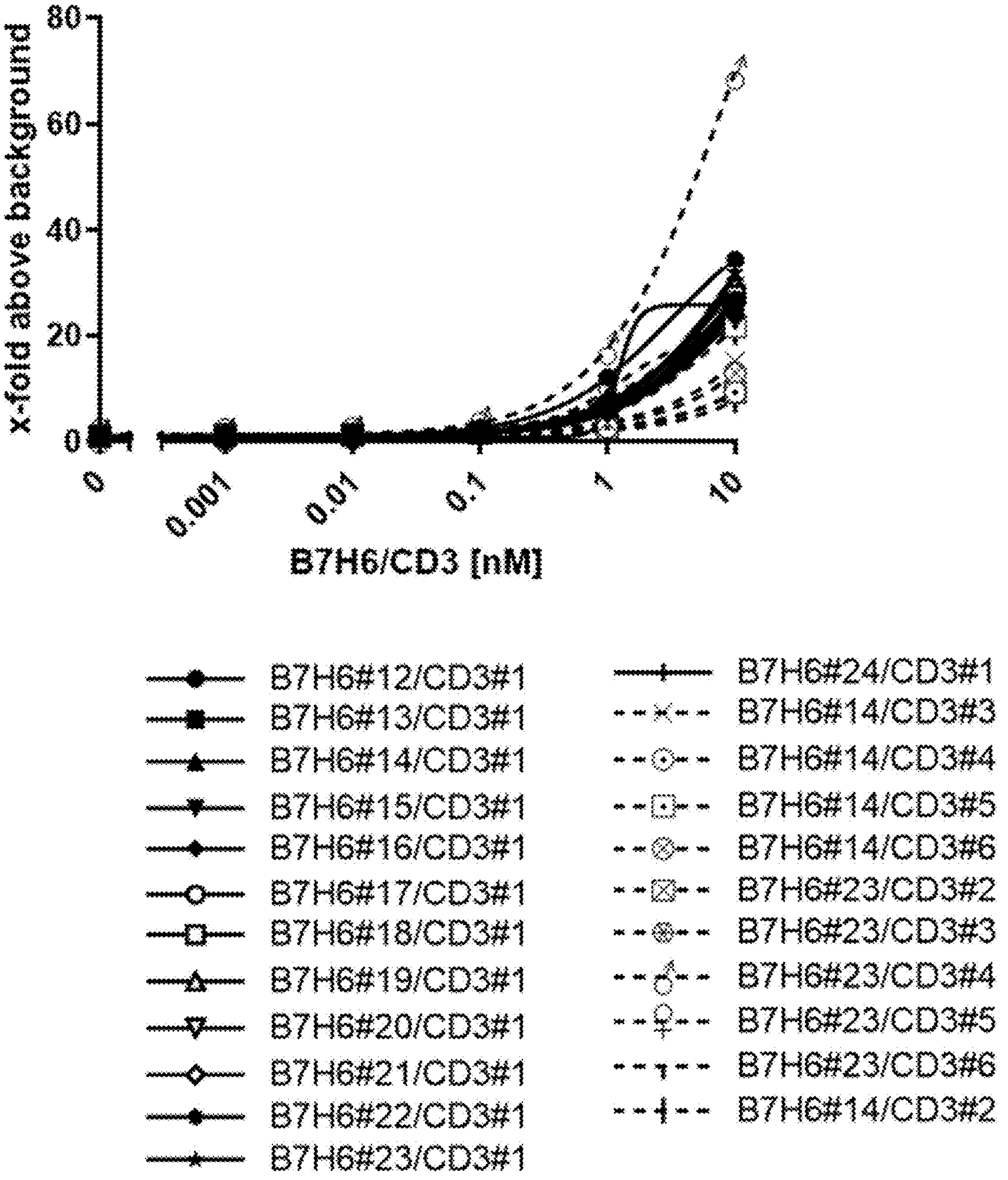
FIG. 7: Binding of 23 exemplary B7H6/CD3 binding proteins to human T-cells expressing CD3.

T-cells were stained with increasing concentrations of two-step purified B7H6/CD3 binding proteins in FACS buffer (PBS/0.5% BSA/0.05% sodium azide). Bound molecules were detected with PE-conjugated anti-human secondary antibody (Sigma-Aldrich, #P8047). FIG. 7 shows binding of exemplary B7H6/CD3 binding proteins (B7H6/CD3 binding proteins comprising a B7H6 chain of SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and a CD3 chain of SEQ ID NO:311, and B7H6 binding proteins comprising a B7H6 chain of SEQ ID NO:230 or SEQ ID NO:239 and a CD3 chain of SEQ ID NO:312, SEQ ID NO:313, SEQ ID NO:314, SEQ ID NO:315, or SEQ ID NO:316, respectively) to human T-cells.

Example 10: Binding Selectivity

Figure 8:
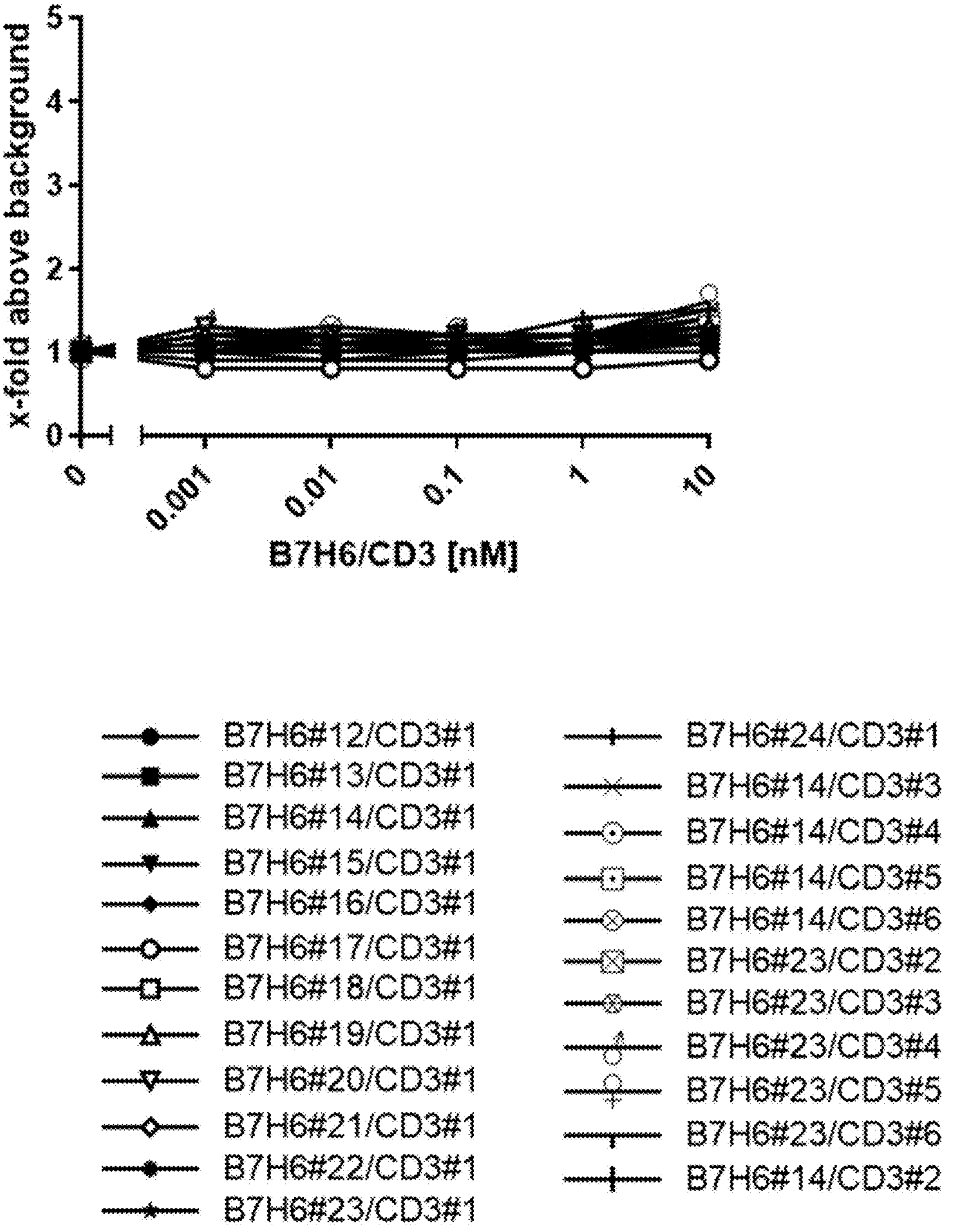
FIG. 8: Binding of 23 exemplary B7H6/CD3 binding proteins to B7H6-negative CHO-K1 cells.

Binding of B7H6/CD3 binding proteins to B7H6- and CD3-negative CHO-K1 cells was tested by flow cytometry analysis. B7H6/CD3 binding proteins were produced, as described in Example 2. CHO-K1 cells were stained with increasing concentrations of two-step purified B7H6/CD3 binding proteins in FACS buffer (PBS/0.5% BSA/0.05% sodium azide). Bound molecules were detected with PE-conjugated anti-human secondary antibody (Sigma-Aldrich, #P8047). FIG. 8 shows binding of exemplary B7H6/CD3 binding proteins (B7H6/CD3 binding proteins comprising a B7H6 chain of SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and a CD3 chain of SEQ ID NO:311, and B7H6 binding proteins comprising a B7H6 chain of SEQ ID NO:230 or SEQ ID NO:239 and a CD3 chain of SEQ ID NO:312, SEQ ID NO:313, SEQ ID NO:314, SEQ ID NO:315, or SEQ ID NO:316, respectively) to CHO-K1 cells.

Example 11: Inhibition of B7H6-Dependent NK Cell Activity

Cell surface expressed B7H6 binds to NKp30 on NK cells, which triggers NKp30-mediated activation of NK cells and NK cell cytotoxicity and cytokine secretion (Brandt et al, J. Exp. Med. 2009; 206(7):1495-1503). To assess B7H6-dependent activation of NK-cells, 96-well flat bottom cell culture plates were coated with 100 nM recombinant human B7H6 protein (R&DSystems #7144-B7-050) overnight at 4° C. On the next day, plates were washed with PBS, subsequently increasing concentrations of B7H6/CD3 binding proteins or recombinant NKp30 protein (R&DSystems #1849-NK-025) were added and incubated for one hour at room temperature. B7H6/CD3 binding proteins were produced, as described in Example 2. After an additional washing step, 100,000 NK92MI (ATCC) cells in 100 μl medium (MEM alpha containing 12.5% fetal bovine serum, 12.5% horse serum, 0.2 mM D-Myo-Inositol, 0.02 mM folic acid and 0.1 mM β-mercaptoethanol) were added per well and incubated for 24 hours. On the next day, IFNγ concentration was quantified using the V-PLEX Human IFN-γ Kit (Meso Scal Discovery). FIGS. 9A+B show the ability of B7H6/CD3 binding proteins (B7H6/CD3 binding proteins comprising a B7H6 chain of SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:226, SEQ ID NO:227, SEQ ID NO:228, SEQ ID NO:230, SEQ ID NO:231, SEQ ID NO:232, SEQ ID NO:235, SEQ ID NO:236, and a CD3 chain of SEQ ID NO:311) to inhibit B7-H6-dependent induction of IFNγ secretion by NK-92MI.

B7H6 binding proteins which do not or only weakly bind to Ala-mutated B7H6 extracellular proteins in which the NKp30 interaction sites were substituted with Alanine (B7-H6/CD3 binding proteins comprising a B7H6 chain of SEQ ID NO:222, SEQ ID NO:223, SEQ ID NO:224, SEQ ID NO:225, SEQ ID NO:226, SEQ ID NO:227, and a CD3 chain of SEQ ID NO:311) (as shown in FIG. 4, Example 6) inhibit the B7-H6-dependent induction of IFNγ secretion by NK-92MI cells, whereas binding protein that show strong binding to Ala-mutated B7H6 extracellular proteins comparable to wild type protein, (B7-H6/CD3 binding proteins comprising a B7H6 chain of SEQ ID NO:217, SEQ ID NO:218, SEQ ID NO:219, SEQ ID NO:220, SEQ ID NO:221, SEQ ID NO:228, SEQ ID NO:230, SEQ ID NO:231, SEQ ID NO:232, SEQ ID NO:235, SEQ ID NO:236, and a CD3 chain of SEQ ID NO:311) (as shown in FIG. 4, Example 6) do not influence the B7-H6-dependent induction of IFNγ secretion by NK-92MI cells.

Example 12: Potency of T-Cell Redirected Lysis Human HCT-15 Cells

Potency of non-stimulated T-cells against HCT-15 cells was determined using lactate-dehydrogenase (LDH) release as readout for cell lysis. In this assay, the B7H6-positive CRC cell line HCT-15 was co-cultured with human T-cells as effector cells and increasing concentrations of B7H6/CD3 binding proteins for 72 hours at an effector to target cell ratio of 10:1. B7H6/CD3 binding proteins were produced, as described in Example 2. Purified T-cells were isolated as described in Example 9. Subsequently, HCT-15 cells and T-cells at a ratio of 1:10 were incubated with B7H6/CD3 binding proteins at concentrations from 0.00001 nM to 10 nM for 72 hours.

Cytotoxic activity was determined using the Cytotoxicity Detection Kit$^{PLUS}$ (Roche), following the manufacturer's instructions. In brief, this method is based on the usage of the release of LDH from dead or plasma-membrane damaged cells. Cell culture supernatant is incubated with the reaction mixture from the kit for 30 minutes and the formation of Formazan, as a result of LDH activity is measured in a spectrophotometer at 500 nm as surrogate for cell lysis. Percentage of cytotoxicity relative to the maximal lysis control was calculated according to the following formula:

$$\text{Cytotoxicity (relative to control)} = \frac{\text{measured value} - \text{background}}{\text{maximal lysis} - \text{minimal lysis}}$$

Background: Target cells+Effector cells
Maximal lysis: Target cells+5% Triton X-100
Minimal lysis: Target cells Using GraphPad®Prism® 5.0 software (GraphPad Sofware, Inc), the percentage of cytotoxicity relative to the maximal lysis control was plotted against the corresponding B7H6/CD3 binding protein concentrations. Dose response curves were analysed with the four-parameter logistic equation model for evaluation of sigmoidal dose-response curve and $EC_{50}$ values were calculated.

FIGS. 10A+B and 11A+B show examples of potency T-cell redirected lysis of HCT-15 cells mediated by exemplary B7H6/CD3 binding proteins (B7H6/CD3 binding proteins comprising a B7H6 chain of SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and a CD3 chain of SEQ ID NO:311, and B7H6 binding proteins comprising a B7H6 chain of SEQ ID NO:230 or SEQ ID NO:239 and a CD3 chain of SEQ ID NO:312, SEQ ID NO:313, SEQ ID NO:314, SEQ ID NO:315, or SEQ ID NO:316, respectively). FIGS. 10 and 11 show that B7H6 binding proteins which bind to the recombinant Ala-mutated B7H6 extracellular proteins, in which the NKp30 interaction sites were substituted with Alanine, comparable as to wt protein, and do not inhibit the B7-H6-dependent secretion of IFNγ by NK92MI cells (B7H6/CD3 binding proteins comprising a B7H6 chain of SEQ ID NO:217, SEQ ID NO:218, SEQ ID NO:219, SEQ ID NO:220, SEQ ID NO:221, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and a CD3 chain of SEQ ID NO:311, and B7H6 binding proteins comprising a B7H6 chain of SEQ ID NO:230 or SEQ ID NO:239 and a CD3 chain of SEQ ID NO:312, SEQ ID NO:313, SEQ ID NO:314, SEQ ID NO:315, or SEQ ID NO:316, respectively) (as shown in, Example 6, 11) show lower $EC_{50}$ values (Tables 4A+B) than B7H6/CD3 binding proteins which do not or only weakly bind to recombinant Ala-mutated B7H6 extracellular proteins and inhibit the B7-H6-dependent secretion of IFNγ by NK92MI cells (B7-H6/CD3 binding proteins comprising of a SEQ ID NO:217, SEQ ID NO:218, SEQ ID NO:219, SEQ ID NO:220, or SEQ ID NO:221, and a CD3 chain of SEQ ID NO:CD3 #1) (as shown in, Example 6, 11). Thus, binding proteins that do not inhibit B7H6 dependent NK cell activation surprisingly show a significantly higher T-cell mediated tumor cell lysis compared to binding proteins that do inhibit B7H6 dependent NK cell activation.

Figure 12:
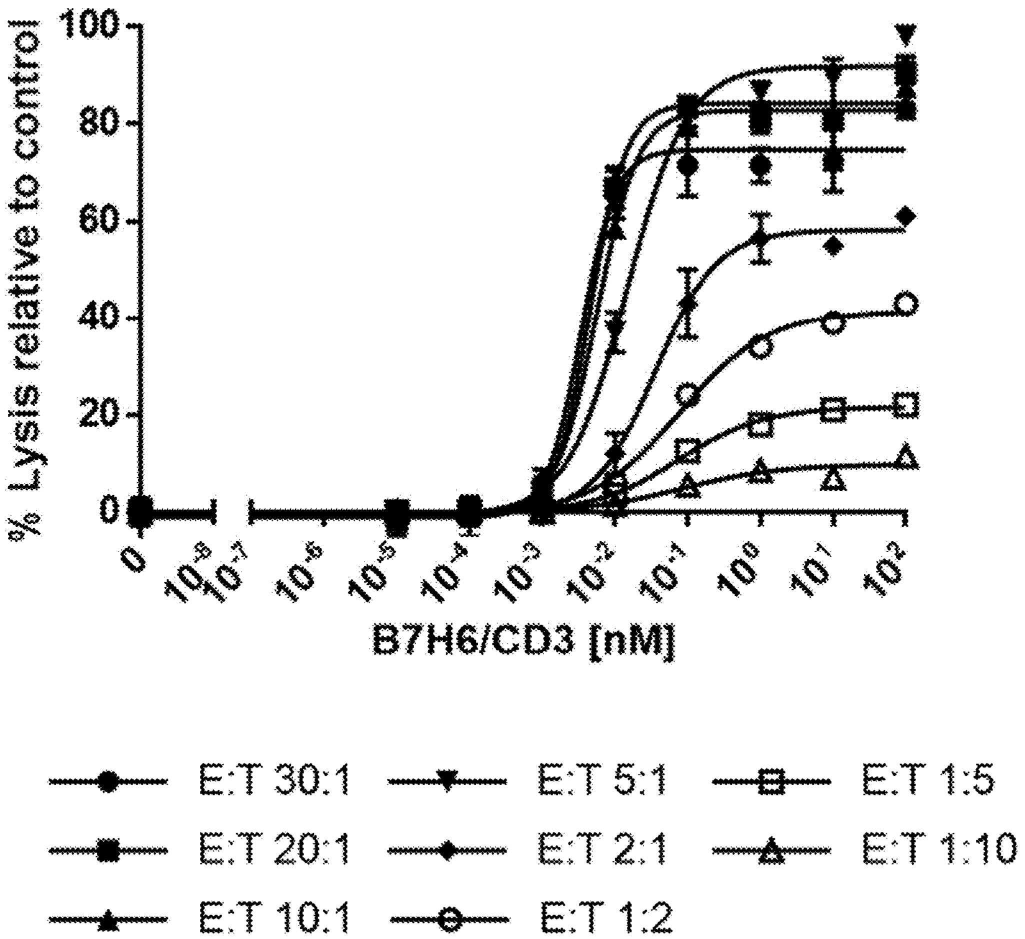
FIG. 12: Potency in lysing target cells of an exemplary B7H6/CD3 binding protein at various effector to target (E:T) cell ratios.

As shown in FIG. 12 with an exemplary B7H6/CD3 binding protein, activity only requires low effector to target cell ratios.

TABLE 4A $EC_{50}$ values [nM] of 11 exemplary B7H6/CD3 binding proteins as measured in 72 hour cytotoxicity assay with non-stimulated T-cells (from Donor #1) as effector cells and HCT-15 cells as target cells.

| B7H6/CD3 | $EC_{50}$ [nM] |
|---|---|
| B7H6#1/CD3#1 | 0.14 |
| B7H6#2/CD3#1 | 0.22 |
| B7H6#3/CD3#1 | 0.40 |
| B7H6#4/CD3#1 | 0.23 |
| B7H6#5/CD3#1 | 0.22 |
| B7H6#6/CD3#1 | 0.46 |
| B7H6#7/CD3#1 | 0.36 |
| B7H6#8/CD3#1 | 0.62 |
| B7H6#9/CD3#1 | 0.44 |

TABLE 4A-continued $EC_{50}$ values [nM] of 11 exemplary B7H6/CD3 binding proteins as measured in 72 hour cytotoxicity assay with non-stimulated T-cells (from Donor #1) as effector cells and HCT-15 cells as target cells.

| B7H6/CD3 | $EC_{50}$ [nM] |
|---|---|
| B7H6#10/CD3#1 | 0.53 |
| B7H6#11/CD3#1 | 0.77 |

TABLE 4B $EC_{50}$ values [nM] of 23 exemplary B7H6/CD3 binding proteins as measured in 72 hour cytotoxicity assay with non-stimulated T-cells (from Donor #2) as effector cells and HCT-15 cells as target cells.

| B7H6/CD3 | $EC_{50}$ [nM] |
|---|---|
| B7H6#12/CD3#1 | 0.004 |
| B7H6#13/CD3#1 | 0.008 |
| B7H6#14/CD3#1 | 0.003 |
| B7H6#15/CD3#1 | 0.004 |
| B7H6#16/CD3#1 | 0.011 |
| B7H6#17/CD3#1 | 0.014 |
| B7H6#18/CD3#1 | 0.014 |
| B7H6#19/CD3#1 | 0.011 |
| B7H6#20/CD3#1 | 0.010 |
| B7H6#21/CD3#1 | 0.010 |
| B7H6#22/CD3#1 | 0.005 |
| B7H6#23/CD3#1 | 0.005 |
| B7H6#24/CD3#1 | 0.005 |
| B7H6#14/CD3#2 | 0.118 |
| B7H6#23/CD3#2 | 0.215 |
| B7H6#14/CD3#3 | 0.069 |
| B7H6#23/CD3#3 | 0.107 |
| B7H6#14/CD3#4 | 0.292 |
| B7H6#23/CD3#4 | 0.447 |
| B7H6#14/CD3#5 | 0.005 |
| B7H6#23/CD3#5 | 0.003 |
| B7H6#14/CD3#6 | 0.081 |
| B7H6#23/CD3#6 | 0.129 |

Example 13: Cross-Reactivity and Selectivity of T-Cell Redirected Lysis

Potency of non-stimulated T-cells against HCT-15 cells was determined using lactate-dehydrogenase (LDH) release as readout for cell lysis as described in Example 12. B7H6/CD3 binding proteins were produced, as described in Example 2. Recombinant cynomolgus B7H6-expressing cell lines were generated as described in Example 5.

Figure 13:
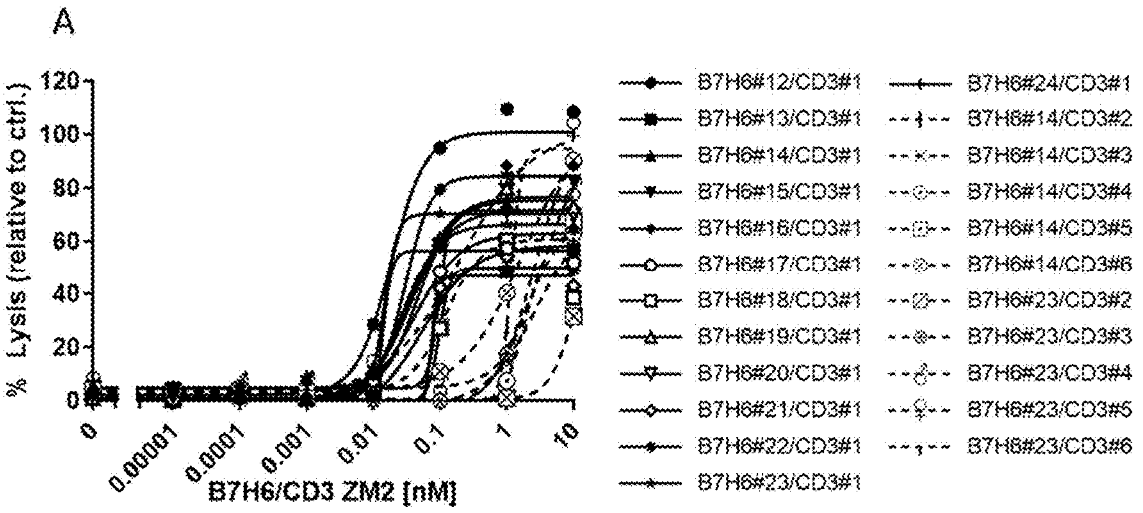
FIG. 13: Potency in lysis cells of 23 exemplary B7H6/CD3 binding proteins redirecting non-stimulated T-cells towards recombinant CHO cells transfected with B7-H6 and Cho wt cells.
Figure 13:
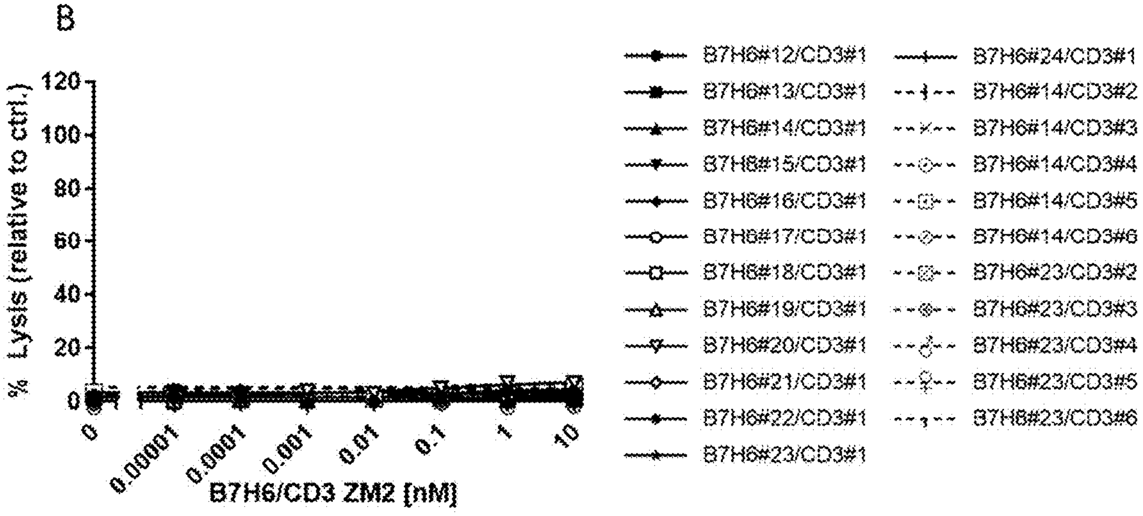

FIG. 13 shows examples of potency of T-cell redirected lysis of cyno B7H6 expressing cells (FIG. 13A) and B7H6-negative parental CHO-K1 cells (FIG. 13B) mediated by exemplary B7H6/CD3 binding proteins a B7H6 chain SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and a CD3 chain of SEQ ID NO:311, and B7H6 binding proteins comprising a B7H6 chain of SEQ ID NO:230 or SEQ ID NO:239 and a CD3 chain of SEQ ID NO:312, SEQ ID NO:313, SEQ ID NO:314, SEQ ID NO:315, or SEQ ID NO:316, respectively).

Example 14: Selectivity of Activation of T Cells

Figure 14:
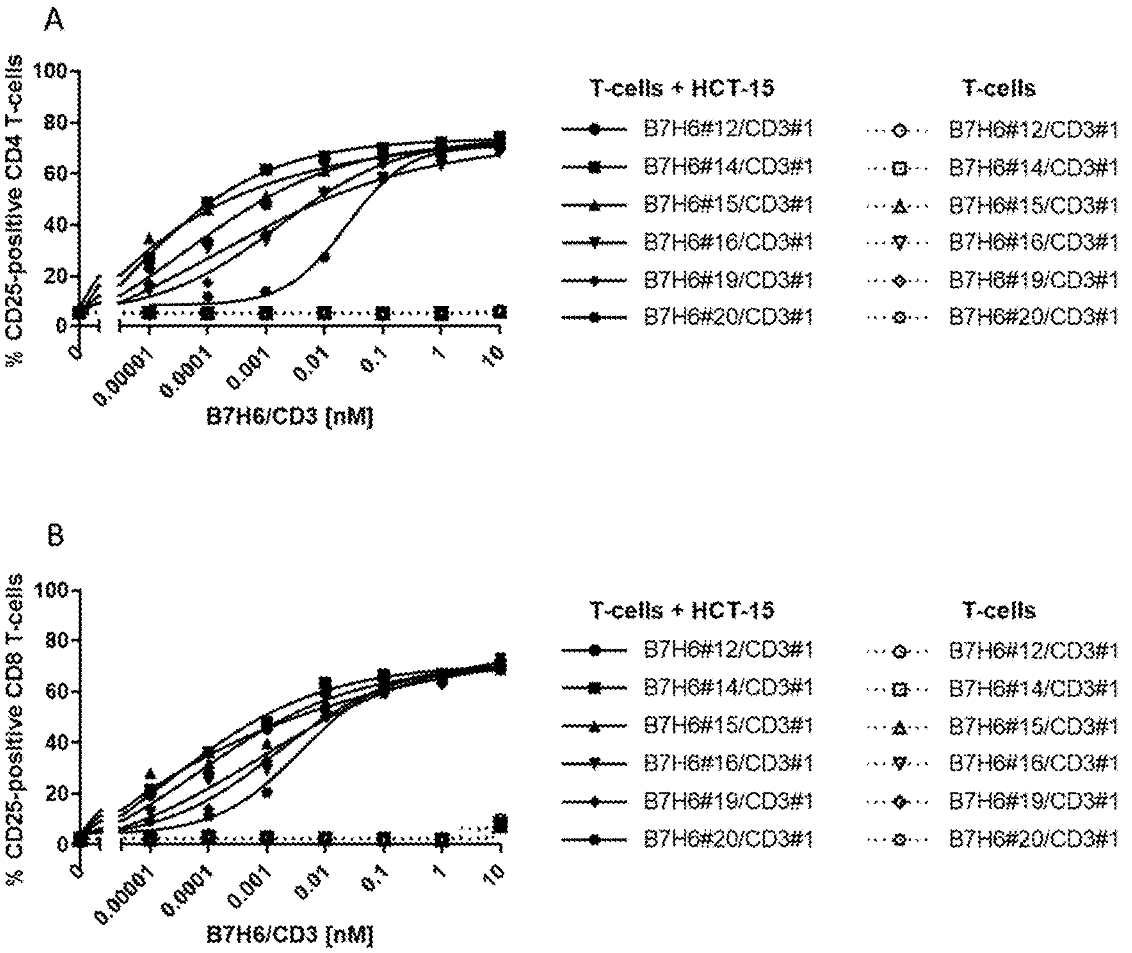
FIG. 14: Potency in upregulation of CD25 expression on T-cells in presence of HCT-15 cells of 6 exemplary B7H6/CD3 binding proteins.

To determine activation of T-cells, a cytotoxicity assay with non-stimulated T-cells and B7H6-positive HCT-15 cells as target cells was setup as described in Example 12. B7H6/CD3 binding proteins were produced, as described in Example 2. To determine T cell activation, cells were centrifuged and stained with antibodies against CD4 (BD #550630), CD8 (BD #557834), and CD25 (BD #340907) and measured by flow-cytometry. FIG. 14 shows examples of potency of activation of CD4+(FIG. 14A) and CD8+(FIG. 14B) cells in presence and absence of B7H6-positive HCT-15 cells mediated by exemplary B7H6/CD3 binding proteins comprising a B7H6 chain of SEQ ID NO:228, SEQ ID NO:230, SEQ ID NO:231, SEQ ID NO:232, SEQ ID NO:235, or SEQ ID NO:236, and a CD3 chain of SEQ ID NO:311.

Example 15: Selectivity of Degranulation of T Cells

Figure 15:
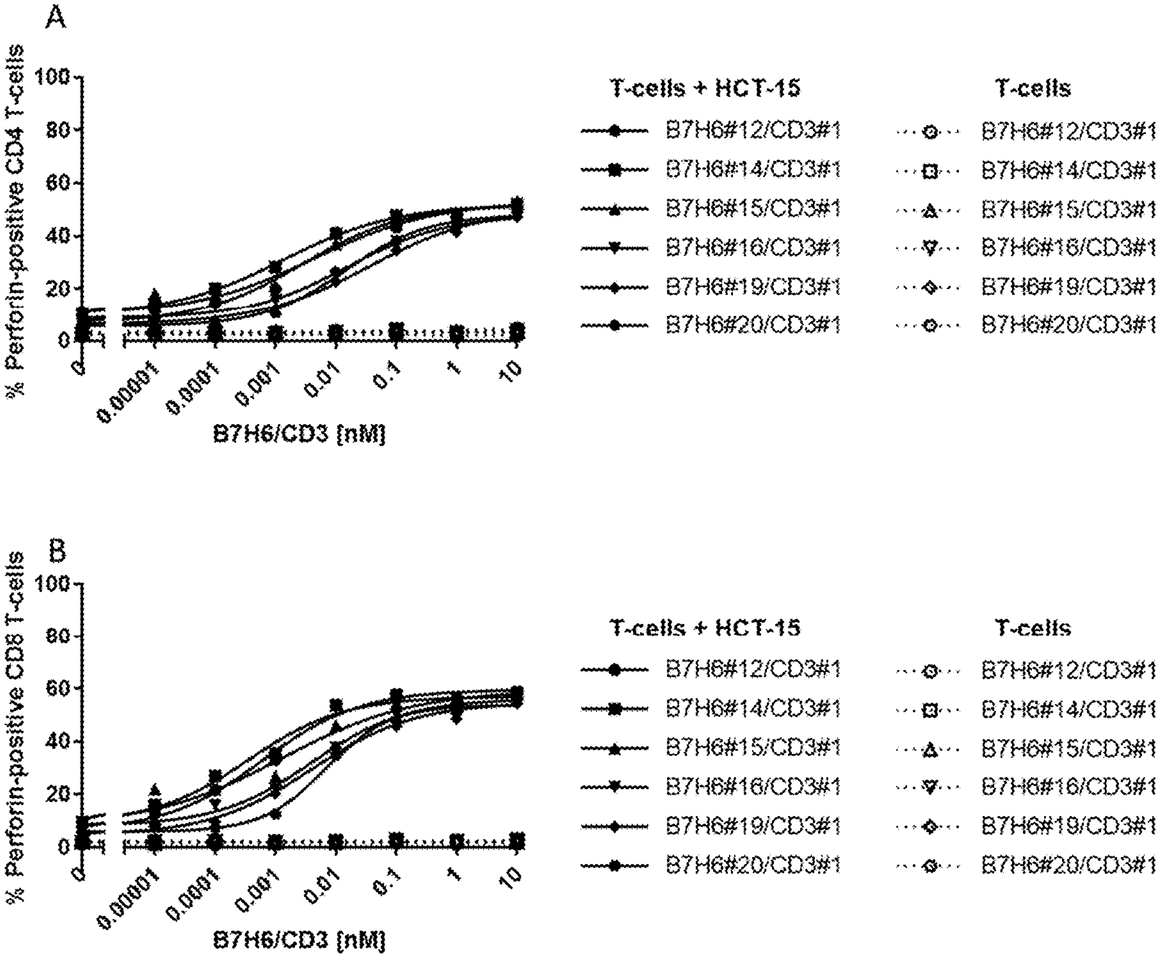
FIG. 15: Potency in upregulation of intracellular Perforin expression in T-cells in presence of HCT-15 cells of 6 exemplary B7H6/CD3 binding proteins.
Figure 16:
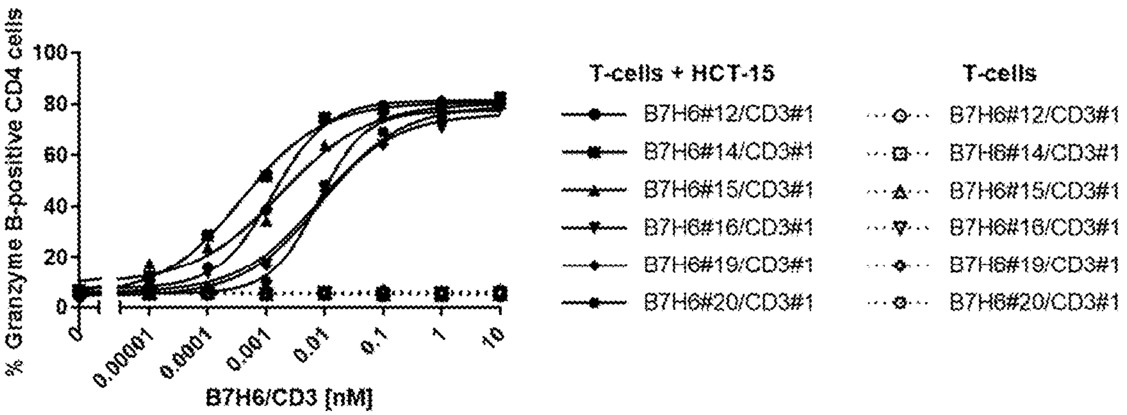
FIG. 16: Potency in upregulation of intracellular Granzyme B expression in T-cells in presence of HCT-15 cells of 6 exemplary B7H6/CD3 binding proteins.
Figure 16:
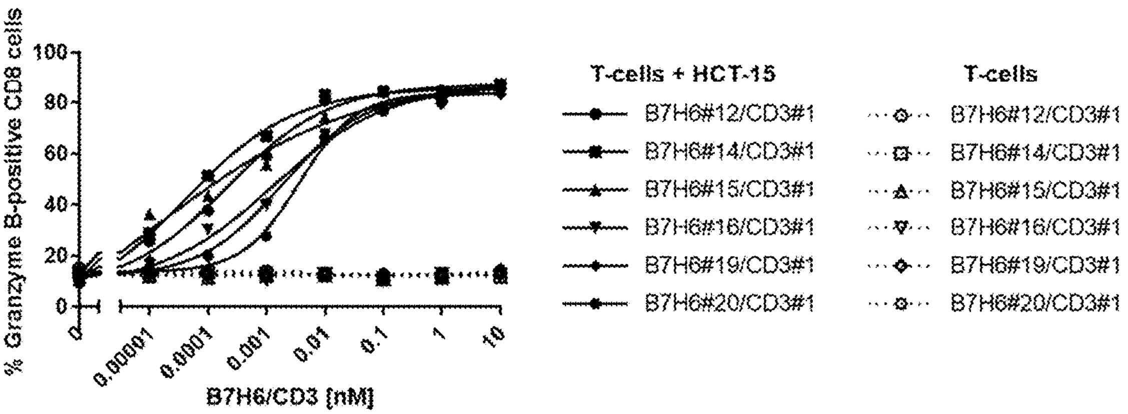

To determine degranulation of T-cells via intracellular expression of Perforin and Granzyme B, a cytotoxicity assay with non-stimulated T-cells and B7H6-positive HCT-15 cells as target cells was setup as described in Example 12. B7H6/CD3 binding proteins were produced, as described in Example 2. To determine intracellular levels of Granzyme B and Perforin, cells were centrifuged and stained with antibodies against CD4 (BD #550630), CD8 (BD #557834), subsequently the cells were permabilized using the Fixation/Permeabilization Solution (BD #554714) and stained with antibodies against Perforin (BioLegend #308120) and Granzyme B (BD #560221) and measured by flow-cytometry. FIG. 15 shows examples of potency of upregulation of intracellular Perforin expression in $CD4^+$ (FIG. 15A) and $CD8^+$ (FIG. 15B) cells, and FIG. 16 shows upregulation of intracellular Granzyme B expression in $CD4^+$ (FIG. 16A) and $CD8^+$ (FIG. 16B) cells in presence and absence of B7H6-positive HCT-15 cells mediated by exemplary B7H6/CD3 binding proteins comprising a B7H6 chain of SEQ ID NO:228, SEQ ID NO:230, SEQ ID NO:231, SEQ ID NO:232, SEQ ID NO:235, or SEQ ID NO:236, and a CD3 chain of SEQ ID NO:311.

Example 16: Induction of T-Cell Proliferation

Figure 17:
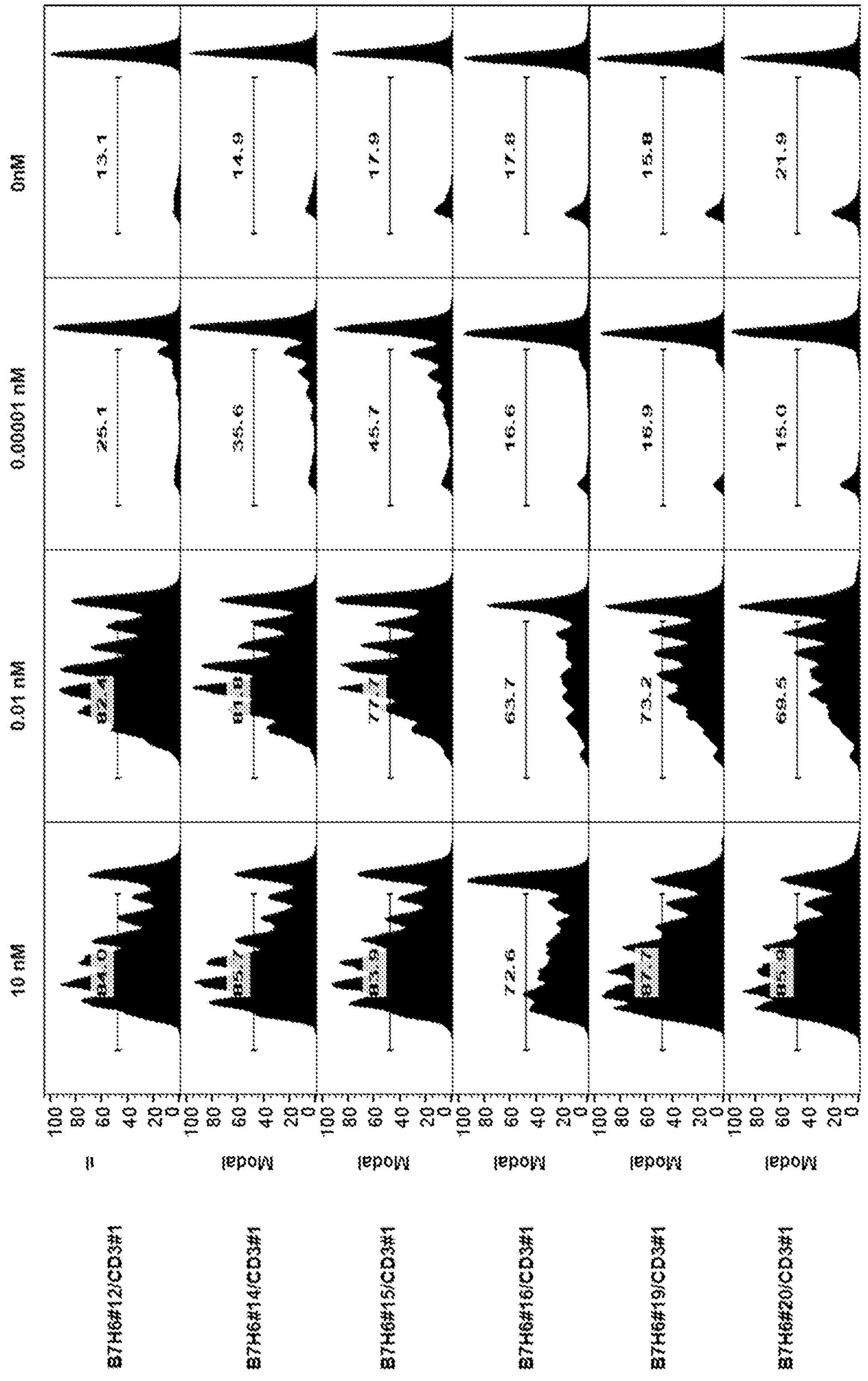
FIG. 17: Potency in proliferation of T-cells in presence of HCT-15 cells of 6 exemplary B7H6/CD3 binding proteins.

A cytotoxicity assay with non-stimulated T-cells and B7H6-positive HCT-15 cells as target cells was setup as described in Example 12. B7H6/CD3 binding proteins were produced, as described in Example 2. To determine the proliferation of T cells, PBMCs were labeled with 5 μM Cell Trace™ CFSE (Invitrogen, C34554) and T cell stained with an anti-CD3 antibody (BioLegend cat #: 317336). Subsequently the labeled PBMCs were incubated with HCT-15 cells at a ratio of 10:1 and increasing concentrations of a B7H6/CD3 binding protein for 6 days. FIG. 17 shows dose-dependent induction of proliferation of T-cells by B7H6-binding proteins by exemplary B7H6/CD3 binding proteins comprising a B7H6 chain of SEQ ID NO:228, SEQ ID NO:230, SEQ ID NO:231, SEQ ID NO:232, SEQ ID NO:235, or SEQ ID NO:236, and a CD3 chain of SEQ ID NO:311 in presence of B7H6-positive HCT-15 cells.

Example 17: Selectivity of IFNγ Secretion

Figure 18:
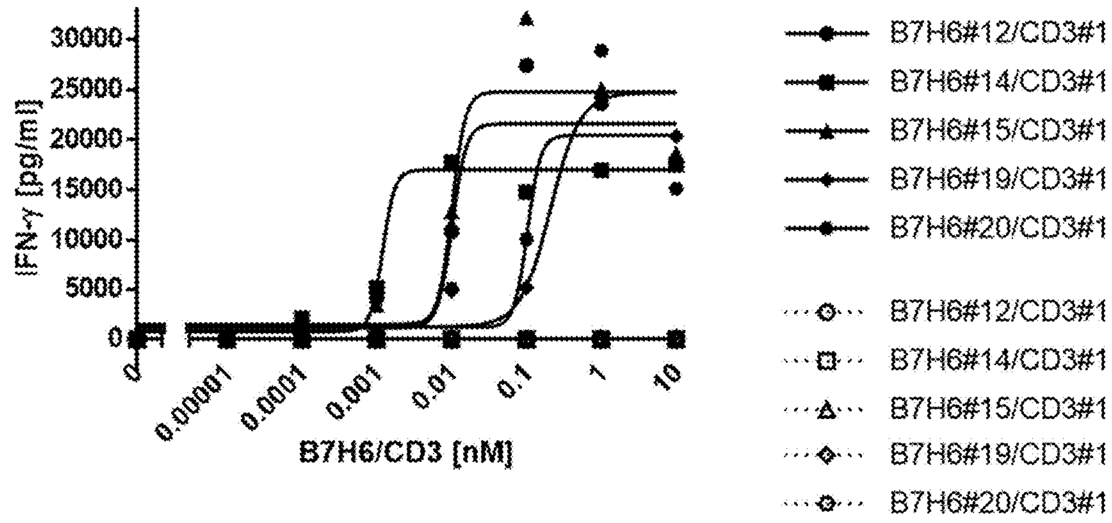
FIG. 18: Potency in secretion of IFNγ by T-cells in presence of HCT-15 cells of 5 exemplary B7H6/CD3 binding proteins.

A cytotoxicity assay with non-stimulated T-cells and B7H6-positive HCT-15 cells as target cells was setup as described in Example 12. B7H6/CD3 binding proteins were produced, as described in Example 2. Cytokine levels in supernatants were determined by V-Plex Human IFN-gamma Kit (MSD, CAT: K151QOD-4). FIG. 18 shows secretion of IFNγ induced by five exemplary B7H6/CD3 binding proteins comprising a B7H6 chain of SEQ ID NO:228, SEQ ID NO:230, SEQ ID NO:231, SEQ ID NO:235, or SEQ ID NO:236, and a CD3 chain of SEQ ID NO:311.

Example 18: Mouse PK

B7H6/CD3 binding proteins were produced, as described in Example 2.

The PK of B7H6/CD3 binding proteins was evaluated in C57BL/6 mice following a single 1 mg/kg i.v. dose. Serum concentrations of B7H6/CD3 binding proteins were determined using a B7H6 capture/CD3 detection assay.

In brief, male C57BL/6 mice received a single 1 mg/kg intravenous (IV) dose (n=3 per molecule). Blood samples were collected pre-dose and 0.25, 2, 6, 24, 48, 96, 168, 240 and 336 hours post-dose. Serum drug levels were measured with an MSD-based ligand binding assay, using biotinylated B7H6 as the capture reagent and sulfo-tagged CD3E as the at detection reagent. Pharmacokinetic (PK) parameters were calculated from serum concentration time-profiles using non-compartmental analysis. The following PK parameters were assessed: AUCtlast (area under the serum concentration-time curve from time zero to the last quantifiable time-point), AUCinf (area under the serum concentration-time curve extrapolated to infinity), CL (systemic clearance), $V_{SS}$ (steady-state volume of distribution) and $T_{1/2}$ (terminal half-life).

Figure 19:
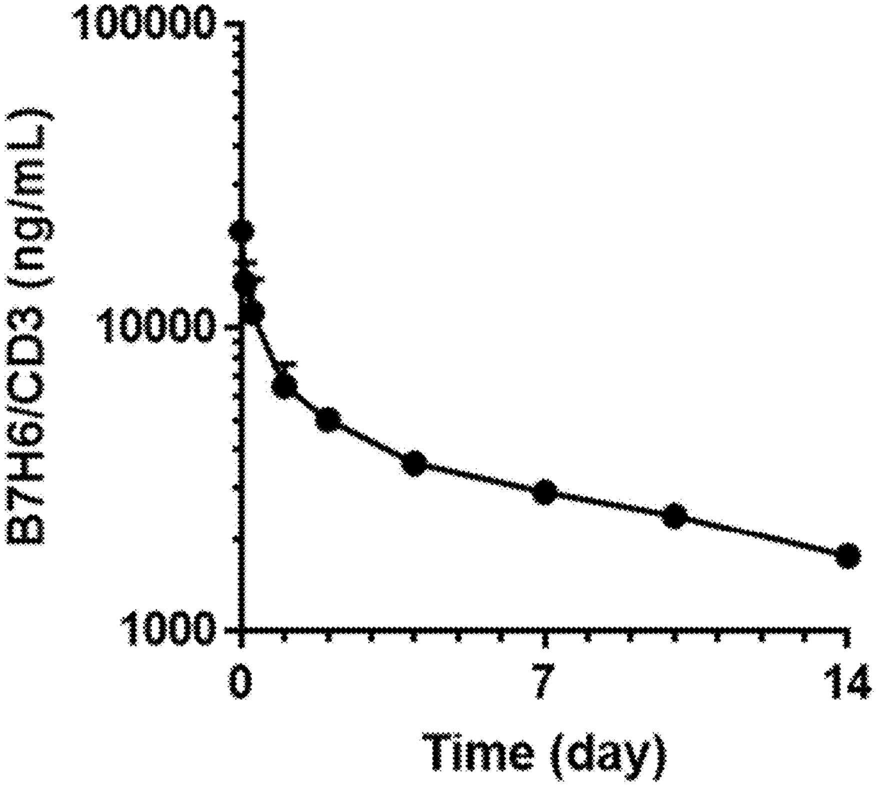
FIG. 19: Pharmacokinetic profile of one exemplary B7H6/CD3 binding protein.

Mean (SD) serum concentration time-profiles for an exemplary B7H6/CD3 binding protein are summarized in FIG. 19. Mean (SD) PK parameters for these exemplary BH6/CD3 binding protein are summarized in Table 5.

TABLE 5

Mean (SD) PK parameters of an exemplary B7H6/CD3 binding protein in male C57BL/6 mice following a single 1 mg/kg intravenous dose

| Dose (mg/kg) | $C_{max}$ (ng/mL) | $AUC_{tlast}$ (ng · hr/mL) | $AUC_{inf}$* (ng · hr/mL) | CL (mL/d/kg) | $V_{ss}$ (mL/kg) | $T_{1/2}$ (day) | MRT (day) |
|---|---|---|---|---|---|---|---|
| 1 | 20500 (458) | 1200000 (78100) | 1840000 (112000) | 13.1 (0.8) | 173 (30) | 10.2 (2.2) | 13.3 (3.0) |

*greater than 20% extrapolated AUC

Example 18A: Mouse PK

Figure 22:
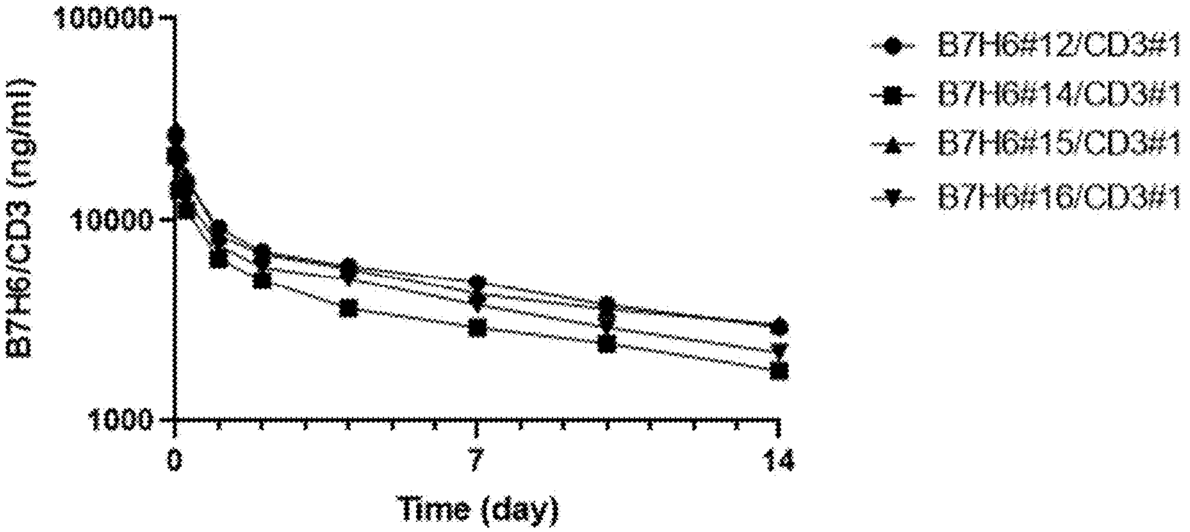
FIG. 22: Pharmacokinetic profile of four exemplary B7H6 binding protein.

The PK of B7H6/CD3 binding proteins was evaluated as described in Example 18. Mean (SD) serum concentration time-profiles for four exemplary B7H6/CD3 binding proteins comprising a B7H6 chain of SEQ ID NO:228, SEQ ID NO:230, SEQ ID NO:231, or SEQ ID NO:232, and a CD3 chain of SEQ ID NO:311 are summarized in FIG. 22.

Example 19: In Vivo Efficacy

Efficacy studies were performed using a human xenograft mouse model reconstituted with human T cells. In detail, human NCI-H716 colorectal cancer cells ($2.5 \times 10^7$) were injected subcutaneously (s.c.) into the right dorsal flank of sub-lethally irradiated (2 Gy, day −1) female NOD.Cg-$Prkdc^{scid}$ $Il2rg^{tm1Sug}$/JicTac mice (Day −16). In parallel, human CD3 positive T cells (isolated from healthy human blood donor) were expanded in vitro.

Human peripheral blood mononuclear cells (PBMCs) were prepared as described in Example 9.

T-cells were isolated by negative selection using the Pan T Cell Isolation Kit II (Miltenyi Biotec #130-096-535). In brief, cells were resuspend in 40 μl buffer PBS/0.5% BSA (Gibco ref #041-94553 M)/2 mM EDTA (Invitrogen ref #15575-038) per $10\times10^6$ cells and incubated with 10 μl of Biotin-Antibody cocktail per $10\times10^6$ cells for 5 min at 4° C. Subsequently, 30 μl buffer and 20 μl anti-biotin MACS® MicroBeads/$10\times10^6$ cells were added and incubated for 10 min at 4° C. Subsequently the mixture was placed in a pre-rinsed 25LS column (Miltenyi Biotec #130-042-401) in the magnetic field of suitable MACS® microbead separator (Miltenyi Biotec). Flow-through was collected and washed in assay medium.

Subsequently T cells were expanded using the T Cell Activation/Expansion Kit human (Miltenyi Biotec Cat #130-091-441) for 17 days. In brief, anti-Biotin MACSi-Bead™ Particles are loaded with CD2-, CD3-, CD28 Biotin and are transferred to the purified T cells in a ratio of 2 cells per particle and incubated in presence of 20 Units recombinant IL-2 (R&D #202-IL-050/CF) at a density of 0.5-$10^6$ cells/ml for 14 days. Cells were supplemented with 20 Units fresh IL-2 every three days. Three days before injection into the animals, T cells were restimulated with anti-Biotin MACSiBead™ Particles are loaded with CD2-, CD3-, CD28 Biotin at a ratio of 1 bead per 4 cells for additional three days. Finally, beads were removed with a MACSiMAG™ Separator (Miltenyi Biotec) and T cells were washed in PBS.

On day −2, animals were randomized into treatment groups based on tumor volume and $2\times10^7$ human T cells were injected intra-peritoneally (i.p.). B7H6/CD3 binding proteins were produced, as described in Example 2. Treatment was started on day 1 and B7H6/CD3 binding protein or Vehicle buffer (50 mM NaOAc, 100 mM NaCl, pH 5.0) was administered in a q7d dosing regimen by intravenous (i.v.) bolus injections into the lateral tail vein. Tumor growth was monitored by external caliper measurements and tumor volumes were calculated using a standard hemi-ellipsoid formula. Animals reaching sacrifice criteria were euthanized early during the studies for ethical reasons. Treatment of tumor-bearing mice with B7H6/CD3 binding proteins once weekly i.v. at 0.05 mg/kg induced significant tumor regression (FIG. 20).

Example 19A: In Vivo Efficacy

Efficacy studies were performed using a human NCI-H716 xenograft mouse model reconstituted with human $CD3^+$ T cells as described in Example 19. Treatment of tumor-mice with B7H6/CD3 binding proteins comprising a B7H6 chain of SEQ ID NO:228, SEQ ID No 230, SEQ ID NO:231, or SEQ ID NO:232, and a CD3 chain of SEQ ID NO:311 once weekly i.v. at 0.05 mg/kg induced significant tumor regression (FIG. 23).

Example 19B: In Vivo Efficacy

Figure 24:
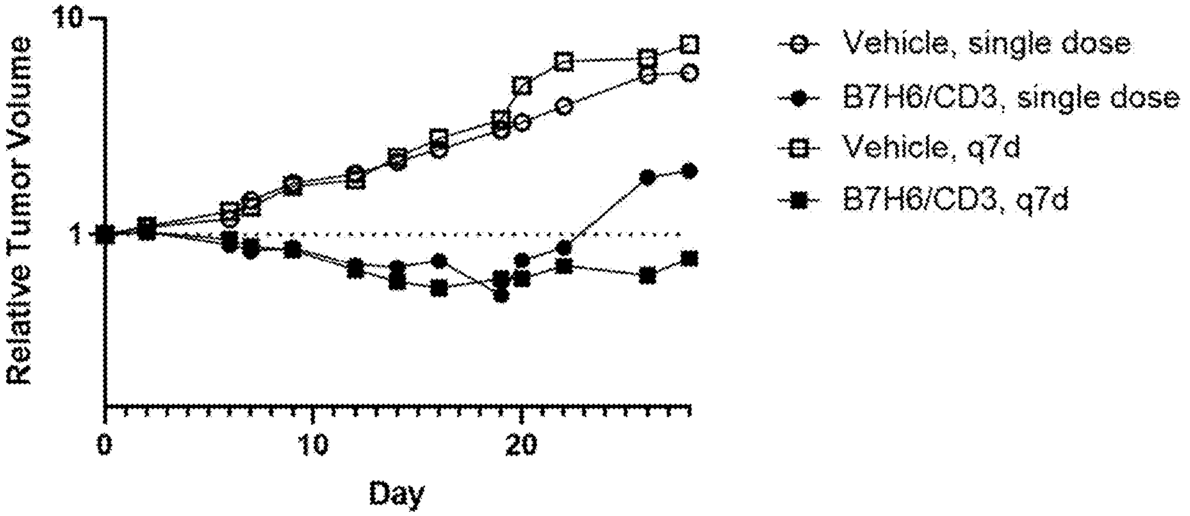
FIG. 24: Anti-tumor activity of an exemplary B7H6/CD3 binding protein in a T-cell engrafted mouse xenograft model administered q7d or as one single dose.

Efficacy studies were performed using a human NCI-H716 xenograft mouse model reconstituted with human $CD3^+$ T cells as described in Example 19. Treatment of tumor-bearing mice with an exemplary B7H6/CD3 binding protein administered once weekly or as a single dose i.v. at 0.05 mg/kg induced significant tumor regression (FIG. 24).

Example 20: Percent Monomer Content of B7H6/CD3 Binding Proteins

Percent monomer was determined for B7H6/CD3 binding proteins (B7H6/CD3 binding proteins comprising a B7H6 chain of SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:225, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and a CD3 chain of SEQ ID NO:311, and B7H6 binding proteins comprising a B7H6 chain of SEQ ID NO:230 or SEQ ID NO:239 and a CD3 chain of SEQ ID NO:312, SEQ ID NO:313, SEQ ID NO:314, SEQ ID NO:315, or SEQ ID NO:316, respectively) by Analytical Size Exclusion Chromatography (aSEC) (shown in Table 6). aSEC was run on a Waters® (Milfrod, Mass., USA) Acquity UPLC® system using a Protein BEH SEC column 200 Å, 1.7 μm, 4.6×150 mm (Cat #186005225). Running conditions were as follows: Mobile phase: 50 mM Sodium Phosphate, 200 mM Arginine and 0.05% Sodium Azide; Flow rate: 0.5 ml/min; Runtime: 5 minutes; Sample loading amount: 10 μg; Peak detection: A280 nm; Automated processing method of chromatograms.

TABLE 6

Percent monomer after first and second purification step

| B7H6 binder | CD3 binder | Percent Monomer after 1st step | Percent Monomer after 2nd step |
|---|---|---|---|
| B7H6#1 | CD3#1 | 70.5 | 98.5 |
| B7H6#2 | CD3#1 | 38.7 | 95.1 |
| B7H6#3 | CD3#1 | 50.1 | 96.6 |
| B7H6#4 | CD3#1 | 56.0 | 99.9 |
| B7H6#5 | CD3#1 | 66.5 | 99.3 |
| B7H6#6 | CD3#1 | 63.7 | 99.1 |
| B7H6#7 | CD3#1 | 43.4 | 97.7 |
| B7H6#8 | CD3#1 | 68.3 | 96.8 |
| B7H6#9 | CD3#1 | 61.3 | 95.7 |
| B7H6#10 | CD3#1 | 66.3 | 97.7 |
| B7H6#11 | CD3#1 | 38.2 | 95.3 |
| B7H6#12 | CD3#1 | 67.4 | 99.9 |
| B7H6#13 | CD3#1 | 61.9 | 99.9 |
| B7H6#14 | CD3#1 | 64.6 | 99.9 |
| B7H6#15 | CD3#1 | 53.8 | 99.9 |
| B7H6#16 | CD3#1 | 52.4 | 99.7 |
| B7H6#17 | CD3#1 | 46.8 | 99.9 |
| B7H6#18 | CD3#1 | 50.1 | 99.8 |
| B7H6#19 | CD3#1 | 64.1 | 99.9 |
| B7H6#20 | CD3#1 | 62.3 | 99.9 |
| B7H6#21 | CD3#1 | 60.4 | 99.9 |
| B7H6#22 | CD3#1 | 57.5 | 99.9 |
| B7H6#23 | CD3#1 | 59.5 | 99.8 |
| B7H6#24 | CD3#1 | 51.7 | 99.9 |
| B7H6#14 | CD3#2 | 71.9 | 99.9 |
| B7H6#14 | CD3#3 | 68.2 | 99.9 |
| B7H6#14 | CD3#4 | 62.2 | 99.6 |
| B7H6#14 | CD3#5 | 76.5 | 99.9 |
| B7H6#14 | CD3#6 | 70.5 | 99.9 |
| B7H6#23 | CD3#2 | 69.8 | 99.8 |
| B7H6#23 | CD3#3 | 67.3 | 99.6 |
| B7H6#23 | CD3#4 | 62.2 | 99.7 |
| B7H6#23 | CD3#5 | 75 | 99.9 |
| B7H6#23 | CD3#6 | 69.6 | 99.9 |

Example 21: Thermostability

Thermostability was determined by Thermal Shift Analysis (TSA) and results of the first melting transitions (Tm1) of B7H6/CD3 binding proteins (B7H6 binding proteins comprising a B7H6 chain of SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and a CD3 chain of SEQ ID NO:311, and B7H6 binding proteins comprising a B7H6 chain of SEQ ID NO:230 or SEQ ID NO:239 and a CD3 chain of SEQ ID NO:312, SEQ ID NO:313, SEQ ID NO:314, SEQ ID NO:315, or SEQ ID NO:316, respectively) are shown in Table 7. The fluorescence intensity profile as a function of temperature was acquired using a QuantStudio™ 6 Flex real-time PCR system (Applied Biosystems, Waltham, Mass.) with SYPRO® Orange protein gel stain (Invitrogen, Carlsbad, Calif.) as the extrinsic fluorophore. Sample was diluted to 0.4 mg/ml in 10 mM histidine, pH 6.0 with 40 mM sodium chloride and 0.02% sodium azide. The melt curve was generated with a thermal ramp from 25° C. to 95° C. at a rate of 2° C./min, with data collected approximately every 0.4° C. through the 'ROX' filter set (Ex: 580±10 nm, Em: 623±14 nm). Data were analyzed using Protein Thermal Shift™ Software Version v1.3 (ThermoFisher Scientific, Waltham, Mass.).

TABLE 7

Thermostability analysis

| B7H6 binder | CD3 binder | Tm1 (° C.) |
|---|---|---|
| B7H6#12 | CD3#1 | 65.3 |
| B7H6#13 | CD3#1 | 65.2 |
| B7H6#14 | CD3#1 | 65.7 |
| B7H6#15 | CD3#1 | 65.4 |
| B7H6#16 | CD3#1 | 65.4 |
| B7H6#17 | CD3#1 | 65.4 |
| B7H6#18 | CD3#1 | 65.0 |
| B7H6#19 | CD3#1 | 64.0 |
| B7H6#20 | CD3#1 | 62.5 |
| B7H6#21 | CD3#1 | 64.9 |
| B7H6#22 | CD3#1 | 58.7 |
| B7H6#23 | CD3#1 | 64.7 |
| B7H6#24 | CD3#1 | 65.3 |
| B7H6#14 | CD3#2 | 61.7 |
| B7H6#14 | CD3#3 | 60.4 |
| B7H6#14 | CD3#4 | 60.3 |
| B7H6#14 | CD3#5 | 61.4 |
| B7H6#14 | CD3#6 | 61.4 |
| B7H6#23 | CD3#2 | 60.1 |
| B7H6#23 | CD3#3 | 64.9 |
| B7H6#23 | CD3#4 | 58.0 |
| B7H6#23 | CD3#5 | 57.9 |
| B7H6#23 | CD3#6 | 57.5 |

Example 22: Predicted Immunogenicity Scores in Silico by Epivax

Immunogenicity of sequences was evaluated in silico with a mathematical algorithm. Specifically, EpiMatrix® Treg-adjusted Scores (EpiVax Inc., Providence R.I.)) as a measure of immunogenicity scores, were determined for B7H6 chains (a B7H6 chain of SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:225, SEQ ID NO:227, SEQ ID NO:228, SEQ ID NO:229, SEQ ID NO:230, SEQ ID NO:231, SEQ ID at NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240) and for CD3 chains (a CD3 chain of SEQ ID NO:311, SEQ ID NO:312, SEQ ID NO:313, SEQ ID NO:314, SEQ ID NO:315, or SEQ ID NO:316) and compared to the scores of various Fc sequences. These scores are taking T-cell epitopes and Treg epitopes into consideration. The lower the immunogenicity score, the less likely a sequence to be immunogenic. In general, a negative score is considered low risk of immunogenicity, while a highly positive score is viewed as indication for potential immunogenicity. As shown in the table 8 and 9 below, exemplary B7H6/CD3 binding proteins described herein have very low immunogenicity scores, indicating that the risk of being immunogenic is low for these binding proteins.

TABLE 8

Adjusted Epivax ® scores of B7H6/CD3 binding proteins

| B7H6 or CD3 binding protein | VH | VL | Full polypeptide chain (VL-CL-linker-VH-CH1-hinge-CH2-CH3) |
|---|---|---|---|
| B7H6#1 B7H6 chain | −9.94 | 17.52 | −29.07 |
| B7H6#2 B7H6 chain | 17.12 | 1.78 | −27.07 |
| B7H6#3 B7H6 chain | 67.70 | 32.77 | −11.61 |
| B7H6#4 B7H6 chain | −20.24 | −6.54 | −34.34 |
| B7H6#5 B7H6 chain | −58.29 | −29.64 | −43.99 |
| B7H6#6 B7H6 chain | 4.77 | −9.90 | −30.99 |
| B7H6#7 B7H6 chain | 16.81 | −13.51 | −28.20 |
| B7H6#8 B7H6 chain | −31.42 | 35.40 | −29.91 |
| B7H6#9 B7H6 chain | −4.61 | −4.44 | −31.45 |
| B7H6#10 B7H6 chain | 10.78 | 3.40 | −26.72 |
| B7H6#11 B7H6 chain | 4.49 | 47.21 | −22.15 |
| B7H6#12 B7H6 chain | −24.63 | −48.50 | −39.76 |
| B7H6#13 B7H6 chain | −19.87 | −48.50 | −39.00 |
| B7H6#14 B7H6 chain | −23.93 | −48.50 | −39.65 |
| B7H6#15 B7H6 chain | −19.71 | −48.50 | −38.98 |
| B7H6#16 B7H6 chain | −17.72 | −48.50 | −38.66 |
| B7H6#17 B7H6 chain | −19.71 | −48.50 | −38.98 |
| B7H6#18 B7H6 chain | −19.71 | −50.41 | −39.25 |
| B7H6#19 B7H6 chain | −22.64 | −48.50 | −39.44 |
| B7H6#20 B7H6 chain | −24.63 | −50.41 | −40.03 |
| B7H6#21 B7H6 chain | −21.94 | −48.50 | −39.33 |
| B7H6#22 B7H6 chain | −23.93 | −50.41 | −39.92 |
| B7H6#23 B7H6 chain | −21.94 | −50.41 | −39.61 |
| B7H6#24 B7H6 chain | −19.71 | −50.41 | −39.25 |
| CD3#1 CD3 chain | −9.68 | −50.52 | −35.25 |
| CD3#2 CD3 chain | −40.29 | −8.95 | −33.62 |
| CD3#3 CD3 chain | −41.48 | −4.54 | −33.15 |
| CD3#4 CD3 chain | −39.06 | −4.54 | −32.77 |
| CD3#5 CD3 chain | −55.51 | −14.24 | −36.83 |
| CD3#6 CD3 chain | −41.48 | −14.24 | −34.60 |

TABLE 9

Adjusted Epivax ® scores of Fc domains

| Fc Protein Chain | Adjusted Epivax score |
|---|---|
| Fc-IgG1-WT | −25.64 |
| Fc-IgG1-LALA | −29.83 |
| Fc-IgG1-LALA-KNOB | −31.76 |
| Fc-IgG1-LALA-HOLE | −18.01 |

Example 23: Non-Specific Binding to Surfaces

The specificity of the B7H6/CD3 binding proteins of the invention was further tested in an surface plasmon resonance (SPR)-based assay using highly charged proteins. A non-specific binding assay was developed using biosensor technology to determine if binding proteins have significant binding to unrelated charged proteins. In this assay, B7H6/CD3 binding proteins were passed over two SPR surfaces, one coated with a negatively charged protein (Trypsin Inhibitor) and one coated with a positively charged protein (Lysozyme). When a protein displays significant non-specific binding to these surfaces, it is likely that the cause of binding is the presence of positive or negative charged surface patches on the candidate. Non-specific binding of proteins may translate to poor pharmacokinetics (PK) and biodistribution and may also have downstream manufacturability impacts.

The experiment was performed on a Biacore® T200 SPR system (GE Healthcare Life Sciences). The dilution, surface preparation, and binding experiments were performed at 25° C. in 1×HBS-EP buffer prepared from 10×HBS-EP. The flow rate for both the immobilization protocol and binding experiment was at 5 μL/min.

To prepare the surface for the non-specific binding experiment, chicken egg white lysozyme and trypsin inhibitor from *Glycine max* soybean were coupled manually to a Biacore® series S CM5 sensor chip (GE Healthcare sciences) with the surface density of 3000-5000 RU using the amine coupling kit according to the manufacture instructions. Samples were prepared at 1 μM in 1×HBS-EP buffer. The samples were injected over activated surfaces with a 10 min association and 15 min dissociation. The data was collected using Biacore® T200 Control Software version 2.0.1 and analyzed using Biacore® T200 Evaluation Software version 3.0 (GE Healthcare Life Sciences).

Table 10 shows no or very low binding to the two highly charged proteins, Trypsin Inhibitor and Lysozyme, of exemplary B7H6/CD3 binding proteins (B7H6 binding proteins comprising a B7H6 chain of SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, or SEQ ID NO:240 and a CD3 chain of SEQ ID NO:311, and B7H6 binding proteins comprising a B7H6 chain of SEQ ID NO:230 or SEQ ID NO:239 and a CD3 chain of SEQ ID NO:312, SEQ ID NO:313, SEQ ID NO:314, SEQ ID NO:315, or SEQ ID NO:316, respectively).

TABLE 10:

Low RU numbers indicate no significant binding to unrelated charged proteins

| B7H6 binder | CD3 binder | Non-specific binding (RU), Lysozyme (positive) | Non-specific binding (RU), Tryp Inhibitor (negative) |
|---|---|---|---|
| B7H6#12 | CD3#1 | 9.2 | 35.4 |
| B7H6#13 | CD3#1 | 7.2 | 30.6 |
| B7H6#14 | CD3#1 | 8.1 | 32.7 |
| B7H6#15 | CD3#1 | 7.2 | 32.8 |
| B7H6#16 | CD3#1 | 8.2 | 42.6 |
| B7H6#17 | CD3#1 | 15.3 | 88.4 |
| B7H6#18 | CD3#1 | 6.6 | 32.8 |
| B7H6#19 | CD3#1 | 8.2 | 40.3 |
| B7H6#20 | CD3#1 | 9.8 | 48.4 |
| B7H6#21 | CD3#1 | 8.1 | 42 |
| B7H6#22 | CD3#1 | 7.8 | 39.5 |
| B7H6#23 | CD3#1 | 8.1 | 45.7 |
| B7H6#24 | CD3#1 | 7.9 | 43.5 |
| B7H6#14 | CD3#2 | 11.2 | 12.2 |
| B7H6#14 | CD3#3 | 12.4 | 26.4 |
| B7H6#14 | CD3#4 | 8.8 | 22.6 |
| B7H6#14 | CD3#5 | 16.2 | 109.6 |
| B7H6#14 | CD3#6 | 15.7 | 34 |
| B7H6#23 | CD3#2 | 37.8 | 47.8 |
| B7H6#23 | CD3#3 | 18.9 | 38.7 |
| B7H6#23 | CD3#4 | 6.8 | 20.7 |
| B7H6#23 | CD3#5 | 15 | 114.7 |
| B7H6#23 | CD3#6 | 57.2 | 96.5 |

Figure 21:
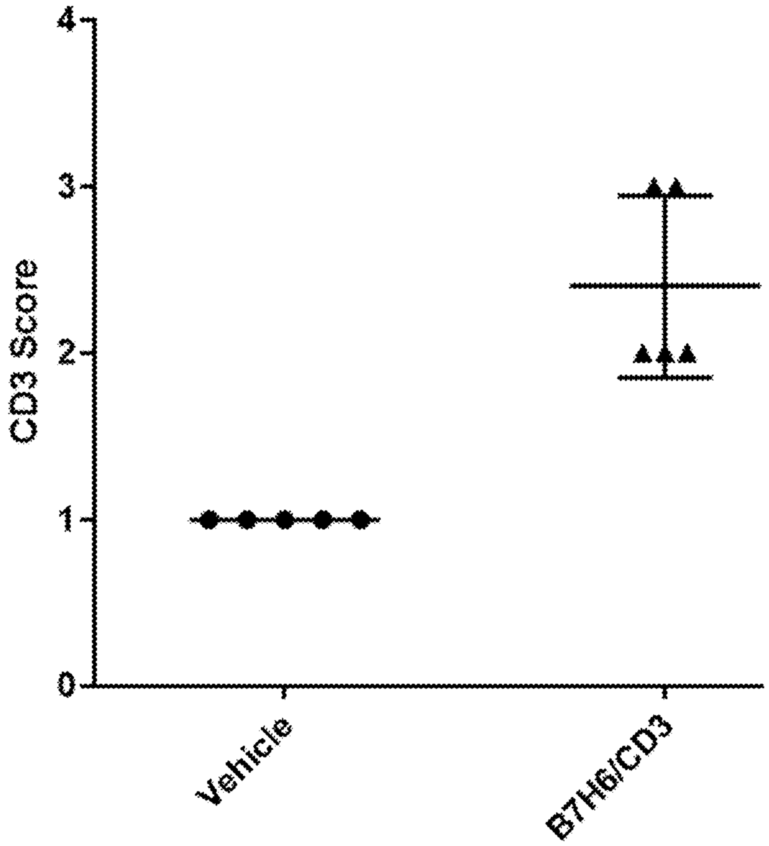
FIG. 21: T cell infiltration in NCI-H716 xenograft tumor tissue with an exemplary B7H6/CD3 binding protein.

Example 24: T Cell Infiltration in SHP77 Xenograft Tumor Tissue with an Exemplary B7H6/CD3 Binding Protein Remaining tumor tissues from mice in the study described in Example 19 were prepared, fixed in formalin and embedded in paraffin. Subsequently tissue sections were prepared and stained for CD3 expression on T cells (anti-CD3 (2GV6), Ventana Medical Systems). T cell infiltration in NCI-H716 xenograft tumor tissue with an exemplary B7H6/CD3 binding protein is shown in FIG. 21. The scoring in Table 11 was used to quantify CD3 expression in xenograft tumor tissues.

TABLE 11

Scoring for quantification of infiltrating CD3-positive T cells

| Score | Description |
|---|---|
| 0 | <5 CD3-positive T-cells per HPF (high-power field) |
| 1 | 5-99 CD3-positive T-cells per HPF (high-power field) |
| 2 | 100-200 CD3-positive T-cells per HPF (high-power field) |
| 3 | >300 CD3-positive T-cells per HPF (high-power field) |

Example 25: Pharmaceutical Formulation for i.v. Administration

Any of the above binding proteins/molecules of the invention can be selected for the manufacture of a pharmaceutical formulation for i.v. application. An example of a suitable pharmaceutical formulation for the antibody of the invention is as follows.

A 10 mL vial contains 10 mg/mL of the B7H6/CD3 binding molecule/protein of the invention, in a buffer comprising histidine, trehalose, polysorbate 20 and water for injection.

The invention claimed is:

1. A protein comprising a first antigen binding unit specifically binding to B7H6 and a second antigen binding unit specifically binding to CD3, wherein said first antigen binding unit specifically binding to B7H6 is selected from the group consisting of i) to xxiv):

i) an antigen binding unit comprising light chain CDRs comprising the amino acid sequences of SEQ ID NO:1 (CDR1), SEQ ID NO:2 (CDR2) and SEQ ID NO:3 (CDR3) and heavy chain CDRs comprising the amino acid sequences of SEQ ID NO:4 (CDR1), SEQ ID NO:5 (CDR2) and SEQ ID NO:6 (CDR3);

ii) an antigen binding unit comprising light chain CDRs comprising the amino acid sequences of SEQ ID NO:7 (CDR1), SEQ ID NO:8 (CDR2) and SEQ ID NO:9 (CDR3) and heavy chain CDRs comprising the amino acid sequences of SEQ ID NO:10 (CDR1), SEQ ID NO:11 (CDR2) and SEQ ID NO:12 (CDR3);

iii) an antigen binding unit comprising light chain CDRs comprising the amino acid sequences of SEQ ID NO:13 (CDR1), SEQ ID NO:14 (CDR2) and SEQ ID NO:15 (CDR3) and heavy chain CDRs comprising the amino acid sequences of SEQ ID NO:16 (CDR1), SEQ ID NO:17 (CDR2) and SEQ ID NO:18 (CDR3);

iv) an antigen binding unit comprising light chain CDRs comprising the amino acid sequences of SEQ ID NO:19 (CDR1), SEQ ID NO:20 (CDR2) and SEQ ID NO:21 (CDR3) and heavy chain CDRs comprising the amino acid sequences of SEQ ID NO:22 (CDR1), SEQ ID NO:23 (CDR2) and SEQ ID NO:24 (CDR3);

v) an antigen binding unit comprising light chain CDRs comprising the amino acid sequences of SEQ ID NO:25 (CDR1), SEQ ID NO:26 (CDR2) and SEQ ID NO:27 (CDR3) and heavy chain CDRs comprising the amino acid sequences of SEQ ID NO:28 (CDR1), SEQ ID NO:29 (CDR2) and SEQ ID NO:30 (CDR3);

vi) an antigen binding unit comprising light chain CDRs comprising the amino acid sequences of SEQ ID NO:31 (CDR1), SEQ ID NO:32 (CDR2) and SEQ ID NO:33 (CDR3) and heavy chain CDRs comprising the amino acid sequences of SEQ ID NO:34 (CDR1), SEQ ID NO:35 (CDR2) and SEQ ID NO:36 (CDR3);

vii) an antigen binding unit comprising light chain CDRs comprising the amino acid sequences of SEQ ID NO:37 (CDR1), SEQ ID NO:38 (CDR2) and SEQ ID NO:39 (CDR3) and heavy chain CDRs comprising the amino acid sequences of SEQ ID NO:40 (CDR1), SEQ ID NO:41 (CDR2) and SEQ ID NO:42 (CDR3);

viii) an antigen binding unit comprising light chain CDRs comprising the amino acid sequences of SEQ ID NO:43 (CDR1), SEQ ID NO:44 (CDR2) and SEQ ID NO:45 (CDR3) and heavy chain CDRs comprising the amino acid sequences of SEQ ID NO:46 (CDR1), SEQ ID NO:47 (CDR2) and SEQ ID NO:48 (CDR3);

ix) an antigen binding unit comprising light chain CDRs comprising the amino acid sequences of SEQ ID NO:49 (CDR1), SEQ ID NO:50 (CDR2) and SEQ ID NO:51 (CDR3) and heavy chain CDRs comprising the amino acid sequences of SEQ ID NO:52 (CDR1), SEQ ID NO:53 (CDR2) and SEQ ID NO:54 (CDR3);

x) an antigen binding unit comprising light chain CDRs comprising the amino acid sequences of SEQ ID NO:55 (CDR1), SEQ ID NO:56 (CDR2) and SEQ ID NO:57 (CDR3) and heavy chain CDRs comprising the amino acid sequences of SEQ ID NO:58 (CDR1), SEQ ID NO:59 (CDR2) and SEQ ID NO:60 (CDR3);

xi) an antigen binding unit comprising light chain CDRs comprising the amino acid sequences of SEQ ID NO:61 (CDR1), SEQ ID NO:62 (CDR2) and SEQ ID NO:63 (CDR3) and heavy chain CDRs comprising the amino acid sequences of SEQ ID NO:64 (CDR1), SEQ ID NO:65 (CDR2) and SEQ ID NO:66 (CDR3);

xii) an antigen binding unit comprising light chain CDRs comprising the amino acid sequences of SEQ ID NO:67 (CDR1), SEQ ID NO:68 (CDR2) and SEQ ID NO:69 (CDR3) and heavy chain CDRs comprising the amino acid sequences of SEQ ID NO:70 (CDR1), SEQ ID NO:71 (CDR2) and SEQ ID NO:72 (CDR3);

xiii) an antigen binding unit comprising light chain CDRs comprising the amino acid sequences of SEQ ID NO:73 (CDR1), SEQ ID NO:74 (CDR2) and SEQ ID NO:75 (CDR3) and heavy chain CDRs comprising the amino acid sequences of SEQ ID NO:76 (CDR1), SEQ ID NO:77 (CDR2) and SEQ ID NO:78 (CDR3);

xiv) an antigen binding unit comprising light chain CDRs comprising the amino acid sequences of SEQ ID NO:79 (CDR1), SEQ ID NO:80 (CDR2) and SEQ ID NO:81 (CDR3) and heavy chain CDRs comprising the amino acid sequences of SEQ ID NO:82 (CDR1), SEQ ID NO:83 (CDR2) and SEQ ID NO:84 (CDR3);

xv) an antigen binding unit comprising light chain CDRs comprising the amino acid sequences of SEQ ID NO:85 (CDR1), SEQ ID NO:86 (CDR2) and SEQ ID NO:87 (CDR3) and heavy chain CDRs comprising the amino acid sequences of SEQ ID NO:88 (CDR1), SEQ ID NO:89 (CDR2) and SEQ ID NO:90 (CDR3);

xvi) an antigen binding unit comprising light chain CDRs comprising the amino acid sequences of SEQ ID NO:91 (CDR1), SEQ ID NO:92 (CDR2) and SEQ ID NO:93 (CDR3) and heavy chain CDRs comprising the amino acid sequences of SEQ ID NO:94 (CDR1), SEQ ID NO:95 (CDR2) and SEQ ID NO:96 (CDR3);

xvii) an antigen binding unit comprising light chain CDRs comprising the amino acid sequences of SEQ ID NO:97 (CDR1), SEQ ID NO:98 (CDR2) and SEQ ID NO:99 (CDR3) and heavy chain CDRs comprising the amino acid sequences of SEQ ID NO:100 (CDR1), SEQ ID NO:101 (CDR2) and SEQ ID NO:102 (CDR3);

xviii) an antigen binding unit comprising light chain CDRs comprising the amino acid sequences of SEQ ID NO:103 (CDR1), SEQ ID NO:104 (CDR2) and SEQ ID NO:105 (CDR3) and heavy chain CDRs comprising the amino acid sequences of SEQ ID NO:106 (CDR1), SEQ ID NO:107 (CDR2) and SEQ ID NO:108 (CDR3);

xix) an antigen binding unit comprising light chain CDRs comprising the amino acid sequences of SEQ ID NO:109 (CDR1), SEQ ID NO:110 (CDR2) and SEQ ID NO:111 (CDR3) and heavy chain CDRs comprising the amino acid sequences of SEQ ID NO:112 (CDR1), SEQ ID NO:113 (CDR2) and SEQ ID NO:114 (CDR3);

xx) an antigen binding unit comprising light chain CDRs comprising the amino acid sequences of SEQ ID NO:115 (CDR1), SEQ ID NO:116 (CDR2) and SEQ ID NO:117 (CDR3) and heavy chain CDRs comprising the amino acid sequences of SEQ ID NO:118 (CDR1), SEQ ID NO:119 (CDR2) and SEQ ID NO:120 (CDR3);

xxi) an antigen binding unit comprising light chain CDRs comprising the amino acid sequences of SEQ ID NO:121 (CDR1), SEQ ID NO:122 (CDR2) and SEQ ID NO:123 (CDR3) and heavy chain CDRs comprising the amino acid sequences of SEQ ID NO:124 (CDR1), SEQ ID NO:125 (CDR2) and SEQ ID NO:126 (CDR3);

xxii) an antigen binding unit comprising light chain CDRs comprising the amino acid sequences of SEQ ID NO:127 (CDR1), SEQ ID NO:128 (CDR2) and SEQ ID NO:129 (CDR3) and heavy chain CDRs comprising the amino acid sequences of SEQ ID NO:130 (CDR1), SEQ ID NO:131 (CDR2) and SEQ ID NO:132 (CDR3);

xxiii) an antigen binding unit comprising light chain CDRs comprising the amino acid sequences of SEQ ID NO:133 (CDR1), SEQ ID NO:134 (CDR2) and SEQ ID NO:135 (CDR3) and heavy chain CDRs comprising the amino acid sequences of SEQ ID NO:136 (CDR1), SEQ ID NO:137 (CDR2) and SEQ ID NO:138 (CDR3); and xxiv) an antigen binding unit comprising light chain CDRs comprising the amino acid sequences of SEQ ID NO:139 (CDR1), SEQ ID NO:140 (CDR2) and SEQ ID NO:141 (CDR3) and heavy chain CDRs comprising the amino acid sequences of SEQ ID NO:142 (CDR1), SEQ ID NO:143 (CDR2) and SEQ ID NO:144 (CDR3).

2. The protein of claim 1, wherein said first antigen binding unit specifically binding to B7H6 is selected from the group consisting of i) to xxiv):

i) a light chain variable domain comprising the amino acid sequence of SEQ ID NO:145 and heavy chain variable domain comprising the amino acid sequence of SEQ ID NO:146;

ii) a light chain variable domain comprising the amino acid sequences of SEQ ID NO:147 and heavy chain variable domain comprising the amino acid sequences of SEQ ID NO:148;

iii) a light chain variable domain comprising the amino acid sequence of SEQ ID NO:149 and heavy chain variable domain comprising the amino acid sequence of SEQ ID NO:150;

iv) a light chain variable domain comprising the amino acid sequence of SEQ ID NO:151 and heavy chain variable domain comprising the amino acid sequence of SEQ ID NO:152;

v) a light chain variable domain comprising the amino acid sequence of SEQ ID NO:153 and heavy chain variable domain comprising the amino acid sequence of SEQ ID NO:154;

vi) a light chain variable domain comprising the amino acid sequence of SEQ ID NO:155 and heavy chain variable domain comprising the amino acid sequence of SEQ ID NO:156;

vii) a light chain variable domain comprising the amino acid sequence of SEQ ID NO:157 and heavy chain variable domain comprising the amino acid sequence of SEQ ID NO:158;

viii) a light chain variable domain comprising the amino acid sequence of SEQ ID NO:159 and heavy chain variable domain comprising the amino acid sequence of SEQ ID NO:160;

ix) a light chain variable domain comprising the amino acid sequence of SEQ ID NO:161 and heavy chain variable domain comprising the amino acid sequence of SEQ ID NO:162;

x) a light chain variable domain comprising the amino acid sequence of SEQ ID NO:163 and heavy chain variable domain comprising the amino acid sequence of SEQ ID NO:164;

xi) a light chain variable domain comprising the amino acid sequence of SEQ ID NO:165 and heavy chain variable domain comprising the amino acid sequence of SEQ ID NO:166;

xii) a light chain variable domain comprising the amino acid sequence of SEQ ID NO:167 and heavy chain variable domain comprising the amino acid sequence of SEQ ID NO:168;

xiii) a light chain variable domain comprising the amino acid sequence of SEQ ID NO:169 and heavy chain variable domain comprising the amino acid sequence of SEQ ID NO:170;

xiv) a light chain variable domain comprising the amino acid sequence of SEQ ID NO:171 and heavy chain variable domain comprising the amino acid sequence of SEQ ID NO:172;

xv) a light chain variable domain comprising the amino acid sequence of SEQ ID NO:173 and heavy chain variable domain comprising the amino acid sequence of SEQ ID NO:174;

xvi) a light chain variable domain comprising the amino acid sequence of SEQ ID NO:175 and heavy chain variable domain comprising the amino acid sequence of SEQ ID NO:176;

xvii) a light chain variable domain comprising the amino acid sequence of SEQ ID NO:177 and heavy chain variable domain comprising the amino acid sequence of SEQ ID NO:178;

xviii) a light chain variable domain comprising the amino acid sequence of SEQ ID NO:179 and heavy chain variable domain comprising the amino acid sequence of SEQ ID NO:180;

xix) a light chain variable domain comprising the amino acid sequence of SEQ ID NO:181 and heavy chain variable domain comprising the amino acid sequence of SEQ ID NO:182;

xx) a light chain variable domain comprising the amino acid sequence of SEQ ID NO:183 and heavy chain variable domain comprising the amino acid sequence of SEQ ID NO:184;

xxi) a light chain variable domain comprising the amino acid sequence of SEQ ID NO:185 and heavy chain variable domain comprising the amino acid sequence of SEQ ID NO:186;

xxii) a light chain variable domain comprising the amino acid sequence of SEQ ID NO:187 and heavy chain variable domain comprising the amino acid sequence of SEQ ID NO:188;

xxiii) a light chain variable domain comprising the amino acid sequence of SEQ ID NO:189 and heavy chain variable domain comprising the amino acid sequence of SEQ ID NO:190; and xxiv) a light chain variable domain comprising the amino acid sequence of SEQ ID NO:191 and heavy chain variable domain comprising the amino acid sequence of SEQ ID NO:192.

3. The protein of claim 1, wherein said second antigen binding unit specifically binding to CD3 is selected from the group consisting of i)-vi):

i) an antigen binding unit comprising light chain CDRs comprising the amino acid sequences of SEQ ID NO:257 (CDR1), SEQ ID NO:258 (CDR2) and SEQ ID NO:259 (CDR3) and heavy chain CDRs comprising the amino acid sequences of SEQ ID NO:260 (CDR1), SEQ ID NO:261 (CDR2) and SEQ ID NO:262 (CDR3);

ii) an antigen binding unit comprising light chain CDRs comprising the amino acid sequences of SEQ ID NO:263 (CDR1), SEQ ID NO:264 (CDR2) and SEQ ID NO:265 (CDR3) and heavy chain CDRs comprising the amino acid sequences of SEQ ID NO:266 (CDR1), SEQ ID NO:267 (CDR2) and SEQ ID NO:268 (CDR3);

iii) an antigen binding unit comprising light chain CDRs comprising the amino acid sequences of SEQ ID NO:269 (CDR1), SEQ ID NO:270 (CDR2) and SEQ ID NO:271 (CDR3) and heavy chain CDRs comprising the amino acid sequences of SEQ ID NO:272 (CDR1), SEQ ID NO:273 (CDR2) and SEQ ID NO:274 (CDR3);

iv) an antigen binding unit comprising light chain CDRs comprising the amino acid sequences of SEQ ID NO:275 (CDR1), SEQ ID NO:276 (CDR2) and SEQ ID NO:277 (CDR3) and heavy chain CDRs comprising the amino acid sequences of SEQ ID NO:278 (CDR1), SEQ ID NO:279 (CDR2) and SEQ ID NO:280 (CDR3);

v) an antigen binding unit comprising light chain CDRs comprising the amino acid sequences of SEQ ID NO:281 (CDR1), SEQ ID NO:282 (CDR2) and SEQ ID NO:283 (CDR3) and heavy chain CDRs comprising the amino acid sequences of SEQ ID NO:284 (CDR1), SEQ ID NO:285 (CDR2) and SEQ ID NO:286 (CDR3); and vi) an antigen binding unit comprising light chain CDRs comprising the amino acid sequences of SEQ ID NO:287 (CDR1), SEQ ID NO:288 (CDR2) and SEQ ID NO:289 (CDR3) and heavy chain CDRs comprising the amino acid sequences of SEQ ID NO:290 (CDR1), SEQ ID NO:291 (CDR2) and SEQ ID NO:292 (CDR3).

4. The protein of claim 1, wherein said second antigen binding unit specifically binding to CD3 is selected from the group consisting of i) to vi):

i) a light chain variable domain comprising the amino acid sequence of SEQ ID NO:293 and a heavy chain variable domain comprising the amino acid sequence of SEQ ID NO:294;

ii) a light chain variable domain comprising the amino acid sequence of SEQ ID NO:295 and a heavy chain variable domain comprising the amino acid sequence of SEQ ID NO:296;

iii) a light chain variable domain comprising the amino acid sequence of SEQ ID NO:297 and a heavy chain variable domain comprising the amino acid sequence of SEQ ID NO:298;

iv) a light chain variable domain comprising the amino acid sequence of SEQ ID NO:299 and a heavy chain variable domain comprising the amino acid sequence of SEQ ID NO:300;

v) a light chain variable domain comprising the amino acid sequence of SEQ ID NO:301 and a heavy chain variable domain comprising the amino acid sequence of SEQ ID NO:302; and vi) a light chain variable domain comprising the amino acid sequence of SEQ ID NO:303 and a heavy chain variable domain comprising the amino acid sequence of SEQ ID NO:304.

5. The protein of claim 1, wherein i) said first antigen binding unit specifically binding to B7H6 comprises from its N- to C-terminus a first light chain variable domain, a first light chain constant domain, a first peptide linker, a first heavy chain variable domain and a first heavy chain constant CH1 domain; and ii) said second antigen binding unit specifically binding to CD3 comprises from its N- to C-terminus a second light chain variable domain, a second light chain constant domain, a second peptide linker, a second heavy chain variable domain and a second heavy chain constant CH1 domain.

6. The protein of claim 5, wherein i) said first antigen binding unit comprises light chain CDRs comprising the amino acid sequences of SEQ ID NO:67 (CDR1), SEQ ID NO:68 (CDR2) and SEQ ID NO:69 (CDR3) and heavy chain CDRs comprising the amino acid sequences of SEQ ID NO:70 (CDR1), SEQ ID NO:71 (CDR2) and SEQ ID NO:72 (CDR3), and said second antigen binding unit comprises light chain CDRs comprising the amino acid sequences of SEQ ID NO:257 (CDR1), SEQ ID NO:258 (CDR2) and SEQ ID NO:259 (CDR3) and heavy chain CDRs comprising the amino acid sequences of SEQ ID NO:260 (CDR1), SEQ ID NO:261 (CDR2) and SEQ ID NO:262 (CDR3); or ii) said first antigen binding unit comprises light chain CDRs comprising the amino acid sequences of SEQ ID NO:79 (CDR1), SEQ ID NO:80 (CDR2) and SEQ ID NO:81 (CDR3) and heavy chain CDRs comprising the amino acid sequences of SEQ ID NO:82 (CDR1), SEQ ID NO:83 (CDR2) and SEQ ID NO:84 (CDR3) and said second antigen binding unit comprises light chain CDRs comprising the amino acid sequences of SEQ ID NO:257 (CDR1), SEQ ID NO:258 (CDR2) and SEQ ID NO:259 (CDR3) and heavy chain CDRs comprising the amino acid sequences of SEQ ID NO:260 (CDR1), SEQ ID NO:261 (CDR2) and SEQ ID NO:262 (CDR3); or iii) said first antigen binding unit comprises light chain CDRs comprising the amino acid sequences of SEQ ID NO:85 (CDR1), SEQ ID NO:86 (CDR2) and SEQ ID NO:87 (CDR3) and heavy chain CDRs comprising the amino acid sequences of SEQ ID NO:88 (CDR1), SEQ ID NO:89 (CDR2) and SEQ ID NO:90 (CDR3) and said second antigen binding unit comprises light chain CDRs comprising the amino acid sequences of SEQ ID NO:257 (CDR1), SEQ ID NO:258 (CDR2) and SEQ ID NO:259 (CDR3) and heavy chain CDRs comprising the amino acid sequences of SEQ ID NO:260 (CDR1), SEQ ID NO:261 (CDR2) and SEQ ID NO:262 (CDR3); or iv) said first antigen binding unit comprises light chain CDRs comprising the amino acid sequences of SEQ ID NO:91 (CDR1), SEQ ID NO:92 (CDR2) and SEQ ID NO:93 (CDR3) and heavy chain CDRs comprising the amino acid sequences of SEQ ID NO:94 (CDR1), SEQ ID NO:95 (CDR2) and SEQ ID NO:96 (CDR3) and said second antigen binding unit comprises light chain CDRs comprising the amino acid sequences of SEQ ID NO:257 (CDR1), SEQ ID NO:258 (CDR2) and SEQ ID NO:259 (CDR3) and heavy chain CDRs comprising the amino acid sequences of SEQ ID NO:260 (CDR1), SEQ ID NO:261 (CDR2) and SEQ ID NO:262 (CDR3).

7. The protein of claim 5, wherein i) said first antigen binding unit comprises a light chain variable domain comprising the amino acid sequence of SEQ ID NO:167 and a heavy chain variable domain comprising the amino acid sequence of SEQ ID NO:168, and said second antigen binding unit comprises a light chain variable domain comprising the amino acid sequence of SEQ ID NO:293 and a heavy chain variable domain comprising the amino acid sequence of SEQ ID NO:294; or ii) said first antigen binding unit comprises a light chain variable domain comprising the amino acid sequence of SEQ ID NO:171 and a heavy chain variable domain comprising the amino acid sequence of SEQ ID NO:172, and said second antigen binding unit comprises a light chain variable domain comprising the amino acid sequence of SEQ ID NO:293 and a heavy chain variable domain comprising the amino acid sequence of SEQ ID NO:294; or iii) said first antigen binding unit comprises a light chain variable domain comprising the amino acid sequence of SEQ ID NO:173 and a heavy chain variable domain comprising the amino acid sequence of SEQ ID NO:174, and said second antigen binding unit comprises a light chain variable domain comprising the amino acid sequence of SEQ ID NO:293 and a heavy chain variable domain comprising the amino acid sequence of SEQ ID NO:294; or iv) said first antigen binding unit comprises a light chain variable domain comprising the amino acid sequence of SEQ ID NO:175 and a heavy chain variable domain comprising the amino acid sequence of SEQ ID NO:176, and said second antigen binding unit comprises a light chain variable domain comprising the amino acid sequence of SEQ ID NO:293 and a heavy chain variable domain comprising the amino acid sequence of SEQ ID NO:294.

8. The protein of claim 5, wherein said first and/or second peptide linker is selected from any one of the linkers in the group consisting of: a peptide linker comprising 26 to 42 amino acids, a peptide linker comprising 30 to 40 amino acids, a peptide linker comprising 34 to 40 amino acids, a peptide linker comprising 36 to 39 amino acids, and a peptide linker comprising 38 amino acids.

9. The protein of claim 5, wherein at least one of said first linker and/or second linker is a Gly-Ser linker, comprising the amino acid sequence of SEQ ID NO:250.

10. The protein of claim 5, wherein the first light chain constant domain and the second light chain constant domain comprise a human kappa or lambda domain.

11. The protein of claim 5, wherein said first antigen binding unit specific for B7H6 comprises an amino acid sequence selected from the group consisting of SEQ ID NO:193, SEQ ID NO:194, SEQ ID NO:195, SEQ ID NO:196 SEQ ID NO:197 SEQ ID NO:198 SEQ ID NO:199 SEQ ID NO:200 SEQ ID NO:201 SEQ ID NO:202 SEQ ID NO:203 SEQ ID NO:204 SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, and SEQ ID NO:216 and said second antigen binding unit specific for CD3 comprises an amino acid sequence selected from the group consisting of SEQ ID NO:305, SEQ ID NO:306, SEQ ID NO:307, SEQ ID NO:308, SEQ ID NO:309, and SEQ ID NO:310.

12. The protein of claim 11, wherein (i) said first antigen binding unit specific for B7H6 comprises an amino acid sequence of SEQ ID NO: 204 and said second antigen binding unit specific for CD3 comprises an amino acid sequence of SEQ ID NO:305; or (ii) said first antigen binding unit specific for B7H6 comprises an amino acid sequence of SEQ ID NO: 206 and said second antigen binding unit specific for CD3 comprises an amino acid sequence of SEQ ID NO.305;

(iii) said first antigen binding unit specific for B7H6 comprises an amino acid sequence of SEQ ID NO: 207 and said second antigen binding unit specific for CD3 comprises an amino acid sequence of SEQ ID NO.305; or (iv) said first antigen binding unit specific for B7H6 comprises an amino acid sequence of SEQ ID NO: 208 and said second antigen binding unit specific for CD3 comprises an amino acid sequence of SEQ ID NO.305.

13. The protein of claim 5, further comprising a first and a second Fc domain, said first Fc domain being covalently linked to said first antigen binding unit.

14. The protein of claim 13, wherein i) said first Fc domain comprises a tyrosine (Y) at position 366 [T366Y], and said second Fc domain comprises a threonine (T) at position 407 [Y407T], or ii) said first Fc domain comprises a tryptophan (W) at position 366 [T366W], and said second Fc domain comprises a serine (S) at position 366 [T366S], an alanine (A) at position 368 [L368A] and a valine (V) at position 407 [Y407V], or iii) said second Fc domain comprises a tyrosine (Y) at position 366 [T366Y], and said first Fc domain comprises a threonine (T) at position 407 [Y407T], or iv) said second Fc domain comprises a tryptophan (W) at position 366 [T366W], and said first Fc domain comprises a serine (S) at position 366 [T366S], an alanine (A) at position 368 [L368A] and a valine (V) at position 407 [Y407V].

15. The protein of claim 13, wherein said first and/or said second Fc domain comprises an alanine at position 234 [L234A] and at position 235 [L235A].

16. The protein of claim 5, comprising a first polypeptide chain specifically binding to B7H6 comprising an amino acid sequence selected from the group consisting of SEQ ID NO:217, SEQ ID NO:218, SEQ ID NO:219, SEQ ID NO:220, SEQ ID NO:221, SEQ ID NO:222, SEQ ID NO:223, SEQ ID NO; 224, SEQ ID NO:225, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, and SEQ ID NO:240 and a second polypeptide chain specifically binding to CD3 comprising the amino acid sequence selected from the group consisting of SEQ ID NO:311, SEQ ID NO:312, SEQ ID NO:313, SEQ ID NO:314, SEQ ID NO:315, and SEQ ID NO:316.

17. The protein of claim 16, wherein (i) said first polypeptide chain specifically binding to B7H6 comprises an amino acid sequence of SEQ ID NO: 228 and said second polypeptide chain specifically binding to CD3 comprises and amino acid sequence of SEQ ID NO:311; or (ii) said first polypeptide chain specifically binding to B7H6 comprises an amino acid sequence of SEQ ID NO: 230 and said second polypeptide chain specifically binding to CD3 comprises and amino acid sequence of SEQ ID NO:311, or (iii) said first polypeptide chain specifically binding to B7H6 comprises an amino acid sequence of SEQ ID NO: 231 and said second polypeptide chain specifically binding to CD3 comprises and amino acid sequence of SEQ ID NO:311; or (iv) said first polypeptide chain specifically binding to B7H6 comprises an amino acid sequence of SEQ ID NO: 232 and said second polypeptide chain specifically binding to CD3 comprises and amino acid sequence of SEQ ID NO:311.

18. The protein of claim 16, wherein said first and said second polypeptide chain are linked via disulfide bonds forming a bispecific, bivalent and heterodimeric protein.

19. A pharmaceutical composition comprising the protein of claim 1 and a pharmaceutically acceptable carrier.

20. An anti-B7H6 antibody molecule comprising i) light chain CDRs comprising the amino acid sequences of SEQ ID NO:1 (CDR1), SEQ ID NO:2 (CDR2) and SEQ ID NO:3 (CDR3) and heavy chain CDRs comprising the amino acid sequences of SEQ ID NO:4 (CDR1), SEQ ID NO:5 (CDR2) and SEQ ID NO:6 (CDR3); or ii) light chain CDRs comprising the amino acid sequences of SEQ ID NO:7 (CDR1), SEQ ID NO:8 (CDR2) and SEQ ID NO:9 (CDR3) and heavy chain CDRs comprising the amino acid sequences of SEQ ID NO:10 (CDR1), SEQ ID NO:11 (CDR2) and SEQ ID NO:12 (CDR3); or iii) light chain CDRs comprising the amino acid sequences of SEQ ID NO:13 (CDR1), SEQ ID NO:14 (CDR2) and SEQ ID NO:15 (CDR3) and heavy chain CDRs comprising the amino acid sequences of SEQ ID NO:16 (CDR1), SEQ ID NO:17 (CDR2) and SEQ ID NO:18 (CDR3); or iv) light chain CDRs comprising the amino acid sequences of SEQ ID NO:19 (CDR1), SEQ ID NO:20 (CDR2) and SEQ ID NO:21 (CDR3) and heavy chain CDRs comprising the amino acid sequences of SEQ ID NO:22 (CDR1), SEQ ID NO:23 (CDR2) and SEQ ID NO:24 (CDR3); or v) light chain CDRs comprising the amino acid sequences of SEQ ID NO:25 (CDR1), SEQ ID NO:26 (CDR2) and SEQ ID NO:27 (CDR3) and heavy chain CDRs comprising the amino acid sequences of SEQ ID NO:28 (CDR1), SEQ ID NO:29 (CDR2) and SEQ ID NO:30 (CDR3); or vi) light chain CDRs comprising the amino acid sequences of SEQ ID NO:31 (CDR1), SEQ ID NO:32 (CDR2) and SEQ ID NO:33 (CDR3) and heavy chain CDRs comprising the amino acid sequences of SEQ ID NO:34 (CDR1), SEQ ID NO:35 (CDR2) and SEQ ID NO:36 (CDR3); or vii) light chain CDRs comprising the amino acid sequences of SEQ ID NO:37 (CDR1), SEQ ID NO:38 (CDR2) and SEQ ID NO:39 (CDR3) and heavy chain CDRs comprising the amino acid sequences of SEQ ID NO:40 (CDR1), SEQ ID NO:41 (CDR2) and SEQ ID NO:42 (CDR3); or viii) light chain CDRs comprising the amino acid sequences of SEQ ID NO:43 (CDR1), SEQ ID NO:44 (CDR2) and SEQ ID NO:45 (CDR3) and heavy chain CDRs comprising the amino acid sequences of SEQ ID NO:46 (CDR1), SEQ ID NO:47 (CDR2) and SEQ ID NO:48 (CDR3); or ix) light chain CDRs comprising the amino acid sequences of SEQ ID NO:49 (CDR1), SEQ ID NO:50 (CDR2) and SEQ ID NO:51 (CDR3) and heavy chain CDRs comprising the amino acid sequences of SEQ ID NO:52 (CDR1), SEQ ID NO:53 (CDR2) and SEQ ID NO:54 (CDR3); or x) light chain CDRs comprising the amino acid sequences of SEQ ID NO:55 (CDR1), SEQ ID NO:56 (CDR2) and SEQ ID NO:57 (CDR3) and heavy chain CDRs comprising the amino acid sequences of SEQ ID NO:58 (CDR1), SEQ ID NO:59 (CDR2) and SEQ ID NO:60 (CDR3); or xi) light chain CDRs comprising the amino acid sequences of SEQ ID NO:61 (CDR1), SEQ ID NO:62 (CDR2) and SEQ ID NO:63 (CDR3) and heavy chain CDRs comprising the amino acid sequences of SEQ ID NO:64 (CDR1), SEQ ID NO:65 (CDR2) and SEQ ID NO:66 (CDR3); or xii) light chain CDRs comprising the amino acid sequences of SEQ ID NO:67 (CDR1), SEQ ID NO:68 (CDR2) and SEQ ID NO:69 (CDR3) and heavy chain CDRs comprising the amino acid sequences of SEQ ID NO:70 (CDR1), SEQ ID NO:71 (CDR2) and SEQ ID NO:72 (CDR3); or xiii) light chain CDRs comprising the amino acid sequences of SEQ ID NO:73 (CDR1), SEQ ID NO:74 (CDR2) and SEQ ID NO:75 (CDR3) and heavy chain CDRs comprising the amino acid sequences of SEQ ID NO:76 (CDR1), SEQ ID NO:77 (CDR2) and SEQ ID NO:78 (CDR3); or xiv) comprising light chain CDRs comprising the amino acid sequences of SEQ ID NO:79 (CDR1), SEQ ID NO:80 (CDR2) and SEQ ID NO:81 (CDR3) and heavy chain CDRs comprising the amino acid sequences of SEQ ID NO:82 (CDR1), SEQ ID NO:83 (CDR2) and SEQ ID NO:84 (CDR3); or xv) light chain CDRs comprising the amino acid sequences of SEQ ID NO:85 (CDR1), SEQ ID NO:86 (CDR2) and SEQ ID NO:87 (CDR3) and heavy chain CDRs comprising the amino acid sequences of SEQ ID NO:88 (CDR1), SEQ ID NO:89 (CDR2) and SEQ ID NO:90 (CDR3); or xvi) light chain CDRs comprising the amino acid sequences of SEQ ID NO:91 (CDR1), SEQ ID NO:92 (CDR2) and SEQ ID NO:93 (CDR3) and heavy chain CDRs comprising the amino acid sequences of SEQ ID NO:94 (CDR1), SEQ ID NO:95 (CDR2) and SEQ ID NO:96 (CDR3); or xvii) light chain CDRs comprising the amino acid sequences of SEQ ID NO:97 (CDR1), SEQ ID NO:98 (CDR2) and SEQ ID NO:99 (CDR3) and heavy chain CDRs comprising the amino acid sequences of SEQ ID NO:100 (CDR1), SEQ ID NO:101 (CDR2) and SEQ ID NO:102 (CDR3); or xviii) light chain CDRs comprising the amino acid sequences of SEQ ID NO:103 (CDR1), SEQ ID NO:104 (CDR2) and SEQ ID NO:105 (CDR3) and heavy chain CDRs comprising the amino acid sequences of SEQ ID NO:106 (CDR1), SEQ ID NO:107 (CDR2) and SEQ ID NO:108 (CDR3); or xix) light chain CDRs comprising the amino acid sequences of SEQ ID NO:109 (CDR1), SEQ ID NO:110 (CDR2) and SEQ ID NO:111 (CDR3) and heavy chain CDRs comprising the amino acid sequences of SEQ ID NO:112 (CDR1), SEQ ID NO:113 (CDR2) and SEQ ID NO:114 (CDR3); or xx) light chain CDRs comprising the amino acid sequences of SEQ ID NO:115 (CDR1), SEQ ID NO:116 (CDR2) and SEQ ID NO:117 (CDR3) and heavy chain CDRs comprising the amino acid sequences of SEQ ID NO:118 (CDR1), SEQ ID NO:119 (CDR2) and SEQ ID NO:120 (CDR3); or xxi) light chain CDRs comprising the amino acid sequences of SEQ ID NO:121 (CDR1), SEQ ID NO:122 (CDR2) and SEQ ID NO:123 (CDR3) and heavy chain CDRs comprising the amino acid sequences of SEQ ID NO:124 (CDR1), SEQ ID NO:125 (CDR2) and SEQ ID NO:126 (CDR3); or xxii) light chain CDRs comprising the amino acid sequences of SEQ ID NO:127 (CDR1), SEQ ID NO:128 (CDR2) and SEQ ID NO:129 (CDR3) and heavy chain CDRs comprising the amino acid sequences of SEQ ID NO:130 (CDR1), SEQ ID NO:131 (CDR2) and SEQ ID NO:132 (CDR3); or xxiii) light chain CDRs comprising the amino acid sequences of SEQ ID NO:133 (CDR1), SEQ ID NO:134 (CDR2) and SEQ ID NO:135 (CDR3) and heavy chain CDRs comprising the amino acid sequences of SEQ ID NO:136 (CDR1), SEQ ID NO:137 (CDR2) and SEQ ID NO:138 (CDR3); or xxiv) light chain CDRs comprising the amino acid sequences of SEQ ID NO:139 (CDR1), SEQ ID NO:140 (CDR2) and SEQ ID NO:141 (CDR3) and heavy chain CDRs comprising the amino acid sequences of SEQ ID NO:142 (CDR1), SEQ ID NO:143 (CDR2) and SEQ ID NO:144 (CDR3).

* * * * *